(12) United States Patent
Hannapel et al.

(10) Patent No.: US 7,265,263 B1
(45) Date of Patent: Sep. 4, 2007

(54) POTATO TRANSCRIPTION FACTORS, METHODS OF USE THEREOF, AND A METHOD FOR ENHANCING TUBER DEVELOPMENT

(75) Inventors: David J. Hannapel, Ames, IA (US); Hao Chen, Ames, IA (US); Faye M. Rosin, Wageningen (NL)

(73) Assignee: Iowa State University Research Foundation, Inc., Ames, IA (US)

( * ) Notice: Subject to any disclaimer, the term of this patent is extended or adjusted under 35 U.S.C. 154(b) by 262 days.

(21) Appl. No.: 10/624,201

(22) Filed: Jul. 21, 2003

Related U.S. Application Data

(60) Provisional application No. 60/397,423, filed on Jul. 19, 2002.

(51) Int. Cl.
| | |
|---|---|
| C12N 15/29 | (2006.01) |
| C12N 15/82 | (2006.01) |
| C12N 15/87 | (2006.01) |
| C12N 5/04 | (2006.01) |
| A01H 5/00 | (2006.01) |
| A01H 5/10 | (2006.01) |

(52) U.S. Cl. ............... 800/278; 800/298; 800/290; 800/287; 800/320; 435/320.1; 435/410; 435/419; 536/23.1; 536/23.6

(58) Field of Classification Search ............ 536/23.1, 536/23.6; 435/320.1, 468, 410, 419; 800/290, 800/278, 298, 287, 320
See application file for complete search history.

(56) References Cited

OTHER PUBLICATIONS

Fourgoux-Nicol et al (1999, Plant Molecular Biology 40 :857-872).*
Bowie et al, Science 247:1306-1310, 1990.*
McConnell et al, Nature 411 (6838):709-713, 2001.*
Chuck et al (1996, The Plant Cell 8:1277-1289).*
Fourgoux-Nicol et al (1999, Plant Molecular Biology 40 :857-872).*
Bowie et al, Science 247:1306-1310, 199.*
McConnell et al, Nature 411 (6838):709-713, 2001.*
Chuck et al (1996, The Plant Cell 8:1277-1289).*
GenBank Accession No. U65648, Feb. 4, 1997.
GenBank Accession No. AF406697, Sep. 2, 2002.
GenBank Accession No. AF406698, Sep. 2, 2002.
GenBank Accession No. AF406699, Sep. 2, 2002.
GenBank Accession No. AF406700, Sep. 2, 2002.
GenBank Accession No. AF406701, Sep. 2, 2002.
GenBank Accession No. AF406702, Sep. 2, 2002.
GenBank Accession No. AF406703, Sep. 2, 2002.
Rosin et al., "Overexpression of a *Knotted*-Like Homeobox Gene of Potato Alters Vegetative Development by Decreasing Gibberellin Accumulation," *Plant Physiology* 132:106-117 (2003).
Smith et al., "Selective Interaction of Plant Homedomain Proteins Mediates High DNA-Binding Affinity," *PNAS* 99:9579-9584 (2002).
Chen et al., "Interacting Transcription Factors from the Three-Amino Acid Loop Extension Superclass Regulate Tuber Formation," *Plant Physiology* 132:1391-1404 (2003).
Amador et al., "Gibberellins Signal Nuclear Import of PHOR1, a Photoperiod-Responsive Protein with Homology to *Drosophila* Armadillo," *Cell* 106:343-354 (2001).
Carrera et al., "Feedback Control and Diurnal Regulation of Gibberellin 20-Oxidase Transcript Levels in Potato," *Plant Physiology* 119:765-773 (1999).
Müller et al., "In vitro Interactions Between Barley TALE Homeodomain Proteins Suggest a Role for Protein-Protein Associations in the Regulation of *Knox* Gene Function," *The Plant Journal* 27:13-23 (2001).
Bellaoui et al., "The Arabidopsis BELL1 and KNOX TALE Homeodomain Proteins Interact Through a Domain Conserved Between Plants and Animals," *The Plant Cell* 13:2455-2470 (2001).
Chen et al., "Interacting Transcription Factors from the TALE Superclass Regulate Processes of Growth in Potato," Poster presentation at ASPB meeting in Denver (2002).
Chen et al., "Interacting Transcription Factors Regulate Tuber Development," Presentation at Potato Genetics Committee meeting in St. Paul, Minnesota, NCR-84 (2001).
Rosin et al., "A Potato *knox* Gene Involved in Plant Development," Oral presentation at the 2001 Annual Meeting of the American Society of Plant Biologists in Providence, Rhode Island (2001).
Rosin, "Transcription Factors Involved in the Development of Potato (*Solanum tuberosum* L.)," Ph.D. Dissertation, Iowa State University (2002).
Hart, "Isolation and Characterization of Genes Belonging to Developmental Regulatory Gene Classes in Potato (*Solanum tuberosum* L.)," Ph.D. Dissertation, Iowa State University (1998).

* cited by examiner

*Primary Examiner*—Stuart F. Baum
(74) *Attorney, Agent, or Firm*—Nixon Peabody LLP

(57) ABSTRACT

The present invention relates to isolated nucleic acid molecules which encode a BEL transcription factor from potato (*Solanum tuberosum* L.) and the amino acid sequences encoded by such nucleic acid molecules. Additional aspects of the present invention relate to methods of using isolated nucleic acid molecules which encode BEL transcription factors from potato to enhance growth and to regulate flowering in plants. The present invention is also directed to a method for enhancing tuber development in a plant. This method includes transforming a tuberous plant with a DNA construct including a nucleic acid molecule encoding a BEL transcription factor or a KNOX transcription factor, and an operably linked promoter and 3' regulatory region, whereby tuber development is enhanced in the plant.

33 Claims, 28 Drawing Sheets

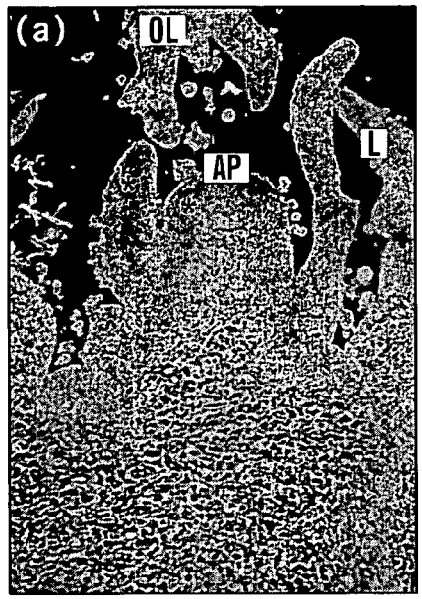
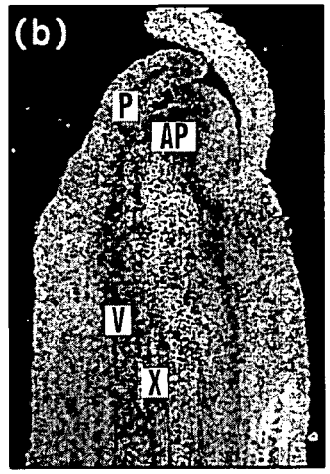
*FIG. 3A*  *FIG. 3B*  *FIG. 3C*
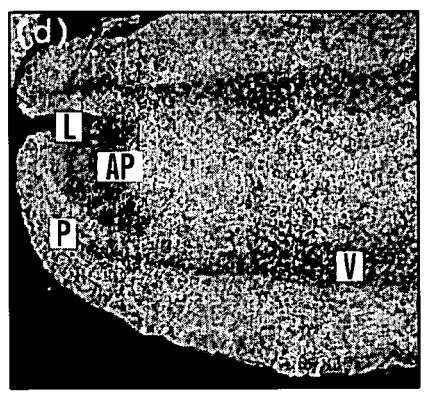
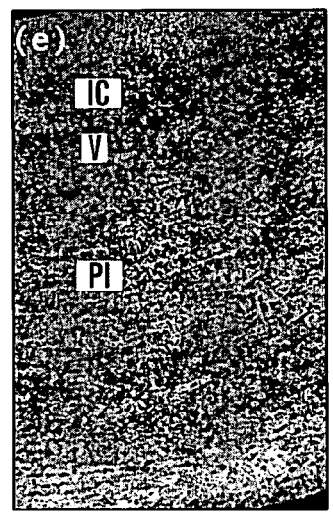
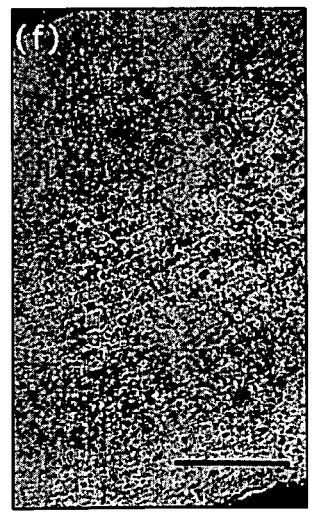
*FIG. 3D*  *FIG. 3E*  *FIG. 3F*

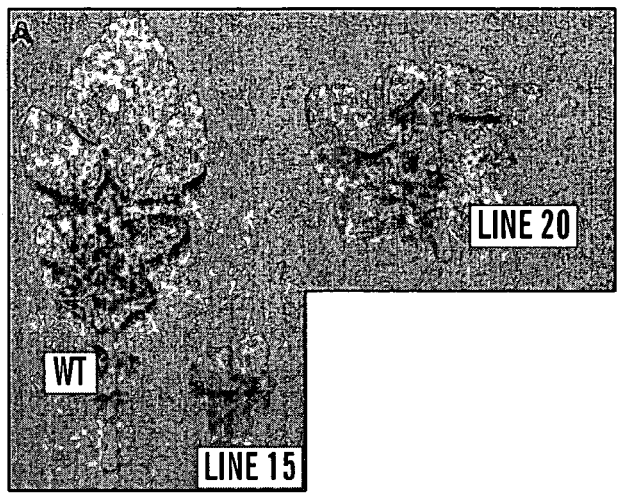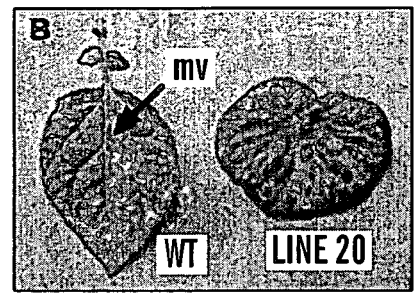
FIG. 5A
FIG. 5B
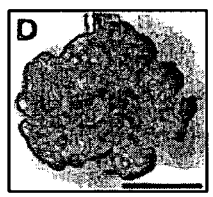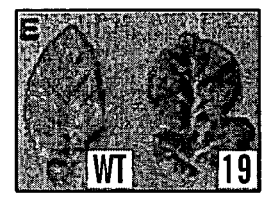
FIG. 5C   FIG. 5D   FIG. 5E
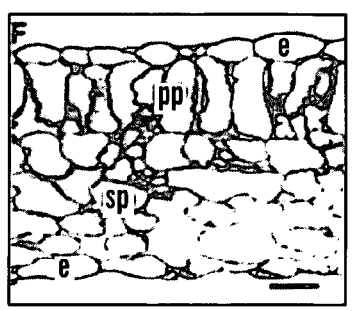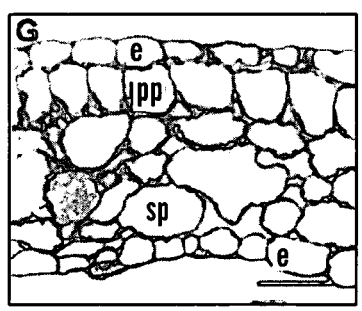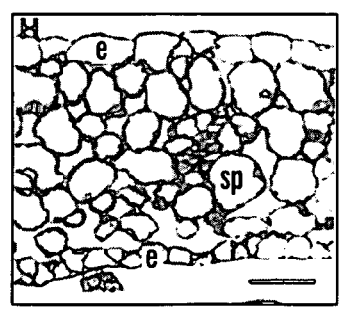
FIG. 5F   FIG. 5G   FIG. 5H

| | GROWTH ON SELECTIVE MEDIA | RELATIVE % β-gal ACTIVITY |
|---|---|---|
| POTH1 (345 aa) | YES | 100 |
| pBHD1 (115-345) | YES | 35 |
| pBHD2 (165-345) | YES | 45 |
| pBHD3 (209-345) | NO | 0 |
| pBHD4 (1-261) | YES | 72 |
| pBHD5 (1-223) | YES | 92 |
| pBHD6 (1-171) | YES | 25 |
| pBHD9 (1-113) | YES | 38 |

*FIG. 10A*

| | GROWTH ON SELECTIVE MEDIA | RELATIVE % β-gal ACTIVITY |
|---|---|---|
| pAD5 (653 aa) | YES | 100 |
| pAD5-1 (230-653) | YES | 45 |
| pAD5-2 (257-653) | NO | 0 |
| pAD5-3 (313-653) | NO | 0 |
| pAD5-4 (348-653) | NO | 0 |
| pAD5-5 (384-653) | NO | 0 |
| pAD5-7 (1-487) | YES | 97 |
| pAD5-8 (1-358) | YES | 57 |
| pAD5-9 (1-315) | YES | 9.1 |
| pAD5-11 (1-286) | YES* | 0 |

*INTERACTION WITH THIS CONSTRUCT PRODUCED A FEW, SLOW GROWING COLONIES BUT NO DETECTABLE β-gal ACTIVITY.

*FIG. 10B*

| DAYS TO TUBERIZE | UNDER LD | - | - | 7 | 7 | 7 | 14 |
|---|---|---|---|---|---|---|---|
| | UNDER SD | 10 | 10 | NA | NA | NA | NA |
| NO. TUBERS* | AFTER 0d | 0 | 0 | 6 | 4 | 5 | 1 |
| | AFTER 7d | 0 | 0 | 10 | 8 | 15 | 4 |
| | AFTER 14d | 6 | 4 | 12 | 14 | 24 | 10 |

| TUBER YIELD PLANT$^{-1}$(mg)* | 18 | 28 | 18 | 95 | 292 | 50 |
|---|---|---|---|---|---|---|

*FROM TWENTY-FOUR PLANTLETS PER LINE, THIRTY-FIVE FOR WT

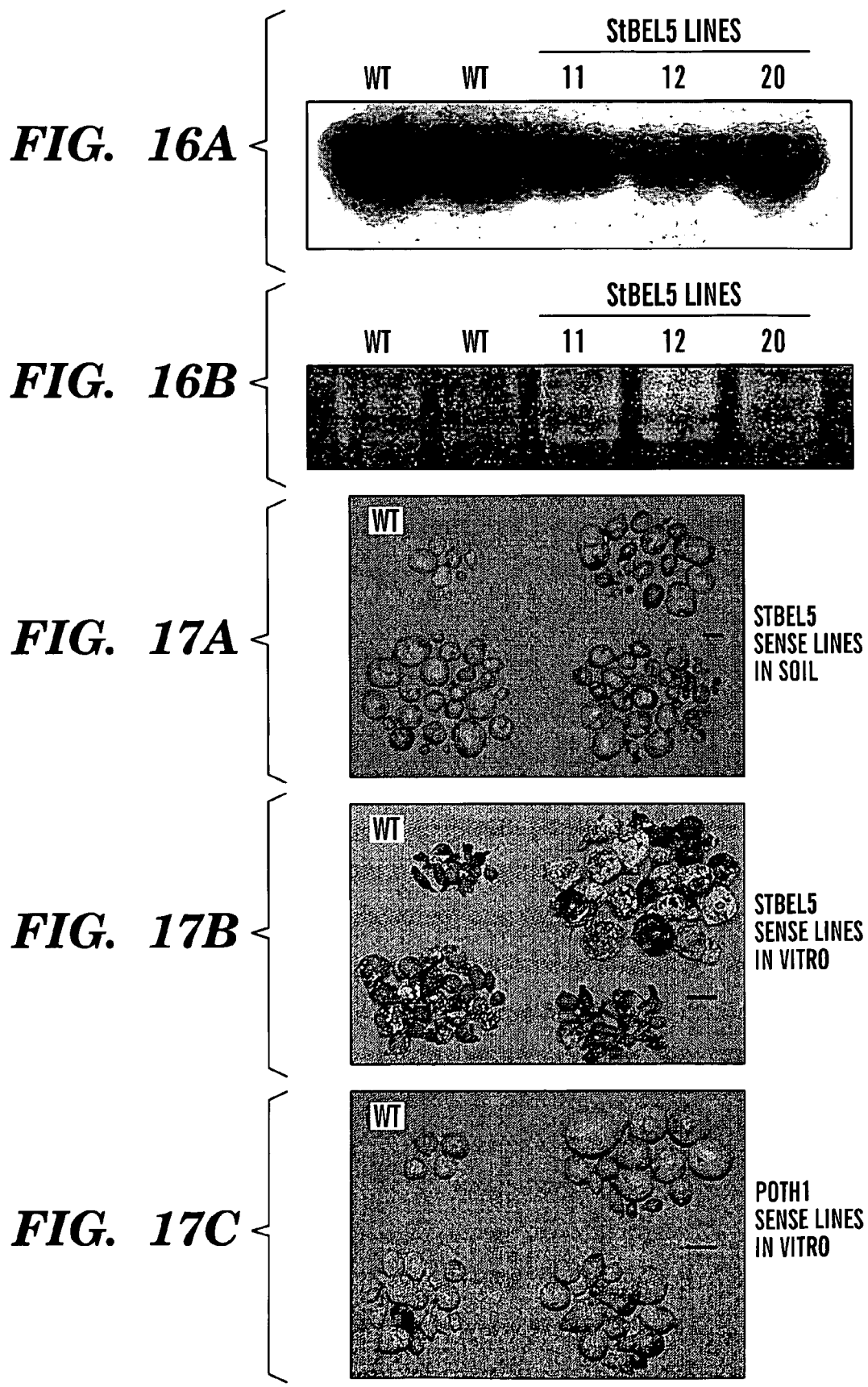

BOTH TFs IN TANDEM ARE NEEDED TO REPRESS THE TARGET GENE
DIAGRAM OF CONSTRUCTS

TGACTTGAC
↓
TGACTTCAC (MUTATED)
FIG. 26A
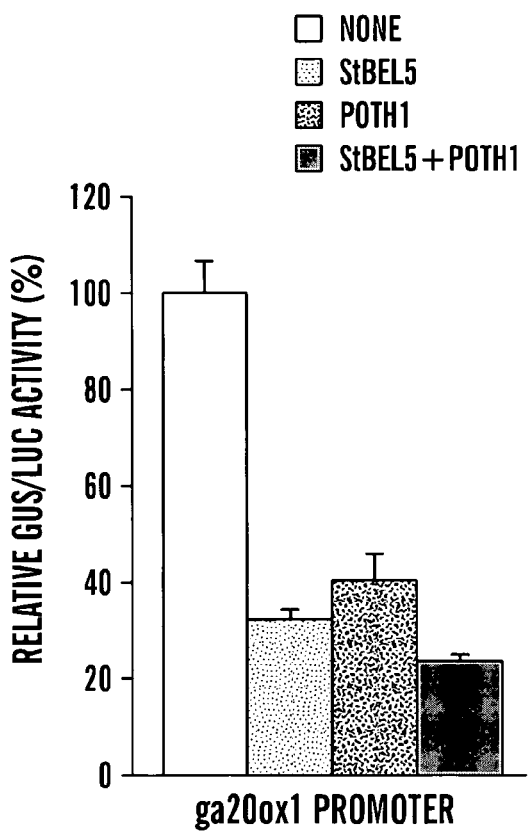
FIG. 26B
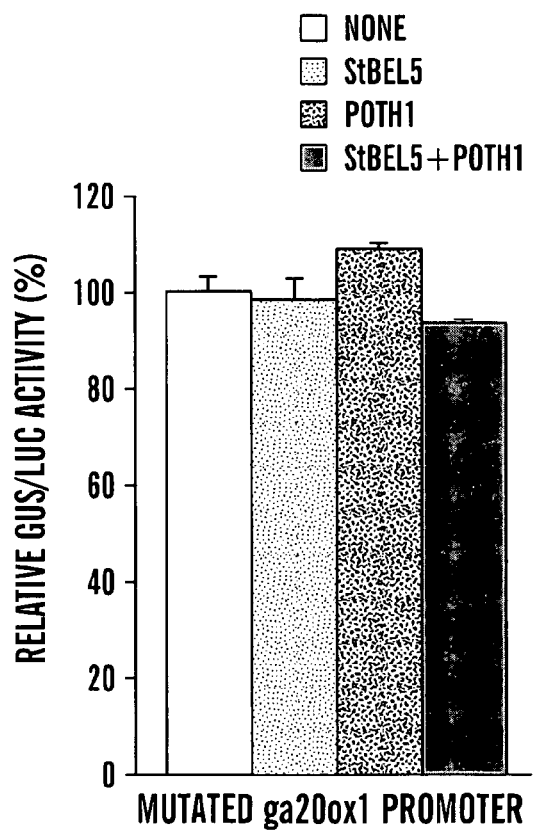
FIG. 26C

POTATO TRANSCRIPTION FACTORS, METHODS OF USE THEREOF, AND A METHOD FOR ENHANCING TUBER DEVELOPMENT

The present invention claims benefit of U.S. Provisional Application Ser. No. 60/397,423, filed Jul. 19, 2002, which is hereby incorporated by reference in its entirety.

The subject matter of this application was made with support from the United States Government under USDA/CSREES Grant Nos. 2002-31100-06019 and 2001-31100-06019. The government may have certain rights.

FIELD OF THE INVENTION

The present invention relates to isolated BEL transcription factors from *Solanum tuberosum*, a method of enhancing tuber development in plants, and methods of regulating flowering and growth in plants.

BACKGROUND OF THE INVENTION

The primary developmental events of plants originate from the shoot apical meristem (SAM) (Clark, "Organ Formation at the Vegetative Shoot Meristem," *Plant Cell* 9:1067-1076 (1997); Kerstetter et al., "Shoot Meristem Formation in Vegetative Development," *Plant Cell* 9:1001-1010 (1997)). The shoot apical meristem (SAM) is responsible for the formation of vegetative organs such as leaves, and may undergo a phase change to form the inflorescence or floral meristem. Many of these events are controlled at the molecular level by transcription factors. Transcription factors (TFs) are proteins that act as developmental switches by binding to the DNA (or to other proteins that bind to the DNA) of specific target genes to modulate their expression. An important family of TFs involved in regulating the developmental events in apical meristems is the knox (knotted-like homeobox) gene family (Reiser et al., "Knots in the Family Tree: Evolutionary Relationships and Functions of Knox Homeobox Genes," *Plant Mol Biol* 42:151-166 (2000)). Knox genes have been isolated from several plant species (reviewed in Reiser et al., "Knots in the Family Tree: Evolutionary Relationships and Functions of knox Homeobox Genes," *Plant Mol. Biol.* 42:151-166 (2000)) and can be divided into two classes based on expression patterns and sequence similarity (Kerstetter et al., "Sequence Analysis and Expression Patters Divide the Maize knotted1-like Homeobox Genes into Two Classes," *Plant Cell* 6:1888-1887 (1994)). Class I knox genes have high similarity to the kn1 homeodomain and generally have a meristem-specific mRNA expression pattern. Class II knox genes usually have a more widespread expression pattern.

Knox genes belong to the group of TFs known as the TALE superclass (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). These TFs are distinguished by a very high level of sequence conservation in the DNA-binding region, designated the homeodomain, and consisting of three α-helices similar to the bacterial helix-loop-helix motif (Kerstetter et al., "Sequence Analysis and Expression Patterns Divide the Maize knotted1-like Homeobox Genes into Two Classes," *Plant Cell* 6:1877-1887 (1994)). The third helix, the recognition helix, is involved in DNA-binding (Mann et al., "Extra Specificity From extradenticle: the Partnership Between HOX and PBX/EXD Homeodomain Proteins," *Trends in Genet* 12:258-262 (1996)). TALE TFs contain a three amino acid loop extension (TALE), proline-tyrosine-proline, between helices I and II in the homeodomain, that has been implicated in protein interactions (Passner et al., "Structure of DNA-Bound Ultrabithorax-Extradenticle Homeodomain Complex," *Nature* 397:714-719 (1999)). There are numerous TFs from plants and animals in the TALE superclass and the two main groups in plants are the KNOX and BEL types (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). Related genes in animal systems play an important role in regulating gene expression.

Expression patterns and functional analysis of mutations support the involvement of knox genes in specific developmental processes of the shoot apical meristem. Kn1 from maize, the first plant homeobox gene to be discovered (Vollbrecht et al., "The Developmental Gene Knotted-1 is a Member of a Maize Homeobox Gene Family," *Nature* 350:241-243 (1991)), is involved in maintenance of the shoot apical meristem and is implicated in the switch from indeterminate to determinate cell fates (Chan et al., "Homeoboxes in Plant Development," *Biochim Biophys Acta* 1442:1-19 (1998); Kerstetter et al., "Loss-of-Function Mutations in the Maize Homeobox Gene, knotted1, are Defective in Shoot Meristem Maintenance," *Development* 124:3045-3054 (1997); Clark et al., The CLAVATA and SHOOT MERISTEMLESS Loci Competitively Regulate Meristem Activity in *Arabidopsis,*" *Development* 122:1567-1575 (1996)). Transcripts of kn1 in maize (Jackson et al., "Expression of Maize KNOTTED1 Related Homeobox Genes in the Shoot Apical Meristem Predicts Patterns of Morphogenesis in the Vegetative Shoot," *Development* 120: 405-413 (1994)), OSH1 in rice (Sentoku et al., "Regional Expression of the Rice KN1-type Homeobox Gene Family During Embryo, Shoot, and Flower Development," *Plant Cell* 11: 1651-1663 (1999)), and NTH15 in tobacco (Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)) were localized by in situ hybridization to undifferentiated cells of the corpus and the developing stem, but were not detected in the tunica or leaf primordia. Overexpression of kn1 in *Arabidopsis* (Lincoln et al., "A knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994)) and in tobacco (Sinha et al., "Overexpression of the Maize Homeobox Gene, KNOTTED-1, Causes a Switch From Determinate to Indeterminate Cell Fates," *Genes Dev* 7:787-795 (1993)), resulted in plants with altered leaf morphologies including lobed, wrinkled or curved leaves with shortened petioles and decreased elongation of veins. Plants were reduced in size and showed a loss of apical dominance. In plants with a severe phenotype, ectopic meristems formed near the veins of leaves indicating a reversion of cell fate back to the indeterminate state (Sinha et al., "Overexpression of the Maize Homeobox Gene, KNOTTED-1, Causes a Switch From Determinate to Indeterminate Cell Fates," *Genes Dev* 7:787-795 (1993)). Overexpression of OSH1 or NTH15 in tobacco resulted in altered morphologies similar to the 35S-kn1 phenotype (Sato et al., "Abnormal Cell Divisions in Leaf Primordia Caused by the Expression of the Rice Homeobox Gene OSH1 Lead to Altered Morphology of Leaves in Transgenic Tobacco," *Mol Gen Genet* 251:13-22

(1996); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)).

Alterations in leaf and flower morphology in 35S-NTH15 or OSH1 transgenic tobacco were accompanied by changes in hormone levels. Whereas levels of all the hormones measured were changed slightly, both gibberellin and cytokinin levels were dramatically altered (Kusaba et al., "Alteration of Hormone Levels in Transgenic Tobacco Plants Overexpressing the Rice Homeobox Gene OSH1," *Plant Physiol* 116:471-476 (1998); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)). RNA blot analysis revealed that the accumulation of GA 20-oxidase1 mRNA was reduced several fold in transgenic plants (Kusaba et al., "Decreased $GA_1$ Content Caused by the Overexpression of OSH1 is Accompanied by Suppression of GA 20-oxidase Gene Expression," *Plant Physiol* 117:1179-1184 (1998); Tanaka-Ueguchi et al., "Overexpression of a Tobacco Homeobox Gene, NTH15, Decreases the Expression of a Gibberellin Biosynthetic Gene Encoding GA 20-oxidase," *Plant J* 15:391-400 (1998)). A KNOX protein of tobacco binds to specific elements in regulatory regions of the GA 20-oxidase1 gene of tobacco to repress its activity (Sakamoto et al., KNOX Homeodomain Protein Directly Suppresses the Expression of a Gibberellin Biosynthesis Gene in the Tobacco Shoot Apical Meristem," *Genes Dev* 15:581-590 (2001)). GA 20-oxidase is a key enzyme in the GA biosynthetic pathway necessary for the production of the physiologically inactive $GA_{20}$ precursor of active $GA_1$ (Hedden et al., "Gibberellin Biosynthesis: Enzymes, Genes and Their Regulation," *Annu Rev Plant Physiol Plant Mol Biol* 48:431-460 (1997)). $GA_1$ and other active GA isoforms are important regulators of stem elongation, the orientation of cell division, the inhibition of tuberization, flowering time, and fruit development (Jackson et al., "Control of Tuberisation in Potato by Gibberellins and Phytochrome," *B. Physiol Plant* 98:407-412 (1996); Hedden et al., "Gibberellin Biosynthesis: Enzymes, Genes and Their Regulation," *Annu Rev Plant Physiol Plant Mol Biol* 48:431-460 (1997); Rebers et al., "Regulation of Gibberellin Biosynthesis Genes During Flower and Early Fruit Development of Tomato," *Plant J* 17:241-250 (1999)).

Another plant homeobox gene family that is closely related to the knox genes is the BEL (BELL) family (Chan et al., "Homeoboxes in Plant Development," *Biochim Biophys Acta* 1442:1-19 (1998); Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). BEL TFs have been implicated in flower and fruit development (Reiser et al., The BELL1 Gene Encodes a Homeodomain Protein Involved in Pattern Formation in the *Arabidopsis* Ovule Primordium," *Cell* 83:735-742 (1995); Dong et al., "MDH1: an Apple Homeobox Gene Belonging to the BEL1 Family," *Plant Mol Biol* 42:623-633 (2000)). Genetic analysis of BEL1 in *Arabidopsis* showed that expression of this TF regulated the development of ovule integuments and overlaps the expression of AGAMOUS (Ray et al., "*Arabidopsis* Floral Homeotic Gene BELL (BEL1) Controls Ovule Development Through Negative Regulation of AGAMOUS Gene (AG)," *Proc Natl Acad Sci USA* 91:5761-5765 (1994); Reiser et al., The BELL1 Gene Encodes a Homeodomain Protein Involved in Pattern Formation in the *Arabidopsis* Ovule Primordium," *Cell* 83:735-742 (1995); Western et al., "BELL1 and AGAMOUS Genes Promote Ovule Identity in *Arabidopsis thaliana*," *Plant J* 18:329-336 (1999)). In COP1 mutants, the photoinduced expression of ATH1, another BEL TF of *Arabidopsis*, was elevated, indicating a possible role in the signal transduction pathway downstream of COP1 (Quaedvlieg et al., "The Homeobox Gene ATH1 of *Arabidopsis* is Depressed in the Photomorphogenic Mutants cop1 and det1," *Plant Cell* 7:117-129 (1995)).

Plants must maintain a great deal of flexibility during development to respond to environmental and developmental cues. Responses to these signals, which include day length, light quality or quantity, temperature, nutrient and hormone levels, are coordinated within the meristem (Kerstetter et al., "Shoot Meristem Formation in Vegatative Development," *Plant Cell* 9:1001-1010 (1997)). In potato, there is a specialized vegetative meristem called the stolon meristem that develops as a horizontal stem and under inductive conditions will form the potato tuber (Jackson, "Multiple Signaling Pathways Control Tuber Induction in Potato," *Plant Physiol.* 119:1-8 (1999); Fernie et al., "Molecular and Biochemical Triggers of Potato Tuber Development," *Plant Physiol.* 127:1459-1465 (2001)). Potato offers an excellent model system for examining how vegetative meristems respond to external and internal factors to control development at the molecular level. In model tuberization systems, synchronous tuber formation occurs under inductive conditions and shoot or stolon formation occurs under noninductive conditions. The cellular and biochemical processes that occur in these model systems have been examined extensively (Vreugdenhil et al., "Initial Anatomical Changes Associated with Tuber Formation on Single-Node Potato (*Solanum tuberosum* L.) Cuttings: A Re-evaluation," *Ann. Bot.* 84:675-680 (1999); Xu et al., "The Role of Gibberellin, Abscisic Acid, and Sucrose in the Regulation of Potato Tuber Formation In vitro," *Plant Physiol.* 117:575-584 (1998); Hannapel, "Characterization of Early Events of Potato Tuber Development," *Physiol. Plant* 83:568-573 (1991); Wheeler et al., "Comparison of Axillary Bud Growth and Patatin Accumulation in Potato Leaf Cuttings as Assays for Tuber Induction," *Ann. Bot.* 62:25-30 (1988)). In addition to being good systems to examine integration of signals at the meristem, understanding the molecular processes controlling tuberization in potato is important. Potato is the fourth largest crop produced in the world, ranking after maize, rice, and wheat, and is a major nutritional source in many countries (Jackson, "Multiple Signaling Pathways Control Tuber Induction in Potato," *Plant Physiol.* 119:1-8 (1999); Fernie et al., "Molecular and Biochemical Triggers of Potato Tuber Development," *Plant Physiol.* 127:1459-1465 (2001)); therefore, research focusing on the process of tuber initiation and development is very important.

Tuber formation in potatoes (*Solanum tuberosum* L.) is a complex developmental process that requires the interaction of environmental, biochemical, and genetic factors. Several important biological processes like carbon partitioning, signal transduction, and meristem determination are involved (Ewing et al., "Tuber Formation in Potato: Induction, Initiation and Growth," *Hort. Rev.* 14:89-198 (1992)). Under conditions of a short-day photoperiod and cool temperature, a transmissible signal is activated that initiates cell division and expansion and a change in the orientation of cell growth in the subapical region of the stolon tip (Ewing et al., "Tuber Formation in Potato: Induction, Initiation and Growth," *Hort. Rev.* 14:89-198 (1992); Xu et al., "Cell Division and Cell Enlargement During Potato Tuber Formation," *J. Expt.*

*Bot.* 49:573-582 (1998)). In this signal transduction pathway, perception of the appropriate environmental cues occurs in leaves and is mediated by phytochrome and gibberellins (van den Berg et al., "Morphology and (14C) gibberellin A-12 Metabolism in Wild-Type and Dwarf *Solanum tuberosum* ssp. *Andigena* Grown Under Long and Short Photoperiods," *J. Plant Physiol.* 146:467-473 (1995); Jackson et al., "Phytochrome B Mediates the Photoperiodic Control of Tuber Formation in Potato," *Plant J.* 9:159-166 (1996); Jackson et al., "Control of Tuberisation in Potato by Gibberellins and Phytochrome," *B. Physiol Plant* 98:407-412 (1996)). Tuber development at the stolon tip is comprised of biochemical and morphological processes. Both are controlled by differential gene expression (Hannapel, "Characterization of Early Events of Potato Tuber Development," *Physiol. Plant* 83:568-573 (1991); Bachem et al., "Analysis of Gene Expression During Potato Tuber Development," *Plant J.* 9:745-753 (1996); Macleod et al., "Characterisation of Genes Isolated from a Potato Swelling Stolon cDNA Library," *Pot. Res.* 42:31-42 (1999)) with most of the work focusing on the biochemical processes, including starch synthesis (Abel et al., "Cloning and Functional Analysis of a cDNA Encoding a Novel 139 kDa Starch Synthase from Potato (*Solanum tuberosum* L.)," *Plant J.* 10:981-991 (1996); Preiss, "ADPglucose Pyrophosphorylase: Basic Science and Applications in Biotechnology," *Biotech. Annu. Rev.* 2:259-279 (1996); Geigenberger et al., "Overexpression of Pyrophosphatase Leads to Increased Sucrose Degradation and Starch Synthesis, Increased Activities of Enzymes for Sucrose-Starch Interconversions, and Increased Levels of Nucleotides in Growing Potato Tubers," *Planta* 205:428-437 (1998)) and storage protein accumulation (Mignery et al., "Isolation and Sequence Analysis of cDNAs for the Major Potato Tuber Protein, Patatin," *Nucl. Acid Res.* 12:7989-8000 (1984); Hendriks et al., "Patatin and Four serine Protease Inhibitor Genes are Differentially Expressed During Potato Tuber Development," *Plant Mol. Biol.* 17:385-394 (1991); Suh et al., "Proteinase-Inhibitor Activity and Wound-Inducible Expression of the 22-kDa Potato-Tuber Proteins," *Planta* 184:423-430 (1991)).

Much less is known about the morphological controls of tuberization, although it is clear that phytohormones play a prominent role (Koda et al., "Potato Tuber-Inducing Activities of Jasmonic Acid and Related Compounds," *Phytochemistry* 30:1435-1438 (1991); Xu et al., "The Role of Gibberellin, Abscisic Acid, and Sucrose in the Regulation of Potato Tuber Formation In vitro," *Plant Physiol.* 117:575-584 (1998), Sergeeva et al., "Tuber Morphology and Starch Accumulation are Independent Phenomena: Evidence from ipt-transgenic Potato Lines," *Physiol. Plant* 108:435-443 (2000)). Gibberellins (GA), in particular, play an important role in regulating tuber development. High levels of GA are correlated with the inhibition of tuberization, whereas low levels are associated with the induction of tuber formation (Jackson et al., "Control of Tuberisation in Potato by Gibberellins and Phytochrome," *B. Physiol Plant* 98:407-412 (1996); Xu et al., "The Role of Gibberellin, Abscisic Acid, and Sucrose in the Regulation of Potato Tuber Formation In vitro," *Plant Physiol.* 117:575-584 (1998)). Specific genes, such as lipoxygenases (Kolomiets et al., "Lipoxygenase is Involved in the Control of Potato Tuber Development," *Plant Cell* 13:613-626 (2001)) and MADS box genes (Kang et al., "Nucleotide Sequences of Novel Potato MADS-box cDNAs and their Expression in vegetative Organs," *Gene* 166:329-330 (1995)) that are involved in regulating tuber formation have been identified.

Three independent research groups have recently confirmed that BEL-like TFs interact via protein binding with their respective knox-types in three separate species (Bellaoui et al., "The *Arabidopsis* BELL1 and KNOX TALE Homeodomain Proteins Interact Through a Domain Conserved Between Plants and Animals," *Plant Cell* 13:2455-2470 (2001); Müller et al., "In vitro Interactions Between Barley TALE Homeodomain Proteins Suggest a Role for Protein-Protein Associations in the Regulation of Knox Gene Function," *Plant J.* 27:13-23 (2001); Smith et al., "Selective Interaction of Plant Homeodomain Proteins Mediates High DNA-Binding Affinity," *Proc. Nat'l. Acad. Sci. USA* 99:9579-9584 (2002)), but to date, there is no published report on the function of this interaction. Moreover, nothing is known about the role of either KNOX or the BEL TFs in the regulation of development of tuberous plants, such as potato.

The present invention is directed to overcoming these and other deficiencies in the art.

SUMMARY OF THE INVENTION

The present invention relates to isolated nucleic acid molecules which encode a BEL transcription factor from potato (*Solanum tuberosum* L.) and the amino acid sequences encoded by such nucleic acid molecules.

Another aspect of the present invention pertains to host cells, DNA constructs, expression vectors, transgenic plants, and transgenic plant seeds containing the isolated nucleic acid molecules of the present invention.

The present invention is also directed to a method for enhancing tuber development in a plant. This method includes transforming a tuberous plant with a first DNA construct including a first nucleic acid molecule encoding a BEL transcription factor or a KNOX transcription factor, and a first operably linked promoter and first 3' regulatory region, whereby tuber development in the plant is enhanced.

A further aspect of the present invention relates to a method for enhancing growth in a plant. This method includes transforming a plant with a DNA construct including a nucleic acid molecule encoding a BEL transcription factor from *Solanum tuberosum* and an operably linked promoter and 3' regulatory region, whereby growth in the plant is enhanced.

Yet another aspect of the present invention relates to a method for regulating flowering in a plant. This method includes transforming a plant with a DNA construct including a nucleic acid molecule encoding a BEL transcription factor from *Solanum tuberosum* and an operably linked promoter and 3' regulatory region, whereby flowering in the plant is regulated.

The present invention relates to transcription factors which can be used to enhance tuber formation, to enhance growth, or to regulate flowering in a plant. In particular, accelerating tuber growth in field plants shortens the time for field cultivation. It can also be used to shorten the timing of a "late" potato variety to produce an earlier harvest. Many desirable breeding lines of potato produce tubers too late in the growing season or with too low a yield. The method of the present invention circumvents these problems, even under noninductive conditions. Enhanced tuberization also has applications for producing food in space under a research initiative directed by NASA (Food and Crop Systems Research, NASA's Advanced Life Support Program). Potato tubers are also being designed as biostorage organs for the production of pharmaceuticals or bioproducts. Enhanced tuber growth would be advantageous in these systems. Moreover, enhancement of growth in plants or regulation of flowering in plants can be used to produce an earlier harvest of plants/flowers.

BRIEF DESCRIPTION OF THE DRAWINGS

FIGS. 3A-F show the localization of POTH1 mRNA in potato plants as revealed by in situ hybridization. The presence of POTH1 mRNA is indicated by an orange/brown stain under dark-field microscopy. All micrographs are of equal magnification. Size bar=300 μm. FIG. 3A shows a longitudinal section through a vegetative shoot apex, probed with antisense POTH1. AP=apical meristem; L=leaf lamina; OL=older leaf lamina. Asterisks indicate leaf primordia (beneath AP) and procambium (to left of AP). FIG. 3B shows unswollen stolon apex, antisense POTH1. AP=apical meristem; P=procambium; asterisk=lamina of young leaf; V=perimedullary parenchyma associated with vascular tissue; X=xylem element. FIG. 3C shows unswollen stolon apex, sense POTH1. FIG. 3D shows swollen stolon apex, antisense POTH1. AP=apical meristem; P=procambium; V=perimedullary parenchyma and vascular tissue; L=lamina of young leaf. FIG. 3E shows swollen stolon, subapical longitudinal section, basal to section in 3D, antisense POTH1. IC=inner cortex; V=perimedullary parenchyma and vascular tissue; PI=pith. FIG. 3F shows swollen stolon, subapical section, sense POTH1.

FIG. 4A shows total RNA (5 μg) from shoot tips of wild-type (WT) and independent transgenic lines, potato subsp. andigena 15, 18, 20, 29, and 11 that were hybridized to a $^{32}$P-labeled POTH1 probe with the ELK or homeodomain deleted. In FIG. 4B, membranes were stripped and hybridized with $^{32}$P-labeled 1.2 kb wheat 18S rRNA to ascertain equal loading and transfer. In FIGS. 4C-F, three plants each of wild-type and overexpression lines, potato subsp. andigena 15, 18, 20, 29, and 11 were examined. Standard error is indicated for each mean. In FIG. 4C, plant height and in FIG. 4D, internode length were examined for 75-day old plants. In FIG. 4E, petiole length and in FIG. 4F, the terminal leaflet length was measured for the sixth expanded leaf of 84-day old plants.

FIGS. 5A-Q show the phenotype of the leaves of POTH1 overexpression lines. FIG. 5A shows that the overall size and shape of leaves from the andigena intermediate and severe overexpression lines, line 20 and line 15, respectively, have been altered compared to wild-type leaves (WT). In FIG. 5B, wild-type leaflets (WT) have a prominent mid-vein (mv) and pinnate venation pattern. The potato subsp. andigena intermediate overexpression mutant (line 20) has a mouse-ear shape, a shortened mid-vein, and palmate venation pattern. FIG. 5C shows the shoot tip of WT potato subsp. andigena line. FIG. 5D shows the severe mutant, potato subsp. andigena line 15, which has a mouse-ear leaf phenotype and shortened petioles causing leaves to cluster closely to the stem. The bars in FIGS. 5C and D are 5 mm. In FIG. 5E, the rachis and associated leaflets were detached from the petiole of a wild-type (WT) and a representative sense line (19), to show a slight increase in the proliferation of leaflets. FIG. 5F shows a cross-section through a wild-type leaf showing the arrangement of cell layers: e=epidermis; sp=spongy parenchyma; pp=palisade parenchyma. Size bar=50 μm. FIG. 5G shows a cross-section through a potato subsp. andigena line 15 leaf after treatment with $GA_3$ showing an intermediate level of cell organization. Bar=50 μm. FIG. 5H shows a cross-section through a potato subsp. andigena line 15 leaf showing that the cell layers lack a palisade parenchyma layer. Size bar=50 μm. In FIGS. 5P-Q, the compound leaf structure is shown for the overexpression mutant, 'FL-1607' line 5. Shoot tips were treated with either 10 μM $GA_3$ in 0.002% (v/v) ethanol (FIG. 5P) or with 0.002% (v/v) ethanol alone (FIG. 5Q). The mid-vein is marked with an arrow in FIG. 5P. Note that the morphology of the $GA_3$-treated leaf (FIG. 5P) is more similar to the wild-type leaf (FIG. 5O) than to 'FL-1607' line S control leaf (FIG. 5Q).

In FIG. 7A, 5 μg of total RNA from the shoot tips of wild-type lines (designated 2, 9, and 10) and the overexpression lines, potato subsp. andigena 11, 15, and 18 were hybridized with a 1.2-kb fragment of the potato GA 20-oxidase1 cDNA, StGA20ox1 (Carrera et al., "Feedback Control and Diurnal Regulation of Gibberellin 20-oxidase Transcript Levels in Potato," *Plant Physiol.* 119:765-773 (1999), which is hereby incorporated by reference in its entirety). In FIG. 7B, the membrane was stripped and re-probed with 18S wheat rRNA to ascertain equal loading and efficient transfer.

FIG. 9A shows selection on a nutrient carbon medium minus histidine, leucine, trytophan, and adenine. The pAD plasmid provides leucine selection, the pBD plasmid (pBridge) provides tryptophan selection, and histidine and adenine selection are activated from the host strain (AH109) chromosomal DNA. The asterisk (*) designation indicates yeast growth with both plasmids transformed together, whereas the pAD plasmids (designated 5, 11, 13, 14, 22, 29, 30) are transformed alone (no growth). SIR4, a transcriptional activator of yeast, is used as a positive control and pBHD is POTH1 in pBridge alone. FIG. 9B shows that POTH1 interacts with all seven BELs as determined by a quantitative yeast two-hybrid assay. LacZ induction in the yeast strain AH109 was assayed in transformed yeast cultures using a quantitative yeast β-galactosidase assay method (Pierce Chemical Company). For each pair, the dark bars on the left represent the pAD or pBHD plasmid alone transformed into yeast. The white bars on the right in each pair represent both plasmids (pAD and pBHD) transformed together. The standard error of the mean is represented by error bars. FIG. 9C shows immunoprecipitates of the in vitro binding of POTH1 to BEL proteins of potato. $^{35}$S-labeled GAD: POTH1 fusion protein and the three BEL1 proteins (p11Z-5, -13, and -30) were synthesized in separate in vitro transcription/translation reactions (lanes 2, 3, 6, and 9, respectively). Each of the three BEL1 proteins were incubated with the GAD:POTH1 protein and immunoprecipitated with anti-GAD antibodies (lanes 5, 8, and 11). None of the three BEL proteins bound to the GAD protein alone (lanes 4, 7, and 10). Labeled proteins were visualized by autoradiography after separation by SDS-PAGE. Molecular size markers are shown on the right.

FIGS. 10A-B show a deletion analysis of the binding regions of POTH1 and a potato BEL1-like protein using the yeast two-hybrid system. In FIG. 10A, deletion constructs of POTH1 in pBridge were tested for expression in the yeast strain AH109 and cotransformed with the full-length BEL cDNA, StBEL-05, in pGAL4 to test for interaction. In FIG. 10B, deletion constructs of StBEL-05 in pGAL4 were cotransformed with the full-length cDNA of POTH1 in pBridge. Interaction was verified with both nutritional selection and β-galactosidase activity. The white box indicates the homeodomain. The gray box indicates the putative protein/protein interaction region (for POTH1, this is the conserved KNOX domain, for StBEL5, the BELL domain). The black boxes are conserved sequences identified in the BEL proteins (see FIG. 13A) and the diagonal hatched boxes in POTH1 represent the ELK domain. The numbers in parentheses represent the amino acids of the full-length sequence included in each construct.

FIGS. 16A-B are a Northern blot analysis of the accumulation of the mRNA of the GA 20-oxidase1 gene of potato (Carerra et al., "Feedback Control and Diurnal Regulation of Gibberellin 20-oxidase Transcript Levels in Potato," *Plant Physiol.* 119:765-773 (1999), which is hereby incorporated by reference in its entirety) in wild-type plants and sense lines 11, 12, and 20 of StBEL-05 (FIG. 16A). Total RNA was extracted from the 2.0 mm distal tip of stolons from plants grown under LD conditions (16 hours of light, 8 hours of dark). Wild-type RNA (WT) was extracted from two separate pools. Ten μg of total RNA were loaded per lane. A gene-specific probe for GA 20-oxidase1 was used for hybridization. All three StBEL-05 lines exhibited enhanced tuber formation. Ethidium bromide-stained rRNA is visualized as a loading control (FIG. 16B).

FIG. 17A shows tubers harvested from independent lines of StBEL-05 transgenic plants (*Solanum tuberosum* spp. *andigena*) grown in soil under a short-day photoperiod. Plants were grown under long days (LD) (16 hours of light, 8 hours of dark) in 10 cm pots until they reached the 16-leaf stage and then transferred to short days. After 14 days under short days, tubers from three plants per independent line were harvested and photodocumented. Tuber numbers and yields increased by at least threefold in these StBEL-05 lines relative to control plants. Starting from the upper left-hand corner and proceeding clockwise are tubers harvested from control plants (WT) and from each of the StBEL-05 overexpression lines 14, 19, and 12. Other than the increase in the rate of tuber formation, the phenotype of these sense lines was similar to wild-type. Reference bar is equivalent to 1.0 cm.

FIG. 17B shows tubers from the same StBEL-05 lines from FIG. 17A harvested after 21 days of culture in vitro under inductive conditions of a short-day photoperiod (8 hours of light, 16 hours of dark) and 6% sucrose in the media. Tubers from 35 control plants and from 25 plants of the StBEL-05 lines are displayed in the same order as shown in FIG. 17A. Tuber yield per plant of line 14 was sixteenfold greater than wild-type. The tubers showed an intense purple color, which is the result of anthocyanin accumulation characteristic of this subspecies. Reference bar is equivalent to 1.0 cm.

FIG. 17C shows tuber production for stolons from overexpression lines of POTH1. Excised stolon tips from plants grown under LD conditions were grown in vitro in the dark in media supplemented with 8% sucrose. Tubers were harvested after 35 days of culture. Starting from the upper left-hand corner and proceeding clockwise are tubers harvested from control plants (WT) and from each of the POTH1 overexpression lines 11, 18, and 20. Twelve stolon tips per independent line were evaluated for tuber production. Reference bar is equivalent to 1.0 cm.

FIGS. 26A-C show a schematic of the mutated base in a 9-bp motif (FIG. 26A) and that mutation in the StBEL-05-POTH1 heterodimer binding site deprived the ga20ox1 promoter of its response to StBEL-05 and POTH1 repression (FIGS. 26B-C). The construct with the LUC gene under the CaMV 35S promoter was used as control. Each transfection was performed three times. Relative GUS-LUC activity was calculated with reporter alone set as 100%. Data are means±SE.

DETAILED DESCRIPTION OF THE INVENTION

Figure 1:
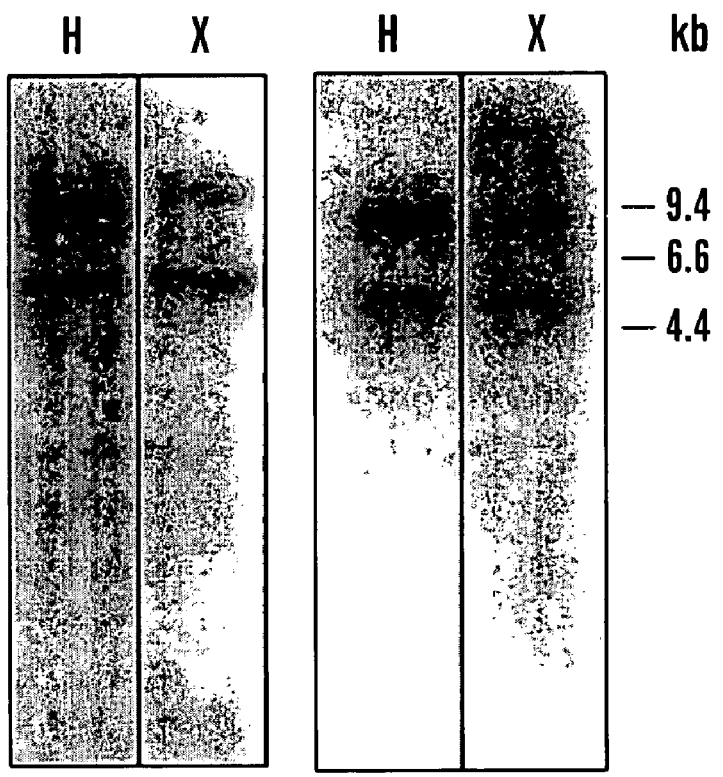
FIG. 1 shows Southern hybridization of POTH1. Genomic DNA (10 μg) was digested with the restriction enzymes, Hind III (H) or Xba I (X) and hybridized to a $^{32}$P-labeled POTH1 probe which did not include the ELK or homeodomain. There is a restriction site for Hind III within the coding sequence of POTH1. Size markers in kb are shown on the right.

The present invention relates to nucleic acid molecules encoding BEL transcription factors from potato (*Solanum tuberosum* L.). BEL transcription factor is a general term used herein to mean a member of the BEL-1-like family of transcription factors, which includes a BELL domain (Bellaoui et al., "The *Arabidopsis* BELL1 and KNOX TALE Homeodomain Proteins Interact Through a Domain Conserved Between Plants and Animals," *Plant Cell* 13(11): 2455-70 (2001), which is hereby incorporated by reference in its entirety) and which regulates growth, in particular, floral development.

In a first embodiment, the BEL transcription factor from *Solanum tuberosum* is identified herein as StBEL-05 and is encoded by a nucleic acid molecule having a nucleotide sequence of SEQ ID NO:1 as follows:

```
  1 catgcagaga taaaaatata gatcagtctg acaagaaggc aacttctcaa agcttagaga
 61 gctaccaccc gaagatagac agttagttac atgtactgtt atagataaaa ggagaaatcc
121 gaagaagaaa gaattttttt tgcagatatg tactatcaag gaacctcgga taatactaat
181 atacaagctg atcatcaaca acgtcataat catgggaata gtaataataa taatattcag
241 acactttatt tgatgaaccc taacaattat atgcaaggct acactacttc tgacacacag
301 cagcagcagc agttacttt cctgaattct tcaccagcag caagcaacgc gctttgccat
361 gcgaatatac aaacgcgcc gctgcaacag cagcacttg tcggtgtgcc tcttccggca
421 gtaagtttgc acgatcagat caatcatcat ggacttttac agcgcatgtg gaacaaccaa
481 gatcaatctc agcaggtgat agtaccatcg tcgacggggg tttctgccac gtcatgtggc
541 gggatcacca cggacttggc gtctcaattg gcgtttcaga ggccgattcc gacaccacaa
601 caccgacagc agcaacaaca gcaaggcggt ctatctctaa gcctttctcc tcagctacaa
661 cagcaaatta gtttcaataa caatatttca tcctcatcac caaggacaaa taatgttact
721 attagggaa cattagatgg aagttctagc aacatggttt taggctctaa gtatctgaaa
781 gctgcacaag agcttcttga tgaagttgtt aatattgttg gaaaaagcat caaaggagat
841 gatcaaaaga aggataattc aatgaataaa gaatcaatgc ctttggctag tgatgtcaac
```

-continued

```
 901 actaatagtt ctggtggtgg tgaaagtagc agcaggcaga aaaatgaagt tgctgttgag
 961 cttacaactg ctcaaagaca agaacttcaa atgaaaaaag ccaagcttct tgccatgctt
1021 gaagaggtgg agcaaaggta cagacagtac catcaccaaa tgcaaataat tgtattatca
1081 tttgagcaag tagcaggaat tggatcagcc aaatcataca ctcaattagc tttgcatgca
1141 atttcgaagc aattcagatg cctaaaggat gcaattgctg agcaagtaaa ggcgacgagc
1201 aagagtttag gtgaagagga aggcttggga gggaaaatcg aaggctcaag actcaaattt
1261 gtggaccatc atctaaggca acaacgcgcg ctgcaacaga taggaatgat gcaaccaaat
1321 gcttggagac cccaaagagg tttacctgaa agagctgtct ctgtccttcg tgcttggctt
1381 ttcgagcatt tcttcatcc ttacccaaag gattcagaca aaatcatgct tgctaagcaa
1441 acggggctaa caaggagcca ggtgtctaac tggttcataa atgctcgagt tcgattatgg
1501 aagccaatgg tagaagaaat gtacttggaa gaagtgaaga atcaagaaca aaacagtact
1561 aatacttcag gagataacaa aaacaaagag accaatataa gtgctccaaa tgaagagaaa
1621 catccaatta ttactagcag cttattacaa gatggtatta ctactactca agcagaaatt
1681 tctacctcaa ctatttcaac ttcccctact gcaggtgctt cacttcatca tgctcacaat
1741 ttctccttcc ttggttcatt caacatggat aatactacta ctactgttga tcatattgaa
1801 aacaacgcga aaaagcaaag aaatgacatg cacaagtttt ctccaagtag tattctttca
1861 tctgttgaca tggaagccaa agctagagaa tcatcaaata aagggtttac taatccttta
1921 atggcagcat acgcgatggg agattttgga aggtttgatc ctcatgatca acaaatgacc
1981 gcgaattttc atggaaataa tggtgtctct cttactttag gacttcctcc ttctgaaaac
2041 ctagccatgc cagtgagcca acaaaattac ctttctaatg acttgggaag taggtctgaa
2101 atggggagtc attacaatag aatgggatat gaaaacattg attttcagag tgggaataag
2161 cgatttccga ctcaactatt accagatttt gttacaggta atctaggaac atgaatacca
2221 gaaagtctcg tattgatagc tgaaaagata aaggaagtt agggatactc ttatattgtg
2281 tgaggccttc tggcccaagt cggaggaccc aatttgatac aacctatcat aggagaaaag
2341 aagtggagac taaattaaag taacaaaatt ttaaagcaca ctttctagta tatatacttc
2401 ttttttttat agtatagaaa agaagagatt ttgtgcttta gtgtatagat agagtctact
2461 tagtataggt tatacttcta gttccttgag aagattgata caactagtag tatttttttt
2521 cttttgggtt ggcttggagt actattttaa gttattggaa actagctata gtaaatgttg
2581 taaagttgtg atattgttcc tctcaatttg catataattt gaaatatttt gtacctacta
2641 gctagtctct aaattatgtt tccattgctt gtaattgcaa ttttatttga attttgtgct
2701 atcattatta gattagcaaa aaaaaaaaaa aaaaa
```

The nucleic acid sequence corresponding to SEQ ID NO:1 encodes a BEL transcription factor isolated from *Solanum tuberosum* identified herein as StBEL-05, which has a deduced amino acid sequence corresponding to SEQ ID NO:2 as follows:

```
Met Tyr Tyr Gln Gly Thr Ser Asp Asn Thr Asn Ile Gln
 1               5                  10

Ala Asp His Gln Gln Arg His Asn His Gly Asn Ser Asn
        15                  20                  25

Asn Asn Asn Ile Gln Thr Leu Tyr Leu Met Asn Pro Asn
            30                  35

Asn Tyr Met Gln Gly Tyr Thr Thr Ser Asp Thr Gln Gln
        40                  45                  50

Gln Gln Gln Leu Leu Phe Leu Asn Ser Ser Pro Ala Ala
            55                  60                  65

Ser Asn Ala Leu Cys His Ala Asn Ile Gln His Ala Pro
                70                  75

Leu Gln Gln Gln His Phe Val Gly Val Pro Leu Pro Ala
        80                  85                  90
```

-continued

Val Ser Leu His Asp Gln Ile Asn His His Gly Leu Leu
            95                  100
Gln Arg Met Trp Asn Asn Gln Asp Gln Ser Gln Gln Val
105                 110                 115
Ile Val Pro Ser Ser Thr Gly Val Ser Ala Thr Ser Cys
            120                 125                 130
Gly Gly Ile Thr Thr Asp Leu Ala Ser Gln Leu Ala Phe
                135                 140
Gln Arg Pro Ile Pro Thr Pro Gln His Arg Gln Gln Gln
145                 150                 155
Gln Gln Gln Gly Gly Leu Ser Leu Ser Leu Ser Pro Gln
            160                 165
Leu Gln Gln Gln Ile Ser Phe Asn Asn Asn Ile Ser Ser
170                 175                 180
Ser Ser Pro Arg Thr Asn Asn Val Thr Ile Arg Gly Thr
            185                 190                 195
Leu Asp Gly Ser Ser Ser Asn Met Val Leu Gly Ser Lys
                200                 205
Tyr Leu Lys Ala Ala Gln Glu Leu Leu Asp Glu Val Val
210                 215                 220
Asn Ile Val Gly Lys Ser Ile Lys Gly Asp Asp Gln Lys
            225                 230
Lys Asp Asn Ser Met Asn Lys Glu Ser Met Pro Leu Ala
235                 240                 245
Ser Asp Val Asn Thr Asn Ser Ser Gly Gly Gly Glu Ser
            250                 255                 260
Ser Ser Arg Gln Lys Asn Glu Val Ala Val Glu Leu Thr
                265                 270
Thr Ala Gln Arg Gln Glu Leu Gln Met Lys Lys Ala Lys
275                 280                 285
Leu Leu Ala Met Leu Glu Glu Val Glu Gln Arg Tyr Arg
            290                 295
Gln Tyr His His Gln Met Gln Ile Ile Val Leu Ser Phe
300                 305                 310
Glu Gln Val Ala Gly Ile Gly Ser Ala Lys Ser Tyr Thr
            315                 320                 325
Gln Leu Ala Leu His Ala Ile Ser Lys Gln Phe Arg Cys
                330                 335
Leu Lys Asp Ala Ile Ala Glu Gln Val Lys Ala Thr Ser
340                 345                 350
Lys Ser Leu Gly Glu Glu Gly Leu Gly Gly Lys Ile
            355                 360
Glu Gly Ser Arg Leu Lys Phe Val Asp His His Leu Arg
365                 370                 375
Gln Gln Arg Ala Leu Gln Gln Ile Gly Met Met Gln Pro
            380                 385                 390
Asn Ala Trp Arg Pro Gln Arg Gly Leu Pro Glu Arg Ala
                395                 400
Val Ser Val Leu Arg Ala Trp Leu Phe Glu His Phe Leu
405                 410                 415
His Pro Tyr Pro Lys Asp Ser Asp Lys Ile Met Leu Ala
            420                 425
Lys Gln Thr Gly Leu Thr Arg Ser Gln Val Ser Asn Trp
430                 435                 440
Phe Ile Asn Ala Arg Val Arg Leu Trp Lys Pro Met Val
            445                 450                 455
Glu Glu Met Tyr Leu Glu Glu Val Lys Asn Gln Glu Gln
                460                 465
Asn Ser Thr Asn Thr Ser Gly Asp Asn Lys Asn Lys Glu
            470                 475                 480
Thr Asn Ile Ser Ala Pro Asn Glu Glu Lys His Pro Ile
                485                 490
Ile Thr Ser Ser Leu Leu Gln Asp Gly Ile Thr Thr Thr
495                 500                 505
Gln Ala Glu Ile Ser Thr Ser Thr Ile Ser Thr Ser Pro
            510                 515                 520
Thr Ala Gly Ala Ser Leu His His Ala His Asn Phe Ser
                525                 530
Phe Leu Gly Ser Phe Asn Met Asp Asn Thr Thr Thr Thr
            535                 540                 545
Val Asp His Ile Glu Asn Asn Ala Lys Lys Gln Arg Asn
                550                 555
Asp Met His Lys Phe Ser Pro Ser Ser Ile Leu Ser Ser
560                 565                 570
Val Asp Met Glu Ala Lys Ala Arg Glu Ser Ser Asn Lys
            575                 580                 585
Gly Phe Thr Asn Pro Leu Met Ala Ala Tyr Ala Met Gly
                590                 595
Asp Phe Gly Arg Phe Asp Pro His Asp Gln Gln Met Thr
            600                 605                 610
Ala Asn Phe His Gly Asn Asn Gly Val Ser Leu Thr Leu
                615                 620
Gly Leu Pro Pro Ser Glu Asn Leu Ala Met Pro Val Ser
625                 630                 635
Gln Gln Asn Tyr Leu Ser Asn Asp Leu Gly Ser Arg Ser
            640                 645                 650
Glu Met Gly Ser His Tyr Asn Arg Met Gly Tyr Glu Asn
                655                 660
Ile Asp Phe Gln Ser Gly Asn Lys Arg Phe Pro Thr Gln
            665                 670                 675
Leu Leu Pro Asp Phe Val Thr Gly Asn Leu Gly Thr
                680                 685

The BEL transcription factor has a molecular mass of approximately 75.7 kDa. StBEL-05, isolated from *Solanum tuberosum*, has a single open reading frame ("ORF") of 2067 bp, extending between nucleotides 148-2214.

In a second embodiment, the BEL transcription factor from *Solanum tuberosum* is identified herein as StBEL-11 and is encoded by a nucleic acid molecule having a nucleotide sequence of SEQ ID NO:3 as follows:

```
   1 atgactttca ggtctagtct tccactagac ctccgtgaaa tttcaacaac aaatcatcaa
  61 gttggaatac tatcatcatc accattacca tcaccaggaa caaataccaa taatatcaat
 121 catactcgag gattaggggc atcatcatct ttttcgattt ctaatgggat gatattgggt
 181 tctaagtacc taaaagttgc acaagatctt cttgatgaag ttgttaatgt tggaaaaaac
 241 atcaaattat cagatggctt agagagtggt gcaaaggaga aacacaaatt ggacaatgaa
 301 ttaatatctt tggctagtga tgatgttgaa agcagcagcc aaaaaaatag tggtgttgaa
 361 cttacaacag ctcaaagaca agaacttcaa atgaagaaag ccaagcttgt tagcatgctt
 421 gatgaggtgg atcaaaggta tagacaatac catcaccaaa tgcaaatgat tgcaacatca
 481 tttgagcaaa caacaggaat tggatcatca aaatcataca cacaacttgc tttgcacaca
 541 atttcaaagc aatttagatg tttaaaagat gcaatttctg gcaaataaa ggacactagc
 601 aaaactttag gggaagaaga aacattggga ggcaaaattg aaggatcaaa gttgaaattt
 661 gtggatcatc atttacgcca acaacgtgca ctacaacaat tagggatgat gcaaaccaat
 721 gcatggaagc ctcaaagagg tttgccagaa agagcggttt cagttctccg cgcttggctt
 781 ttcgagcatt tcttcatcc gtatcccaaa gattcagata aaatcatcct tgctaagcaa
 841 acagggctaa caaggagcca ggtatcaaat tggtttataa atgctagagt tagactatgg
 901 aagccaatgg tagaagaaat gtacatggaa gaagtgaaga aaaacaatca agaacaaaat
 961 attgagccta ataacaatga aattgttggc tcaaaatcaa gtgttccaca agagaaatta
1021 ccaattagta gcaatattat tcataatgct tctccaaatg atatttctac ttccaccatt
1081 tcaacatctc cgacgggtgg cggcggttcg attccgactc agacggttgc aggtttctcc
1141 ttcattaggt cattaaacat ggagaacatt gatgatcaaa ggaacaacaa aaaggcaaga
1201 aatgagatgc aaaattgttc aactagtact attctctcaa tggaaagaga atcataaat
1261 aaagttgtgc aagatgagac aatcaaaagt gaaaagttca acaacacaca aacaagagaa
1321 tgttactctc taatgactcc aaattacaca atggatgatc aatttggaac aaggttcaat
1381 aatcaaaatc atgaacaatt ggcaacaaca acaacttttc atcaaggaaa tggtcatgtt
1441 tctcttactt tagggcttcc accaaattct gaaaaccaac acaattacat tggattggaa
1501 aatcattaca atcaacctac acatcatcca aatattagct atgaaaacat tgattttcag
1561 agtggaaagc gatacgccac tcaactatta caagattttg tttcttgatg atatatataa
1621 tttgcaggta aatcagcttg aaattacatc atgacaggtc ttgaataaaa gaagggagt
1681 tgagatttag tgatcatata aatatgtata ggtagaaatt ttagttagta tataggtt
1741 atacttctag tttcttaatg aagatacaag ttttgttgtt atttttgtat tgaggtaact
1801 agctagcttg gattatttaa agttggtgca tgcaactaaa gaagaagaaa aaataatcta
1861 tatatgcaaa ctacagtata ttgtaaattt tgtgcttc
```

The nucleic acid sequence corresponding to SEQ ID NO:3 encodes a BEL transcription factor isolated from *Solanum tuberosum* identified herein as StBEL-11, which has a deduced amino acid sequence corresponding to SEQ ID NO:4 as follows:

```
Met Thr Phe Arg Ser Ser Leu Pro Leu Asp Leu Arg Glu
 1               5                  10
Ile Ser Thr Thr Asn His Gln Val Gly Ile Leu Ser Ser
        15                  20                  25
Ser Pro Leu Pro Ser Pro Gly Thr Asn Thr Asn Asn Ile
                30                  35
Asn His Thr Arg Gly Leu Gly Ala Ser Ser Ser Phe Ser
    40                  45                  50
Ile Ser Asn Gly Met Ile Leu Gly Ser Lys Tyr Leu Lys
        55                  60                  65
Val Ala Gln Asp Leu Leu Asp Glu Val Val Asn Val Gly
                70                  75
```

-continued

```
            Lys Asn Ile Lys Leu Ser Asp Gly Leu Glu Ser Gly Ala
             80                  85                  90
            Lys Glu Lys His Lys Leu Asp Asn Glu Leu Ile Ser Leu
                     95                 100
            Ala Ser Asp Asp Val Glu Ser Ser Ser Gln Lys Asn Ser
            105                 110                 115
            Gly Val Glu Leu Thr Thr Ala Gln Arg Gln Glu Leu Gln
                    120                 125                 130
            Met Lys Lys Ala Lys Leu Val Ser Met Leu Asp Glu Val
                        135                 140
            Asp Gln Arg Tyr Arg Gln Tyr His His Gln Met Gln Met
            145                 150                 155
            Ile Ala Thr Ser Phe Glu Gln Thr Thr Gly Ile Gly Ser
                        160                 165
            Ser Lys Ser Tyr Thr Gln Leu Ala Leu His Thr Ile Ser
            170                 175                 180
            Lys Gln Phe Arg Cys Leu Lys Asp Ala Ile Ser Gly Gln
                        185                 190                 195
            Ile Lys Asp Thr Ser Lys Thr Leu Gly Glu Glu Glu Asn
                            200                 205
            Ile Gly Gly Lys Ile Glu Gly Ser Lys Leu Lys Phe Val
                    210                 215                 220
            Asp His His Leu Arg Gln Gln Arg Ala Leu Gln Gln Leu
                        225                 230
            Gly Met Met Gln Thr Asn Ala Trp Lys Pro Gln Arg Gly
            235                 240                 245
            Leu Pro Glu Arg Ala Val Ser Val Leu Arg Ala Trp Leu
                        250                 255                 260
            Phe Glu His Phe Leu His Pro Tyr Pro Lys Asp Ser Asp
                            265                 270
            Lys Ile Ile Leu Ala Lys Gln Thr Gly Leu Thr Arg Ser
            275                 280                 285
            Gln Val Ser Asn Trp Phe Ile Asn Ala Arg Val Arg Leu
                        290                 295
            Trp Lys Pro Met Val Glu Glu Met Tyr Met Glu Glu Val
            300                 305                 310
            Lys Lys Asn Asn Gln Glu Gln Asn Ile Glu Pro Asn Asn
                        315                 320                 325
            Asn Glu Ile Val Gly Ser Lys Ser Ser Val Pro Gln Glu
                            330                 335
```

```
            Lys Leu Pro Ile Ser Ser Asn Ile Ile His Asn Ala Ser
                        340                 345                 350
            Pro Asn Asp Ile Ser Thr Ser Thr Ile Ser Thr Ser Pro
                            355                 360
            Thr Gly Gly Gly Gly Ser Ile Pro Thr Gln Thr Val Ala
            365                 370                 375
            Gly Phe Ser Phe Ile Arg Ser Leu Asn Met Glu Asn Ile
                        380                 385                 390
            Asp Asp Gln Arg Asn Asn Lys Lys Ala Arg Asn Glu Met
                            395                 400
            Gln Asn Cys Ser Thr Ser Thr Ile Leu Ser Met Glu Arg
                405                 410                 415
            Glu Ile Ile Asn Lys Val Val Gln Asp Glu Thr Ile Lys
                        420                 425
            Ser Glu Lys Phe Asn Asn Thr Gln Thr Arg Glu Cys Tyr
            430                 435                 440
            Ser Leu Met Thr Pro Asn Tyr Thr Met Asp Asp Gln Phe
                        445                 450                 455
            Gly Thr Arg Phe Asn Asn Gln Asn His Glu Gln Leu Ala
                            460                 465
            Thr Thr Thr Thr Phe His Gln Gly Asn Gly His Val Ser
                470                 475                 480
            Leu Thr Leu Gly Leu Pro Pro Asn Ser Glu Asn Gln His
                        485                 490
            Asn Tyr Ile Gly Leu Glu Asn His Tyr Asn Gln Pro Thr
                495                 500                 505
            His His Pro Asn Ile Ser Tyr Glu Asn Ile Asp Phe Gln
                        510                 515                 520
            Ser Gly Lys Arg Tyr Ala Thr Gln Leu Leu Gln Asp Phe
                            525                 530
            Val Ser
            535
```

The BEL transcription factor has a molecular mass of approximately 59 kDa. StBEL-11, isolated from *Solanum tuberosum*, has a single open reading frame ("ORF") of 1608 bp, extending between nucleotides 1-1608.

In a third embodiment, the BEL transcription factor from *Solanum tuberosum* is identified herein as StBEL-13 and is encoded by a nucleic acid molecule having a nucleotide sequence of SEQ ID NO:5 as follows:

```
  1  ggggagcgag tggttccgac aaggtatggt aatgggtgga ggtgcaagta
 51  gtcaacaatt gggatatgca aaaaatcata ctcctaatgt ggcggagtcc
101  atgcaacttt ttctaatgaa tccacaacca aggtcacctt ctccatctcc
151  tcctaattca acttcttcta cgcttcacat gttgttacca aacccatcat
201  ctacttcaac acttcaaggg tttcctaatc cggccgaagg atctttcggt
251  caattcatta catgggggaa tggaggagca agtgctgcca cagccaccca
301  tcatctcaat gcccagaatg aaatcggagg agtaaacgtt gtagaaagtc
351  aaggcctatc tctatccttg tcttcttcgt tacagcacaa ggcggaggaa
```

-continued

```
 401   ttacaaatga gcggagaagc tggaggaatg atgttcttca atcaaggagg
 451   gtctagtact tccgggcagt atcgatacaa gaatttgaat atgggtggat
 501   caggagtaag cccaaacatt catcaagtcc atgttgggta tgggtcatca
 551   ttaggagtgg tcaatgtgtt gaggaattcc aaatacgcga aagctgccca
 601   agaactactg gaagaattct gcagtgttgg aagaggtaaa ttgaagaaga
 651   ctaacaacaa agcagcagcc aataaccta atacgaaccc tagtggcgct
 701   aacaatgaag cttcttcaaa agatgttcct actttgtccg ctgctgatag
 751   aattgagcat cagagaagga aggtcaaact tttatctatg gttgatgagg
 801   tagataggag gtacaatcat tactgtgaac aaatgcagat ggttgtaaat
 851   tcgtttgatt tagtgatggg tttcggcaca gcagttccct acacagcact
 901   tgcacagaag gcaatgtcaa gacatttcag gtgtttaaag gatgcaatag
 951   gagcacaatt gaagcagagt tgtgagttat taggagaaa agatgcagga
1001   aattcgggat tgactaaagg agaaactccg aggcttaaga tgcttgaaca
1051   aagtttgagg caacaaaggg cgtttcacca aatgggaatg atggaacaag
1101   aagcttggag accacaaaga ggcttacctg aacgttctgt caacatttta
1151   agagcttggc tttttgagca ttttctacac ccgtatccaa gtgatgctga
1201   taaacatctg ttggcaagac agactggtct ctccagaaat caggtatcaa
1251   attggttcat taatgctagg gttcggttgt ggaaacccat ggtagaagat
1301   atgtatcaac aagaagccaa agatgaagat ggagatggag atgagaagag
1351   ccaaagccaa aacagtggca ataacataat tgcacaaaca ccaacgccta
1401   atagcctgac taacacttca tctactaata tgacgacgac aacagcccct
1451   acaactacga cagctctagc tgctgcagag acaggaacag ctgccactcc
1501   cataactgtt acctcaagca aaagatccca aatcaatgcc acggatagtg
1551   accccttcact tgtagcaatc aattccttct ctgaaaacca agctactttt
1601   ccgaccaaca ttcatgatcc cgacgattgc cgtcgcggca acttatccgg
1651   tgacgacggg accaccacac atgatcatat ggggtccacc atgataaggt
1701   ttgggaccac tgctggtgac gtgtcactca ccttagggtt acgacatgca
1751   ggaaatttac cagagaatac tcatttcttt ggttaattaa tacgtatttt
1801   ccccatagta attaattaaa actgaatttg cttgagctca tcataattta
1851   tgcattgctt tttgttataa gaaattccat aaattagctt tgtgttaaaa
1901   aaaaaaaaaa aaaaaaaaa
```

The nucleic acid sequence corresponding to SEQ ID NO:5 encodes a BEL transcription factor isolated from *Solanum tuberosum* identified herein as StBEL-13, which has a deduced amino acid sequence corresponding to SEQ ID NO:6 as follows:

```
Met Val Met Gly Gly Gly Ala Ser Ser Gln Gln Leu Gly Tyr Ala Lys
  1               5                  10                  15

Asn His Thr Pro Asn Val Ala Glu Ser Met Gln Leu Phe Leu Met Asn
             20                  25                  30
```

Pro Gln Pro Arg Ser Pro Ser Pro Ser Pro Pro Asn Ser Thr Ser Ser
            35                  40                  45

Thr Leu His Met Leu Leu Pro Asn Pro Ser Ser Thr Ser Thr Leu Gln
        50                  55                  60

Gly Phe Pro Asn Pro Ala Glu Gly Ser Phe Gly Gln Phe Ile Thr Trp
65                  70                  75                  80

Gly Asn Gly Gly Ala Ser Ala Ala Thr Ala Thr His His Leu Asn Ala
                85                  90                  95

Gln Asn Glu Ile Gly Gly Val Asn Val Val Glu Ser Gln Gly Leu Ser
                100                 105                 110

Leu Ser Leu Ser Ser Leu Gln His Lys Ala Glu Glu Leu Gln Met
        115                 120                 125

Ser Gly Glu Ala Gly Gly Met Met Phe Phe Asn Gln Gly Gly Ser Ser
    130                 135                 140

Thr Ser Gly Gln Tyr Arg Tyr Lys Asn Leu Asn Met Gly Gly Ser Gly
145                 150                 155                 160

Val Ser Pro Asn Ile His Gln Val His Val Gly Tyr Gly Ser Ser Leu
                165                 170                 175

Gly Val Val Asn Val Leu Arg Asn Ser Lys Tyr Ala Lys Ala Ala Gln
                180                 185                 190

Glu Leu Leu Glu Glu Phe Cys Ser Val Gly Arg Gly Lys Leu Lys Lys
        195                 200                 205

Thr Asn Asn Lys Ala Ala Ala Asn Asn Pro Asn Thr Asn Pro Ser Gly
        210                 215                 220

Ala Asn Asn Glu Ala Ser Ser Lys Asp Val Pro Thr Leu Ser Ala Ala
225                 230                 235                 240

Asp Arg Ile Glu His Gln Arg Arg Lys Val Lys Leu Leu Ser Met Val
                245                 250                 255

Asp Glu Val Asp Arg Arg Tyr Asn His Tyr Cys Glu Gln Met Gln Met
                260                 265                 270

Val Val Asn Ser Phe Asp Leu Val Met Gly Phe Gly Thr Ala Val Pro
        275                 280                 285

Tyr Thr Ala Leu Ala Gln Lys Ala Met Ser Arg His Phe Arg Cys Leu
    290                 295                 300

Lys Asp Ala Ile Gly Ala Gln Leu Lys Gln Ser Cys Glu Leu Leu Gly
305                 310                 315                 320

Glu Lys Asp Ala Gly Asn Ser Gly Leu Thr Lys Gly Glu Thr Pro Arg
                325                 330                 335

Leu Lys Met Leu Glu Gln Ser Leu Arg Gln Gln Arg Ala Phe His Gln
            340                 345                 350

Met Gly Met Met Glu Gln Glu Ala Trp Arg Pro Gln Arg Gly Leu Pro
        355                 360                 365

Glu Arg Ser Val Asn Ile Leu Arg Ala Trp Leu Phe Glu His Phe Leu
    370                 375                 380

His Pro Tyr Pro Ser Asp Ala Asp Lys His Leu Leu Ala Arg Gln Thr
385                 390                 395                 400

Gly Leu Ser Arg Asn Gln Val Ser Asn Trp Phe Ile Asn Ala Arg Val
                405                 410                 415

Arg Leu Trp Lys Pro Met Val Glu Asp Met Tyr Gln Gln Glu Ala Lys
            420                 425                 430

Asp Glu Asp Gly Asp Gly Asp Glu Lys Ser Gln Ser Gln Asn Ser Gly
        435                 440                 445

```
Asn Asn Ile Ile Ala Gln Thr Pro Thr Pro Asn Ser Leu Thr Asn Thr
    450                 455                 460

Ser Ser Thr Asn Met Thr Thr Thr Ala Pro Thr Thr Thr Thr Ala
465             470                 475                 480

Leu Ala Ala Ala Glu Thr Gly Thr Ala Ala Thr Pro Ile Thr Val Thr
            485                 490                 495

Ser Ser Lys Arg Ser Gln Ile Asn Ala Thr Asp Ser Asp Pro Ser Leu
            500                 505                 510

Val Ala Ile Asn Ser Phe Ser Glu Asn Gln Ala Thr Phe Pro Thr Asn
        515                 520                 525

Ile His Asp Pro Asp Asp Cys Arg Arg Gly Asn Leu Ser Gly Asp Asp
    530                 535                 540

Gly Thr Thr His Asp His Met Gly Ser Thr Met Ile Arg Phe Gly
545             550                 555                 560

Thr Thr Ala Gly Asp Val Ser Leu Thr Leu Gly Leu Arg His Ala Gly
            565                 570                 575

Asn Leu Pro Glu Asn Thr His Phe Phe Gly
            580                 585
```

The BEL transcription factor has a molecular mass of approximately 64.5 kDa. StBEL-13, isolated from *Solanum tuberosum*, has a single open reading frame ("ORF") of 1759 bp, extending between nucleotides 26-1784.

In a fourth embodiment, the BEL transcription factor from *Solanum tuberosum* is identified herein as StBEL-14 and is encoded by a nucleic acid molecule having a nucleotide sequence of SEQ ID NO:7 as follows:

```
   1  aaccnaaaaa agagatcgaa ttcggcacga gtgatcatgg tccttcgtct
  51  tctaagaaca ttattagtga acaattttac caacatggta gtcatgaaaa
 101  tatgttgaca acaacaacta ctcatcatga tgatcatcaa ggctcgtggc
 151  atcacgataa taacagaaca ttacttgttg atgatccatc tatgagatgt
 201  gttttcccct gtgaaggaaa tgaaaggcca agtcatggac tttcattatc
 251  tctttgttcc tcaaatccat caagtattgg tttacaatct tttgaactta
 301  gacatcaaga tttgcaacaa ggattaatac atgatggatt tttgggtaaa
 351  tctacaaata tacaacaagg gtattttcat catcatcatc aagttaggga
 401  ctcgaaatat ttaggtccgg ctcaagagtt gctcagtgag ttctgtagtc
 451  tcggaataaa gaagaataat gatcattctt cttcaaaagt acttctaaag
 501  caacatgaga gtactgctag tacttcaaaa aagcaacttt tacagtctct
 551  tgaccttttg gaacttcaaa aagaaagac aaaattgctt caaatgcttg
 601  aagaggtgga tagaaggtac aagcattatt gtgatcaaat gaaggctgtt
 651  gtatcatcat ttgaagcagt ggctggaaat ggagcagcaa cagtttactc
 701  agccttagca tcaagggcta tgtcaaggca ttttagatgt ttaagagatg
 751  gaattgtggc acaaattaag gccacaaaaa tggctatggg agaaaaagac
 801  agtactagta ctcttattcc tggttcaaca agaggtgaaa caccaagact
 851  cagacttctt gatcaaactt taaggcaaca aaaggctttc caacagatga
 901  atatgatgga gactcatcca tggagaccgc aacgtggtct cccagaaaga
 951  tcagtctccg ttctccgcgc ttggctcttt gaacactttc ttcacccgta
1001  cccaagtgat gttgataaac acattttagc tcgccaaact ggtctttcaa
1051  gaagccaggt gtctaattgg ttcattaatg caagggtaag gctatggaag
```

-continued

```
1101  ccaatggtgg aagaaatgta cttagaagaa acaaaagaag aagaaaatgt
1151  tggatctcca gatggatcaa aagccctaat tgatgacatg acaattcatc
1201  aatcacacat tgatcatcat caagctgatc aaaagccaaa tcttgtaaga
1251  attgactctg aatgcatatc ttccatcata aatcatcaac ctcatgagaa
1301  aaatgatcaa aactatggag taattagagg tggagatcaa tcgtttggcg
1351  cgattgagct agatttttca acaaatattg cttatggtac tagtggtggt
1401  gaccatcatc atcatggagg gggtgtttct ttaacattgg gattacaaca
1451  acatggtgga agtggtggat catcaatggg gttaactaca ttttcatcac
1501  aaccatctca taatcaaagt tcactttttt atccaagaga tgatgatcaa
1551  gttcaatatt catcactttt ggatagtgaa atcagaatt tgccatatag
1601  aaaccttgat gggggcacaa cttcttcatg atttggctgg ttaaaaaatg
1651  acagagattc ttcattttgg accttattat atactctaat tttaatatat
1701  attggtgatg aatgatgata aaaaaaaaaa aaaaaaaaaa aaaaaaaaaa
1751  aaaaaaaaaa acctcgancc cggtcgactn tanancccta tagngagtcg
1801  tnttnctgca nanatctntg aatcgtaaat nctgaaaaac cccgcaagtt
1851  cacttcaact gngcatcgng cnccatctca atttctttca tttatncatc
1901  gttttgcctt nttttatgta actatnctcc tntaagtttc aatcttggcc
1951  atgtaacctn tgatctntaa aattttttaa atgactanaa ttaatgccca
2001  tntttttttt ggacctaaat tnttcatgaa aatntnttnc nagggcttnt
2051  tcaaaanctt tggacttntt cnccanaggt ttggtcaagt ntccaatcaa
2101  ggt
```

The nucleic acid sequence corresponding to SEQ ID NO:7 encodes a BEL transcription factor isolated from *Solanum tuberosum* identified herein as StBEL-14, which has a deduced amino acid sequence corresponding to SEQ ID NO:8 as follows:

```
Met Val Asn His Gln Leu Gln Asn Phe Glu Thr Asn Pro Glu Met Tyr
 1               5                  10                  15

Asn Leu Ser Ser Thr Thr Ser Ser Met Asp Gln Met Ile Gly Phe Pro
                20                  25                  30

Pro Asn Asn Asn Pro His His Val Leu Trp Lys Gly Asn Phe Pro
            35                  40                  45

Asn Lys Ile Asn Gly Val Asp Asp Asp His Gly Pro Ser Ser Ser
        50                  55                  60

Lys Asn Ile Ile Ser Glu Gln Phe Tyr Gln His Gly Ser His Glu Asn
65                  70                  75                  80

Met Leu Thr Thr Thr Thr His His Asp Asp His Gln Gly Ser Trp
                85                  90                  95

His His Asp Asn Asn Arg Thr Leu Leu Val Asp Asp Pro Ser Met Arg
            100                 105                 110

Cys Val Phe Pro Cys Glu Gly Asn Glu Arg Pro Ser His Gly Leu Ser
            115                 120                 125

Leu Ser Leu Cys Ser Ser Asn Pro Ser Ser Ile Gly Leu Gln Ser Phe
        130                 135                 140
```

-continued

```
Glu Leu Arg His Gln Asp Leu Gln Gln Gly Leu Ile His Asp Gly Phe
145                 150                 155                 160

Leu Gly Lys Ser Thr Asn Ile Gln Gln Gly Tyr Phe His His His
            165                 170                 175

Gln Val Arg Asp Ser Lys Tyr Leu Gly Pro Ala Gln Glu Leu Leu Ser
            180                 185                 190

Glu Phe Cys Ser Leu Gly Ile Lys Lys Asn Asn Asp His Ser Ser Ser
            195                 200                 205

Lys Val Leu Leu Lys Gln His Glu Ser Thr Ala Ser Thr Ser Lys Lys
210                 215                 220

Gln Leu Leu Gln Ser Leu Asp Leu Leu Glu Leu Gln Lys Arg Lys Thr
225                 230                 235                 240

Lys Leu Leu Gln Met Leu Glu Glu Val Asp Arg Arg Tyr Lys His Tyr
                245                 250                 255

Cys Asp Gln Met Lys Ala Val Val Ser Ser Phe Glu Ala Val Ala Gly
                260                 265                 270

Asn Gly Ala Ala Thr Val Tyr Ser Ala Leu Ala Ser Arg Ala Met Ser
                275                 280                 285

Arg His Phe Arg Cys Leu Arg Asp Gly Ile Val Ala Gln Ile Lys Ala
                290                 295                 300

Thr Lys Met Ala Met Gly Glu Lys Asp Ser Thr Ser Thr Leu Ile Pro
305                 310                 315                 320

Gly Ser Thr Arg Gly Glu Thr Pro Arg Leu Arg Leu Asp Gln Thr
                325                 330                 335

Leu Arg Gln Gln Lys Ala Phe Gln Gln Met Asn Met Glu Thr His
                340                 345                 350

Pro Trp Arg Pro Gln Arg Gly Leu Pro Glu Arg Ser Val Ser Val Leu
                355                 360                 365

Arg Ala Trp Leu Phe Glu His Phe Leu His Pro Tyr Pro Ser Asp Val
370                 375                 380

Asp Lys His Ile Leu Ala Arg Gln Thr Gly Leu Ser Arg Ser Gln Val
385                 390                 395                 400

Ser Asn Trp Phe Ile Asn Ala Arg Val Arg Leu Trp Lys Pro Met Val
                405                 410                 415

Glu Glu Met Tyr Leu Glu Glu Thr Lys Glu Glu Asn Val Gly Ser
                420                 425                 430

Pro Asp Gly Ser Lys Ala Leu Ile Asp Asp Met Thr Ile His Gln Ser
                435                 440                 445

His Ile Asp His His Gln Ala Asp Gln Lys Pro Asn Leu Val Arg Ile
            450                 455                 460

Asp Ser Glu Cys Ile Ser Ser Ile Ile Asn His Gln Pro His Glu Lys
465                 470                 475                 480

Asn Asp Gln Asn Tyr Gly Val Ile Arg Gly Gly Asp Gln Ser Phe Gly
                485                 490                 495

Ala Ile Glu Leu Asp Phe Ser Thr Asn Ile Ala Tyr Gly Thr Ser Gly
                500                 505                 510

Gly Asp His His His Gly Gly Val Ser Leu Thr Leu Gly Leu
            515                 520                 525

Gln Gln His Gly Gly Ser Gly Gly Ser Ser Met Gly Leu Thr Thr Phe
            530                 535                 540

Ser Ser Gln Pro Ser His Asn Gln Ser Ser Leu Phe Tyr Pro Arg Asp
545                 550                 555                 560
```

-continued

```
Asp Asp Gln Val Gln Tyr Ser Ser Leu Leu Asp Ser Glu Asn Gln Asn
            565                 570                 575

Leu Pro Tyr Arg Asn Leu Asp Gly Gly Thr Thr Ser Ser
            580                 585
```

The BEL transcription factor has a molecular mass of approximately 64.8 kDa. StBEL-14, isolated from *Solanum tuberosum*, has a single open reading frame ("ORF") of 1768 bp, extending between nucleotides 85-1852.

In a fifth embodiment, the BEL transcription factor from *Solanum tuberosum* is identified herein as StBEL-22 and is encoded by a nucleic acid molecule having a nucleotide sequence of SEQ ID NO:9 as follows:

```
   1  acgagcgttt atgagacagc cggggttgttg tctgaaatgt tcaattttca gacaacatcc
  61  acggctgcaa ctgaattgtt gcagaatcaa ttgtcaaata actatagaca cccgaatcaa
 121  cagccacatc atcaacctcc gaccagggag tggtttggta acagacaaga gatcgtagtt
 181  ggtggaagtt tgcaggtaac atttggggat acaaaagatg atgtgaatgc gaaggtatta
 241  ttgagtaacc gtgatagtgt aactgattat tatcagcgtc aacacaatca agtaccaagt
 301  ataaataccg cggagtccat gcaactttt cttatgaatc cacaaccaag ttcaccatca
 361  caatctactc cttcaactct tcatcaaggg ttttctagcc cggtcggagg gcattttagt
 421  caattcatgt gtggaggagc aagtacttct tcaaatccaa ttggaggagt aaatgtgatt
 481  gatcaagggc aaggtctttc attgtccttg tcatctactt tacaacattt ggaagcatcc
 541  aaagtggaag atttgaggat gaatagtgga ggagaaatgt tgttttttcaa tcaagaaagt
 601  caaaatcatc ataatattgg ttttgggtca tcactaggac tagtcaatgt gttgaggaat
 661  tcaaagtatg tcaaagcaac acaagagttg ttggaagagt tttgttgtgt tgggaagggt
 721  caattgttca agaaaatcaa caaagtttct aggaataaca acacaagtac atcacccatt
 781  attaaccccta gtggaagtaa taacaataat tcatcttctt caaaggctat tatccctcct
 841  aatttgtcaa ctgcagagag acttgatcat caaagaagga aggtcaaact tttatccatg
 901  cttgatgagg tagagaaaag atacaaccac tattgtgaac aaatgcagat ggtagtaaac
 961  tcattcgatc tagtgatggg ttttggagct gcagttcctt acacagcact agcacagaaa
1021  gccatgtcta ggcatttcaa gtgtttaaaa gatggcgtgg cggcgcaatt gaagaagaca
1081  tgtgaggcac taggtgaaaa agatgcaagc agtagttcag gactgactaa aggagaaaca
1141  ccaaggctta aggtgcttga acaaagcttg aggcaacaaa gagcttttca acaaatggga
1201  atgatggaac aagaagcttg gaggccacaa agaggattgc ctgaacgatc tgtcaatatt
1261  ttaagagctt ggcttttcga acatttctca catccgtatc caagtgatgc agataagcat
1321  cttttggcac gacagactgg tctctccaga aaccaggtag caaactggtt cataaatgcg
1381  agggtgagat tgtggaaacc catggtagaa gaaatgtatc aaagagaggt taatgaagat
1441  gatgttgatg acatgcaaga aaaccaaaac agtacaaata cacaaatacc aacgcctaat
1501  attattatta caaccaattc taacattaca gaaacaaaat cagctgccac tgccacaatt
1561  gcttcagaca aaaaccccca aatcaatgtc tctgaaattg acccttcaat tgtcgcaatg
1621  aatacacatt attcttcctc tatgccaact caattaacca atttccccac tattcaagat
1681  gagtccgacc acatcttata tcgccgcagt ggagcggaat atgggaccac aaatatggct
1741  agtaattctg aaattggatc caacatgata acatttggga ccactacggc tagtgatgtt
1801  tcacttacct taggactgcg ccatgcgggt aatttacctg agaatactca ttttttccggt
```

-continued

```
1861  taattaagat agtgtattca aacactgcta cataaattat gattttatat atatatat
1921  tgtcatccga ttagtttat
```

The nucleic acid sequence corresponding to SEQ ID NO:9 encodes a BEL transcription factor isolated from *Solanum tuberosum* identified herein as StBEL-22, which has a deduced amino acid sequence corresponding to SEQ ID NO:10 as follows:

```
Thr Ser Val Tyr Glu Thr Ala Gly Leu Leu Ser Glu Met Phe Asn Phe
 1               5                  10                  15

Gln Thr Thr Ser Thr Ala Ala Thr Glu Leu Leu Gln Asn Gln Leu Ser
                20                  25                  30

Asn Asn Tyr Arg His Pro Asn Gln Gln Pro His His Gln Pro Pro Thr
            35                  40                  45

Arg Glu Trp Phe Gly Asn Arg Gln Glu Ile Val Val Gly Gly Ser Leu
        50                  55                  60

Gln Val Thr Phe Gly Asp Thr Lys Asp Val Asn Ala Lys Val Leu
65                  70                  75                  80

Leu Ser Asn Arg Asp Ser Val Thr Asp Tyr Tyr Gln Arg Gln His Asn
                85                  90                  95

Gln Val Pro Ser Ile Asn Thr Ala Glu Ser Met Gln Leu Phe Leu Met
            100                 105                 110

Asn Pro Gln Pro Ser Ser Pro Ser Gln Ser Thr Pro Ser Thr Leu His
        115                 120                 125

Gln Gly Phe Ser Ser Pro Val Gly Gly His Phe Ser Gln Phe Met Cys
    130                 135                 140

Gly Gly Ala Ser Thr Ser Ser Asn Pro Ile Gly Gly Val Asn Val Ile
145                 150                 155                 160

Asp Gln Gly Gln Gly Leu Ser Leu Ser Leu Ser Ser Thr Leu Gln His
                165                 170                 175

Leu Glu Ala Ser Lys Val Glu Asp Leu Arg Met Asn Ser Gly Gly Glu
            180                 185                 190

Met Leu Phe Phe Asn Gln Glu Ser Gln Asn His His Asn Ile Gly Phe
        195                 200                 205

Gly Ser Ser Leu Gly Leu Val Asn Val Leu Arg Asn Ser Lys Tyr Val
    210                 215                 220

Lys Ala Thr Gln Glu Leu Leu Glu Glu Phe Cys Cys Val Gly Lys Gly
225                 230                 235                 240

Gln Leu Phe Lys Lys Ile Asn Lys Val Ser Arg Asn Asn Asn Thr Ser
                245                 250                 255

Thr Ser Pro Ile Ile Asn Pro Ser Gly Ser Asn Asn Asn Ser Ser
            260                 265                 270

Ser Ser Lys Ala Ile Ile Pro Pro Asn Leu Ser Thr Ala Glu Arg Leu
        275                 280                 285

Asp His Gln Arg Arg Lys Val Lys Leu Leu Ser Met Leu Asp Glu Val
    290                 295                 300

Glu Lys Arg Tyr Asn His Tyr Cys Glu Gln Met Gln Met Val Val Asn
305                 310                 315                 320

Ser Phe Asp Leu Val Met Gly Phe Gly Ala Ala Val Pro Tyr Thr Ala
                325                 330                 335

Leu Ala Gln Lys Ala Met Ser Arg His Phe Lys Cys Leu Lys Asp Gly
            340                 345                 350
```

-continued

```
Val Ala Ala Gln Leu Lys Lys Thr Cys Glu Ala Leu Gly Glu Lys Asp
            355                 360                 365

Ala Ser Ser Ser Gly Leu Thr Lys Gly Glu Thr Pro Arg Leu Lys
    370                 375                 380

Val Leu Glu Gln Ser Leu Arg Gln Gln Arg Ala Phe Gln Gln Met Gly
385                 390                 395                 400

Met Met Glu Gln Glu Ala Trp Arg Pro Gln Arg Gly Leu Pro Glu Arg
                405                 410                 415

Ser Val Asn Ile Leu Arg Ala Trp Leu Phe Glu His Phe Leu His Pro
                420                 425                 430

Tyr Pro Ser Asp Ala Asp Lys His Leu Leu Ala Arg Gln Thr Gly Leu
        435                 440                 445

Ser Arg Asn Gln Val Ala Asn Trp Phe Ile Asn Ala Arg Val Arg Leu
    450                 455                 460

Trp Lys Pro Met Val Glu Met Tyr Gln Arg Glu Val Asn Glu Asp
465                 470                 475                 480

Asp Val Asp Met Gln Glu Asn Gln Asn Ser Thr Asn Thr Gln Ile
                485                 490                 495

Pro Thr Pro Asn Ile Ile Ile Thr Thr Asn Ser Asn Ile Thr Glu Thr
            500                 505                 510

Lys Ser Ala Ala Thr Ala Thr Ile Ala Ser Asp Lys Lys Pro Gln Ile
        515                 520                 525

Asn Val Ser Glu Ile Asp Pro Ser Ile Val Ala Met Asn Thr His Tyr
    530                 535                 540

Ser Ser Ser Met Pro Thr Gln Leu Thr Asn Phe Pro Thr Ile Gln Asp
545                 550                 555                 560

Glu Ser Asp His Ile Leu Tyr Arg Arg Ser Gly Ala Gly Tyr Gly Thr
                565                 570                 575

Thr Asn Met Ala Ser Asn Ser Glu Ile Gly Ser Asn Met Ile Thr Phe
            580                 585                 590

Gly Thr Thr Thr Ala Ser Asp Val Ser Leu Thr Leu Gly Leu Arg His
        595                 600                 605

Ala Gly Asn Leu Pro Glu Asn Thr His Phe Ser Gly
    610                 615                 620
```

The BEL transcription factor has a molecular mass of approximately 67.3 kDa. StBEL-22, isolated from *Solanum tuberosum*, has a single open reading frame ("ORF") of 1863 bp, extending between nucleotides 1-1863.

In a sixth embodiment, the BEL transcription factor from *Solanum tuberosum* is identified herein as StBEL-29 and is encoded by a nucleic acid molecule having a nucleotide sequence of SEQ ID NO: 11 as follows:

```
  1  caagggcttt cacttagcct gtcctcgtcc cagcagccgg ggtttgggaa cttcacggcg
 61  gcgcgtgagc ttgtttcttc gccttcgggt tcggcttcag cttcagggat acaacaacaa
121  caacagcaac aacagagtat tagtagtgtg cctttgagtt ctaagtacat gaaggctgca
181  caagagctac ttgatgaagt tgtaaatgtt ggaaaatcaa tgaaaagtac taatagtact
241  gatgttgttg ttaataatga tgtcaagaaa tcgaagaata tgggcgatat ggacggacag
301  ttagacggag ttggagcaga caaagacgga gctccaacaa ctgagctaag tacaggggag
361  agacaagaaa ttcaaatgaa gaaagcaaaa cttgttaaca tgcttgacga ggtggagcag
421  aggtatagac attatcatca ccaaatgcag tcagtgatac attggttaga gcaagctgct
481  ggcattggat cagcaaaaac atatacagca ttggctttgc agacgatttc gaagcaattt
541  aggtgtctta aggacgcgat aattggtcaa atacgatcag caagccagac gttaggcgaa
```

-continued

```
 601  gaagatagtt tgggagggaa gattgaaggt tcaaggctta aatttgttga taatcagcta
 661  agacagcaaa gggctttgca acaattggga atgatccagc ataatgcttg gagacctcag
 721  agaggattgc ccgaacgagc tgtttctgtt cttcgcgctt ggcttttga acatttcctc
 781  catccttatc ccaaggattc agacaaaatg atgctagcaa acaaacagg actaactagg
 841  agtcaggtgt cgaattggtt catcaatgct cgagttcgtc tttggaagcc aatggtggaa
 901  gagatgtact tggaagagat aaaagaacac gaacagaatg ggttgggtca agaaaagacg
 961  agcaaattag gtgaacagaa cgaagattca acaacatcaa gatccattgc tacacaagac
1021  aaaagccctg gttcagatag ccaaaacaag agttttgtct caaaacagga caatcatttg
1081  cctcaacaca accctgcttc accaatgccc gatgtccaac gccacttcca taccctatc
1141  ggtatgacca tccgtaatca gtctgctggt ttcaacctca ttggatcacc agagatcgaa
1201  agcatcaaca ttactcaagg gagtccaaag aaaccgagga acaacgagat gttgcattca
1261  ccaaacagca ttccatccat caacatggat gtaaagccta acgaggaaca aatgtcgatg
1321  aagtttggtg atgataggca ggacagagat ggattctcac taatgggagg accgatgaac
1381  ttcatgggag gattcggagc ctatcccatt ggagaaattg ctcggtttag caccgagcaa
1441  ttctcagcac catactcaac cagtggcaca gtttcactca ctcttggcct accacataac
1501  gaaaacctct caatgtctgc aacacaccac agtttccttc caattccaac acaaaacatc
1561  caaattggaa gtgaaccaaa tcatgagttt ggtagcttaa acacaccaac atcagctcac
1621  tcaacatcaa gcgtctatga aaccttcaac attcagaaca gaaagaggtt cgccgcaccc
1681  ttgttaccag attttgttgc ctgatcacaa aaacaaaaac aggttttggc aacagacaaa
1741  cttctgtcgc taaacaagga catgatttag cgacagataa cttcagtcgc taacttagcg
1801  actgaaaact tctgtcgcta agcatgaaca tgtattagcg acatacagta tgcaactgta
1861  tgtcactaaa caagaacatg atgaattagt gacggacaac ttctgtcgct aaacaacaaa
1921  aaaaaatcca tgttttagta tattgtttct cattctatca tatcatggta gtgtaaagaa
1981  tcaagaaaca agttttacat agtaacagtc tttatacatt ggagatgaag aaccatttaa
2041  gttcttcaaa atagatagat tttctaggtt acttctanaa gatatatata tggttgaggg
2101  tttgtatatt aaaaaaaaaa aaaaaaaa
```

The nucleic acid sequence corresponding to SEQ ID NO:11 encodes a BEL transcription factor isolated from *Solanum tuberosum* identified herein as StBEL-29, which has a deduced amino acid sequence corresponding to SEQ ID NO:12 as follows:

```
Gln Gly Leu Ser Leu Ser Leu Ser Ser Gln Gln Pro Gly Phe Gly
  1               5                  10                  15

Asn Phe Thr Ala Ala Arg Glu Leu Val Ser Ser Pro Ser Gly Ser Ala
             20                  25                  30

Ser Ala Ser Gly Ile Gln Gln Gln Gln Gln Gln Gln Ser Ile Ser
         35                  40                  45

Ser Val Pro Leu Ser Ser Lys Tyr Met Lys Ala Ala Gln Glu Leu Leu
     50                  55                  60

Asp Glu Val Val Asn Val Gly Lys Ser Met Lys Ser Thr Asn Ser Thr
 65                  70                  75                  80
```

-continued

```
Asp Val Val Asn Asn Asp Val Lys Lys Ser Lys Asn Met Gly Asp
                85                  90                  95

Met Asp Gly Gln Leu Asp Gly Val Gly Ala Asp Lys Asp Gly Ala Pro
            100                 105                 110

Thr Thr Glu Leu Ser Thr Gly Glu Arg Gln Glu Ile Gln Met Lys Lys
            115                 120                 125

Ala Lys Leu Val Asn Met Leu Asp Glu Val Glu Gln Arg Tyr Arg His
130                 135                 140

Tyr His His Gln Met Gln Ser Val Ile His Trp Leu Glu Gln Ala Ala
145                 150                 155                 160

Gly Ile Gly Ser Ala Lys Thr Tyr Thr Ala Leu Ala Leu Gln Thr Ile
                165                 170                 175

Ser Lys Gln Phe Arg Cys Leu Lys Asp Ala Ile Ile Gly Gln Ile Arg
                180                 185                 190

Ser Ala Ser Gln Thr Leu Gly Glu Glu Asp Ser Leu Gly Gly Lys Ile
                195                 200                 205

Glu Gly Ser Arg Leu Lys Phe Val Asp Asn Gln Leu Arg Gln Gln Arg
210                 215                 220

Ala Leu Gln Gln Leu Gly Met Ile Gln His Asn Ala Trp Arg Pro Gln
225                 230                 235                 240

Arg Gly Leu Pro Glu Arg Ala Val Ser Val Leu Arg Ala Trp Leu Phe
                245                 250                 255

Glu His Phe Leu His Pro Tyr Pro Lys Asp Ser Asp Lys Met Met Leu
                260                 265                 270

Ala Lys Gln Thr Gly Leu Thr Arg Ser Gln Val Ser Asn Trp Phe Ile
                275                 280                 285

Asn Ala Arg Val Arg Leu Trp Lys Pro Met Val Glu Glu Met Tyr Leu
290                 295                 300

Glu Glu Ile Lys Glu His Glu Gln Asn Gly Leu Gly Gln Glu Lys Thr
305                 310                 315                 320

Ser Lys Leu Gly Glu Gln Asn Glu Asp Ser Thr Thr Ser Arg Ser Ile
                325                 330                 335

Ala Thr Gln Asp Lys Ser Pro Gly Ser Asp Ser Gln Asn Lys Ser Phe
                340                 345                 350

Val Ser Lys Gln Asp Asn His Leu Pro Gln His Asn Pro Ala Ser Pro
                355                 360                 365

Met Pro Asp Val Gln Arg His Phe His Thr Pro Ile Gly Met Thr Ile
                370                 375                 380

Arg Asn Gln Ser Ala Gly Phe Asn Leu Ile Gly Ser Pro Glu Ile Glu
385                 390                 395                 400

Ser Ile Asn Ile Thr Gln Gly Ser Pro Lys Lys Pro Arg Asn Asn Glu
                405                 410                 415

Met Leu His Ser Pro Asn Ser Ile Pro Ser Ile Asn Met Asp Val Lys
                420                 425                 430

Pro Asn Glu Glu Gln Met Ser Met Lys Phe Gly Asp Asp Arg Gln Asp
                435                 440                 445

Arg Asp Gly Phe Ser Leu Met Gly Gly Pro Met Asn Phe Met Gly Gly
                450                 455                 460

Phe Gly Ala Tyr Pro Ile Gly Glu Ile Ala Arg Phe Ser Thr Glu Gln
465                 470                 475                 480

Phe Ser Ala Pro Tyr Ser Thr Ser Gly Thr Val Ser Leu Thr Leu Gly
                485                 490                 495
```

```
Leu Pro His Asn Glu Asn Leu Ser Met Ser Ala Thr His His Ser Phe
            500                 505                 510
Leu Pro Ile Pro Thr Gln Asn Ile Gln Ile Gly Ser Glu Pro Asn His
            515                 520                 525
Glu Phe Gly Ser Leu Asn Thr Pro Thr Ser Ala His Ser Thr Ser Ser
            530                 535                 540
Val Tyr Glu Thr Phe Asn Ile Gln Asn Arg Lys Arg Phe Ala Ala Pro
545                 550                 555                 560
Leu Leu Pro Asp Phe Val Ala
                565
```

The BEL transcription factor has a molecular mass of approximately 56.2 kDa. StBEL-29, isolated from *Solanum tuberosum*, has a single open reading frame ("ORF") of 1704 bp, extending between nucleotides 1-1704.

In a seventh embodiment, the BEL transcription factor from *Solanum tuberosum* is identified herein as StBEL-30 and is encoded by a nucleic acid molecule having a nucleotide sequence of SEQ ID NO:13 as follows:

```
   1  atctccaagt aaaaaggtta ttgagaaaag taacacagat ggcgacttat tttcctagtc
  61  caaacaatca aagagatgct gatcagacat ttcaatattt taggcaatct ttgcctgagt
 121  cttattcaga agcttcaaat gctccagaaa acatgatggt attcatgaac tattcttctt
 181  ctggggcata ttcagatatg ttgacgggta cttcccaaca acaacacaac tgcatcgata
 241  tcccatctat aggagccacg cctttcaaca catcccaaca agaaatattg tcaaatcttg
 301  gaggatcgca gatggggatt caggattttt cttcatggag agatagcaga aatgagatgc
 361  tagctgataa tgtcttttcaa gttgcacaaa atgtgcaggg tcaaggatta tccctcagtc
 421  ttggctccaa tataccatct ggaattggaa tttcacatgt ccaatctcag aatcctaacc
 481  aaggtggcgg ttttaacatg tcctttggag atggtgataa ttcccaacca aaagaacaaa
 541  gaaatgcaga ttatttttcct ccggataatc ctggaaggga cttggatgct atgaaagggt
 601  ataattctcc atatggtacg tcgagtattg caaggaccat tcccagctcg aagtatttga
 661  aagcagctca atatttgctt gatgaggttg ttagtgtcag aaaggccatc aaggagcaaa
 721  attctaagaa agagttgaca aaggattcca gagagtctga tgtggactcg aaaaatatat
 781  catcagatac tcctgcaaat ggggggttcaa atcctcatga gtccaaaaac aaccaaagtg
 841  aactttcacc taccgagaag caagaagtgc agaacaaact ggccaaactt ctgtcaatgc
 901  tggatgagat tgatagaagg tacagacaat attatcatca gatgcaaata gtggtttcat
 961  catttgatgt ggtagctgga gaaggagcag ctaaaccata cacagctctt gctctccaga
1021  caatttcccg acacttccgt tgcttgcgtg atgcaatctg cgatcagatt cgagcatcac
1081  gaagaagtct tggagagcaa gatgcttcag aaaacagcaa agcgattgga atatcacgcc
1141  tgcgttttgt ggatcatcat attagacagc agagagccct gcagcagctt ggtatgatgc
1201  aacaacatgc ctggaggcct cagaggggat tgcctgaaag ctctgtttca gttttgcgtg
1261  cttggctctt tgagcacttt cttcatccct acccgaaaga ttctgacaaa attatgctag
1321  caaggcaaac tggcttaacg agaagtcagg tatcaaattg gttcataaat gcacgggtgc
1381  gtctttggaa acccatggtt gaggaaatgt acaaagaaga ggctggtgat gctaaaatag
1441  actcaaattc ttcatcggat gttgccccca gacttgcaac aaaagactca aaagttgaag
1501  aaagaggaga attgcaccag aatgcagctt cagaatttga gcagtacaat agtggccaaa
1561  tcctggagtc aaaatctaac catgaagctg atgtagaaat ggagggagca agtaatgcag
```

-continued

```
1621  aaactcaaag tcaatctgga atggaaaacc aaacaggcga acccctgcct gctatggata
1681  attgcaccct ttttcaggac gcatttgttc aaagcaacga tagattctca gaatttggta
1741  gttttggaag tggaaatgta ctacccaatg gagtttcact tacattgggg ctgcagcaag
1801  gtgaaggaag caacctacct atgtccatcg aaactcacgt tagttatgta ccattaaggg
1861  cagatgacat gtatagtaca gcacctacta ctatggtccc tgaaacagca gaattcaact
1921  gcttggattc tgggaatagg cagcaaccat tttggctcct accatctgct acatgatttt
1981  gtatgtgttg tagaattaaa ctgcaagttt tgagtacatc aacattcatc ttcaaaaaaa
2041  aaaaaaaaaa aaaaaaaaaa aaaaa
```

The nucleic acid sequence corresponding to SEQ ID NO:13 encodes a BEL transcription factor isolated from *Solanum tuberosum* identified herein as StBEL-30, which has a deduced amino acid sequence corresponding to SEQ ID NO:14 as follows:

```
Met Ala Thr Tyr Phe Pro Ser Pro Asn Asn Gln Arg Asp Ala Asp Gln
 1               5                  10                  15

Thr Phe Gln Tyr Phe Arg Gln Ser Leu Pro Glu Ser Tyr Ser Glu Ala
                20                  25                  30

Ser Asn Ala Pro Glu Asn Met Met Val Phe Met Asn Tyr Ser Ser Ser
            35                  40                  45

Gly Ala Tyr Ser Asp Met Leu Thr Gly Thr Ser Gln Gln Gln His Asn
        50                  55                  60

Cys Ile Asp Ile Pro Ser Ile Gly Ala Thr Pro Phe Asn Thr Ser Gln
65                  70                  75                  80

Gln Glu Ile Leu Ser Asn Leu Gly Gly Ser Gln Met Gly Ile Gln Asp
                85                  90                  95

Phe Ser Ser Trp Arg Asp Ser Arg Asn Glu Met Leu Ala Asp Asn Val
            100                 105                 110

Phe Gln Val Ala Gln Asn Val Gln Gly Gln Gly Leu Ser Leu Ser Leu
        115                 120                 125

Gly Ser Asn Ile Pro Ser Gly Ile Gly Ile Ser His Val Gln Ser Gln
    130                 135                 140

Asn Pro Asn Gln Gly Gly Gly Phe Asn Met Ser Phe Gly Asp Gly Asp
145                 150                 155                 160

Asn Ser Gln Pro Lys Glu Gln Arg Asn Ala Asp Tyr Phe Pro Pro Asp
                165                 170                 175

Asn Pro Gly Arg Asp Leu Asp Ala Met Lys Gly Tyr Asn Ser Pro Tyr
            180                 185                 190

Gly Thr Ser Ser Ile Ala Arg Thr Ile Pro Ser Ser Lys Tyr Leu Lys
        195                 200                 205

Ala Ala Gln Tyr Leu Leu Asp Glu Val Val Ser Val Arg Lys Ala Ile
    210                 215                 220

Lys Glu Gln Asn Ser Lys Lys Glu Leu Thr Lys Asp Ser Arg Glu Ser
225                 230                 235                 240

Asp Val Asp Ser Lys Asn Ile Ser Ser Asp Thr Pro Ala Asn Gly Gly
                245                 250                 255

Ser Asn Pro His Glu Ser Lys Asn Asn Gln Ser Glu Leu Ser Pro Thr
            260                 265                 270
```

-continued

```
Glu Lys Gln Glu Val Gln Asn Lys Leu Ala Lys Leu Leu Ser Met Leu
        275                 280                 285
Asp Glu Ile Asp Arg Arg Tyr Arg Gln Tyr Tyr His Gln Met Gln Ile
    290                 295                 300

Val Val Ser Ser Phe Asp Val Val Ala Gly Glu Gly Ala Ala Lys Pro
305                 310                 315                 320
Tyr Thr Ala Leu Ala Leu Gln Thr Ile Ser Arg His Phe Arg Cys Leu
                325                 330                 335
Arg Asp Ala Ile Cys Asp Gln Ile Arg Ala Ser Arg Arg Ser Leu Gly
            340                 345                 350

Glu Gln Asp Ala Ser Glu Asn Ser Lys Ala Ile Gly Ile Ser Arg Leu
        355                 360                 365

Arg Phe Val Asp His His Ile Arg Gln Gln Arg Ala Leu Gln Gln Leu
    370                 375                 380

Gly Met Met Gln Gln His Ala Trp Arg Pro Gln Arg Gly Leu Pro Glu
385                 390                 395                 400
Ser Ser Val Ser Val Leu Arg Ala Trp Leu Phe Glu His Phe Leu His
                405                 410                 415
Pro Tyr Pro Lys Asp Ser Asp Lys Ile Met Leu Ala Arg Gln Thr Gly
            420                 425                 430

Leu Thr Arg Ser Gln Val Ser Asn Trp Phe Ile Asn Ala Arg Val Arg
        435                 440                 445
Leu Trp Lys Pro Met Val Glu Glu Met Tyr Lys Glu Glu Ala Gly Asp
    450                 455                 460

Ala Lys Ile Asp Ser Asn Ser Ser Ser Asp Val Ala Pro Arg Leu Ala
465                 470                 475                 480
Thr Lys Asp Ser Lys Val Glu Glu Arg Gly Glu Leu His Gln Asn Ala
                485                 490                 495
Ala Ser Glu Phe Glu Gln Tyr Asn Ser Gly Gln Ile Leu Glu Ser Lys
            500                 505                 510

Ser Asn His Glu Ala Asp Val Glu Met Glu Gly Ala Ser Asn Ala Glu
        515                 520                 525
Thr Gln Ser Gln Ser Gly Met Glu Asn Gln Thr Gly Glu Pro Leu Pro
    530                 535                 540

Ala Met Asp Asn Cys Thr Leu Phe Gln Asp Ala Phe Val Gln Ser Asn
545                 550                 555                 560
Asp Arg Phe Ser Glu Phe Gly Ser Phe Gly Ser Gly Asn Val Leu Pro
                565                 570                 575

Asn Gly Val Ser Leu Thr Leu Gly Leu Gln Gln Gly Glu Gly Ser Asn
            580                 585                 590

Leu Pro Met Ser Ile Glu Thr His Val Ser Tyr Val Pro Leu Arg Ala
        595                 600                 605
Asp Asp Met Tyr Ser Thr Ala Pro Thr Thr Met Val Pro Glu Thr Ala
    610                 615                 620

Glu Phe Asn Cys Leu Asp Ser Gly Asn Arg Gln Gln Pro Phe Trp Leu
625                 630                 635                 640
Leu Pro Ser Ala Thr
                645
```

The BEL transcription factor has a molecular mass of approximately 71 kDa. StBEL-30, isolated from *Solanum tuberosum*, has a single open reading frame ("ORF") of 1938 bp, extending between nucleotides 39-1976.

Fragments of the above BEL transcription factors are encompassed by the present invention.

Suitable fragments can be produced by several means. In one method, subclones of the genes encoding the BEL transcription factors of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein, fragments of a BEL transcription factor encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for a BEL transcription factor being produced. Alternatively, subjecting a full length BEL transcription factor to high temperatures and pressures will produce fragments. These fragments can then be separated by conventional procedures (e.g., chromatography, SDS-PAGE).

Another example of suitable fragments of the nucleic acids of the present invention are fragments of the genes which have been identified as conserved ("con") regions of the proteins, or alternatively, those portions of nucleotide sequences that have been identified as variable ("var") regions. Conserved regions in accordance with the present invention include the homeodomain region (including the proline-tyrosine-proline loop between helices I and II), the amino-terminal SKY box, the BELL domain, and the carboxy-terminal VSLTLGL-box (SEQ ID NO:15), as described in Examples 20-32, below. Thus, one embodiment of the present invention relates to an isolated nucleic acid molecule encoding a protein having at least 85%, preferably 90%, similarity to the homeodomain region, the amino-terminal SKY box, the BELL domain, and the carboxy-terminal VSLTLGL-box (SEQ ID NO:15) in either SEQ ID NO:2, SEQ ID NO:4, SEQ ID NO:6, SEQ ID NO:8, SEQ ID NO:10, SEQ ID NO:12, or SEQ ID NO:14 by basic BLAST using default parameters analysis. Sequences identified using DNAStar Mega alignment program as either variable or conserved in a gene can be amplified using standard PCR methods using forward and reverse primers designed to amplify the region of choice and which include a restriction enzyme sequence to allow ligation of the PCR product into a vector of choice. Combinations of amplified conserved and variable region sequences can be ligated into a single vector to create a "cassette" which contains a plurality of DNA molecules in one vector.

Mutations or variants of the above polypeptides or proteins are encompassed by the present invention. Variants may be made by, for example, the deletion or addition of amino acids that have minimal influence on the properties, secondary structure, and hydropathic nature of a polypeptide or protein. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as an isolated nucleic acid molecule according to the present invention is a nucleic acid molecule having a nucleotide sequence that is at least 55% similar, preferably at least 80% similar, and most preferably, at least 90% similar, to the nucleotide sequence of SEQ ID NO:1, SEQ ID NO:3, SEQ ID NO:5, SEQ ID NO:7, SEQ ID NO:9, SEQ ID NO:11, or SEQ ID NO:13 by basic BLAST using default parameters analysis.

Suitable nucleic acid molecules are those that hybridize to a nucleic acid molecule comprising a nucleotide sequence of SEQ ID NO:1, SEQ ID NO:3, SEQ ID NO:5, SEQ ID NO:7, SEQ ID NO:9, SEQ ID NO:11, or SEQ ID NO:13 under stringent conditions. For the purposes of defining the level of stringency, reference can conveniently be made to Sambrook et al., *Molecular Cloning: a Laboratory Manual*, 2$^{nd}$ Edition, Cold Spring Harbor, N.Y., Cold Spring Harbor Laboratory Press, at 11.45 (1989). An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at >45° C. for 2-3 hours. An example of high stringency conditions includes 0.1-1×SSC/0.1% w/v SDS at 60° C. for 1-3 hours. The skilled artisan is aware of various parameters which may be altered during hybridization and washing and which will either maintain or change the stringency conditions. Other examples of high stringency conditions include: 4-5×SSC/0.1% w/v SDS at 54° C. for 1-3 hours and 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C.

The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

A BEL transcription factor of the present invention is preferably produced in purified form (e.g., at least about 80%, more preferably 90% pure) by conventional techniques. For example, a BEL transcription factor of the present invention may be secreted into the growth medium of recombinant host cells. To isolate the BEL transcription factor, a protocol involving a host cell such as *Escherichia coli* may be used, in which protocol the *E. coli* host cell carrying a recombinant plasmid is propagated, homogenized, and the homogenate is centrifuged to remove bacterial debris. The supernatant is then subjected to sequential ammonium sulfate precipitation. The fraction containing the BEL transcription factor of the present invention is subjected to gel filtration in an appropriately sized dextran or polyacrylamide column to separate the proteins or polypeptides. If necessary, the protein fraction may be further purified by high performance liquid chromatography ("HPLC").

The present invention relates to a DNA construct that contains a DNA molecule encoding for a BEL transcription factor. This involves incorporating one or more of the nucleic acid molecules of the present invention, or a suitable portion thereof, into host cells using conventional recombinant DNA technology. Generally, this involves inserting the nucleic acid molecule into an expression system to which the nucleic acid molecule is heterologous (i.e. not normally present). The expression system contains the necessary elements for the transcription and translation of the inserted protein-coding sequences.

The present invention also relates to an expression vector containing a nucleic acid molecule encoding a BEL transcription factor of the present invention. The nucleic acid molecules of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for transformation. The selection of a vector will depend on the preferred transformation technique and target cells for transfection.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/-or KS +/- (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), pCB201, and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Thus, certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. A constitutive promoter is a promoter that directs expression of a gene throughout the development and life of an organism. An inducible promoter is a promoter that is capable of directly or indirectly activating transcription of one or more DNA sequences or genes in response to an inducer. In the absence of an inducer, the DNA sequences or genes will not be transcribed or will only be minimally transcribed.

The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promoter, lac promotor, trp promotor, recA promotor, ribosomal RNA promotor, the PR and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Other examples of some constitutive promoters that are widely used for inducing expression of transgenes include the nopoline synthase (NOS) gene promoter, from *Agrobacterium tumefaciens*, (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter derived from the cellular elongation factor 1α gene.

Bacterial host cell strains and expression vectors may be chosen which inhibit the action of the promoter unless specifically induced. In certain operations, the addition of specific inducers is necessary for efficient transcription of the inserted nucleic acid. For example, the lac operon is induced by the addition of lactose or IPTG (isopropylthiobeta-D-galactoside). A variety of other operons, such as trp, pro, etc., are under different controls.

Other examples of some inducible promoters, induced, for examples by a chemical agent, such as a metabolite, growth regulator, herbicide or phenolic compound, or a physiological stress/physical means, such as cold, heat, salt, toxins, or through the action of a pathogen or disease agent such as a virus or fungus, include a glucocorticoid-inducible promoter (Schena et al., *Proc. Natl. Acad. Sci.* 88:10421-5 (1991), which is hereby incorporated by reference in its entirety), the heat shock promoter ("Hsp"), IPTG or tetracycline ("Tet on" system), the metallothionine promoter, which is activated by heavy metal ions, and hormone-responsive promoters, which are activated by treatment of certain hormones. A host cell containing an inducible promoter may be exposed to an inducer by externally applying the inducer to the cell. In addition, "tissue-specific" promoters can be used, which are promoters that function in a tissue specific manner to regulate the gene of interest within selected tissues of the host. Examples of such tissue specific promoters include seed, flower, or root specific promoters as are well known in the field (e.g., U.S. Pat. No. 5,750,385 to Shewmaker et al., which is hereby incorporated by reference in its entirety). Promoters of the nucleic acid construct of the present invention may be either homologous (derived from the same species as the host cell) or heterologous (derived from a different species than the host cell).

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

The constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid of the present invention.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A nucleic acid molecule of the preset invention, promoter of choice, an appropriate 3' regulatory region, and, if desired, a reporter gene, can be incorporated into a vector-expression system to contain a nucleic acid of the present invention, or a suitable fragment thereof, using standard cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology* John Wiley & Sons, New York, N.Y., which are hereby incorporated by reference in their entirety. The transcriptional and translational elements are operably linked to the nucleic acid molecule of the present invention or a fragment thereof, meaning that the resulting vector expresses the BEL transcription factor when placed in a suitable host cell.

Once an isolated DNA molecule encoding a BEL transcription factor has been cloned into an expression vector, it is ready to be incorporated into a host cell. Such incorporation can be carried out by the various forms of transformation noted above, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like.

Thus, the present invention also relates to a host cell incorporating one or more of the isolated nucleic acid molecules of the present invention. In one embodiment, the isolated nucleic acid molecule is heterologous to the host cell. Such incorporation can be carried out by the various forms of transformation noted above, depending upon the vector/host system, and using the various host cells described above.

Methods of transformation may result in transient or stable expression of the DNA under control of the promoter. Preferably, the nucleic acid of the present invention is stably inserted into the genome of the host cell as a result of the transformation, although transient expression can serve an important purpose.

One approach to transforming host cells with a nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression, because the population of cells is very high (on the order of $10^6$). To deliver DNA inside protoplasts, several methodologies have been proposed, but the most common are electroporation (Fromm et al., *Proc. Natl. Acad. Sci. USA* 82:5824-5828 (1985), which is hereby incorporated by reference in its entirety) and polyethylene glycol (PEG) mediated DNA uptake (Krens et al., *Nature* 296:72-74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the nucleic acid molecule of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA* 76:3348-52 (1979), which is hereby incorporated by reference in its entirety).

Stable transformants are preferable for the methods of the present invention. An appropriate method of stably introducing the nucleic acid molecule into plant cells is to infect a plant cell with *Agrobacterium tumefaciens* or *Agrobacterium rhizogenes* previously transformed with a DNA construct of the present invention. Under appropriate conditions known in the art, the transformed plant cells are grown to form shoots or roots, and develop further into plants.

Plant tissues suitable for transformation include without limitation, floral buds, leaf tissue, root tissue, meristems, zygotic and somatic embryos, megaspores, callus, protoplasts, tassels, pollen, embryos, anthers, and the like. The means of transformation chosen is that most suited to the tissue to be transformed.

Suitable plants include dicots and monocots. Monocots suitable for the present invention include Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, *freesia*, *crocus*, and *watsonia*), and Orchidacea (e.g., orchid). Examples of dicots suitable for the present invention include Salicaceae (e.g., willow, and poplar), Ranunculaceae (e.g., *Delphinium*, *Paeonia*, *Ranunculus*, *Anemone*, *Clematis*, columbine, and marsh marigold), Magnoliaceae (e.g., tulip tree and *Magnolia*), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, *wisteria*, lupine, black locust, and *acacia*), Malvaceae (e.g., cotton, okra, and mallow), Umbelliferae (e.g., carrot, parsley, parsnips, and hemlock), Labiatae (e.g., mint, peppermints, spearmint, thyme, sage, and lavender), Solanaceae (e.g., potato, tomato, pepper, eggplant, tobacco, henbane, *atropa*, *physalis*, *datura*, and *Petunia*), Cucurbitaceae (e.g., melon, squash, pumpkin, and cucumber), Compositae (e.g., sunflower, endive, artichoke, lettuce, safflower, aster, marigold, dandelions, sage brush, *Dalia*, *Chrysanthemum*, and *Zinna*), and Rubiaceae (e.g., coffee).

After transformation, the transformed plant cells can be selected and regenerated. Preferably, transformed cells are first identified using a selection marker simultaneously introduced into the host cells along with the DNA construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of a compound identifiable are suitable. The most widely used reporter gene for gene fusion experiments has been uidA, a gene from *Escherichia coli* that encodes the β-glucuronidase protein, also known as GUS (Jefferson et al., *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. It is known that practically all plants can be regenerated from cultured cells or tissues. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures*, Vol. 1: (MacMillan Publishing Co., New York, 1983); and Vasil I. R. (ed.), *Cell Culture and Somatic Cell Genetics of Plants*, Acad. Press, Orlando, Vol. 1, 1984, and Vol. III (1986), which are hereby incorporated by reference in their entirety.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds or propagules (e.g., cuttings) are recovered from the transgenic plants. The seeds can then be planted in the soil and cultivated using conventional procedures to produce transgenic plants.

The present invention is also directed to a method for enhancing tuber development in a plant. This method includes transforming a tuberous plant with a first DNA construct including a first nucleic acid molecule encoding a BEL transcription factor or a KNOX transcription factor, and a first operably linked promoter and first 3' regulatory region, whereby tuber development in the plant is enhanced.

Suitable BEL transcription factors include BEL transcription factors from potato, as described above. Other suitable BEL transcription factors include, but are not limited to, those from tobacco, tomato (see, e.g., GenBank Accession Nos. AF375964, AF375965, and AF375966), *Arabidopsis*, rice, barley, apple, and bago (*Gnetum gnemon*).

As used herein, a KNOX transcription factor is encoded by a Knotted-like homeobox (knox) gene and includes a KNOX domain. KNOX transcription factors regulate growth, in particular, leaf architecture and meristem growth. KNOX transcription factors have been isolated from several plant species (reviewed in Reiser et al., "Knots in the Family Tree: Evolutionary Relationships and Functions of knox Homeobox Genes," *Plant Mol. Biol.* 42:151-166 (2000), which is hereby incorporated by reference in its entirety) and can be divided into two classes based on expression patterns and sequence similarity (Kerstetter et al., "Sequence Analysis and Expression Patterns Divide the Maize knotted1-like Homeobox Genes into Two Classes," *Plant Cell* 6:1877-1887 (1994), which is hereby incorporated by reference in its entirety). Class I knox genes have high similarity to the maize knotted1 (kn1) homeodomain and generally have a meristem-specific mRNA expression pattern. Class II knox genes usually have a more widespread expression pattern. Knox genes are members of the three amino acid loop extension (TALE) superclass of homeobox genes (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). Knox genes share conserved regions outside of the homeodomain including the MEINOX and ELK domains.

Suitable KNOX transcription factors include, but are not limited to, POTH1, POTH15, POTH2, HO9, NTH Types (1, 9, 15, 20, 22) (Nishamura et al., *Plant J.* 18:337-347 (1999), which is hereby incorporated by reference in its entirety), those from *Arabidopsis*, maize, barley, tobacco, tomato, pea, cabbage, *Ipomoea, Helianthus, Medicago*, and *Dendrobium*.

In one embodiment, the KNOX transcription factor is POTH1 and is encoded by a nucleic acid molecule having a nucleotide sequence of SEQ ID NO:16 as follows:

```
   1  gagtttctct cccttttaaa aagaaaaaa aaaacacaac acccacttca aatatcaaac
  61  aaatttctca tttgattatt tctaagtgat ttacactact ttgtattttt gtttgttttt
 121  ttttagatat atatatggat gatgaaatgt atggttttca ttcaacaaga gacgattacg
 181  cggataaagc tttgatgtca ccggagaatt tgatgatgca aactgagtac aacaatttcc
 241  acaactatac caactcgtcc atcttgactt ctaatccgat gatgtttgga tccgatgata
 301  ttcaattatc atcggaacaa actaattctt tcagtactat gactcttcaa aataatgata
 361  atatttatca aattagaagt ggaaattgtg gcggaggcag tggcagtggt ggtagcagta
 421  aggatcataa tgataataac aataataatg aagattatga tgaagatggt tcaaatgtta
 481  tcaaggctaa aatcgtctca catccttatt atcctaaatt actcaacgct tatattgatt
 541  gccaaaaggt tggagcacca gcgggtatag taaatctgct ggaagaaata aggcaacaaa
 601  ctgattttcg taaaccaaac gctacttcta tatgtatagg agctgatcct gaacttgatg
 661  agtttatgga aacgtattgt gatatattgt tgaagtataa gtccgatctg tctaggcctt
 721  ttgatgaagc aacaacgttc ctcaacaaga ttgaaatgca actaggtaat ctttgcaaag
 781  atgatggtgg tgtatcatca gatgaggagt taagttgtgg tgaggcagat gcatcaatga
 841  gaagtgagga taatgaactc aaagatagac tcctacgtaa gtttggaagt catttaagta
 901  gtctaaagtt ggaattttca aagaaaaaga agaaagggaa gctaccaaaa gaggcaaggc
 961  aaatgttact tgcatggtgg gatgatcact ttagatggcc ttaccctacg gaggctgata
1021  agaattcact agcagaatca acaggacttg atccaaagca gatcaacaat tggtttataa
1081  atcaaaggaa gagacattgg aaaccatcag agaatatgca gttagctgtt atggataatc
1141  taagctctca gttcttctca tcagatgatt gagtttgaat ggaaattgtg aaaatactgc
1201  tcttcatttc tcttttattt atatataata tataaatagt atatttttgg gaaagaaaga
1261  agttatttta ttaatcaaaa tctctataaa taatggtaga gattaattaa tgttgaattc
1321  ttcttgatca tgtaaatatt caatctagct aattgtcaaa attaatgctt acctaaaaaa
1381  aaa
```

The cDNA (Genbank Accession #U65648) includes an open reading frame of 1035 nt coding for a 345-residue protein estimated to have a mass of 37.95 kDa having an amino acid sequence corresponding to SEQ ID NO:17 as follows:

altered leaf morphology. In these circumstances, specific expression in the stolon, for example, may be desirable.

In one embodiment of this method of the present invention, the tuberous plant is transformed with one or more

```
Met Asp Asp Glu Met Tyr Gly Phe His Ser Thr Arg Asp Asp Tyr Ala
 1               5                  10                  15

Asp Lys Ala Leu Met Ser Pro Glu Asn Leu Met Met Gln Thr Glu Tyr
            20                  25                  30

Asn Asn Phe His Asn Tyr Thr Asn Ser Ser Ile Leu Thr Ser Asn Pro
            35                  40                  45

Met Met Phe Gly Ser Asp Asp Ile Gln Leu Ser Ser Glu Gln Thr Asn
        50                  55                  60

Ser Phe Ser Thr Met Thr Leu Gln Asn Asn Asp Asn Ile Tyr Gln Ile
 65                 70                  75                  80

Arg Ser Gly Asn Cys Gly Gly Gly Ser Gly Ser Gly Gly Ser Ser Lys
                85                  90                  95

Asp His Asn Asp Asn Asn Asn Asn Glu Asp Tyr Asp Glu Asp Gly
                100                 105                 110

Ser Asn Val Ile Lys Ala Lys Ile Val Ser His Pro Tyr Tyr Pro Lys
            115                 120                 125

Leu Leu Asn Ala Tyr Ile Asp Cys Gln Lys Val Gly Ala Pro Ala Gly
    130                 135                 140

Ile Val Asn Leu Leu Glu Glu Ile Arg Gln Gln Thr Asp Phe Arg Lys
145                 150                 155                 160

Pro Asn Ala Thr Ser Ile Cys Ile Gly Ala Asp Pro Glu Leu Asp Glu
                165                 170                 175

Phe Met Glu Thr Tyr Cys Asp Ile Leu Leu Lys Tyr Lys Ser Asp Leu
                180                 185                 190

Ser Arg Pro Phe Asp Glu Ala Thr Thr Phe Leu Asn Lys Ile Glu Met
            195                 200                 205

Gln Leu Gly Asn Leu Cys Lys Asp Asp Gly Gly Val Ser Ser Asp Glu
    210                 215                 220

Glu Leu Ser Cys Gly Glu Ala Asp Ala Ser Met Arg Ser Glu Asp Asn
225                 230                 235                 240

Glu Leu Lys Asp Arg Leu Leu Arg Lys Phe Gly Ser His Leu Ser Ser
                245                 250                 255

Leu Lys Leu Glu Phe Ser Lys Lys Lys Lys Gly Lys Leu Pro Lys
                260                 265                 270

Glu Ala Arg Gln Met Leu Leu Ala Trp Trp Asp Asp His Phe Arg Trp
            275                 280                 285

Pro Tyr Pro Thr Glu Ala Asp Lys Asn Ser Leu Ala Glu Ser Thr Gly
    290                 295                 300

Leu Asp Pro Lys Gln Ile Asn Asn Trp Phe Ile Asn Gln Arg Lys Arg
305                 310                 315                 320

His Trp Lys Pro Ser Glu Asn Met Gln Leu Ala Val Met Asp Asn Leu
                325                 330                 335

Ser Ser Gln Phe Phe Ser Ser Asp Asp
                340                 345
```

In accordance with the present invention, the BEL or KNOX transcription factor may be expressed throughout the plant to achieve enhanced tuber development (see Examples below). Alternatively, the BEL or KNOX transcription factor may be expressed in an organ-specific manner. This is beneficial when, for example with POTH1, expression throughout the plant results in dwarf transgenic plants with DNA constructs which include nucleic acid molecules encoding both a BEL transcription factor and a KNOX transcription factor. Alternatively, a plant expressing one or more of a BEL transcription factor or a KNOX transcription factor may be transformed with a DNA construct including a nucleic acid molecule encoding only one of a BEL transcription factor or a KNOX transcription factor.

Tuberous plants suitable for use in this method of the present invention include potato, dahlia, caladium, Jerusalem artichoke (*Helianthus tuberosus*), yam (*Dioscorea alta*), sweet potato (*Impomoea batatus*), cassava (*Manihot esculenta*), tuberous begonia, cyclamen, and other *solanum* species (e.g., wild potato).

Another aspect of the present invention relates to a method of enhancing growth in a plant. This method includes transforming a plant with a DNA construct including a nucleic acid molecule encoding a BEL transcription factor from *Solanum tuberosum* and an operably linked promoter and 3' regulatory region, whereby growth in the plant is enhanced.

Suitable plants which may be transformed in this method of the present invention include Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, *freesia, crocus,* and *watsonia*), Orchidacea (e.g., orchid), Salicaceae (e.g., willow, and poplar), Ranunculaceae (e.g., *Delphinium, Paeonia, Ranunculus, Anemone, Clematis,* columbine, and marsh marigold), Magnoliaceae (e.g., tulip tree and *Magnolia*), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, *wisteria*, lupine, black locust, and *acacia*), Malvaceae (e.g., cotton, okra, and mallow), Umbelliferae (e.g., carrot, parsley, parsnips, and hemlock), Labiatae (e.g., mint, peppermints, spearmint, thyme, sage, and lavender), Solanaceae (e.g., potato, tomato, pepper, eggplant, tobacco, henbane, *atropa, physalis, datura,* and *Petunia*), Cucurbitaceae (e.g., melon, squash, pumpkin, and cucumber), Compositae (e.g., sunflower, endive, artichoke, lettuce, safflower, aster, marigold, dandelions, sage brush, *Dalia, Chrysanthemum,* and *Zinna*), and Rubiaceae (e.g., coffee). In one particular embodiment, the plant transformed is a solanaceous species.

Yet another embodiment of the present invention relates to a method of regulating flowering in a plant. This method includes transforming a plant with a DNA construct including a nucleic acid molecule encoding a BEL transcription factor from *Solanum tuberosum* and an operably linked promoter and 3' regulatory region, whereby flowering in the plant is regulated.

Suitable plants in accordance with this method of the present invention are described above.

The BEL transcription factors from *Solanum tuberosum* of the present invention appear to play a diverse role in plant growth by regulating the development of both reproductive and vegetative meristems. Accordingly, they can be used in the methods for enhancing growth or regulating flowering of the present invention. In particular, the BEL transcription factors of the present invention are involved in regulating photoperiodic responses in potato (tuberization), and BEL transcription factors have previously been identified as contributing to flower development (Müller et al., "In vitro Interactions Between Barley TALE Homeodomain Proteins Suggest a Role for Protein-Protein Associations in the Regulation of Knox Gene Function," *Plant J.* 27:13-23 (2001); Mondrusan et al., "Homeotic Transformation of Ovules into Carpel-Like Structures in *Arabidopsis,*" *Plant Cell* 6:333-349 (1994); Reiser et al., "The BELL1 Gene Encodes a Homeodomain Protein Involved in Patterns Formation in the *Arabidopsis* Ovule Primordium," *Cell* 83:735-742 (1995), which are hereby incorporated by reference in their entirety) and are present in numerous photoperiodic flowering species (e.g., rice, tobacco, morning glory, *Arabidopsis*), thus it appears that they contribute to regulating flower induction in many plants.

EXAMPLES

Example 1—Amplification of Potato Homeobox Fragment for Use as Probe

Two primers, Primer 1 (5'-AAGAAGAAGAA-GAAAGGGAA) (SEQ ID NO:18) and Primer 2 (5'-AT-GAACCAGTTGTTGAT) (SEQ ID NO:19) were designed based on comparison of the homeobox regions of five class I homeobox genes (KN1, KNAT1, KNAT2, OSH1, and SBH1) to correspond to the most highly conserved portions of the homeobox, and were synthesized at the DNA Synthesis Facility at Iowa State University. Template DNA was prepared from a mass in vivo excision of a 4-day axillary bud tuber λZAP®II cDNA library (Stratagene, La Jolla, Calif.) from potato cv. Superior. The potato homeobox fragment was amplified using an annealing temperature of 45° C. and cloned into the pCR2.1 vector of the TA Cloning® Kit (Invitrogen, Carlsbad, Calif.).

Example 2—Library Screening and Sequence Analysis

The early tuberization stage library was constructed as described in Kang et al., "A Novel MADS-box Gene of Potato (*Solanum tuberosum* L.) Expressed During the Early Stages of Tuberization," *Plant Mol. Biol.* 31: 379-386 (1996), which is hereby incorporated by reference in its entirety. Screening of 400,000 pfu was accomplished using 100 ng of $^{32}$P-labeled PCR-generated probe in 50% formamide (50% deionized formamide, 6×SSC, 3.4× Denhardt's solution, 25 mM sodium phosphate buffer, pH 7.0, 120 µg/ml denatured salmon sperm DNA, 0.4% SDS) at 42° C. for 48 hours. Membranes were washed with 2×SSC/0.1% SDS, at 25° C. for 5 minutes; then twice with 2×SSPE/0.1% SDS, at 65° C. for 20 minutes.

POTH1 was sequenced at the Nucleic Acid Sequencing Facility at Iowa State University. Sequence analyses performed included BLAST (Altschul et al., "Basic Local Alignment Search Tool," *J. Mol. Biol.* 215:403-410 (1990), which is hereby incorporated by reference in its entirety) and GAP [Genetics Computer Group (GCG), Madison, Wis.].

Example 3—RNA Isolation and Northern Blot Analysis

Total RNA was isolated (Dix et al., "In vivo Transcriptional Products of the Chloroplast DNA of *Euglena gracilis,*" *Curr. Genet.* 7:265-273 (1983), which is hereby incorporated by reference in its entirety) from potato (*Solanum tuberosum* L.) plants grown in the greenhouse at 20 to 25° C. under 16 hours of light. Total RNA was enriched for poly (A)+ RNA by separation over an oligo-dT column and northern gel electrophoresis was performed using methyl mercury as a denaturant. Ethidium bromide staining under UV light was used to ascertain equal gel loading and efficient transfer to nylon membranes. The Genius™ non-radioactive nucleic acid labeling and detection system (Roche Biochemicals, Indianapolis, Ind.) was used. Fifteen ng/ml of digoxygenin-UTP-labeled antisense RNA probe in 50% formamide was hybridized to filters at 55° C. overnight. Membranes were washed twice for 5 minutes in 2×SSC, 0.1% SDS at 25° C., and then washed twice for 15 minutes in 0.1×SSC, 0.1% SDS at 68° C. The membranes were then incubated 30 minutes in blocking solution:maleic acid buffer pH 7.5 (1:10), 30 minutes in anti-digoxygenin-alkaline-phosphatase conjugate:maleic acid buffer (1:10, 000), washed twice for 15 minutes in maleic acid buffer, and equilibrated 5 minutes in detection buffer before addition of disodium 3-[4-metho xyspiro {1,2-dioxetane-3,2'-[5'-chloro]tricyclo [3.3.1.1$^{3,7}$]decan}-4-yl] phenyl phosphate (CSPD) substrate solution. Membranes were exposed to film for 30 to 45 minutes at 25° C.

Example 4—In Situ Hybridization Analysis

Preparation of tissue samples and in situ hybridizations were performed as described in Cañas et al., "Nuclear Localization of the *Petunia* MADS Box Protein FBP1," *Plant J.* 6:597-604 (1994), which is hereby incorporated by reference in its entirety. Digoxygenin-UTP-labeled RNA probes, both sense and antisense, were transcribed with RNA polymerases according to instructions (Roche Biochemicals, Indianapolis, Ind.), and hydrolyzed using 0.2 M sodium carbonate and 0.2 M sodium bicarbonate at 65° C. for 51 minutes. Unincorporated nucleotides were removed over a Sephadex G-50 column.

For immunological detection, the slides were incubated in buffer 1 (1% blocking solution, 100 mM Tris pH 7.5, 150 mM NaCl) for one hour, then equilibrated with buffer 2 (100 mM Tris pH 7.5, 150 mM NaCl, 0.5% BSA, and 0.3% Triton X-100). Tissue sections were then incubated with anti-digoxygenin-alkaline-phosphatase conjugate diluted 1:1000 in buffer 2 in a humidified box for two hours, then washed three times for 20 minutes in 100 mM Tris pH 7.5, 150 mM NaCl. The tissue sections were equilibrated in buffer 3 (100 mM Tris pH 9.5, 100 mM NaCl, 50 mM $MgCl_2$) for 10 minutes, then incubated in 3.2 µg/ml 5-bromo-4-chloro-3-indolyl-phosphate (BCIP):6.6 µg/ml nitro-blue tetrazolium salt (NBT) in buffer 3 in a humidified box for 13 hours (above-ground tissues) or 7 hours (underground tissues). Accumulation of POTH1 mRNA was visualized as an orange/brown stain under dark field illumination. Sections were viewed and photodocumented using the dark field mode on the Leitz Orthoplan light microscope.

Example 5—35S-POTH1 Transformation of Potato Plants

The full length POTH1 cDNA was cloned into the binary vector, pCB201 (Xiang et al., "A Mini Binary Vector Series for Plant Transformation," *Plant Mol. Biol.* 40:711-718 (1999), which is hereby incorporated by reference in its entirety) between the CaMV 35S promoter and the nos terminator. Two potato cultivars, *Solanum tuberosum* ssp. *andigena* and cv. FL-1607, were transformed by the *Agrobacterium tumefaciens* (strain GV2260) mediated leaf-disk transformation method (Liu et al., "Transformation of *Solanum Brevidens* Using *Agrobacterium Tumefaciens*," *Plant Cell Reports* 15:196-199 (1995), which is hereby incorporated by reference in its entirety). A total of thirty independent transgenic lines from *andigena* and twenty independent transgenic lines from 'FL-1607' were screened for insertion of the transgene and accumulation of POTH1 mRNA. Five independent transgenic lines of *S. tuberosum* spp. *andigena* and 4 lines of *S. tuberosum* cv. FL-1607 that showed high levels of POTH1 mRNA accumulation were selected for further analysis. Untransformed tissue culture plants were used as controls.

Example 6—Nucleic Acid Hybridizations

Genomic DNA was isolated using the cetyltrimethylammonium bromide (CTAB) mini-plant DNA extraction method (Doyle et al., "A Rapid DNA Isolation Procedure for Small Quantities of Fresh Leaf Tissue," *Phytochem. Bull.* 19:11-15 (1987), which is hereby incorporated by reference in its entirety). DNA (10 µg) was digested with Hind III or Xba I (Promega, Madison, Wis.), and gel electrophoresis was performed. DNA was denatured and blotted according to the methods described by Kolomiets et al., "A Leaf Lipoxygenase of Potato Induced Specifically by Pathogen Infection," *Plant Physiol.* 124:1121-1130 (2000), which is hereby incorporated by reference in its entirety. Total RNA was isolated with TriPure Isolation Reagent (Roche Biochemicals, Indianapolis, Ind.) and gel electrophoresis was performed using 10 mM methyl mercury (II) hydroxide as a denaturant. For hybridization with STGA20ox1, shoot tip samples were collected at the same time of day to avoid variations due to diurnal regulation. Probes were labeled with [α-$^{32}$P]dCTP (RadPrime DNA Labeling System, Gibco BRL, Gaithersburg, Md.). POTH1 probes were generated by using the 730 nt EcoR I fragment of POTH1 from the pCR2.1 vector (Invitrogen, Carlsbad, Calif.) with the ELK and homeodomains deleted. The 1.5 kb EcoR I-Xho I fragment of StGA20ox1 cDNA (Carrera et al., "Feedback Control and Diurnal Regulation of Gibberellin 20-oxidase Transcript Levels in Potato," *Plant Physiol.* 119:765-773 (1999), which is hereby incorporated by reference in its entirety) was provided by Salomé Prat (Barcelona, Spain). All membranes were hybridized at 42° C. for 70 hours in 50% formamide. The membranes were rinsed in 2×SSC/0.1% SDS, at 25° C., followed by 1×SSC/0.1% SDS for 0-20 minutes at 65° C., then 0.1×SSC/0.1% SDS for 20-30 minutes at 65° C. Film was exposed for 4 to 7 days.

Example 7—Light Microscopy

Leaf tissue was fixed in 2% glutaraldehyde, 2% paraformaldehyde in 0.1 M sodium phosphate buffer pH 7.0 at 4° C. for 72 hours, dehydrated in a graded ethanol series, and embedded in LR White resin (Electron Microscopy Sciences, Ft. Washington, Pa.). One µm thick sections were cut on an ultramicrotome (Reichert/Leica, Deerfield, Ill.) and stained with 1% toludine blue. Sections were viewed and photodocumented using bright field microscopy.

Example 8—GA Analysis

Three replicates of shoot tips down to the sixth expanded leaf (10 g each), were harvested in liquid nitrogen and frozen at −80° C. The tissue was ground with 80% methanol (MeOH) and incubated at 4° C. overnight. [$^2H_2$]-GA internal standards were added in the following amounts in ng/g fwt: $GA_1$: 1, $GA_8$: 10, $GA_{19}$: 10, $GA_{20}$: 20, and $GA_{53}$: 5. The extract was filtered through Highflo Supercel and washed with 80% MeOH. After evaporation of the MeOH in vacuo, 0.5 M $Na_2HPO_4$ was added to bring the pH to about 8.5, followed by addition of 20 mL of hexane. The flask was mixed well and the hexanes were evaporated off in vacuo. The solution was than acidified to pH 3-3.5 with glacial $CH_3COOH$ (acetic acid) and incubated for 15 minutes. The sample was then filtered through polyvinylpolypyrrolidone (PVPP) and washed with 0.2% acetic acid. The eluate was loaded onto a prepared Baker SPE ($C_{18}$) cartridge and washed with 0.2% acetic acid. The sample was eluted off the column with 7 mL of 80% MeOH, evaporated to dryness, and dissolved in 1 mL 100% MeOH. The MeOH-insoluble precipitate was removed by centrifugation and the supernatant was evaporated to dryness, redissolved in 0.8 mL 0.2% acetic acid, and filtered through a 45 µm filter. A one mL loop was used to load the sample onto the $C_{18}$ HPLC column (Econosphere: Phenomenex, Torrance, Calif.) run with the following 0.2% acetic acid to acetonitrile gradient: 5%-20% over 2 minutes; 20-35% over 15 minutes; 35-75% over 15 minutes. Fractions for the following GAs were taken as follows: 10-14.3 minutes for $GA_8$; 15.3-17.45 minutes for $GA_1$; 23-27 minutes for $GA_{19}$ and $GA_{20}$; 27-29.3 minutes for $GA_{53}$. Fractions were collected separately and methylated with diazomethane in ether. Samples were dried, redissolved in 1 mL ethyl acetate, and partitioned against water. The aqueous phase was partitioned against another 1 mL of ethyl acetate and the ethyl acetate fractions were combined. The samples were dried and placed under high vacuum over $P_2O_5$. The samples were dissolved in 2 µL dry pyridine and 10 µL BSTFA [bis(trimethylsilyl)trifluoroacetamide] with 1% TMCS (trimethylchlorosilane) (Sylon BFT: Pierce, Rockford, Ill.) and heated at 80° C. for 20 minutes. Samples were analyzed by GC-SIM on a GC-MS (HewlettPackard 5890 GC+5970B M) with a 15 m Zebron ZB1 column (Phenomenex, Torrance, Calif.). The carrier gas, He, was set at a flow rate of approximately 35 cm/sec. The initial column temperature was 60° C. for one minute and then increased at a rate of 30° C./minute to 240° C., and then to 290° C. at a rate of 4° C./minute. The injector temperature was 225° C. and the temperature of the detector was 300° C. Concentrations of $GA_{53}$, $GA_{19}$, $GA_{20}$, $GA_1$, and $GA_8$ were determined by calculating the area of the peaks, 448/450, 434/436, 418/420, 506/508, and 594/596, respectively, at the correct Kovats retention indices. Reference spectra were obtained from Gaskin et al., "GC-MS of the Gibberellins and Related Compounds: Methodology and a Library of Spectra," Bristol UK: Cantock's Enterprises (1991), which is hereby incorporated by reference in its entirety. Cross-ion corrections were calculated according to the following formula where: $R_1$=% endogenous ion in final; $R_2$=% heavy ion in final; $A_1$=% endogenous ion in natural unlabelled sample; $A_2$=% heavy ion in natural unlabelled sample; B=heavy isotope internal standard.

$$\text{Amount of natural compound }(A) = \frac{[R1]}{[R2 \times A1 - R1 \times A2]} \times \text{Amount of } B \text{ added}$$

Example 9—In Vitro Tuberization

Cuttings of transgenic and control plants were placed in Murashige-Skoog (MS) media plus 6% sucrose (Konstantinova et al., "Photoperiodic Control of Tuber Formation in Potato Solanum Tuberosum ssp. Andigena in vivo and in vitro," Russian J. Plant Physiol. 46:763-766 (1999), which is hereby incorporated by reference in its entirety). After 2 weeks under long days (16 hours of light, 8 hours of dark) to promote rooting, plants were cultured separately under either long or short day (8 hours of light, 16 hours of dark) conditions. Plants were examined for tuber activity (percentage of plants that produced either swollen stolons or tubers) and the number of tubers were counted.

Example 10—Results: Isolation and Characterization of POTH1

An early stage tuber cDNA library (Kang et al., "Nucleotide Sequences of Novel Potato (Solanum tuberosum L.) MADS-box cDNAs and Their Expression in Vegetative Organs," Gene 166:329-330 (1995), which is hereby incorporated by reference in its entirety) from Solanum tuberosum 'Superior' was screened for members of the homeobox gene family. PCR primers were designed from the consensus sequence of the homeoboxes of the class I genes kn1 from maize (Vollbrecht et al., "The Developmental Gene Knotted-1 is a Member of a Maize Homeobox Gene Family," Nature 350:241-243 (1991), which is hereby incorporated by reference in its entirety), KNAT1 and KNAT2 from Arabidopsis (Lincoln et al., "A Knotted1-like Homeobox Gene in Arabidopsis is Expressed in the Vegetative Meristem and Dramatically Alters Leaf Morphology When Overexpressed in Transgenic Plants," Plant Cell 6:1859-1876 (1994), which is hereby incorporated by reference in its entirety), OSH1 from rice (Matsuoka et al., "Expression of a Rice Homeobox Gene Causes Altered Morphology of Transgenic Plants," Plant Cell 5:1039-1048 (1993), which is hereby incorporated by reference in its entirety), and SBH1 from soybean (Ma et al., "Identification of a Homeobox-Containing Gene With Enhanced Expression During Soybean (Glycine max L.) Somatic Embryo Development," Plant Mol. Biol. 24:465-473 (1994), which is hereby incorporated by reference in its entirety). A mass excision of the tuber cDNA library was performed, and this DNA was used as the PCR template. A band corresponding to the expected size of 158 nt was purified, cloned, and sequenced. This potato homeobox fragment was 87% identical to the conserved positions of the consensus sequence created from the five class I genes, and was used as a probe to screen the cDNA library. Library screening resulted in the isolation of a truncated, 1053-nt homeobox cDNA from the library, which was used as a probe to screen the library again. Three clones were isolated, and the full-length 1383-nt potato homeobox cDNA, POTH1, was selected for further study. The cDNA (Genbank Accession #U65648) includes an open reading frame of 1035 nt coding for a 345-residue protein estimated to have a mass of 37.95 kDa. It contains a 134-nt 5'-untranslated region, and a 216-nt 3'-untranslated region, including the poly-A tail. The coding sequence of the protein includes the 97-aa MEINOX domain, the 22-aa ELK domain, and the 64-aa homeodomain.

To identify proteins with similarity to POTH1, a BLAST analysis (Altschul et al., "Basic Local Alignment Search Tool," J. Mol. Biol. 215:403-410 (1990), which is hereby incorporated by reference in its entirety), was performed on the protein sequence and GAP analysis [Wisconsin Package Version 9.1, Genetics Computer Group (GCG), Madison, Wis.] was used to determine percent similarity. POTH1 shares 86% similarity with the homeodomain of KN1, classifying it as a class I homeobox protein (Kerstetter et al., "Sequence Analysis and Expression Patterns Divide the Maize Knotted1-like Homeobox Genes Into Two Classes," Plant Cell 6:1877-1887 (1994), which is hereby incorporated by reference in its entirety). However, over the entire protein sequence, POTH1 shares only 51% similarity with KN1. The five proteins with the most similarity to POTH1 include TKN3 from tomato (U76408), NTH22 of tobacco (Nishimura et al., "The Expression of Tobacco Knotted1-type Class I Homeobox Genes Correspond to Regions Predicted by the Cytohistological Zonation Model," Plant J. 18: 337-347 (1999), which is hereby incorporated by reference in its entirety), PKN2 of Ipomoea nil (AB016000), KNAT2 of Arabidopsis (Lincoln et al., "A Knotted1-like Homeobox Gene in Arabidopsis is Expressed in the Vegetative Meristem and Dramatically Alters Leaf Morphology When Overexpressed in Transgenic Plants," Plant Cell 6:1859-1876 (1994), which is hereby incorporated by reference in its entirety) and NTH15 of tobacco (Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997), which is hereby incorporated by reference in its entirety) with 94, 88, 73, 69, and 56% similarity overall, respectively. As expected, relatively high levels of conservation were observed in the homeodomains (97 to 83%) and in the MEINOX domains (95 to 63%) of this group.

Example 11—Results: Southern Analysis

To study the complexity of the POTH1 gene family in the tetraploid potato genome, Southern analysis was performed. Genomic DNA from both *S. tuberosum* cv. FL-1607 and spp. *andigena* was digested with Hind III and Xba I. For both species, only two bands hybridized to a gene-specific probe for POTH1 (FIG. 1), indicating that POTH1 is a member of a small gene family. A Hind III site is located within the cDNA sequence of POTH1.

Example 12—Results: Accumulation of POTH1 mRNA

Figure 2:
FIG. 2 shows POTH1 mRNA accumulation in various organs of the potato plants. Poly(A)-enriched RNA (5 μg in each lane) was hybridized to a digoxygenin-rUTP-labeled POTH1 RNA antisense probe with the ELK and homeodomain deleted. MT, mature tuber; S, stem; R, root; IN, inflorescence; ML, mature leaf; SA, shoot apex; SS, swollen stolon apex. Equal loading of intact poly(A)+ RNA in each lane was confirmed by ethidium bromide staining. The hybridizing bands are approximately 1.3 kb in length.

Northern blot analysis was used to determine the pattern of POTH1 mRNA accumulation in various organs of potato (FIG. 2). Poly(A)+ enriched RNA samples were hybridized with a digoxygenin-UTP labeled 780-nt RNA antisense probe with the conserved ELK region, homeobox region, and poly-A tail deleted. A single band, approximately 1.3 kb in length, representing POTH1 mRNA, was present in RNA extracted from stem, root, inflorescence, shoot apex, and swollen stolon apex (FIG. 2, lanes 2, 3, 4, 6, and 7, respectively). POTH1 transcripts were not detected in either mature leaf or mature tuber RNA (FIG. 2, lanes 1 and 5). Equal loading and the quality of the RNA loaded were ascertained via ethidium bromide staining. This autoradiograph was representative of several replicate hybridization blots.

To determine more precisely the location of POTH1 mRNA accumulation, in situ hybridization was performed on vegetative meristems of potato (FIG. 3). The potato SAM is comprised of two tunica layers, which divide anticlinally to produce the epidermis and contribute to lateral organs such as leaves, and three corpus layers, which divide both periclinally and anticlinally to contribute to lateral organ and stem development (Esau, "The Stem: Primary State of Growth. In Wiley, eds., *Anatomy of Seed Plants,* 2nd Edition New York: pp. 243-294 (1977); Sussex, "Morphogenesis in *Solanum Tuberosum* L.: Apical Structure and Developmental Pattern of the Juvenile Shoot," *Phytomorphology* 5:253-273 (1955), which are hereby incorporated by reference in their entirety). POTH1 mRNA accumulates in the two tunica and three corpus layers of the SAM, the leaf primordia, the procambium, and the lamina of young leaves (FIG. 3A). Lower levels of POTH1 transcript can also be detected in the developing leaflets of an older leaf (FIG. 3A, OL). A slightly lower level of POTH1 transcript can be detected in the central zone of the SAM, where initials divide less rapidly than adjacent cells.

Potato plants produce underground stems that grow horizontally, called stolons (Jackson, "Multiple Signaling Pathways Control Tuber Induction in Potato," *Plant Physiol.* 119:1-8 (1999), which is hereby incorporated by reference in its entirety). Under optimum conditions, the subapical region of the stolon tip will begin to swell and eventually develop into a tuber. A nontuberizing stolon will elongate with most of its growth occurring in the tunica and corpus layers. The greatest concentration of POTH1 signal can be detected in the apical meristem of the elongating stolon (FIG. 3B). Expression levels are also high in the lamina of the youngest leaf, the procambium, and the perimedullary parenchyma associated with the vascular tissue (FIG. 3B). Differentiation of the procambium into mature vascular tissue is marked by the appearance of xylem elements (Esau, "The Stem: Primary State of Growth. In Wiley, eds., *Anatomy of Seed Plants,* 2nd Edition New York: pp. 243-294 (1977), which is hereby incorporated by reference in its entirety), and POTH1 transcript accumulates in this differentiated tissue as well (FIG. 3B). No signal is detected in an elongating stolon tip hybridized with a sense POTH1 probe (FIG. 3C).

The apex of a tuberizing stolon, visibly swollen in FIG. 3D, continues to accumulate POTH1 mRNA in the apical meristem, the procambium, the lamina of new leaves, and the perimedullary parenchyma, but the signal is less intense than in the elongating stolon apical meristem (FIG. 3B). In the subapical portion of the swollen stolon tip (FIG. 3E), where rapid radial expansion is occurring (Xu et al., "Cell Division and Cell Enlargement During Potato Tuber Formation," *J. Exp. Bot.* 49:573-582 (1998), which is hereby incorporated by reference in its entirety), POTH1 signal is detected, especially in the perimedullary parenchyma, associated with the vascular tissue. There is some signal as well in the pith and inner cortex (FIG. 3E). FIG. 3F is the sense probe control corresponding to the section in FIG. 3E. Similar results were observed with sense probe controls in each section examined. The data presented in FIG. 3 is representative of several independent replications. Because FIGS. 3A-D are longitudinal sections through various apices at the same magnification, the location of labeled tissues is similar from one apex to the next.

Example 13—Results: The Overexpression of POTH1 in Transgenic Potato Plants

Figure 4A:
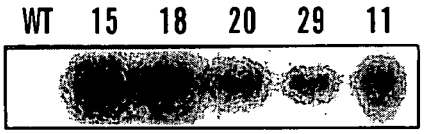
FIGS. 4A-F show POTH1 mRNA accumulation in transgenic potato plants and the evaluation of leaf and stem traits in POTH1 overexpression lines.
Figure 4B:

To determine the effect of POTH1 overexpression on the development of potato, the full-length POTH1 sequence was placed under the control of the CaMV 35S promoter in the binary vector, pCB201 (Xiang et al., "A Mini Binary Vector Series for Plant Transformation," *Plant Mol. Biol.* 40:711-718 (1999), which is hereby incorporated by reference in its entirety). To examine the role of POTH1 in tuberization, two cultivars of potato (*Solanum tuberosum* cv. FL-1607 and *S. tuberosum* ssp. *andigena*) were selected for transformation. *Andigena* plants are photoperiod sensitive, tuberizing only under short-day conditions (Carrera et al., "Changes in GA 20-oxidase Gene Expression Strongly Affect Stem Length, Tuber Induction and Tuber Yield of Potato Plants," *Plant J.* 22:1-10 (2000), which is hereby incorporated by reference in its entirety), whereas 'FL-1607' plants tuberize under both long- and short-day photoperiods. A total of thirty independent transgenic lines from *andigena* and twenty independent transgenic lines from 'FL-1607' were generated and screened for increased POTH1 mRNA expression. Among 10 sense lines of *andigena* and 15 lines of 'FL-1607' that showed high levels of POTH1 mRNA accumulation, five independent transgenic lines of *andigena* and 4 lines of 'FL-1607' were chosen for further analysis. An aberrant phenotype was observed only in those lines with detectable levels of POTH1 mRNA from total RNA samples. Two transgenic lines, *andigena* lines 15 and 18 had the highest levels of POTH1 mRNA accumulation (FIG. 4A), whereas *andigena* lines 11, 20, and 29 had intermediate levels of POTH1 mRNA (FIG. 4A). Similar high levels of POTH1 accumulation were observed in 'FL-1607' overexpression lines that exhibited mutant phenotypes. Equivalent loading of RNA samples was verified by using an 18S rRNA probe from wheat (FIG. 4B).

Example 14—Results: Phenotype of POTH1 Overexpression Lines

Figure 4C:
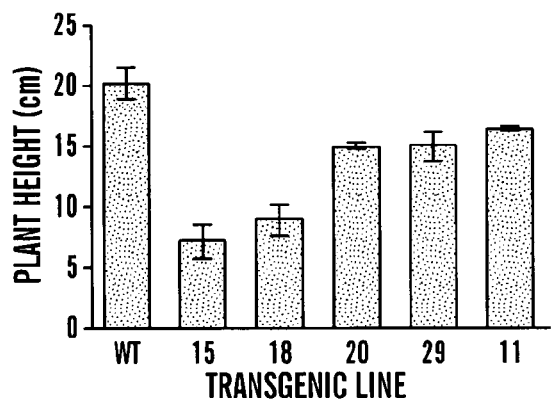
Figure 4D:
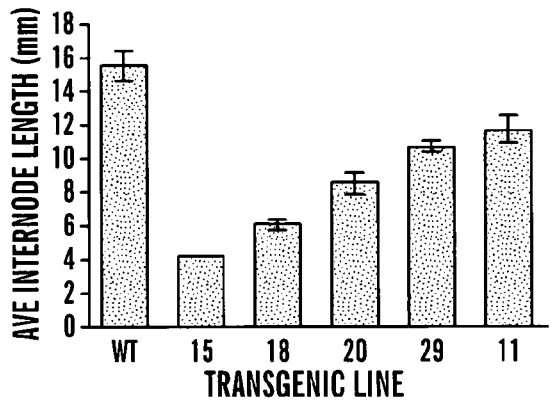
Figure 4E:
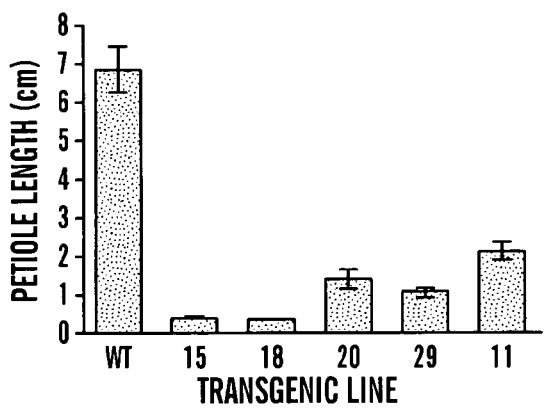
Figure 4F:
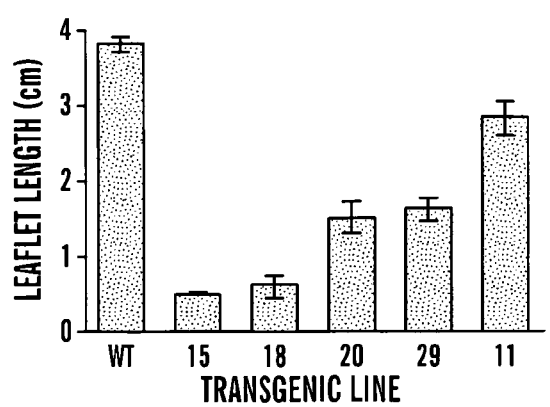

Overexpression of POTH1 resulted in a phenotype characterized by a reduction in plant height and leaf size (FIGS. 4C-F). Lines with the most abundant POTH1 RNA levels had the greatest reduction in overall height. The height of potato subsp. *andigena* lines 15 and 18 was reduced by at least 64% compared with wild-type plants (FIG. 4C). Transgenic lines with an intermediate phenotype (*andigena* lines 20, 29, and 11) showed a 20 to 25% reduction in plant height (FIG. 4C). The decrease in plant height was due to a corresponding decrease in internode elongation (FIG. 4D). The average internode length of the severe mutant, *andigena* line 15, was 4.0 mm compared to 16 mm for wild-type *andigena* plants. The same pattern was observed for petiole and leaflet length (FIGS. 4E and 4F) with the severe phenotypes displaying the greatest reduction in size. Among the five sense lines, petiole length was reduced by 70 to 96%, whereas leaflet length was reduced by 29 to 87% compared to wild-type. The sixth expanded leaf from the shoot apex was used to measure petiole and terminal leaflet length. Similar results were seen for 'FL-1607' overexpression lines.

Transgenic plants that overexpressed POTH1 also exhibited malformed leaves. The overall size of the leaflets was greatly reduced and they were rounded, curved, and wrinkled (FIGS. 5A-B). Wild-type leaflets have an ovate form and display pinnate venation with a prominent midvein (FIG. 5B, left). In the overexpression mutants, the midvein is less prominent and the most severe phenotypes exhibited a 'mouse-ear' leaf phenotype (FIGS. 5B-D). The leaflets are heart-shaped with a shortened mid-vein. In addition, there has been a switch from pinnate to palmate venation (FIG. 5B). The phyllotaxy is not altered in overexpression lines, although, compared with wild-type plants (FIG. 5C), the leaves are clustered closer to the stem due to shortened petioles (FIG. 5D). In tomato, the dominant mutations, Mouse-ear (Me) and Curl (Cu), were caused by a change in the spatial and temporal expression of the tomato knox gene TKn2/LeT6 (Parnis et al., "The Dominant Developmental Mutants of Tomato, Mouse-ear and Curl, are Associated With Distinct Modes of Abnormal Transcriptional Regulation of a Knotted Gene," *Plant Cell* 9:2143-2158 (1997); Chen et al., "A Gene Fusion at a Homeobox Locus: Alterations in Leaf Shape and Implications for Morphological Evolution," *Plant Cell* 9:1289-1304 (1997), which are hereby incorporated by reference in their entirety). Overexpression of kn1 (Hareven et al., "The Making of a Compound Leaf: Genetic Manipulation of Leaf Architecture in Tomato," *Cell* 84:735-744 (1996), which is hereby incorporated by reference in its entirety) in tomato caused up to a six-fold increase in the level of leaf compoundness resulting in a leaf bearing 700-2000 leaflets. Such a marked increase in the level of compoundness was not observed in POTH1 overexpression lines. Increased proliferation of leaflets from sense lines, however, was common (compare wild-type and line 19 leaflets in FIG. 5E).

To determine whether POTH1 overexpression affected the leaf at the cellular level, leaf cross-sections of the severe mutant, potato subsp. *andigena* line 15, were examined. Wild-type leaves consist of a palisade parenchyma layer on the adaxial side and a spongy parenchyma layer on the abaxial side (FIG. 5F). The cells of the palisade layer are aligned in a vertical orientation and are tightly packed, whereas the spongy parenchyma cells are more loosely arranged (FIG. 5F). In leaves of potato subsp. *andigena* line 15, the palisade parenchyma layer is absent and the spongy parenchyma cells are more closely packed (FIG. 5H). Overall cell size in the leaves of *andigena* line 15 is reduced by about one half.

Figure 5I:
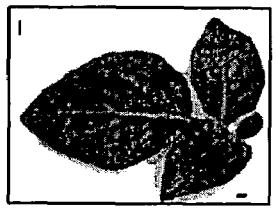
FIG. 5I shows a wild-type leaf from potato subsp. andigena showing the morphology of a compound leaf.
Figure 5J:
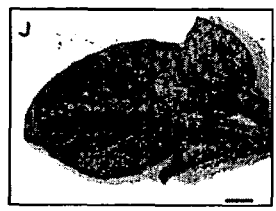
In FIGS. 5J and K, the compound leaf structure is shown for the overexpression mutant, potato subsp. andigena line 15. Shoot tips were treated with either 10 μM $GA_3$ in 0.002% (v/v) ethanol (FIG. 5J) or with 0.002% (v/v) ethanol alone (FIG. 5K). Terminal leaflets from compound leaves of wild-type plants (FIG. 5L), $GA_3$-treated line 15 (FIG. 5M), and untreated line 15 (FIG. 5N) are shown. The mid-vein is marked with an arrow in FIG. 5M. Note that the morphology and venation of the $GA_3$-treated leaf (FIGS. 5J and M) is more similar to the wild-type leaf (FIGS. 5I and L) than to the potato subsp. andigena line 15 untreated leaf (FIGS. 5K and N). Bars in FIGS. 5I through 5K=1.0 mm. The second expanded leaf was used for the leaf samples in FIGS. 5F through 5N.
Figure 5K:
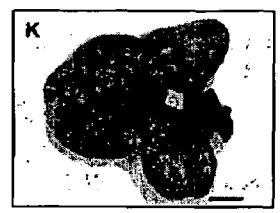
Figure 5L:
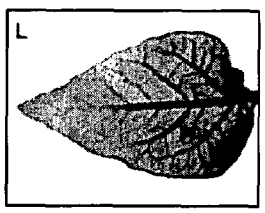
Figure 5M:
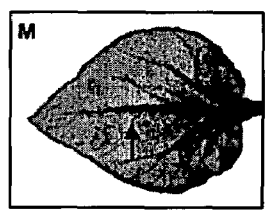
Figure 5N:
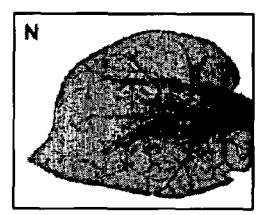
Figure 5O:
FIG. 5O is a wild-type leaf from Solanum tuberosum cv. FL-1607 ('FL-1607') showing the morphology of a compound leaf.
Figure 5P:
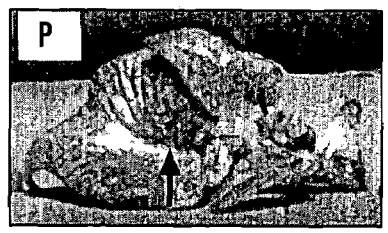
Figure 5Q:
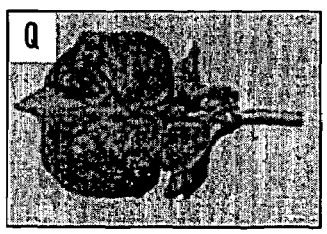

Many of the traits of the phenotypes observed in POTH1 overexpression lines were similar to GA-deficient mutants. These similarities included decreased plant height, decreased internode length, and darker green coloration of the leaves (van den Berg et al., "Morphology and [$^{14}$C] Gibberellin $A_{12}$ Metabolism in Wild-Type and Dwarf *Solanum Tuberosum* ssp. *Andigena* Grown Under Long and Short Photoperiods," *J. Plant Physiol.* 146:467-473 (1995), which is hereby incorporated by reference in its entirety). Because of this, exogenous $GA_3$ was applied to determine whether the overexpression lines were responsive to GA treatment. The shoot apex of overexpression lines was sprayed to runoff with 10 μM $GA_3$ in 0.002% (v/v) ethanol or with 0.002% (v/v) ethanol alone. Application of $GA_3$ not only caused plants with a severe phenotype to increase in height, but also partially rescued the leaf morphology of both severe and intermediate phenotypes. Palisade and spongy parenchyma organization is partially rescued in leaves from line 15 treated with $GA_3$ (FIG. 5G). The compound leaf structure of the of the potato subsp. *andigena* wild-type leaf is shown in FIG. 5I. The $GA_3$-treated leaf (FIG. 5J) of the severe mutant, line 15, is more similar in morphology to the wild-type leaf (FIG. 5K). Leaflets are more ovate in form rather than the typical mouse-ear shape. Wild-type leaves have a prominent mid-vein (FIG. 5L), whereas the mid-vein (FIG. 5M, arrow) is more prominent in the mutant $GA_3$-treated leaf than in the mutant untreated leaf (FIG. 5N). The compound leaf structure of the 'FL-1607' wild-type leaf is shown in FIG. 5O. The $GA_3$-treated leaf (FIG. 5P) of the severe mutant, 'FL-1607' line 5, is more similar in morphology to the wild-type leaf than to the mutant control leaf (FIG. 5Q). Leaflets are more ovate in form rather than the typical 'mouse-ear' shape. The mid-vein (arrow) is more prominent in the $GA_3$-treated leaf (FIG. 5P) than in the mutant leaf (FIG. 5Q).

Figure 6:
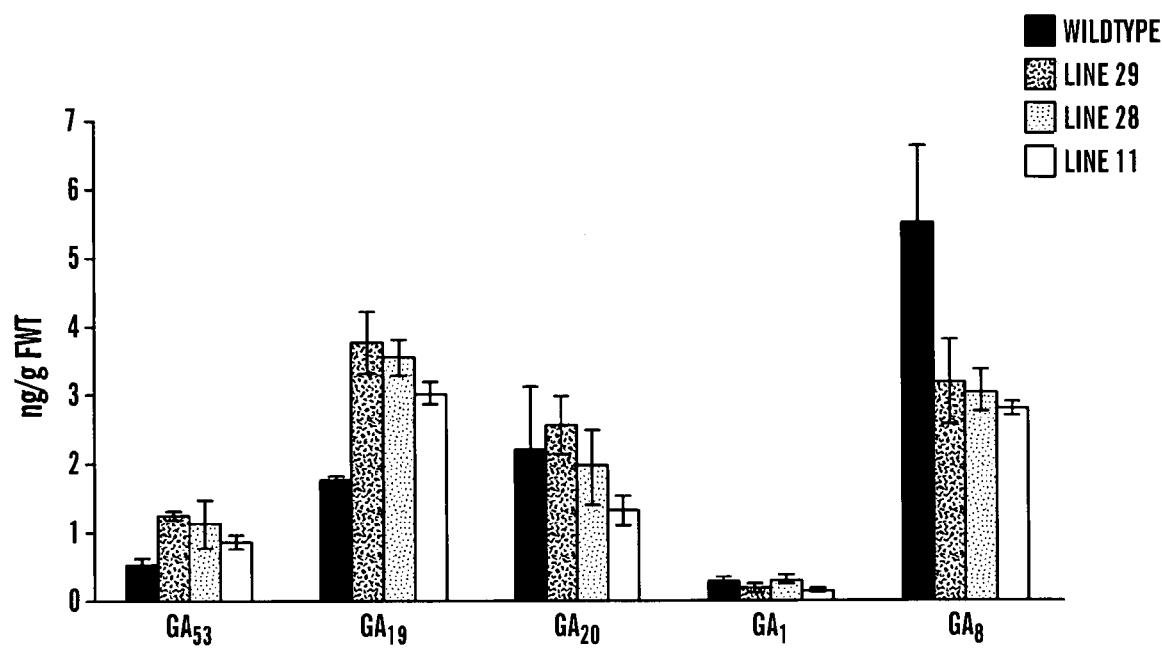
FIG. 6 shows the levels of intermediates in the GA biosynthetic pathway. GAs were extracted from shoot tips down to the sixth expanded leaf from wild-type and potato subsp. andigena POTH1 overexpression lines 29, 20, and 11. GAs were separated by HPLC and levels were measured by gas chromatography-mass spectrometry (GC-MS). $GA_{53}$, $GA_{19}$, and $GA_{20}$ are precursors to $GA_1$, the physiologically active GA, whereas $GA_8$ is the inactive metabolite. $GA_{53}$ and $GA_{19}$ levels increased, whereas $GA_{20}$, $GA_1$, and $GA_8$ levels decreased in POTH1 overexpression lines. Measurements are the average of three replications. Standard error is indicated for each mean. Concentrations of $GA_{53}$, $GA_{19}$, $GA_{20}$, $GA_1$ and $GA_8$ were determined by calculating the area of the peaks at the correct Kovats retention indices (KRI) at 448/450 (KRI=2,497), 434/436 (2,596), 418/420 (2,482), 506/508 (2,669), and 594/596 (2,818), respectively.

To determine whether GA biosynthesis was disrupted in POTH1 overexpression lines, levels of intermediates in the GA biosynthesis pathway in potato (van den Berg et al., "Metabolism of Gibberellin A12 and A12-aldehyde and the Identification of Endogenous Gibberellins in Potato (*Solanum tuberosum* ssp. *andigena*) Shoots," *J. Plant Physiol.* 146:459-466 (1995), which is hereby incorporated by reference in its entirety) were measured. Levels of the intermediates $GA_{53}$ and $GA_{19}$ increased in POTH1 overexpression lines, whereas $GA_1$ and $GA_8$ levels decreased (FIG. 6). In potato subsp. *andigena* lines 29 and 20, $GA_{53}$ and $GA_{19}$ levels increased approximately 2-fold compared with wild-type lines (FIG. 6). The levels of $GA_1$ and $GA_8$ present in potato subsp. *andigena* overexpression lines were approximately one-half that of wild-type levels (FIG. 6). Accumulation of $GA_{53}$ and $GA_{19}$ with a concomitant decrease in $GA_1$ and $GA_8$ indicates that the GA biosynthetic pathway is blocked at the oxidation of $GA_{19}$ to $GA_{20}$, leading to a decrease in the levels of bioactive $GA_1$. Similar patterns of accumulation for GA intermediates were also observed for potato subsp. *andigena* sense line 15 (in andigena line 15, $GA_{53}$ and $GA_{19}$ levels increased 4.8× and 2.1×, respectively, compared to wild-type).

Figure 7A:
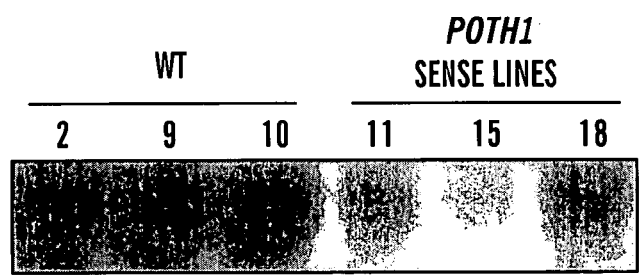
FIGS. 7A-B show the accumulation of mRNA for GA 20-oxidase1 in transgenic plants that overexpress the potato knox gene, POTH1.
Figure 7B:

Overexpression lines were deficient in bioactive GAs, but were responsive to the exogenous application of $GA_3$. This indicates that GA biosynthesis is inhibited in the overexpression lines. In addition, accumulation of $GA_{53}$ and $GA_{19}$, with a decrease in $GA_{20}$, $GA_1$, and $GA_8$ (FIG. 6), indicates that the activity of the biosynthetic gene, GA 20-oxidase, may be suppressed. GA 20-oxidase catalyzes the oxidation of carbon 20 of $GA_{53}$ to $GA_{44}$ to $GA_{19}$ to $GA_{20}$. The enzyme GA 3-oxidase then converts $GA_{20}$ to the active $GA_1$ (Hedden et al., "Gibberellin Biosynthesis: Enzymes, Genes and Their Regulation," *Annu. Rev. Plant Physiol. Plant Mol. Biol.* 48:431-460 (1997), which is hereby incorporated by reference in its entirety). To determine whether POTH1 overexpression causes a change in GA 20-oxidase mRNA levels, RNA blot analysis was performed using one of the potato genes encoding GA 20-oxidase, StGA20ox1, as a probe (Carrera et al., "Feedback Control and Diurnal Regulation of Gibberellin 20-oxidase Transcript Levels in Potato," *Plant Physiol.* 119:765-773 (1999), which is hereby incorporated by reference in its entirety). In the overexpression lines, StGA20ox1 mRNA levels were reduced substantially compared to levels in wild-type lines (FIG. 7).

GA is involved in regulating cell growth in a tuberizing stolon (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety) and in contributing to the control of the photoperiodic response of tuber formation (Martinez-Garcia et al., "The Interaction of Gibberellins and Photoperiod in the Control of Potato Tuberization," *J. Plant Growth Regul.* 20:377-386 (2001), which is hereby incorporated by reference in its entirety). Because levels of active GAs were reduced in transgenic plants, an in vitro tuberization assay (Konstantinova et al., "Photoperiodic Control of Tuber Formation in Potato *Solanum Tuberosum* ssp. *Andigena* in vivo and in vitro," *Russian J. Plant Physiol.* 46:763-766 (1999), which is hereby incorporated by reference in its entirety) was used to determine the effect of POTH1 overexpression on tuberization. After 2 weeks under a 16 hour light/8 hour dark photoperiod to induce rooting, plants were cultured on 6% (w/v) sucrose under either an 8 hour light/16 hour dark (inductive) or 16 hour light/8 hour dark (noninductive) photoperiod. After 10 days, the overexpression lines had 60 to 82% and 19 to 68% tuber activity under short and long days, respectively, compared to 0% activity for wild-type plants (Table 1).

TABLE 1

In vitro tuberization of POTH1 overexpression lines. *S. tuberosum* spp. *andigena* transgenics were placed on Murashige-Skoog media supplemented with 6% sucrose under either short-day (SD) or long-day (LD) conditions. At least 12 plants per line were monitored for total number of tubers that formed and tuber activity (percentage of plants that produced either swollen stolons or tubers). Numbers in parentheses are the average number of tubers produced per plant.

| | # tubers (tubers/plant) | | % tuber activity | | |
|---|---|---|---|---|---|
| line | 14d SD | 14d LD | line | 10d SD | 10d LD |
| control | 1(.08) | 1(.06) | control | 0 | 0 |
| 1200-29 | 21(1.4) | 14(.88) | 1200-29 | 60 | 40 |
| 1200-11 | 13(.72) | 22(1.2) | 1200-11 | 78 | 68 |
| 1200-15 | 17(1.5) | 2(.12) | 1200-15 | 82 | 19 |
| 1200-18 | 12(.86) | 8(.57) | 1200-18 | 79 | 43 |

TABLE 1-continued

In vitro tuberization of POTH1 overexpression lines. *S. tuberosum* spp. *andigena* transgenics were placed on Murashige-Skoog media supplemented with 6% sucrose under either short-day (SD) or long-day (LD) conditions. At least 12 plants per line were monitored for total number of tubers that formed and tuber activity (percentage of plants that produced either swollen stolons or tubers). Numbers in parentheses are the average number of tubers produced per plant.

| line | 21d SD | 21d LD |
|---|---|---|
| control | (0.66) | (0.43) |
| 1200-29 | (1.70) | (1.25) |
| 1200-11 | (0.88) | (1.30) |
| 1200-15 | (2.30) | (0.38) |
| 1200-18 | (1.50) | (0.86) |

Tuber activity was calculated as the percentage of plants that formed either a swollen stolon or a tuber. At 14 days, overexpression lines produced an average of 0.7 to 1.5 tubers per plant under short days, whereas wild-type plants produced an average of 0.08 tubers per plant (Table 1). Similar results were observed under long days and after 21 days in culture (Table 1). Overall, the POTH1 overexpression lines could produce more tubers in less time than controls and apparently, also overcome the negative effects of a long-day photoperiod on tuber formation. The potato cv FL-1607 overexpression lines also exhibited increased tuber activity under both photoperiods.

Example 15—Discussion: POTH1 has a Widespread mRNA Expression Pattern

Isolated from an early stage tuber cDNA library, POTH1 is a homeobox gene belonging to the knox gene family. It contains the conserved homeodomain, ELK, and MEINOX domains. The homeodomain contains the invariant residues, PYP, between helices 1 and 2, making it a member of the TALE superclass. Because of its close sequence match with the KN1 homeodomain, POTH1 is classified as a knox class I homeobox gene.

Even though POTH1 is classified as a class I knox gene, it has a more widespread mRNA expression pattern than other class I genes. POTH1 is expressed in actively growing organs, but not in mature leaves or tubers. Unlike the mRNA expression pattern of kn1 which is limited to corpus cells of the apical meristem (Jackson et al., "Expression of Maize KNOTTED1 Related Homeobox Genes in the Shoot Apical Meristem Predicts Patterns of Morphogenesis in the Vegetative Shoot," *Development* 120:405-413 (1994), which is hereby incorporated by reference in its entirety), in situ hybridization showed that POTH1 mRNA accumulates in the meristematic and indeterminate cells of the SAM, determinate leaf primordia, the expanding lamina of new leaves, and developing leaflets of older leaves. The expression pattern of POTH1 mRNA in the unswollen stolon is similar to that seen in the shoot apical meristem. Signal was highest in undetermined, meristematic cells, but was also detected in the lamina of young leaves and the vascular tissue of the stem. Once tuberization has been initiated, the signal becomes less intense at the stolon apex, but is present in the vascular tissue in the subapical portion of the stolon. At this stage of tuberization, elongation of the meristem has stopped, and rapid, radial expansion occurs in the subapical region (Reeve et al., "Anatomy and Compositional Variation Within Potatoes I. Developmental Histology of the Tuber,"

Amer. Pot. J. 46:361-373 (1969), which is hereby incorporated by reference in its entirety).

Most class I knox genes have a more limited pattern of mRNA expression, restricted to undifferentiated cells of the meristem (Reiser et al., "Knots in the Family Tree: Evolutionary Relationships and Functions of Knox Homeobox Genes," *Plant Mol. Biol.* 42:151-166 (2000), which is hereby incorporated by reference in its entirety). Members of the tobacco knox family have distinct expression patterns within the SAM. NTH15 and NTH1 are expressed throughout the corpus, NTH20 is expressed in the peripherary zone, and NTH9 is expressed in the rib zone of the SAM (Nishimura et al., "The Expression of Tobacco Knotted1-type Class1 Homeobox Genes Correspond to Regions Predicted by the Cytohistological Zonation Model," *Plant J.* 18: 337-347 (1999), which is hereby incorporated by reference in its entirety). The tomato knox class I genes, TKn1 and TKn2/LeT6, have a expression pattern similar to POTH1 with transcripts detectable in meristematic and differentiated cells. Expression of TKn2/LeT6 was detected in the corpus of the meristem, developing leaf primordia, leaflet primordia and margins, and the vascular cells of the leaf (Chen et al., "A Gene Fusion at a Homeobox Locus: Alterations in Leaf Shape and Implications for Morphological Evolution," *Plant Cell* 9:1289-1304 (1997); Janssen et al., "Overexpression of a Homeobox Gene, LeT6, Reveals Indeterminate Features in the Tomato Compound Leaf," *Plant Physiol.* 117: 771-786 (1998), which are hereby incorporated by reference in their entirety). This expanded expression pattern in tomato has been attributed to the differences in compound leaf development compared to simple leaf development and the expansion of undifferentiated tissues to include developing leaflets. Potato is unique because it forms compound leaves from the vegetative shoot apical meristem above ground, but forms simple, scale leaves from the stolon meristem below ground (Sussex, "Morphogenesis in *Solanum Tuberosum* L.: Apical Structure and Developmental Pattern of the Juvenile Shoot," *Phytomorphology* 5:253-273 (1955), which is hereby incorporated by reference in its entirety). Expression of POTH1 is detected in young leaves that arise from both the shoot apical and stolon meristems. This indicates that POTH1 mRNA expression alone is not the determining factor for the development of compound leaves in potato. In the shoot or stolon meristem, the activity of POTH1 may be regulated differently through interaction with partner proteins specific for shoot or stolon meristem development.

Example 16—Discussion: Phenotype of POTH1 Overexpression Transgenic Lines

Overexpression of POTH1 resulted in altered leaf morphology, dwarfism, and increased rates of in vitro tuberization. Leaves were small, wrinkled, and curved. Both severe and intermediate phenotypes were characterized by a 'mouse-ear' leaf phenotype. Leaves were heart-shaped with a decreased midvein and palmate venation. The petioles were reduced in length resulting in leaves clustering closer to the stems. Overexpression lines exhibited dwarfism as a result of reduced internode length. The severity of the phenotype was correlated with the greatest levels of POTH1 sense transcript accumulation. Cross-sections of leaves revealed that the mesophyll cell organization was disrupted with the palisade parenchyma layer missing in POTH1 overexpression lines. The tightly packed cells were about half the size of the wild-type cells. A similar disruption in leaf parenchyma cell layers was observed in sense mutants of KNAT1 and KNAT2 (Chuck et al., "KNAT1 Induces Lobed Leaves With Ectopic Meristems When Overexpressed in *Arabidopsis*," *Plant Cell* 8:1277-1289 (1996); Frugis et al., "Overexpression of KNAT1 in Lettuce Shifts Leaf Determinate Growth to a Shoot-like Indeterminate Growth Associated With an Accumulation of Isopentenyl-type Cytokinins," *Plant Physiol.* 126:1370-1380 (2001); Pautot et al., "KNAT2: Evidence for a Link Between Kknotted-like Genes and Carpel Development," *Plant Cell* 13:1719-1734 (2001), which are hereby incorporated by reference in their entirety). Because class I knox genes are implicated in maintaining the undifferentiated state of cells (Chan et al., "Homeoboxes in Plant Development," *Biochim. Biophys. Acta* 1442:1-19 (1998), which is hereby incorporated by reference in its entirety), disruption in leaf architecture is likely a result of a defect in the normal differentiation program.

Based on overexpression phenotypes, POTH1 and NTH22 of tobacco (Nishimura et al., "Over-Expression of Tobacco Knotted1-type Class1 Homeobox Genes Alter Various Leaf Morphology," *Plant Cell Physiol.* 41:583-590 (2000), which is hereby incorporated by reference in its entirety) appear to have similar functions that overlap, but are distinct from, the class I knox genes, kn1, NTH15, OSH1, and KNAT1. Like overexpression of POTH1 in potato and NTH22 in tobacco, overexpression of kn1, NTH15, OSH1, KNAT1 in tobacco or *Arabidopsis* (Sinha et al., "Overexpression of the Maize Homeo Box Gene, KNOTTED-1, Causes a Switch From Determinate to Indeterminate Cell Fates," *Genes Dev.* 7:787-795 (1993); Sato et al., "Abnormal Cell Divisions in Leaf Primordia Caused by the Expression of the Rice Homeobox Gene OSH1 Lead to Altered Morphology of Leaves in Transgenic Tobacco," *Mol. Gen. Genet.* 251:13-22 (1996); Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997); Chuck et al., "KNAT1 Induces Lobed Leaves With Ectopic Meristems When Overexpressed in *Arabidopsis*," *Plant Cell* 8:1277-1289 (1996); Lincoln et al., "A Knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994), which are hereby incorporated by reference in their entirety) resulted in dwarfism, decreased internode elongation, shortened petioles, and small deformed leaves. Additional phenotypes, including ectopic meristem formation, loss of apical dominance, and delayed senescence, however, were not observed in POTH1 or NTH22 overexpression transgenic lines. Whereas there seems to be some redundancy in function between different members of the knox gene family, (for example, regulation of GA biosynthesis), POTH1 is not likely to have an identical function to kn1, NTH15, or OSH1. Rather, these genes are likely to have different subsets of target genes, which is reflected in their differences in homeodomain sequence (83 to 86% match to POTH1's homeodomain, compared to a 98% match for NTH22).

Example 17—Discussion: Ectopic Expression of POTH1 Results in GA Deficiency

Similar to the knox genes NTH15 of tobacco and OSH1 of rice, the results above indicate that POTH1 is a negative regulator of GA biosynthesis. POTH1 overexpression transgenic lines share many phenotypes with GA-deficient mutants including dwarfism, decreased internode elongation, and darker leaf coloration (van den Berg et al., "Morphology and [$^{14}$C]Gibberellin A$_{12}$ Metabolism in Wild-Type and Dwarf *Solanum Tuberosum* ssp. *Andigena* Grown Under Long and Short Photoperiods," *J. Plant Physiol.* 146:467-473 (1995), which is hereby incorporated by reference in its entirety). Exogenous application of GA$_3$ partially rescued the aberrant leaf phenotype indicating that overexpression lines were responsive to GA. Levels of the bioactive GA, GA$_1$, were reduced in overexpression lines, whereas intermediates prior to GA$_{20}$ in the pathway accumulated. Additionally, the mRNA levels of a key GA biosynthetic enzyme, GA 20-oxidase1, were reduced in overexpression lines. When NTH15 and OSH1 were overexpressed in tobacco, the levels of the hormones, auxin, cytokinin, abscisic acid, and GA were altered. GA$_1$ levels were reduced to 1.4% and 0.4-3.5% of controls in intermediate 35S-NTH15 and severe or mild 35S-OSH1 transgenics, respectively (Kusaba et al., "Alteration of Hormone Levels in Transgenic Tobacco Plants Overexpressing the Rice Homeobox Gene OSH1," *Plant Physiol.* 116:471-476 (1998); Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997), which are hereby incorporated by reference in their entirety). In tobacco, NTH15 affects plant growth by negatively regulating GA levels by suppressing the transcription of the tobacco GA 20-oxidase gene through a direct interaction with regulatory elements (Sakamoto et al., "KNOX Homeodomain Protein Directly Suppresses the Expression of a Gibberellin Biosynthetic Gene in the Tobacco Shoot Apical Meristem," *Genes Dev.* 15:581-590 (2001), which is hereby incorporated by reference in its entirety).

POTH1 overexpression lines exhibited an increase in both the rate of tuberization and the total number of tubers formed under both short- and long-day photoperiods. These sense lines appear to have the capacity to overcome the negative effects of a long-day photoperiod on tuberization in vitro. Enhanced tuberization can be partially attributed to the decrease in GA$_1$ levels caused by POTH1 suppression of GA 20-oxidase1. Pytochrome B (PHYB) and GAs are involved in inhibiting tuberization under long-day photoperiods. A long-day photoperiod is sensed by the leaves and an inhibitory signal mediated by PHYB is transmitted from the leaves to the stolons to inhibit tuberization (Jackson, "Multiple Signaling Pathways Control Tuber Induction in Potato," *Plant Physiol.* 119:1-8 (1999), which is hereby incorporated by reference in its entirety). GA activity is regulated by light, decreasing under short-day photoperiods (Railton et al., "Effects of Daylength on Endogenous Gibberellins in Leaves of *Solanum Andigena* I. Changes in Levels of Free Acidic Gibberellin-like Substances," *Physiol. Plant.* 28:88-94 (1973), which is hereby incorporated by reference in its entirety) and is involved in the photoperiodic control of stolon growth. High levels of GA in the stolon tip favor elongation of stolon meristems, whereas decreasing levels are required for initiation of tuberization (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety). GA 20-oxidase is a key enzyme in the GA biosynthetic pathway. In potato, the GA 20-oxidase genes are regulated by GA$_1$ feedback inhibition, blue light, and PHYB (Jackson et al., "Regulation of Transcript Levels of a Potato Gibberellin 20-Oxidase Gene by Light and Phytochrome B," *Plant Physiol.* 124:423-430 (2000), which is hereby incorporated by reference in its entirety). Whereas PHYB antisense plants were able to form tubers under both long- and short-day photoperiods (Jackson et al., "Phytochrome B Mediates the Photoperiodic Control of Tuber Formation in Potato," *Plant J.* 9:159-166 (1996), which is hereby incorporated by reference in its entirety), transgenic antisense *andigena* plants with suppressed levels of GA 20-oxidase1 (StGA20ox1) were not able to overcome the negative effects of photoperiod on tuberization in soil-grown plants (Carrera et al., "Changes in GA 20-oxidase Gene Expression Strongly Affect Stem Length, Tuber Induction and Tuber Yield of Potato Plants," *Plant J.* 22:1-10 (2000), which is hereby incorporated by reference in its entirety). While the experiments described above involved an in vitro assay rather than soil grown plants, Konstantinova et al., "Photoperiodic Control of Tuber Formation in Potato *Solanum Tuberosum* ssp. *Andigena* in vivo and in vitro," *Russian J. Plant Physiol.* 46:763-766 (1999), which is hereby incorporated by reference in its entirety, demonstrated that an in vitro assay for tuber formation is a reliable method for ascertaining the effect of photoperiod on tuberization in a photoperiod responsive cultivar. While it is possible that GA levels are not reduced sufficiently in antisense GA 20-oxidase1 plants, an additional signal may be involved in the long-day-photoperiod inhibition of tuberization. This indicates that in addition to reducing GA levels, POTH1 overexpression may enhance tuberization under long days by overcoming the effects of other negative regulators.

Example 18—Discussion: Regulation of POTH1 Activity During Development

Overexpression of POTH1 potentially regulates development in the SAM and in underground stolons through a reduction in bioactive GA levels in vegetative meristems. Whereas GA levels are high in the elongating unswollen stolon and decrease in swollen stolons (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety), POTH1 mRNA accumulates in both unswollen and swollen stolons. If POTH1 is a negative regulator of GA synthesis, how can its expression mediate a decrease in GA levels in the swollen stolon leading to tuberization, but not in the elongating unswollen stolon tip? With other TFs, an interaction with a partner protein can regulate development by affecting the binding of the homeodomain(s) to the DNA of a target gene. In *Antirrhinum*, for example, formation of a ternary complex consisting of the MADS box proteins, SQUA, DEF, and GLO, greatly increases DNA binding compared to SQUA homodimers or DEF/GLO heterodimers alone (Egea-Cortines et al., "Ternary Complex Formation Between the MADS-box Proteins SQUAMOSA, DEFICIENS and GLOBOSA is Involved in the Control of Floral Architecture in *Antirrhinum majus*," *EMBO J.* 18:5370-5379 (1999), which is hereby incorporated by reference in its entirety). The interaction of HOX proteins with PBC proteins in animals modulates the affinity of the HOX proteins for specific DNA binding sites (Chang et al., "Meis Proteins are Major in vivo DNA Binding Partners for Wild-Type but not Chimeric Pbx Proteins," *Mol. Cell. Biol.* 17:5679-5687 (1997), which is hereby incorporated by reference in its entirety). HOX homodimers have different DNA binding sites than HOX-PBC heterodimers (Mann et al., "Extra Specificity From Extradenticle: the Partnership Between HOX and PBX/EXD Homeodomain Proteins," *Trends Genet.* 12:258-262 (1996), which is hereby incorporated by reference in its entirety) indicating that the target gene (and function) is dependent on protein-protein interactions. Additionally, HOX-PBC complexes can be activators or repressors of transcription depending on the cell-type and the presence of a third interacting partner (Saleh et al., "Cell Signaling Switches HOX-PBX Complexes From Repressors to Activators of Transcription Mediated by Histone Deacetylases and Histone Acetyltransferases," *Mol. Cell. Biol.* 20:8623-8633 (2000), which is hereby incorporated by reference in its entirety). With the formation of different combinations of heterodimers and ternary complexes, the potential to regulate growth by interacting with different target genes is greatly increased.

It is clear that the interaction of KNOX proteins with other proteins is an important mechanism for regulating development. Protein-protein interactions between BEL-type TFs and KNOX proteins have been reported in barley (Müller et al., "In vitro Interactions Between Barley TALE Homeodomain Proteins Suggest a Role for Protein-protein Associations in the Regulation of Knox Gene Function," *Plant J.* 27:13-23 (2001), which is hereby incorporated by reference in its entirety) and *Arabidopsis* (Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety). Homodimerization of KNOX proteins of barley (Müller et al., "In vitro Interactions Between Barley TALE Homeodomain Proteins Suggest a Role for Protein-protein Associations in the Regulation of Knox Gene Function," *Plant J.* 27:13-23 (2001), which is hereby incorporated by reference in its entirety) and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety) has also been demonstrated. Sakamoto et al., "The Conserved KNOX Domain Mediates Specificity of Tobacco KNOTTED1-type Homeodomain Proteins," *Plant Cell* 11:1419-1431 (1999), which is hereby incorporated by reference in its entirety, showed by expressing chimeric proteins in transgenic tobacco plants that the region of the MEINOX domain (designated KNOX2) involved in protein interaction was more important than the homeodomain in determining the severity of the mutant phenotype. By using a yeast two-hybrid library screen, as described in Examples 20-32, below, seven unique proteins were isolated from potato stolons that interact with POTH1. These seven proteins are homeobox genes of the BEL1-like family and members of the TALE superclass. Whereas POTH1 has a widespread mRNA expression pattern, the seven potato BELs have a differential pattern of expression. It is possible that POTH1 interacts with one BEL protein to negatively regulate GA levels in the tuberizing stolon, but interacts with a different BEL partner in the elongating stolon or SAM. Overexpression of one of the POTH1-interacting proteins, StBEL-05, enhances tuberization under both long- and short-day photoperiods; but unlike POTH1 overexpression, leaf morphology is not altered (see below). In a tandem complex with a specific BEL partner, POTH1 could activate transcription of a set of target genes in one organ or set of cells and with another partner suppress those same genes in a different organ.

Figure 8:
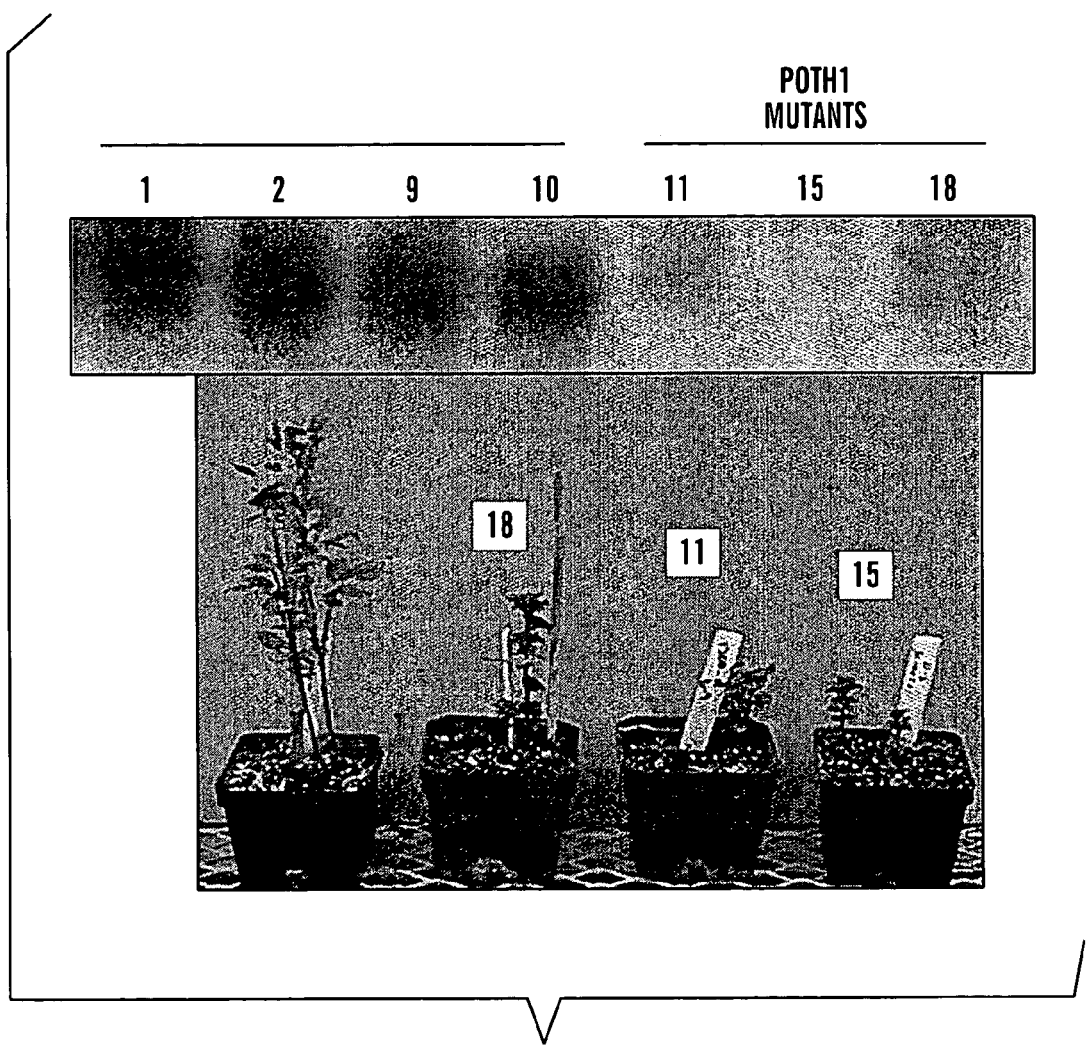
FIG. 8 shows GA 20-oxidase1 mRNA accumulation in shoot tips of POTH1 overexpressers (plants #11, 15, and 18) with a severe phenotype (dwarf with small, curled leaves). Total RNA (10 µg in each lane) was hybridized to $^{32}$P-labeled GA 20-oxidase1 (Carrera et al., "Feedback Control and Diurnal Regulation of Gibberellin 20-oxidase Transcript Level in Potato," *Plant Physiol.* 119:765-773 (1999), which is hereby incorporated by reference) probe. Standard procedures for RNA blot hybridization were used. The plants shown are 8 weeks old. These same plants had reduced levels of $GA_{20}$ and $GA_1$ and increased levels of $GA_{53}$ and $GA_{19}$.

Example 19—Overexpression of POTH1 Negatively Regulates GA Levels and Affects Vegetative Morphology To further examine the function of POTH1, transformed potato plants (*Solanum tuberosum* spp. *andigena*) that overexpressed POTH1 mRNA were analyzed. For these experiments, the full-length cDNA sequence of POTH1 in a sense orientation driven by the CaMV-35S promoter in the binary vector, pCB201 (Xiang et al., "A Mini Binary Vector Series for Plant Transformation," *Plant Mol. Biol.* 40:711-718 (1999), which is hereby incorporated by reference in its entirety) was used. The accumulation of the POTH1 mRNA was tightly correlated with a change in phenotype. These overexpressing lines were characterized by distorted, smaller leaves, and dwarfism (FIG. 8). The mutant leaf traits are designated "mouse-ear" or "curled" phenotype as reported previously in other knox mutants (Parnis et al., "The Dominant Developmental Mutants of Tomato, Mouse-Ear and Curl, Are Associated with Distinct Modes of Abnormal Transcriptional regulation of a knotted Gene," *Plant Cell* 9:2143-2158 (1997); Tamaoki et al., "Ectopic Expression of a Tobacco Homeobox Gene, NTH15, Dramatically Alters Leaf Morphology and Hormone Levels in transgenic Tobacco," *Plant Cell Physiol.* 38:917-927 (1997), which are hereby incorporated by reference in their entirety). Application of $GA_3$ produced a partial reversal of the leaf phenotype and completely rescued the dwarf phenotype (see above).

Because of the similarity of this POTH1 phenotype to those reported in tobacco (Tanaka-Ueguchi et al., "Overexpression of a Tobacco Homeobox Gene, NTH15, Decreases the Expression of a Gibberellin Biosynthetic Gene Encoding GA 20-oxidase," *Plant J.* 15:391-400 (1998); Tamaoki et al., "Transgenic Tobacco Over-Expressing a Homeobox Gene Shows a Developmental Interaction Between Leaf Morphogenesis and Phyllotaxy," *Plant Cell Physiol.* 40:657-557 (1999), which are hereby incorporated by reference in their entirety), the effect of GA 20-oxidase mRNA accumulation in these POTH1 overexpressers was examined. GA 20-oxidase is a key biosynthetic enzyme in the GA pathway, catalyzing the conversion of $GA_{53}$ to $GA_{20}$ via $GA_{44}$ and $GA_{19}$ (Hedden et al., "Gibberellin Biosynthesis: Enzymes, Genes and Their Regulation," *Ann. Rev. Plant Physiol. Plant Mol. Biol.* 48:431-460 (1997), which is hereby incorporated by reference in its entirety). Using a probe for the potato GA 20-oxidase1 gene (Carrera et al., "Feedback Control and Diurnal Regulation of Gibberellin 20-oxidase Transcript Level in Potato," *Plant Physiol.* 119:765-773 (1999), which is hereby incorporated by reference in its entirety), a reduction in GA 20-oxidase1 mRNA in shoots of the most severe mutant phenotypes was observed (FIG. 8). Both internode length and overall plant height were reduced approximately threefold in these mutant plants relative to controls. In addition, in a biochemical analysis performed in collaboration with Dr. Peter Davies, Cornell University, the levels of $GA_{53}$ and $GA_{19}$ increased, whereas the levels of $GA_{20}$ and $GA_1$ decreased in shoot tips of these plants. These results indicate that POTH1 is a negative regulator of GA biosynthesis and that it plays a role in controlling vegetative pattern formation.

Example 20—Two-Hybrid Selection and Deletion Analysis

The Matchmaker two-hybrid system (Clontech, Calif.) was used for the yeast two-hybrid screen. Yeast transformation and plasmid rescue into DH5-α *E. coli* cells were according to the manufacturer's instructions. Full-length POTH1 was cloned into the pBridge (Clontech, Calif.) vector and used as bait to screen the potato (*S. tuberosum* 'Desireé') stolon cDNA library in pAD-GAL4-2.1 (Stratagene, Calif.). Positive interactions were confirmed by cotransforming yeast strain AH109 with each purified pAD plasmid and pBridge: POTH1 and plating on -leucine/-tryptophan (transformation control) and -leucine/-tryptophan/-histidine/-adenine (selection) nutrient medium. Induction of the AH109 reporter gene, lacZ, was measured with a yeast β-galactosidase assay kit (Pierce Chemicals). β-galactosidase activity (FIG. 9B) was determined from a known density of yeast cells and calculated as $1000 \times OD_{420}$/time of color reaction (minutes)×volume of yeast culture (ml)×$OD_{600}$.

The StBEL-05 deletion constructs were amplified by PCR, then cloned into the vector, pGAD, in-frame with the GAL4 activation domain. POTH1 deletion constructs were amplified by PCR, and cloned into pBridge (Clontech) in-frame with the GAL4 binding domain. Sequencing of selected cDNAs and constructs was performed at the Iowa State University DNA Facility. For deletion analysis, modified constructs of POTH1 were cloned into the pBridge vector for fusion with the DNA-binding domain of GAL4 (FIG. 10A). For StBEL-05, constructs were cloned into the pGAD vector for fusion with the activating domain of GAL4 (FIG. 10B). Deletion constructs were made from both the amino and carboxy termini. These mutants were then tested for interaction in the yeast two-hybrid system by cotransforming into yeast strain AH109 with the corresponding full-length partner (StBEL-05 in pGAL4 or POTH1 in pBridge). All constructs were sequenced to verify that they were in-frame. Positive interactions were verified for lacZ induction by using a β-galactosidase assay (Pierce Chemical Company). For POTH1, seven deletion constructs were tested (FIG. 10A). For the BEL TFs, a fusion construct of StBEL-05 (653 aa of StBEL-05 sequence) and nine deletion constructs were tested (FIG. 10B).

GenBank accession numbers for StBEL-05, -11, -13, -14, -22, -29, and -30 are AF406697, AF406698, AF406699, AF406700, AF406701, AF406702, AF406703, respectively.

Example 21—In Vitro Binding Assay

In vitro binding experiments were performed as described by Ni et al., "PIF3, a Phytochrome-Interacting Factor Necessary for Normal Photoinduced Signal Transduction, is a Novel Basic *Helix*-Loop-Helix Protein," *Cell* 95:657-667 (1998), which is hereby incorporated by reference in its entirety. The full-length sequence for POTH1 was cloned into a pET17b/GAD fusion cassette and transcribed under the control of the T7 promoter. The BEL cDNAs were cloned into pGEM11Z vectors and were transcribed under the control of the T7 promoter. $^{35}$S-methionine labeled bait and prey proteins were synthesized using the TnT in vitro transcription-translation kit (Promega) according to the manufacturer's protocols. Each 50 μl TnT reaction contained 2.0 μg of template plasmid DNA and 20 μmol (20 μCi) of labeled $^{35}$S-methionine. The POTH1:GAD/BEL complex was immunoprecipitated with anti-GAD antibodies (Santa Cruz Biotechnology, Calif.). The proteins from the pellet (one-half the fraction) and for the prey (one-fourth of the reaction volume) were resolved on a 10% SDS-PAGE gel and visualized by autoradiography.

Example 22—Hybridization Blot Analysis

Total RNA was extracted from various organs of *Solanum tuberosum* ssp. *andigena* plants grown under a long-day photoperiod by using TR1 REAGENT® according to the manufacturer's manual (Molecular Research Center, Inc., Cincinnati, Ohio). Swollen stolons (newly formed tubers) and tubers were harvested from short-day plants. For FIG. 11B, RNA was extracted from leaves and stolons that were harvested from the photoperiod-responsive species *Solanum tuberosum* ssp. *andigena* grown under a short-day photoperiod. Total RNA was size-fractionated via electrophoresis through a 1.4% agarose gel that contained 5.0 mM methylmercury hydroxide and transferred onto a MagnaGraph nylon membrane (Micron Separations Inc., Westboro, Mass.). Hybridization and washing conditions were the same as described by Kolomiets et al., "Lipoxygenase is Involved in the Control of Potato Tuber Development," *Plant Cell* 13:613-626 (2001), which his hereby incorporated by reference in its entirety. For autoradiography, membranes were exposed to X-ray film with intensifying screens for three to six days at −80° C. A 1.2 kb wheat 18S ribosomal RNA probe was used to confirm uniform loading of RNA for the blots in FIG. 11A. Blots presented are representative examples of at least two independent experiments.

Example 23—Plant Transformation

Transformation and regeneration of plants was undertaken on leaf sections from *Solanum tuberosum* ssp. *andigena* line 7540 as described by Liu et al., "Transformation of *Solanum brevidens* Using *Agrobacterium tumefaciens*," *Plant Cell Reports* 15:196-199 (1995), which is hereby incorporated by reference in its entirety. These autotetraploid *andigena* plants, strictly photoperiodic for tuberization, were obtained from the Institut für Pflanzenbau und Pflanzenzüchtung, Braunchsweig, Germany. The sense constructs were made from a 2.0 kb fragment from the StBEL-05 cDNA and cloned into the binary vector pCB201 (Xiang et al., "A Mini Binary Vector Series for Plant Transformation," *Plant Mol Biol* 40:711-718 (1999), which is hereby incorporated by reference in its entirety) driven by the constitutive CaMV-35S promoter. Constructs were checked by using PCR with clone-specific primers. Positive recombinants were transferred to the *Agrobacterium tumefaciens* strain GV2260 by using the procedure of direct transformation (An et al., *Binary vectors. in Plant Mol. Biol. Manual* pp. A3:1-19, Kluwer Academic, Belgium (1988), which is hereby incorporated by reference in its entirety). Control plants in the tuberization study were *andigena* plants regenerated in vitro. Functional transformants were identified by PCR analysis of genomic DNA and by detection of the accumulation of sense transcripts of StBEL-05 in shoot tip samples. From among these positives, the seven independent transformants (lines 7, 11, 12, 14, 16, 19, and 20 for StBEL-05) used in this study were selected on the basis of abundant accumulation of sense mRNA in shoot tips. Quantitative analysis of cytokinins was performed by using liquid chromatography as described above. Three replicate 200 mg (fresh wt) samples of shoot tips down to the fourth visible expanded leaf were collected, frozen in liquid nitrogen, lyophilized, and analyzed.

Example 24—Evaluation of Tuber Formation

For in vitro tuberization, cultured transgenic plants were grown on a Murashige and Skoog medium with 6.0% sucrose under a long-day photoperiod (16 hours of light, 8 hours of dark) in a growth chamber for two weeks and then transferred to a short-day photoperiod (8 hours of light, 16 hours of dark) in the same growth chamber. For tuber induction, plants were evaluated daily for tuber formation. Soil-grown plants were grown in 10-cm pots under long days (16 hours of light, 8 hours of dark) in the greenhouse supplemented with high pressure sodium HID lamps until they reached the 16-leaf stage and then transferred to short days in the growth chamber. After 14 days under short days, plants were evaluated for tuber formation.

Example 25—Results: Isolation of Potato KNOX Interactive Proteins

Figure 9A:
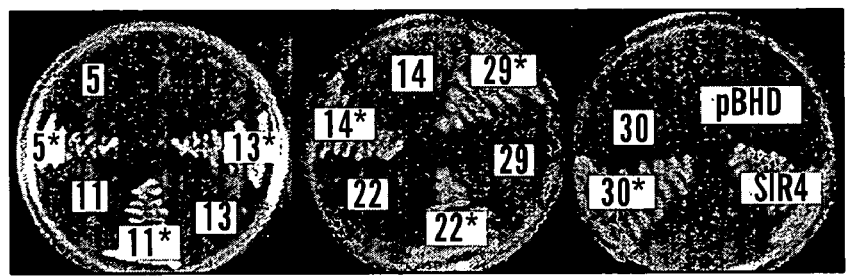
FIGS. 9A-C show the specific interaction of POTH1 with seven BEL1-like proteins of potato.
Figure 9B:
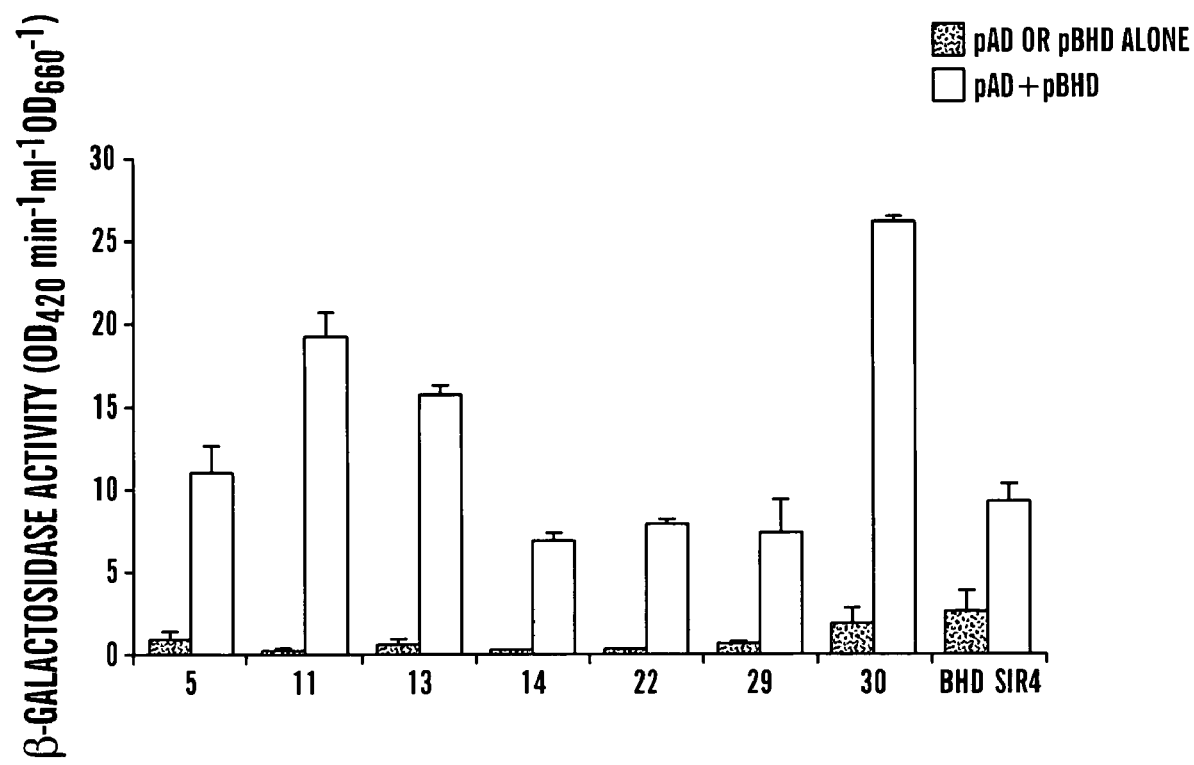
Figure 9C:
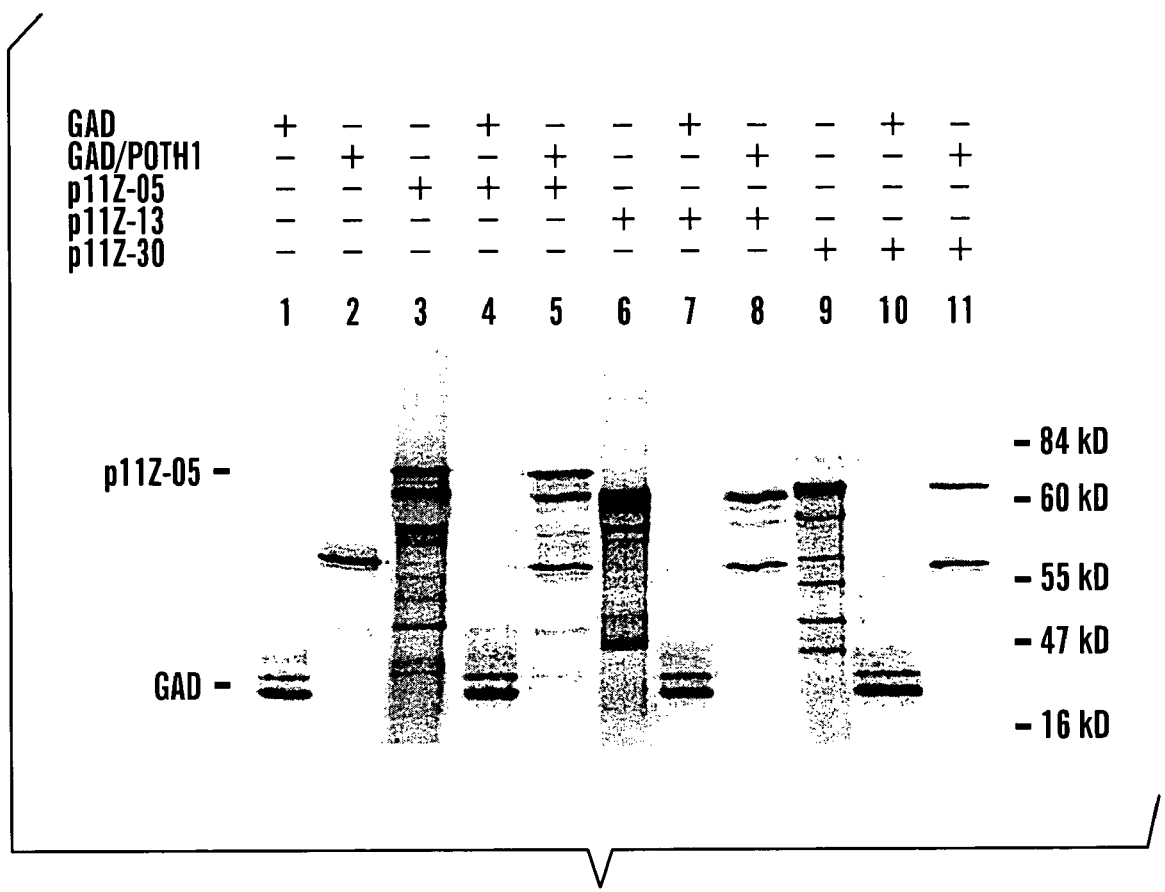

Making use of the two-hybrid selection system in yeast, approximately $10^6$ transformants from a stolon cDNA library of potato were screened using POTH1 in the GAL4-binding domain vector, pBridge (Clontech), as bait. Thirty-eight positive clones that grew on selective media were identified. Of the 38 that were sequenced, 23 clones could be grouped into seven unique genes encoding different members of the TALE superclass of transcription factors (Chan et al., "Homeoboxes in Plant Development," *Biochim Biophys Acta* 1442:1-19 (1998), which is hereby incorporated by reference in its entirety). All seven, designated StBEL-05, -11, -13, -14, -22, -29, and -30 (GenBank accession numbers AF406697, AF406698, AF406699, AF406700, AF406701, AF406702, AF406703, respectively) showed selective interaction when tested in the yeast system both for nutritional markers and for lacZ activation (FIGS. 9A and 9B). Interaction occurred also when the prey cDNAs were cloned into pBridge and transformed with POTH1 in a GAL4-activation domain vector. As a test for autoactivation, the pAD transformants (5, 11, 13, 14, 22, 29, 30) did not grow on -histidine, -adenine, and -leucine medium and the pBD transformant did not grow on -histidine, -tryptophan, and -adenine medium. In vitro binding experiments verified the results of the two-hybrid selection. POTH1 pulled down three representative StBEL proteins with divergent sequence similarity in the BELL domain (5, 13, and 30) and synthesized by in vitro transcription/translation in immunoprecipitation assays (FIG. 9C).

Figure 12:
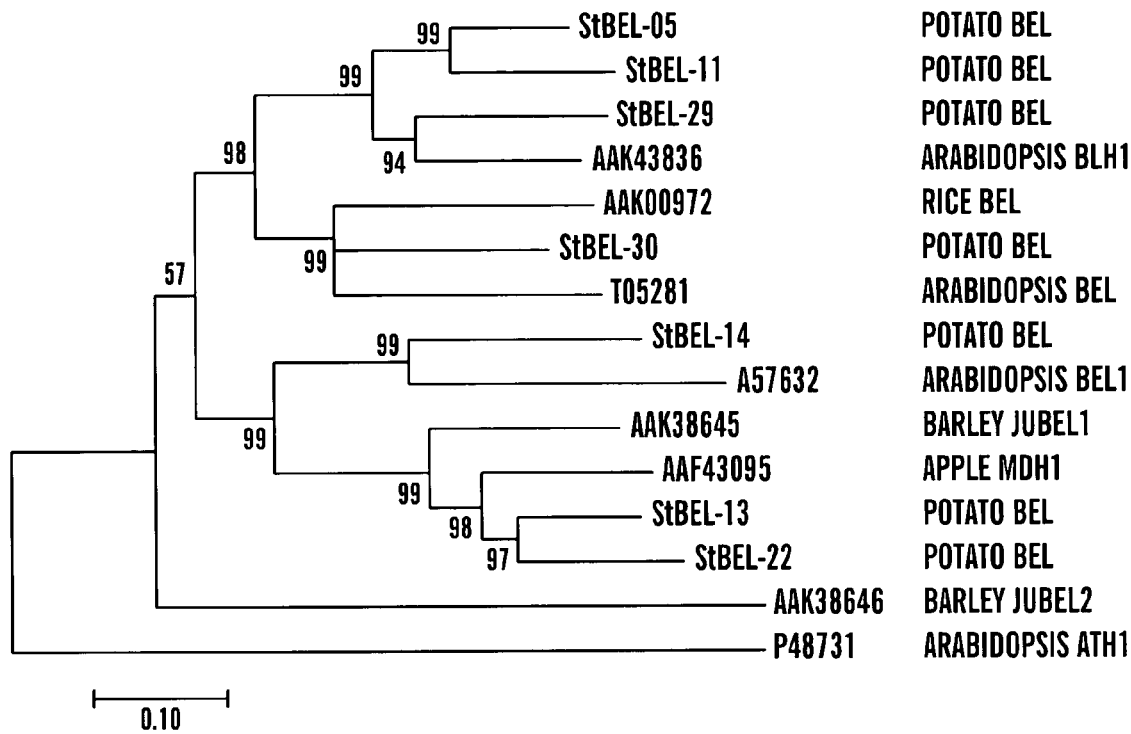
FIG. 12 shows the phylogenetic tree of the BEL1-like proteins of potato (*Solanum tuberosum* L.). The amino acid sequence of seven potato BEL-like proteins was analyzed and compared to BEL proteins of plants. These data were organized into a phylogenetic tree with the ME-Boot program of the MEGA package (version 1.0) and the neighbor-joining program (Saitou and Nei, 1987). The numbers listed at the branching points are boot-strapping values which indicate the level of significance (%) for the separation of two branches. The length of the branch line indicates the extent of difference according to the scale at the lower left-hand side. Databank accession numbers are listed on the dendrogram and the common name of the species is listed in the right-hand column.
Figure 13A:
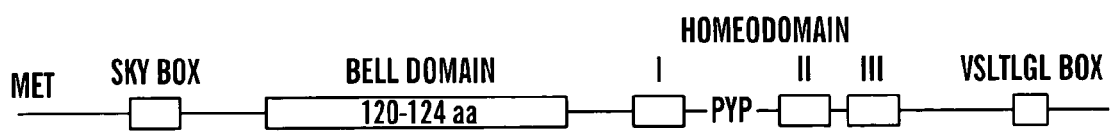
FIG. 13A shows a schematic of the amino acid sequence of the BEL1-like proteins of potato. Boxed regions represent conserved sequences identified by aligning all seven BELs. Helices I, II, and III of the homeodomain are designated. The proline-tyrosine-proline (PYP) loop extension is located between helices I and II. For clarity in labeling, the sequence is not drawn to scale.

Example 26—Results: The Proteins that Interact with the Potato KNOX Protein are Members of the BEL Family of Transcription Factors A phylogenetic analysis of the sequences of the seven interacting proteins identified them as members of the BEL1-like family of transcription factors (FIG. 12). These seven can be organized into four subgroups based on amino acid sequence similarity. Three clones (StBEL-05, -11, and -29) had 60-69% similarity to each other overall and two other clones had a 78% match (StBEL-13 and -22). These two groups range in similarity to the others from 45-53% and a third (StBEL-30) has about 51% similarity to the others. The sequence similarity of StBEL-14 to the other six ranged from 45 to 56%. The amino acid sequence of StBEL-05 has overall 56% similarity to BLH1 of *Arabidopsis* that interacts with KNAT1 (GenBank accession number AAK43836), StBEL-13 matches an apple BEL (Dong et al., "MDH1: an Apple Homeobox Gene Belonging to the BEL1 Family," *Plant Mol Biol* 42:623-633 (2000), which is hereby incorporated by reference in its entirety, GenBank accession number AAF43095) at 74% similarity, and StBEL-30 matches another *Arabidopsis* BEL (GenBank accession number T05281) at 59% similarity. The close match of all seven to the conserved homeodomain and the presence of the proline-tyrosine-proline (P-Y-P) loop between helices I and II (FIG. 13A) distinguish these novel proteins as BEL types in the TALE superclass (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). The homeodomain region is nearly identical among these seven (FIG. 13A, encompassing helices I, II, and III). Other regions of conserved sequence identity are shown schematically in FIG. 13A. These include the amino-terminal SKY box consisting of 20 aa (from ser-207 to lys-226 in StBEL-05), the 120-aa domain starting at leu-272 of the StBEL-05 sequence, and the carboxy-terminal VSLTLGL-box (SEQ ID NO:15) beginning at val-620. Three α-helices were predicted from the conserved 120-aa region of the BEL protein StBEL-05 (underlined sequence of FIG. 13B). Among the seven BELs, the percent similarity of the amino acid sequence in this conserved 120-aa domain ranged from 58 to 90%. Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by referenced in its entirety, referred to this region as the BELL domain.

Figure 13B:
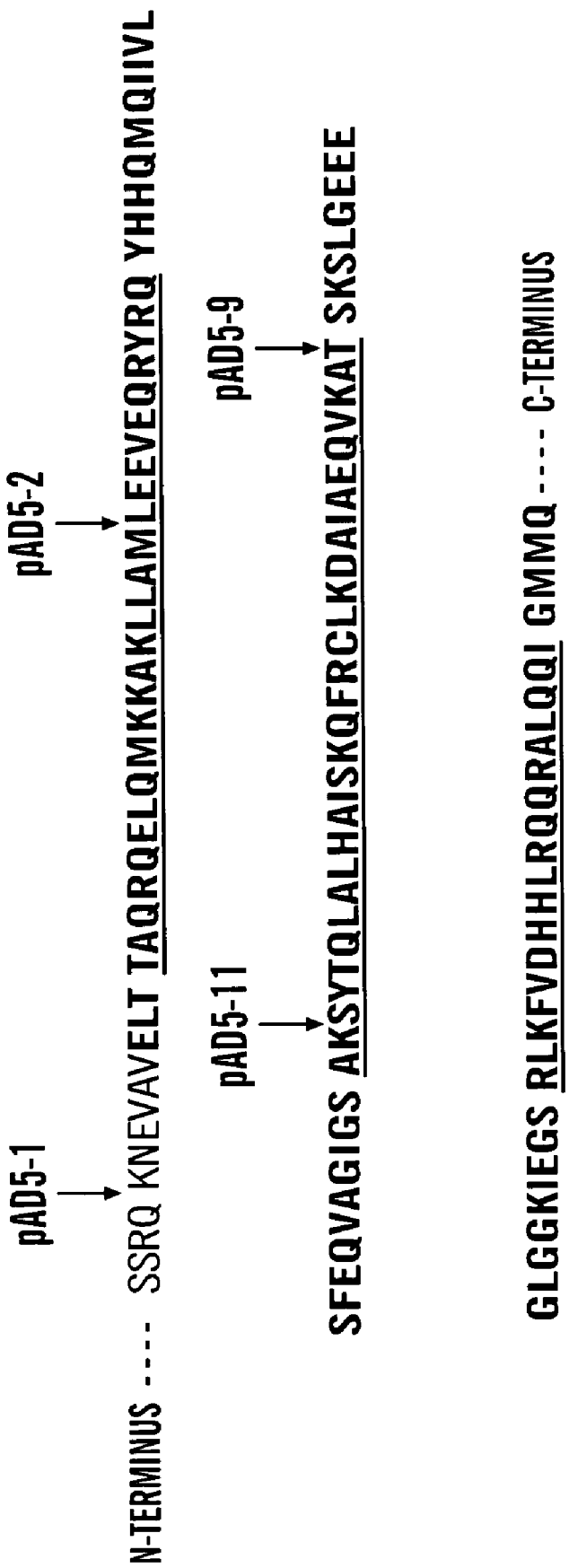
FIG. 13B shows predicted helices of the putative protein-binding region (BELL domain) of the BEL1 protein StBEL-05. The bold letters represent amino acids conserved in other plant BEL1 proteins based on a BLAST analysis of StBEL-05. The underlined portion of the sequence represents a predicted α-helix. A consensus for the prediction of the sequence structure was derived by using three software programs for amino acid sequence analysis: sspal, ssp, and nnssp. Four deletion constructs from FIG. 14B are designated with arrows. Construct pAD5-1 contains aa 230 through 653 of pAD-05 (interaction with POTH1), and pAD5-2 contains aa 257 through 653 of pAD-05 (no interaction). Construct pAD5-11 consists of aa 1 through 286 of pAD-05 (no interaction), and pAD5-9 consists of aa 1 through 315 (interaction with POTH1).
Figure 13C:
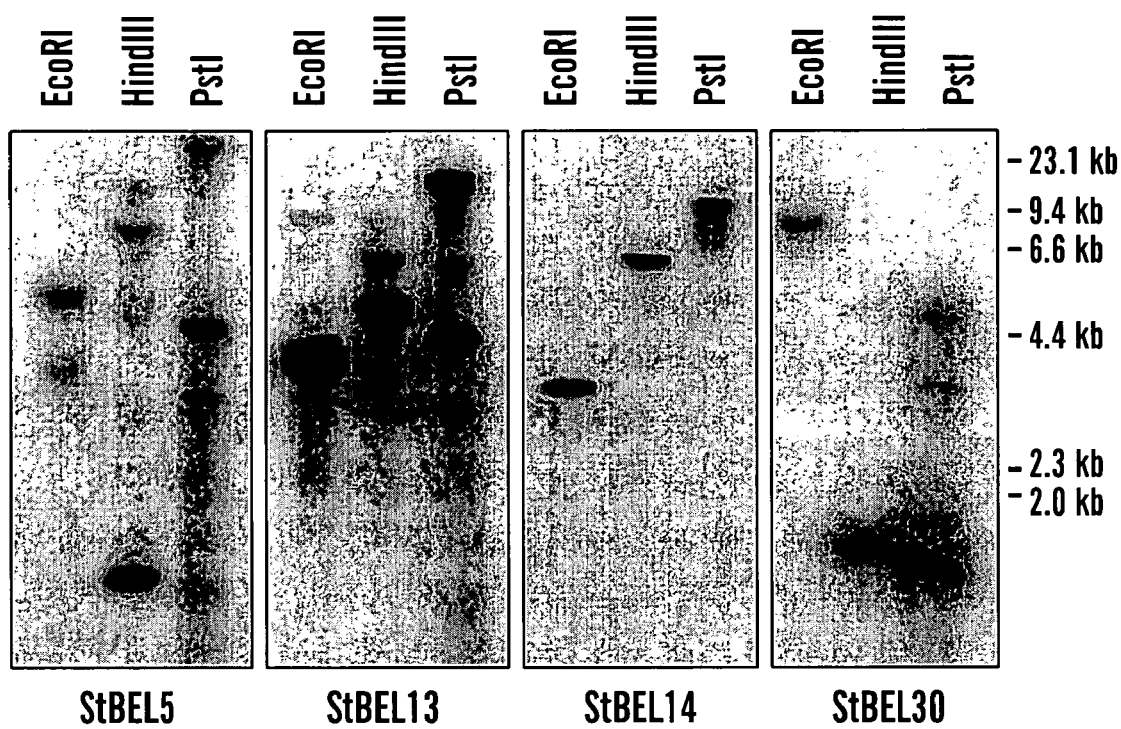
FIG. 13C is a Southern blot analysis of BEL-like genes of potato. Genomic DNA (10 μg per lane) was digested with EcoRI, HindIII, and PstI. Each blot was hybridized with a $^{32}$P-labeled gene-specific probe from each of the four StBEL cDNAs. DNA size markers in kilobases are indicated on the right.

The deduced lengths of the seven original cDNAs are 688 aa for StBEL-05, 535 aa for StBEL-11, 586 aa for StBEL-13, 589 aa for StBEL-14, 620 aa for StBEL-22, 567 aa for StBEL-29, and 645 aa for StBEL-30. Five-RACE was used to verify the full-length of StBEL-05, -13, -14 and -30. For blot hybridizations, a representative clone from each of the four subgroups (StBEL-05, -13, -14, and -30) was used. Southern blot analysis revealed that these genes are unique and belong to small gene subfamilies, based on the complexity of bands detected by gene-specific probes from each of the cDNAs (FIG. 13C).

Example 27—Results: Patterns of mRNA Accumulation for the Potato BELs

Figure 11A:
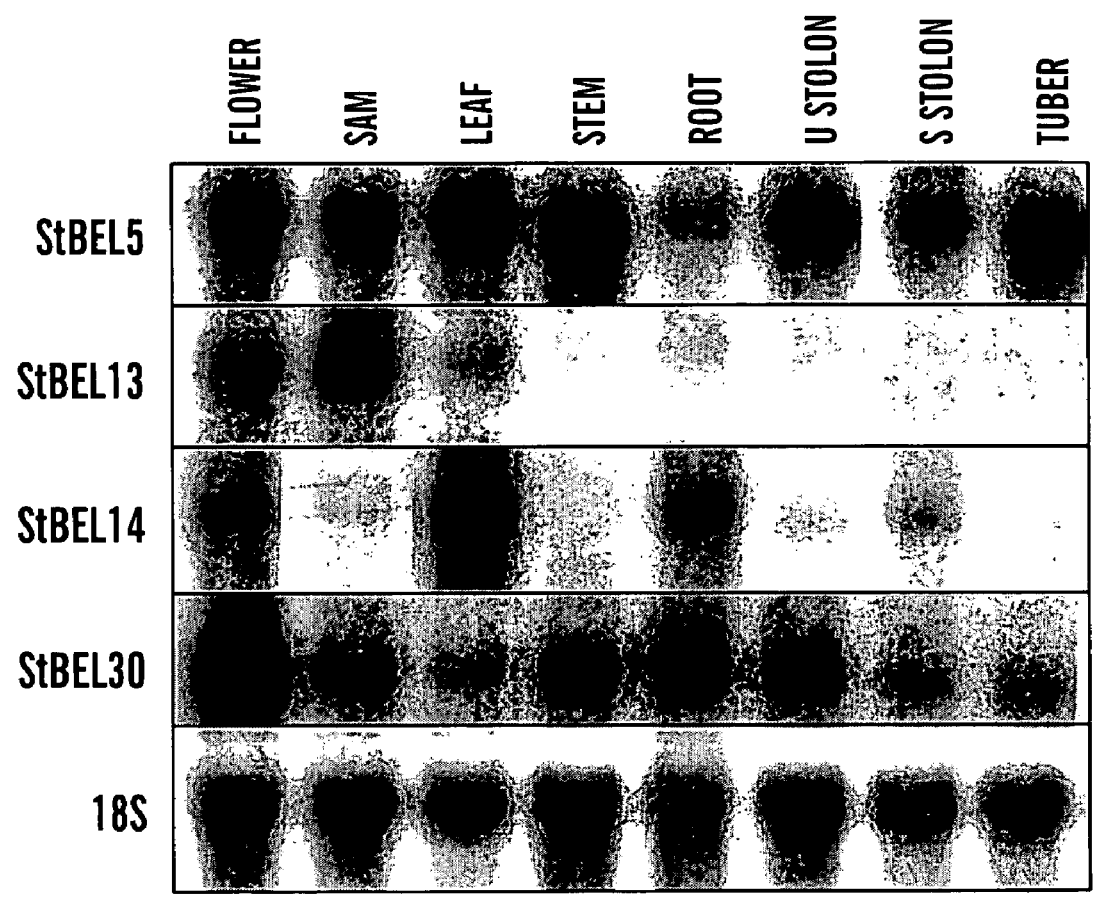
FIG. 11A shows a Northern blot analysis of the accumulation of mRNA for four BEL1-like cDNAs (StBEL-05, -13, -14, and -30) in potato organs. Ten µg of total RNA from flowers, shoot tips (SAM), leaves, stems, roots, unswollen stolons (U stolon), swollen stolons (S stolon), and tubers were loaded per lane. Swollen stolons represent an early stage of tuber formation. A probe for the 18S ribosomal RNA was used to verify equal loading of RNA samples (bottom panel).
Figure 11B:
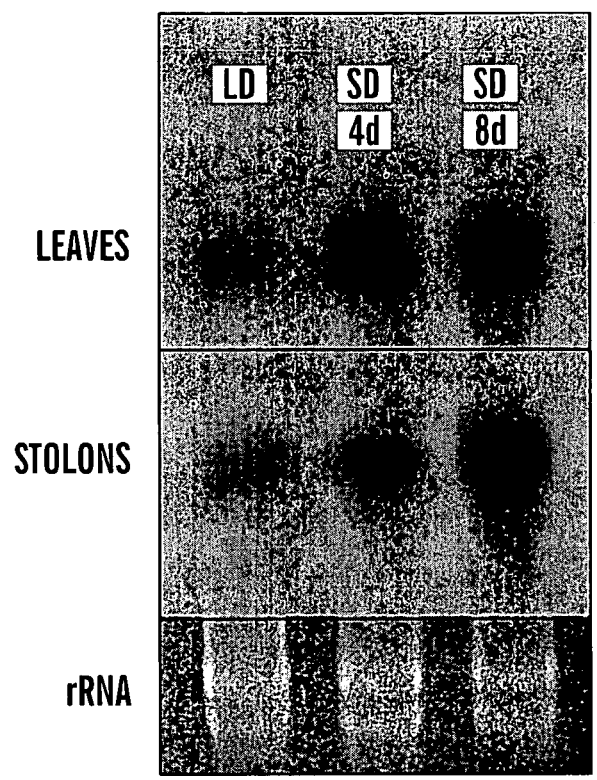
FIG. 11B shows a Northern blot analysis of the accumulation of the mRNA of StBEL-05 in leaves and stolons of WT plants grown under long days (LD, 16 hours of light, 8 hours of dark) and short days (SD, 8 hours of light, 16 hours of dark). Ten µg of total RNA from stolons were loaded per lane. Leaves and stolons were harvested from the photoperiod-responsive potato species, *Solanum tuberosum* ssp. *andigena*, 4 and 8 days after the plants were transferred to short-day conditions. Samples were harvested one hour after the end of the dark period. A gene-specific probe for each BEL cDNA was used. Ethidium bromide-stained ribosomal RNA is visualized as a loading control.
Figure 11C:
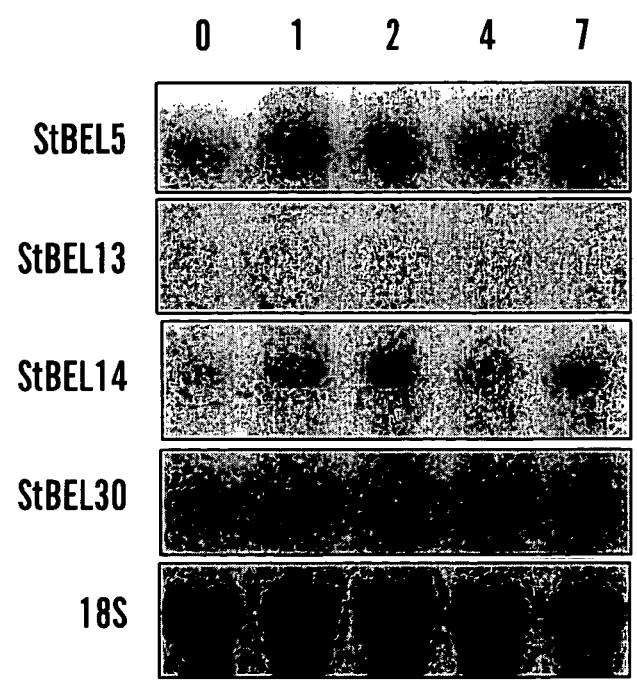
FIG. 11C shows a Northern blot analysis of the accumulation of the mRNA of potato BEL-like cDNAs (StBEL-05, StBEL-13, StBEL-14, and StBEL-30) in tuberizing stolons. Ten µg of total RNA from stolons were loaded per lane. Stolons were harvested from the photoperiod-responsive potato species, *Solanum demissum*, 1, 2, 4, or 7 days after the plants were transferred to short-day conditions. A gene-specific probe for each BEL cDNA was used. A probe for the 18S ribosomal RNA was used to verify equal loading of RNA samples (bottom panels).

The BEL1-like gene represented by StBEL-05 exhibited mRNA accumulation in all organs examined, with the greatest levels in leaves and stems (FIG. 11A). Transcript accumulation of StBEL-11 and StBEL-29 was similar to the pattern of StBEL-05. Transcripts for StBEL-13 accumulated to the highest levels in the SAM and in fully formed flowers but were barely detectable in other organs (FIG. 11A). The autoradiographs for StBEL-13 were exposed two-times longer than the other StBELs. For StBEL-14, transcripts were detected in flowers, leaves, roots, and stolons. The greatest accumulation of StBEL-30 was in flowers with detectable levels in all organs examined. To examine more closely the dynamics of StBEL expression during tuber induction, a temporal study was undertaken for the accumulation of StBEL-05 transcripts in leaves and stolons of the photoperiod-sensitive potato species *S. tuberosum* ssp. *andigena* grown under short-day conditions. Steady-state levels of StBEL-05 mRNA increased in both leaves and stolons after exposing the plants to short-day (SD) conditions (FIG. 11B). Visible tuber formation for the plants grown under SD conditions was observed between 10 to 14 days. In this study, the accumulation of mRNA for the BEL cDNA, StBEL-05, was linked to the induction of tuber formation in the leaves and stolons of a potato species responsive to a SD photoperiod. In addition, a temporal study was undertaken for the accumulation of BEL transcripts in stolons of the photoperiod-sensitive potato species *S. demissum* grown under short-day conditions. The induction of StBEL-05, StBEL-14, and StBEL-30 expression was first detected in stolons one day after exposing the plants to short-day (SD) conditions (FIG. 11C). This increase in RNA levels remained steady through 7 days. Transcripts for StBEL-13 were not detected in stolons in any stage of development (FIG. 11C). Visible tuber formation for the plants grown under SD conditions was observed between 10 to 14 days. In this study, the accumulation of mRNA for the BEL cDNAs, StBEL-05, StBEL-14, and StBEL-30 was linked to the induction of tuber formation in the stolons of a potato species responsive to a SD photoperiod.

Example 28—Results: Determining the Protein Binding Regions in POTH1 and the BEL-Like Proteins Interaction with StBEL-05 was observed with all deletions outside the KNOX domain, with pBHD2 (missing the amino-terminus and the first 48 aa of the KNOX domain, FIG. 10A), with pBHD6 (missing the carboxy terminus and 52 aa of the carboxy-end of the KNOX domain), and with pBHD-9 (first amino-terminal 114 aa but no KNOX domain sequence). No interaction was observed with pBHD3 (missing all of the KNOX domain and the first 114 aa). Control experiments identified the first 114 aa of the N-terminus (pBHD9) as a transcriptional activator. This construct transformed alone into AH109 exhibited nutrient selection on -histidine, -tryptophan, and -adenine medium. Co-transformation of pBHD9 with an empty pGAD cassette produced transformants capable of growth on -histidine, -tryptophan, -adenine, and -leucine medium and induction of lacZ. None of the other constructs containing this domain were capable of growing on selection media without StBEL-05. Using the in vitro binding protocol, both the pBHD6 construct, containing the amino-terminal half of the KNOX domain, and the pBHD9 construct were unable to pull-down StBEL-05. When the pBDH9 construct was cloned into the pGAD vector, no interaction was observed with StBEL-05 in pBridge.

Fusion constructs of StBEL-05 that dissected the 120-aa domain (pAD5-2, -3, -4, -9, and -11) were tested because this is one of the regions that is conserved in BEL TFs from other plant species (Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety; FIG. 13B). Interaction with POTH1 was observed with all constructs that had deletions exclusively outside of the conserved 120-aa box (FIG. 10B). The only exception to this was with pAD5-9 that demonstrated an interaction and included a 43-aa deletion from the carboxy end of the 120-aa domain. Even with as little as a 27-aa deletion from the amino end of the 120-aa domain, interaction did not occur (FIG. 13B, FIG. 10B, pAD5-2). Similar to the results of Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety, deletion of the SKY box (construct pAD5-1) resulted in a 55% decrease in the induction of the lacZ marker as measured by β-galactosidase activity relative to the full-length construct, StBEL-05 (FIG. 10B).

Example 29—Results: Enhanced Tuber Formation in Transgenic Plants that Overexpress the BEL cDNA, StBEL-05

Figures 14A, 14B, 14C:
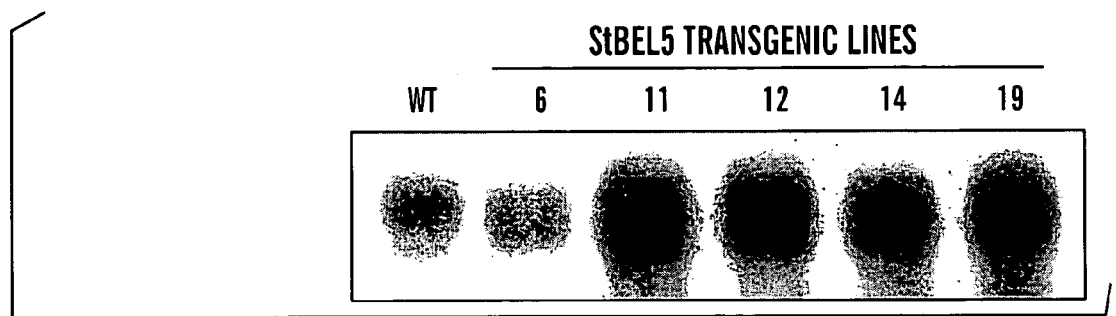
FIGS. 14A-C show in vitro tuberization of transgenic plants that overexpress sense transcripts of StBEL-05. Northern blot analysis for the accumulation of mRNA for StBEL-05 was performed by using 10 μg of total RNA/lane from vegetative meristems of in vitro plantlets and gene-specific probes for StBEL-05 (see FIG. 14A). Equal loading of RNA samples was verified by visualizing ethidium bromide-stained rRNA bands with UV light. The rate of tuberization (days to tuberize) was determined by the first appearance of tubers from among twenty-four replicates (see FIG. 14B). The number of tubers was scored after 2 weeks of LD conditions (0 d), and after 7 (7 d) and 14 days (14 d) of SD conditions (see FIG. 14B). Tubers were harvested and weighed after 21 days (see FIG. 14C) from the StBEL-05 overexpression (24 plants each) and wild-type lines (35 plants). Cultured transgenic plants of *Solanum tuberosum* ssp. *andigena* were grown on a Murashige and Skoog medium with 6% sucrose under a long-day photoperiod (16 hours of light, 8 hours of dark) in a growth chamber for two weeks. For tuber induction, plants were transferred to a Murashige and Skoog medium supplemented with 6% sucrose and evaluated daily for tuber formation under a short-day photoperiod (8 hours of light, 16 hours of dark) in the growth chamber until tubers formed. All numbered lines were verified as transgenic by using PCR with transgene-specific primers. Control plants were both nontransgenic (WT) and transgenic (StBEL-05 line 6).

To examine the function of the potato BELs, transformed potato plants (*Solanum tuberosum* ssp. *andigena*) that over expressed StBEL-05 from a constitutive promoter were analyzed. This BEL gene was selected because of its moderate level of activity in stolons and tubers and its increase in RNA levels in response to inductive conditions for tuber formation (FIG. 11). For these experiments, a 2000-bp fragment of the coding sequence of StBEL-05 in a sense orientation driven by the CaMV-35S promoter in the binary vector pCB201 (Xiang et al., "A Mini Binary Vector Series for Plant Transformation," *Plant Mol Biol* 40:711-718 (1999), which is hereby incorporated by reference in its entirety) was used. Transformants were identified by PCR analysis of genomic DNA and by detection of the accumulation of sense transcripts of StBEL-05 in RNA samples from vegetative meristems. From among approximately twenty-five positives, four independent lines with the highest levels of StBEL-05 mRNA accumulation (FIG. 14A) were selected for evaluation of tuber formation in vitro under both inductive (SD) and noninductive (LD) conditions. The highest expressers of StBEL-05 sense transcripts (lines 11, 12, 14, and 19) exhibited tuber formation under LD conditions (FIG. 14B). Control plants (WT and line 6) produced tubers only under SD conditions. The highest overexpressers of StBEL-05 also produced more tubers than control plants over the course of this experiment and were more responsive to inductive conditions. After seven days under SD conditions, the control plants had produced no tubers, whereas the overexpression mutants (lines 11, 12, 14, and 19) had produced 10, 8, 15, and 4 tubers, respectively (FIG. 14B). After 14 days under SD, controls had increased to 6 and 4 tubers, whereas the overexpression lines had increased to 12, 14, 24, and 10 tubers, respectively. Tuber yields (fr wt) also increased in overexpression lines 12, 14, and 19 (FIG. 14C). The greatest tuber production was exhibited by lines 12 and 14 with a five- and sixteenfold increase, respectively, relative to wild-type plants (FIG. 14B, bottom panel). Tubers from the overexpression lines grew larger than controls. Select tubers from line 14 reached fresh weights of almost 700 mg, whereas the largest control tuber reached only 140 mg.

With whole plants grown in soil under SD conditions for 14 days, StBEL-05 overexpression lines produced an average of three- to fivefold more tubers per plant and more than a threefold greater tuber yield per plant than controls (Table 2).

TABLE 2

Rate of tuberization for overexpression lines of StBEL-05 under soil-grown, short-day conditions. Plants were grown in 10-cm pots under long days (16 hours of light, 8 hours of dark) until they reached the 16-leaf stage and then transferred to short days (8 hours of light, 16 hours of dark). After 14 days under short days, four plants per independent line were evaluated for tuber formation. Standard errors of the mean are shown.

| Plant line | Number tubers plant$^{-1}$ | Tuber yield plant$^{-1}$ (g) |
| --- | --- | --- |
| Wild-type | 2.2 ± 1.4 | 1.4 ± 0.9 |
| StBEL5-12 | 8.0 ± 0.8 | 5.4 ± 1.3 |
| StBEL5-14 | 8.3 ± 0.9 | 4.6 ± 1.3 |
| StBEL5-19 | 11.5 ± 2.1 | 4.7 ± 1.4 |

Increased yields (as high as 50%) were maintained for these lines even after six weeks of growth in soil. Seven overexpressing sense lines (lines 7, 11, 12, 14, 16, 19, and 20) also exhibited tuber activity (swollen stolons or tuber formation) on soil-grown plants under LD greenhouse conditions. Five of these plants produced tubers, whereas control plants exhibited no tuber activity. In addition, the rate of tuberization for plants grown in vitro under short-day conditions for 21 days is shown in Table 3, below.

TABLE 3

Rate of tuberization for overexpression lines of StBEL-05. Plants were grown in vitro under short days in media with 6% sucrose for 21 days and scored for tuber formation. Twenty-five plants per independent line were evaluated, thirty-five for controls.

| Plant line | Number tubers plant$^{-1}$ | Tuber yield plant$^{-1}$ (mg) |
|---|---|---|
| Control | 0.4 | 18 |
| StBEL-05-12 | 0.9 | 95 |
| StBEL-05-14 | 1.3 | 292 |
| StBEL-05-19 | 0.9 | 50 |

Figure 15:
FIG. 15 shows overexpression mutant lines for the potato KNOX gene, POTH1 (lines 15 and 18), and for the BEL1-like protein, StBEL-05 (lines 12, 14, and 19). These StBEL-05 sense lines had a leaf phenotype similar to wild-type plants (WT). These are 8-week plants grown under long-day conditions (16 hours of light, 8 hours of dark) in the greenhouse supplemented with high pressure sodium HID lamps. The StBEL-05 plants ranged in height from 34 to 39 cm, whereas, the POTH1 lines were 7 to 10 cm in height.

Similar to POTH1 overexpressers (see above), these results show that the accumulation of StBEL-05 mRNA is correlated with an increased rate of tuber formation. Other than this enhanced capacity for tuberization, the StBEL-05 overexpression lines in Table 2 did not exhibit the phenotype characteristic of KNOX gene overexpressers, including extreme dwarfism and abnormal leaf morphology (FIG. 15). The abnormal phenotype of KNOX overexpressers is mediated by changes in hormone levels, specifically, a reduction in gibberellins and an increase in cytokinins (see above; Sato et al., "Abnormal Cell Divisions in Leaf Primordia Caused by the Expression of the Rice Homeobox Gene OSH1 Lead to Altered Morphology of Leaves in Transgenic Tobacco," *Mol Gen Genet* 251:13-22 (1996); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997); Frugis et al., "Overexpression of KNAT1 in Lettuce Shifts Leaf Determinate Growth to a Shoot-like Indeterminate Growth Associated With an Accumulation of Isopentenyl-type Cytokinins," *Plant Physiol* 126:1370-1380 (2001), which are hereby incorporated by reference in their entirety). With the exception of two StBEL-05 sense mutants (lines 11 and 20), the leaf and stem growth of the StBEL-05 overexpression lines was similar to wild-type plants (FIG. 15). All five StBEL-05 lines exhibited an enhanced rate of growth comparable to control plants (Table 4).

TABLE 4

Plant height (cm) and fresh weight (g) of overexpression lines of StBEL-05 under soil-grown, long-day conditions. Plants were grown in 10-cm pots under long days (16 hours of light, 8 hours of dark) and plant height was measured after 10 and 45 days. Four plants per independent line were evaluated for growth. Fresh weight of leaves and stems was measured after 45 days. Standard errors of the mean are shown.

| Plant Line | Plant height (cm) at 10 d | Plant height (cm) at 45 d | Fresh weight (g) of stem and leaves |
|---|---|---|---|
| Wild type | 5.3 ± 0.3 | 35.2 ± 2.2 | 18.0 ± 2.6 |
| StBEL5-11 | 7.3 ± 0.4 | 31.9 ± 3.0 | 19.6 ± 1.3 |
| StBEL5-20 | 6.3 ± 0.6 | 32.2 ± 2.0 | 10.8 ± 0.5 |
| StBEL5-12 | 7.1 ± 0.7 | 44.9 ± 0.9 | 23.3 ± 1.2 |
| StBEL5-14 | 6.2 ± 0.2 | 38.2 ± 1.2 | 29.2 ± 1.0 |
| StBEL5-19 | 7.1 ± 0.5 | 48.7 ± 1.9 | 25.5 ± 3.5 |

The average height of line 19 plants was 13.5 cm greater than control plants after 45 days. Fresh weights of leaves and stems of lines 12, 14, and 19 were 29 to 62% greater than control plants. Lines 11 and 20 exhibited a more rapid rate of growth early (10 days) and then growth rate dropped off by 45 days (Table 4). Accumulation of StBEL-05 transgenic mRNA in line 20 was equivalent to line 11. Three-month old plants from lines 11 and 20 exhibited a slight reduction in leaf size and stem height as a result of decreased apical dominance. To examine the mechanism for this reduced leaf morphology, cytokinin analysis was performed on shoot apices down to the fourth visible true leaf. Similar to POTH1 overexpressers, shoot tips of both StBEL-05 lines 11 and 20 exhibited a two- to fivefold increase in the bioactive forms of cytokinin (Table 5).

TABLE 5

Cytokinin content (picomoles g fr wt$^{-1}$) in shoot tips of POTH1 and StBEL-05 overexpression lines grown under long days (16 hours of light, 8 hours of dark) in the greenhouse. Wild-type lines are nontransformed *Solanum tuberosum* spp. *andigena*. Zeatin types include zeatin, zeatin riboside, dihydrozeatin, and dihyrozeatin riboside. Isopentenyl types include isopentenyl and isopentenyladenine. Standard error was calculated on three replicates.

| Sample | Zeatin types | Isopentenyl types |
|---|---|---|
| Wild-type | 10.5 ± 1.0 | 12.0 ± 1.5 |
| POTH1-15 | 42.5 ± 15 | 35.5 ± 7.0 |
| POTH1-29 | 34.0 ± 12 | 30.0 ± 6.0 |
| StBEL5-11 | 55.5 ± 30 | 31.5 ± 11 |
| StBEL5-20 | 30.5 ± 6.0 | 29.5 ± 6.5 |

The overall magnitude increases in the cytokinin types among the four StBEL and POTH1 mutant lines were remarkably consistent.

POTH1 sense lines had increased levels of $GA_{53}$ and $GA_{19}$ and decreased levels of $GA_{20}$ and $GA_1$ in shoot tips, indicating a down-regulation of the biosynthetic enzyme GA 20-oxidase1 (see above). Using a probe for the potato GA 20-oxidase1 gene (Carrera et al., "Changes in GA 20-oxidase Genes Expression Strongly Affect Stem Length, Tuber Induction and Tuber Yield of Potato Plants," *Plant J.* 22:1-10 (2000), which is hereby incorporated by reference in its entirety), a reduction in GA 20-oxidase1 mRNA in shoots of the most severe mutant phenotypes for POTH1 sense lines was observed (see above, FIG. 15). To determine the effect of overexpression of the POTH1 partner, StBEL-05, RNA levels for GA 20-oxidase1 were examined in the stolons of StBEL-05 sense lines grown under long-day photoperiod conditions. All three of the StBEL-05 lines examined (lines 11, 12, and 20) exhibited a reduction in GA 20-oxidase1 mRNA in stolon tips comparable to controls (FIG. 16). No such reduction in the levels of GA 20-oxidase1 mRNA was observed in shoot tips of StBEL-05 lines grown under long days.

To determine the effect of upregulating StBEL-05 mRNA levels on POTH1 RNA accumulation, northerns were performed on total RNA extracted from StBEL-05 sense lines 12, 14, 19, and 20 using POTH1 as a probe. There were no changes in the levels of POTH1 mRNA in both shoot tips and stolon tips of these StBEL-05 lines relative to wild-type plants. These results indicate that the enhancement of tuber formation in StBEL-05 overexpression lines is not mediated by an indirect increase in POTH1 expression.

Example 30—Discussion: Seven BEL Proteins Interact with a KNOX Protein of Potato Using a yeast two-hybrid library screen, seven unique proteins from potato stolons that interact with the knotted-like protein, POTH1, were identified. Sequence analysis revealed that these interacting proteins are from the BEL1-like family in the TALE superclass of homeodomain proteins. These proteins have conserved regions in common with other TALE proteins, including the homeodomain (comprised of three α-helices) and the proline-tyrosine-proline "TALE" (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). These sequences have been implicated in DNA-binding and protein/protein interactions, respectively (Mann et al., "Extra Specificity From extradenticle: the Partnership Between HOX and PBX/EXD Homeodomain Proteins," *Trends in Genet* 12:258-262 (1996); Passner et al., "Structure of DNA-Bound Ultrabithorax-Extradenticle Homeodomain Complex," *Nature* 397:714-719 (1999), which are hereby incorporated by reference in their entirety). A second conserved region of 120 aa just upstream from the homeodomain (designated the BELL domain by Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety) was identified among BEL proteins by using a BLAST analysis (FIG. 13B, bold letters). Sequence analysis of the predicted secondary structure of this domain reveals the presence of three putative α-helices within the 120 residues (FIG. 13B, underlined sequence). Not all BEL proteins conserve the third helix, however, including the *Arabidopsis* BEL, ATH1 (Quaedvlieg et al., "The Homeobox Gene ATH1 of *Arabidopsis* is Depressed in the Photomorphogenic Mutants cop1 and det1," *Plant Cell* 7:117-129 (1995), which is hereby incorporated by reference in its entirety) and the barley BEL, JUBEL2 (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety). Protein interaction using the two-hybrid system demonstrated that the first 80 aa of this domain (up to QVKAT of the STBEL-05 sequence and comprising the first two predicted helices of this region) are necessary to mediate interaction with POTH1 (interaction of construct pAD5-9 with POTH1). Deletion of as little as the first 20 aa of this domain (comprising a major portion of the first predicted helix) interfered with the interaction with POTH1 (FIGS. 13B and 10B, construct pAD5-2). The results also showed that deletion of 43 aa from the carboxy-end of the 120-aa domain (see FIG. 10B, construct pAD5-9; comprising the third helical structure) did not affect protein interaction. Deletion of the two carboxyl-terminal helices in this region (construct pAD5-11) resulted in a loss of interaction. It appears that all three helical structures contribute to specific binding affinity for POTH1 but that only the amino-terminal two-thirds of the 120-aa domain are necessary for binding to occur. Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety, identified a coiled-coil region in a BEL protein of barley that was involved in the interaction with KNOX proteins. This coiled-coil domain overlaps with 48 of the 80 aa (and comprising the first helix) identified as essential for interaction to occur.

Sequence differences in this putative protein-binding region appear to contribute to the regulation of POTH1 activity by affecting binding affinity to a shared partner. In the interaction between PIF3, a basic helix-loop-helix factor, and phytochrome A and B, phytochrome B has tenfold greater binding affinity for the PIF3 partner than phytochrome A (Zhu et al., "Phytochrome B Binds With Greater Affinity Than Phytochrome A to the Basic Helix-loop-helix Factor PIF3 in a Reaction Requiring the PAS Domain of PIF3," *Proc Natl Acad Sci USA* 97:13419-13424 (2000), which is hereby incorporated by reference in its entirety). A comparison of this 120-aa domain in the potato BELs revealed that StBEL-05 (expressed ubiquitously) has a 58% similarity match to StBEL-13 (expressed predominately in the SAM and flower only) and that StBEL-13 has a 63% match to StBEL-30 in this conserved region. Such differences in sequence may mediate binding affinities to shared partners and, coupled with expression patterns, could reflect organ-specific differences in function.

Conservation in sequence among these seven proteins was also identified in two short amino acid sequence motifs, one near the carboxyl-end of the protein (VSLTLGL) (SEQ ID NO:15) and another just upstream of the BELL domain (SKY box, FIG. 13A). Both of these regions are conserved among other plant BELs. Protein interaction studies showed that the VSLTLGL (SEQ ID NO:15) box is not involved in protein interaction with POTH1 and its function remains unknown. Consistent with Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety, it was observed that, whereas binding occurred without the 229 aa at the amino terminus of StBEL-05 (construct pAD5-1), this 229 aa sequence alone, containing the SKY box, was sufficient to mediate an interaction with POTH1 (and other class I KNOX proteins). This 229-aa sequence, however, did not interact with a class II KNOX protein. Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety, identified the SKY-box sequence in the barley BEL protein to be a part of the KNOX-interacting domain. Our deletion analysis indicates that the SKY box enhances the binding affinity of StBEL-05 to KNOX partners.

Example 31—Discussion: The Protein Binding Region of POTH1

In addition to the homeodomain, KNOX TFs also contain a conserved region of approximately 100 aa, upstream from the homeodomain, known as the KNOX (MEINOX) domain, and postulated to be involved in protein/protein interaction (Bürglin, "The PBC Domain Contains a MEI-NOX Domain: Coevolution of Hox and TALE Homeobox Genes," *Dev Genes Evol* 208:113-116 (1998), which is hereby incorporated by reference in its entirety). Using deletion mutants in the two-hybrid yeast system, regions of amino acid sequence in the KNOX domain of the class I KNOX protein, POTH1, that are involved in an interaction with the BEL TFs have been identified. Binding to the BEL partner is mediated by the KNOX domain but is not dependent on the presence of the first half of the 120 aa KNOX region (FIG. 10A). Similar results were obtained by Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety. Sakamoto et al., "The Conserved KNOX Domain Mediates Specificity of Tobacco KNOTTED1-type Homeodomain Proteins," *Plant Cell* 11: 1419-1431 (1999), which is hereby incorporated by reference in its entirety, showed by using chimeric proteins that the second half of the KNOX domain (designated KNOX2) of a tobacco KNOX protein (NTH15, with 63% similarity to POTH1 in the KNOX region) was most important for determining the severity of the mutant phenotype. Their results indicated that this conserved domain was even more important in determining the phenotype than the DNA-binding domain. The deletion analysis for POTH1 in the present study combined with the results of Sakamoto et al., "The Conserved KNOX Domain Mediates Specificity of Tobacco KNOTTED1-type Homeodomain Proteins," *Plant Cell* 11:1419-1431 (1999), which is hereby incorporated by reference in its entirety, indicate that the interaction of the BEL proteins with the KNOX domain is a prominent control mechanism for mediating KNOX activity and maintaining stable development of the vegetative meristem. KNOX2 contains 18 aa that are predicted to form an α-helix and are conserved among all tobacco and potato KNOX proteins. POTH1 has a close sequence match to members of the family of KNOX proteins of tobacco (Nishimura et al., Over-expression of Tobacco Knotted1-type Class1 Homeobox Genes Alters Various Leaf Morphology," *Plant Cell Physiol* 41:583-590 (2000), which is hereby incorporated by reference in its entirety), with an overall sequence similarity ranging from 60 to 73% and an even greater match in the conserved KNOX and homeodomain regions. Using the two-hybrid system, all seven BELs of potato interacted with four other tobacco class I-type KNOX proteins. Unlike KNOX proteins of barley (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety) and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety), however, POTH1 did not form homodimers in vitro. Structural similarities to the MEIS domain of animal homeodomain proteins (Bürglin, "The PBC Domain Contains a MEINOX Domain: Coevolution of Hox and TALE Homeobox Genes," *Dev Genes Evol* 208:113-116 (1998), which is hereby incorporated by reference in its entirety) suggest that sequences in the KNOX domain of plants are important for interactions with other proteins (Sakamoto et al., "The Conserved KNOX Domain Mediates Specificity of Tobacco KNOTTED1-type Homeodomain Proteins," *Plant Cell* 11:1419-1431 (1999), which is hereby incorporated by reference in its entirety). These results confirm the function of this domain in an interaction with a BEL1-like protein of potato.

Example 32—Discussion: The Function of the BEL/POTH1 Interaction

Through both molecular and genetic analyses, the BEL proteins are known to function in the development of ovules. Reiser et al., "The BELL1 Gene Encodes a Homeodomain Protein Involved in Pattern Formation in the *Arabidopsis* Ovule Primordium," *Cell* 83:735-742 (1995), which is hereby incorporated by reference in its entirety, showed that BELL1 of *Arabidopsis* was involved in the pattern formation of ovule primordium. More specifically, the expression of NOZZLE (a nuclear protein and putative TF) and BELL are spatially linked and interact with other transcription factors to determine distal-proximal pattern formation during ovule development (Balasubramanian et al., "NOZZLE Links Proximal-Distal and Adaxial-Abaxial Pattern Formation During Oovule Development in *Arabidopsis thaliana*," *Development* 129:4291-4300 (2002), which is hereby incorporated by reference in its entirety). Both NOZZLE and BELL are chalazal identity genes that share overlapping functions (Balasubramanian et al., "NOZZLE Regulates Proximal-Distal Formation, Cell Pproliferation and Early Sporogenesis During Oovule Development in *Arabidopsis thaliana*," *Development* 127:4227-4238 (2000), which is hereby incorporated by reference in its entirety). In bell mutants, the chalazal domain undergoes altered development and growth of the integuments is replaced by irregular outgrowths (Mondrusan et al., "Homeotic Transformation of Ovules into Carpel-like Structures in *Arabidopsis*," *Plant Cell* 6:333-349 (1994), which is hereby incorporated by reference in its entirety). Overexpression of an apple BEL gene (MDH1) in *Arabidopsis* produced plants that were dwarf, had reduced fertility, and exhibited changes in both carpel and fruit shape (Dong et al., "MDH1: an Apple Homeobox Gene Belonging to the BEL1 Family," *Plant Mol Biol* 42:623-633 (2000), which is hereby incorporated by reference in its entirety). Overall, these results support that BEL proteins function in controlling the formation of carpellate tissues and plant fertility. Overexpression of a cDNA of a barley BEL in tobacco produced plants that were dwarf and exhibited malformed leaves and reduced apical dominance (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety). This BEL1-like cDNA isolated from floral meristems produced a sense phenotype similar to a class I knox overexpresser (Chan et al., "Homeoboxes in Plant Development," *Biochim Biophys Acta* 1442:1-19 (1998), which is hereby incorporated by reference in its entirety). All seven of the BEL TFs in this study were isolated from stolons, a vegetative organ. Based on these results and the patterns of mRNA accumulation in potato, it appears that the BEL1 TFs of potato play a diverse role in plant growth by regulating the development of both reproductive and vegetative meristems.

Because the BEL TFs of potato and POTH1 interact, the function of one provides a clue to the function of the other. The KNOX protein of tobacco, NTH15, affects plant growth by regulating GA levels through a direct interaction with a specific motif in regulatory sequences of the GA 20-oxidase1 gene, a key GA biosynthetic enzyme (Sakamoto et al., KNOX Homeodomain Protein Directly Suppresses the Expression of a Gibberellin Biosynthesis Gene in the Tobacco Shoot Apical Meristem," *Genes Dev* 15:581-590 (2001), which is hereby incorporated by reference in its entirety). NTH15 directly suppresses the expression of GA 20-oxidase1 within specific cells of the SAM to maintain the indeterminate state of corpus cells. The knotted1-like protein of potato, POTH1, is also involved in the regulation of GA synthesis and acts as a developmental switch during tuber formation. Transgenic plants that overexpressed POTH1 had reduced levels of GA 20-oxidase1 mRNA, altered levels of GA intermediates, and exhibited a phenotype that could be partially rescued by $GA_3$ treatment (see above). These plants were dwarf and developed malformed leaves. Under both short-day (inductive conditions) and long-day (noninductive) photoperiods, POTH1 overexpressing lines produced more tubers than controls (see above).

Figure 17D:
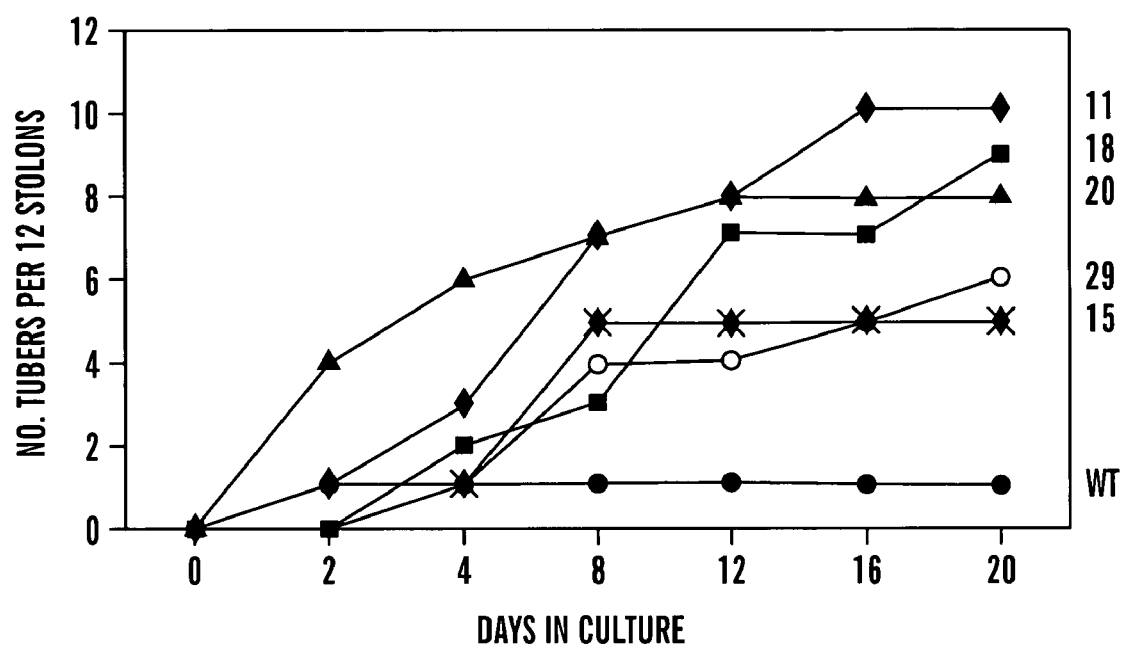
FIG. 17D shows the rate of tuberization for stolons from overexpression lines 11, 18, 20, 29, and 15 of POTH1 and from wild-type plants (WT). Excised stolon tips (approximately 1.5 cm in length) from plants grown under long-day conditions were grown in vitro in the dark in media supplemented with 8% (w/v) sucrose and monitored for 20 days.

These sense lines exhibited a capacity for enhanced tuber formation. Lines that overexpressed StBEL-05 produced tubers even under LD in vitro conditions, whereas control plants produced tubers only after 10 days of SD conditions. Overall, the BEL sense lines produced more tubers at a faster rate than controls even on soil-grown plants. After 14 days of SD conditions, soil-grown StBEL-05 overexpressers exhibited a threefold increase in tuber production relative to wild-type plants (Table 2). Thus, both POTH1 and StBel-05 overexpression lines produced more tubers at a faster rate than controls (see FIGS. 17A-D). In FIG. 17D, stolon tips excised from in vitro plantlets overexpressing POTH1 that were not tuberizing were cultured. After a 20-day incubation in the dark on 8% (w/v) sucrose, stolons from all five POTH1 sense lines produced more tubers than wild-type stolons. Line 11 exhibited almost a 10-fold increase in tuber yield (262 mg stolon tip-1) after 35 days in culture compared with wild-type plants (27 mg stolon tip-1).

All of the above results show that that the expression of both POTH1 and its protein partner, STBEL-05, is associated with an enhanced rate of tuber formation. In addition to enhanced tuber production, select StBEL-05 lines exhibited increases in cytokinin levels and a reduction in GA 20-oxidase1 mRNA similar to POTH1 overexpression lines. This increase in cytokinin levels could explain the enhanced rate of growth for the StBEL-05 lines, although excessive accumulation may have led to the reduction in growth exhibited by mature plants of lines 11 and 20. GA is involved in regulating cell growth in a tuberizing stolon (Xu et al., "The Role of Gibberellin, Abscisic Acid, and Sucrose in the Regulation of Potato Tuber Formation in vitro," *Plant Physiol* 117:575-584 (1998), which is hereby incorporated by reference in its entirety) and in contributing to the control of the photoperiodic response of tuber formation (Jackson et al., "Control of Tuberisation in Potato by Gibberellins and Phytochrome," *B. Physiol Plant* 98:407-412 (1996), Martinez-Garcia et al., "The Interaction of Gibberellins and Photoperiod in the Control of Potato Tuberization," *J Plant Growth Regul* 20:377-386 (2001), which are hereby incorporated by reference in their entirety). Low levels of GA in the stolon tip are correlated with tuber induction (Xu et al., "The Role of Gibberellin, Abscisic Acid, and Sucrose in the Regulation of Potato Tuber Formation in vitro," *Plant Physiol* 117:575-584 (1998), which is hereby incorporated by reference in its entirety). Tuberization is also affected by cytokinin accumulation, with high levels inhibiting and moderate levels promoting tuber formation (Gális et al., "The Effect of an Elevated Cytokinin Level Using the ipt Gene and $N^6$-Benzyladenine on Single Node and Intact Potato Plant Tuberization in vitro," *J Plant Growth Regul* 14:143-150 (1995); Romanov et al., "Effect of Indole-3-Acetic Acid and Kinetin on Tuberisation Parameters of Different Cultivars and Transgenic Lines of Potato in vitro," *Plant Growth Reg* 32:245-251 (2000), which are hereby incorporated by reference in their entirety). Local accumulation of cytokinins in axillary buds of transgenic tobacco produced truncated, tuberizing lateral branches (Guivarc'h et al., "Local Expression of the ipt Gene in Transgenic Tobacco (*Nicotiana tabacum* L. cv. SR1) Axillary Buds Establishes a Role for Cytokinins in Tuberization and Sink Formation," *J Exp Bot* 53:621-629 (2002), which is hereby incorporated by reference in its entirety). Through an interaction with POTH1, the BEL protein encoded by StBEL-05 may also function to regulate hormone levels in stolons or leaves to favor the formation of tubers.

The results set forth above indicate that the physical interaction between the KNOX and BEL proteins provides a molecular basis for regulating processes of growth in the potato and that overexpression of each partner alone affects vegetative development and enhances tuber formation.

Example 33—Both POTH1 and StBEL-05 Interact to Repress Transcriptional Activity of the GA20 Oxidase1 Gene of Potato—Preliminary Results If POTH1 and StBEL physically interact and their overexpression produces transgenic plants that exhibit similar developmental pathways, it is reasonable to assume that they target the same gene. Using gel mobility shift assays (FIG. 18), it is shown that in tandem POTH1 and StBEL-05 bind to the P1 region of the GA20 oxidase1 promoter. In tandem, StBEL-05 and POTH1 had a greater binding affinity for the ga20ox1 promoter than either alone. The StBEL-05-POTH1 heterodimer bound specifically to a composite sequence TT<u>GAC</u>TT<u>GAC</u> (SEQ ID NO: 20) containing two adjacent TGAC cores in the P1 region. Using a transcription assay with GUS reporter driven by the ga20ox1 promoter in tobacco protoplasts, StBEL-05 and POTH1 alone suppressed the activity of the ga20ox1 promoter by more than 50%, together about 80%. The binding affinity of POTH1 and StBEL-05 represses the transcriptional activity of the promoter (FIG. 19).

Figure 19:
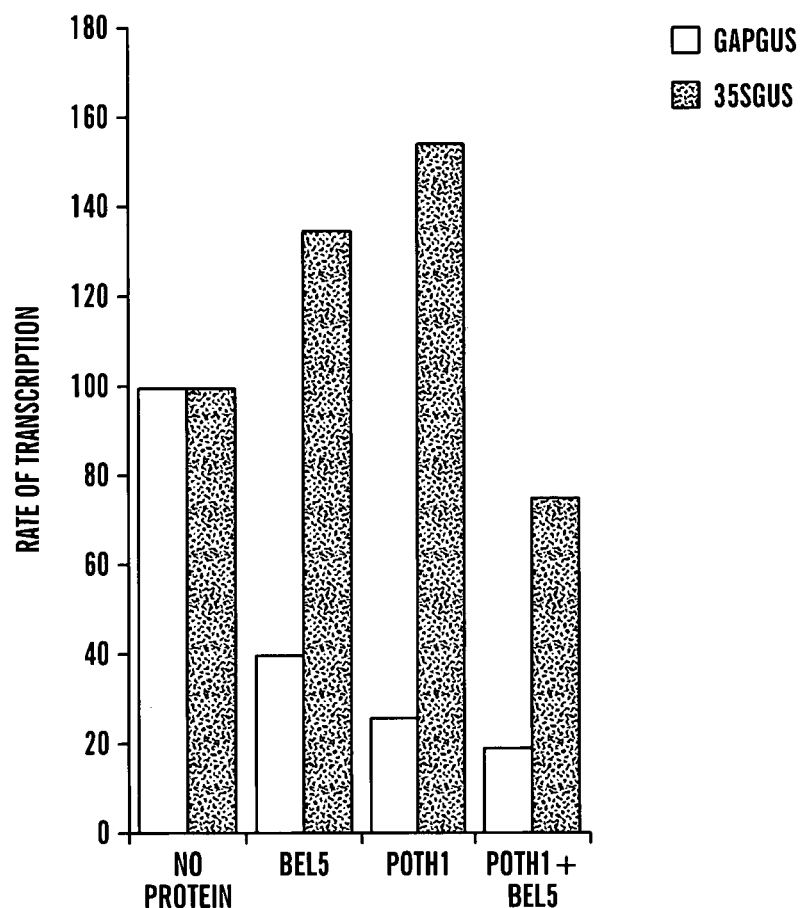
FIG. 19 shows the effect of binding two transcription factors to the GA20 oxidase1 promoter on the rate of transcription. The potato GA20 oxidase1 promoter (1170 bp) plus an enhancer was fused to a GUS marker (GAPGUS, gray bars). The two transcription factors, POTH1 and StBEL-05, were cloned and expressed in separate protein expression vectors. All constructs were transformed into tobacco protoplasts through electroporation. Whereas, repression of transcription was affected by each TF alone, expression of the proteins in tandem resulted in the greatest repression of transcription. Activity of the 35SGUS construct (black bars) was used as a baseline control. The "no protein" protoplasts are designated as 100% transcriptional activity. All activities are calculated in relation to a luciferase internal control.
Figure 20:
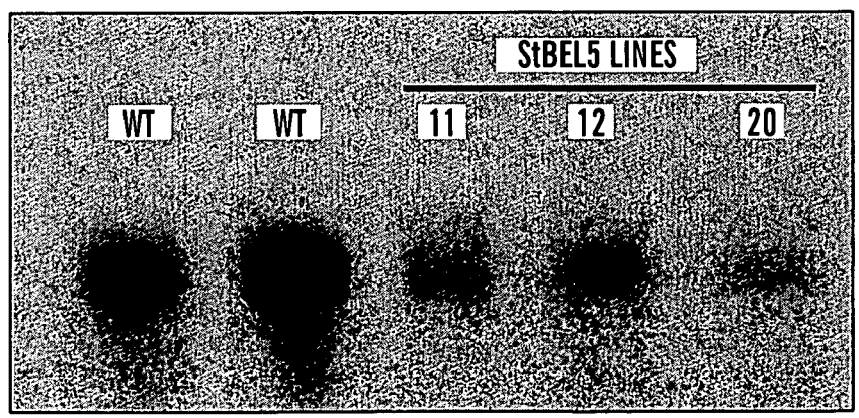
FIG. 20 shows GA20 oxidase1 mRNA accumulation in stolon tips of plants grown under long-day conditions. Ten μg of total RNA was probed with a $^{32}$P-fragment specific for the potato GA20 oxidase1 cDNA. These StBEL-05 lines all exhibited enhanced tuber formation.

Consistent with the in vitro results of StBeL/POTH1 repression of the GA20 oxidase1 promoter/GUS marker (FIG. 19), GA20 oxidase1 mRNA levels are also reduced in stolons of the StBEL-05 sense lines gown under long days (FIG. 20). This reduction in mRNA will lead to a reduction in bioactive GA and result in facilitating tuber formation. StBEL-05 mRNA levels were found to increase in both stolons and leaves of WT plants in response to the inductive conditions of short days. These results are consistent with the proposed role of GA in mediating photoperiodic responses in potato (Martinez-Garcia et al., "The Interaction of Gibberellins and Photoperiod in the Control of Potato Tuberization," *J. Plant Growth Regul.* 20:377-386 (2002), which is hereby incorporated by reference in its entirety).

These preliminary data show that POTH1 and StBEL-05 proteins interact in vitro and that overexpression of each separately, produces plants that are enhanced in their capacity to form tubers. Both proteins interact to repress the transcriptional activity of a key GA biosynthetic gene. Because expression of the BEL TFs appears to be differential, the BELs appear to act in tandem with POTH1 (or other KNOX proteins) to regulate growth differently in the various organs or cells of the potato. A more detailed description of the above experiments is provided in Examples 34-43, below.

Example 34-BEL and KNOX Interaction Mediates Transcriptional Activity of the Potato ga20ox1 Promoter—Plant Materials Tobacco 'Petit Havana' plants were maintained in Murashige and Skoog basal medium (1962) supplemented with 2% sucrose and incubate d at 25° C., un der 16 hour photoperiods for three to four weeks.

Example 35—BEL and KNOX Interaction Mediates Transcriptional Activity of the Potato ga20ox1 Promoter—Protein Expression and Purification in *E. coli*

Glutathione S-transferase (GST) fusion constructs were generated by introducing full-length cDNAs of StBEL-05 and POTH1 in frame with GST into the pGEX-5X-2 expression vector (Roche, Indianapolis, Ind. and transformed into BL21 (DE3) *E. coli* cells (Stratagene, La Jolla, Calif.). Cells were grown at 30° C. until the $OD_{600}$ reached 0.6, induced with 1.0-mM isopropyl-β-D-thiogalactopyranoside, and cultured for 5 hours. The manufacturer's protocol (Roche) was followed for cell lysis and affinity purification by using glutathione sepharose 4B beads. The GST portion of the fusion protein was cleaved by Factor Xa protease (Promega, Madison, Wis.). Purified StBEL-05 and POTH1 protein were frozen in liquid $N_2$ and stored at −80° C.

Example 36—BEL and KNOX Interaction Mediates Transcriptional Activity of the Potato ga20ox1 Promoter—Gel Retardation Assay The first intron with partial flanking exon sequence (450 bp) of potato ga20ox1 and its promoter (981 bp, provided by Dr. Salomé Prat, CSIC Cantoblanco Campus, Univ. of Madrid, Spain) were used for gel mobility shift assays. Polymerase chain reaction (PCR) was used to amplify three regions of the promoter: -981 to 636 (P1), -660 to 307 (P2), and -331 to 0 (P3). About a 25-bp overlap was maintained between P1 and P2 or P2 and P3 in the chance that the protein-binding site would span the overlapped region. The first intron of this gene was amplified from potato genomic DNA by using PCR and the oligos 5'-GGATCCT-TGAAGTGGCTCTTCTCT-3' (SEQ ID NO:21) and 5'-AATCTAGAGACACTCTCTTTTTCGT-3' (SEQ ID NO:22) as primers. These primers were designed based on the site of the first intron of the tobacco GA20 oxidase gene Ntc12. The four fragments were purified on a 1.4% agarose gel and labeled with $\alpha^{32}$P-dATP using Klenow fragment. DNA-binding reactions were set up on ice in 20 μL containing 10-mM Tris-HCl (pH 7.5), 5% glycerol, 0.5-mM EDTA, 0.5-mM DTT, 0.05% NP-40, 50-mM NaCl, 50-mg·$L^{-1}$ poly (dG-dC)•poly (dG-dC) (Amersham Pharmacia Biotech, Piscataway, N.J.), 100-ng protein, and 1-fmol labeled DNA. After incubation on ice for 30 minutes, the reactions were resolved on a 6% native polyacrylamide gel in 1×TGE (Tris-Glycine-EDTA) buffer. The gel was dried and exposed to X-ray film.

In the competition assays, unlabeled double-stranded DNA fragments (10×, 25×, 50×, 100×) were incubated with the recombinant protein before the addition of the radioactive probe. The dissociation rates were determined by adding 500-fold more cold DNA fragments to the DNA-binding reactions that were being incubated on ice, and loaded onto the running gel every 10 minutes. Mutated oligos for binding sites were synthesized by the DNA Sequencing and Synthesis Facility, Iowa State University (Ames, Iowa).

Example 37—BEL and KNOX Interaction Mediates Transcriptional Activity of the Potato ga20ox1 Promoter—Transcription Assay Generation of Reporters and Effectors The cauliflower mosaic virus (CaMV) 35S promoter in pBI221 (Clontech, Palo Alto, Calif.) was replaced by an enhancer fragment (-832 to -50) of the 35S promoter plus 980 bp of the ga20ox1 promoter to generate the pGAOP::β-glucuronidase (GUS) reporter construct. With this construct, the reporter GUS transcription level is augmented but its transcription may still be affected by the ga20ox1 promoter. A CaMV 35S promoter-driven luciferase (LUC) construct 35S-LUC (obtained from Dr. Takahashi, Dept. of Biological Sciences, Graduate School of Science, Univ. of Tokyo, Japan) was used as an internal control. Effector constructs were also generated by using pBI221 vector as a backbone, with the GUS gene replaced by the full-length cDNAs of either StBEL-05 or POTH1, downstream of the CaMV 35S promoter. Truncated cDNAs that encode the N-terminal protein-binding domains of StBEL-05 or POTH1 were used to generate the dominant negative constructs, StBEL5ΔC295 and POTH1ΔC122, respectively. The reporter construct with the mutated promoter was generated by site-directed PCR mutagenesis with oligos 5'-CTATTTGACTTC*ACACGGTTATTT-3' (SEQ ID NO:23) and 5'-AAATAACCGTGTG*AAGTCAAATAG-3' (SEQ ID NO:24).

Transfection Assay

Fully expanded leaves from three- to four-week-old tobacco plants were excised and placed in K3 basal media (Kao et al., "Nutritional Requirements for Growth of *Vicia hajastana* Cells and Protoplasts at a Very Low Density in Liquid Media," *Planta* 126:105-110 (1975), which is hereby incorporated by reference in its entirety) supplemented with 0.4 M sucrose, 0.25% (w-v) cellulases (Karlan Research Products, Santa Rosa, CA), and 0.05% (w-v) macerases (Calbiochem, La Jolla, Calif.) and incubated for overnight at 28° C. After incubation, the liberated protoplasts were filtered through sterile cheesecloth into a Babcock bottle, and centrifuged for 10 minutes at 1000 rpm. Protoplasts were collected from the bottleneck area and washed once in K3 media with 0.4 M sucrose and resuspended in K3 media containing 0.4 M glucose to a final concentration of $4 \times 10^6$ protoplasts per milliliter.

For each transfection analysis, 700 μL of tobacco protoplasts (prepared as described above) were mixed with 30 μL 2 M KCl and plasmid DNA in an electroporation cuvette with 0.4-cm electrode gap. The plasmid DNA was a mixture of 2 μg of the pGAOP::GUS reporter construct, 0.1 μg of the 35S-LUC construct as internal control, and a different combination of 2 μg of each effector plasmid. After electroporation (voltage=170 V, capacitance=125 μF, Gene Pulser Transfection Apparatus; Bio-Rad, Hercules, Calif.), 4.0 mL of Murashige and Skoog (1962) basal media was added, and the protoplasts were incubated in the dark at room temperature for 40 to 48 hours before conducting GUS and LUC activity assays. Transfections were performed three times for each effector combination.

Luciferase assays were performed by injecting 100-μL luciferase substrate (Promega, Madison, Wis.) into 20 μL of extract and measuring the emitted photons for 15 seconds in a TD-20 luminometer (Turner Designs, Sunnyvale, Calif.). Fluorometric GUS assays were performed as described (Jefferson, "Assaying Chimeric Genes in Plants: The GUS Gene Fusion System," *Plant Mol. Biol. Rep.* 5:387-405 (1987), which is hereby incorporated by reference in its entirety). A fluorescence multiwell plate reader, Fluoroskan II (MTX labs, Vienna, Va.), was used to measure GUS activity at 365 nm (excitation) and 455 nm (emission). Each sample was measured three times for both LUC and GUS activity. Relative GUS-LUC activity was calculated by dividing the ratio of GUS activity to LUC activity from different effectors with the ratio from reporter plasmid alone. Relative activities calculated from three transfection replications were presented as a mean±SE.

Example 38—Results: StBEL-05 and POTH1 Bind to the Regulatory Regions of ga20ox1

Figure 18A:
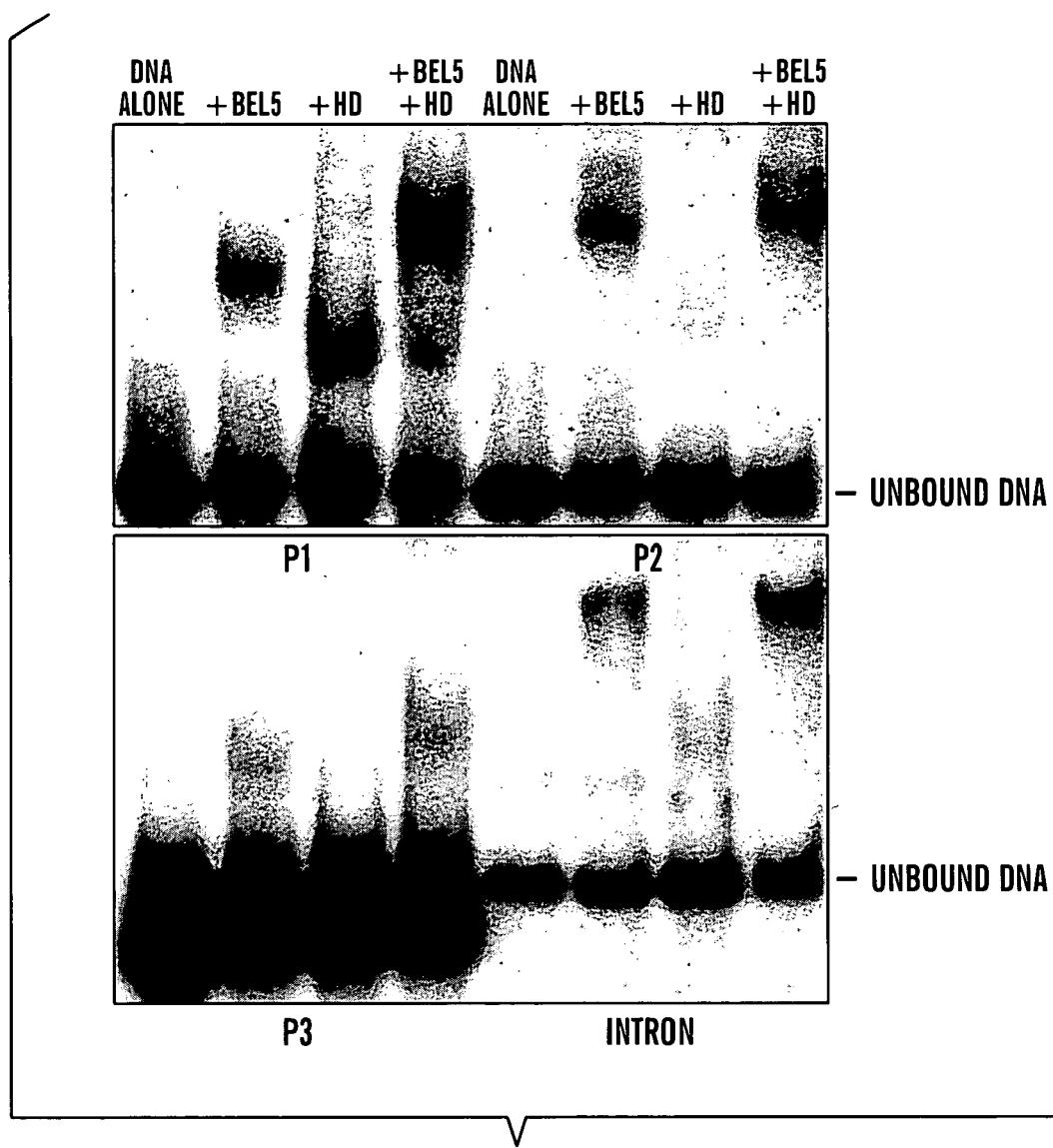
FIGS. 18A-B show gel mobility shift assays (FIG. 18A) for the binding of two transcription factors of potato, POTH1 (HD) and StBEL-05, to regions of the GA20 oxidase1 promoter and the first intron (FIG. 18B). Each DNA probe is tested for binding in four sets: DNA alone, with StBEL-05 only, with POTH1 (HD) only, and with both StBEL-05 and POTH1. The two proteins appear to bind in tandem to the P1 region. Two-hundred μg of purified protein and $^{32}$P-labeled DNA fragments were used in each binding reaction. The protein/DNA mix was run on a nondenaturing polyacrylamide gel. These results are representative of several replications. The GA20 ox1 promoter was provided by Salomé Prat, Barcelona.
Figure 21A:
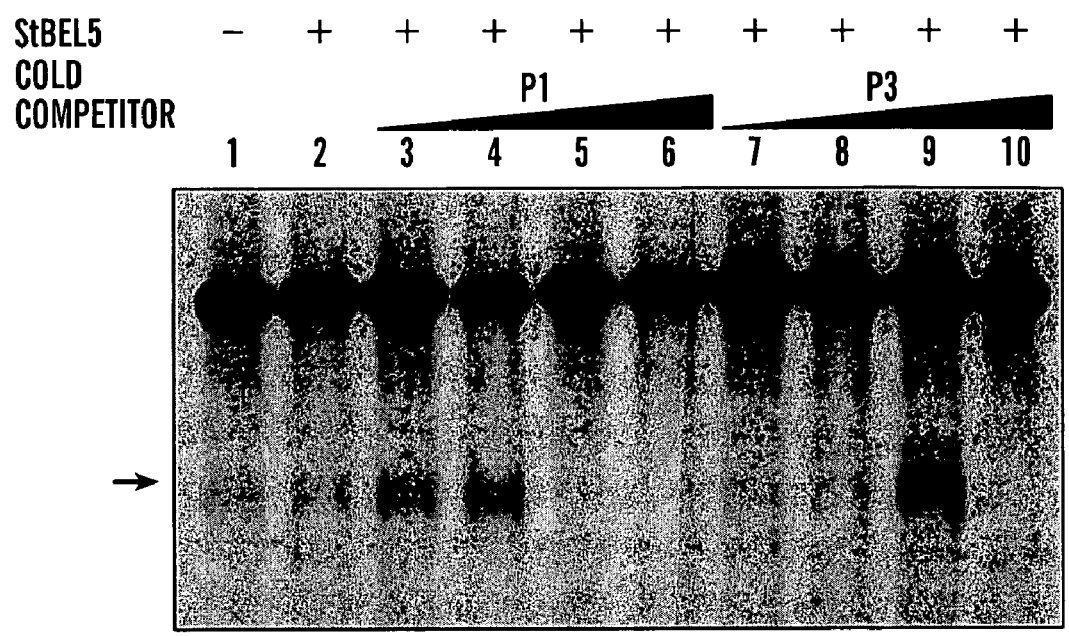
FIGS. 21A-B show a competition gel-retardation assay of P1 with cold P1 or P3 in the presence of StBEL-05 (FIG. 21A) or POTH1 (FIG. 21B). Lane 1 is labeled P1 alone, lane 2 is the labeled P1 with either StBEL-05 (FIG. 21A) or POTH1 (FIG. 21B). Increased amounts (10×, 25×, 50×, 100×) of unlabeled P1 or P3 were added to lanes 3 to 6 and 7 to 10, respectively. The DNA-protein complexes are indicated with arrowheads.
Figure 21B:
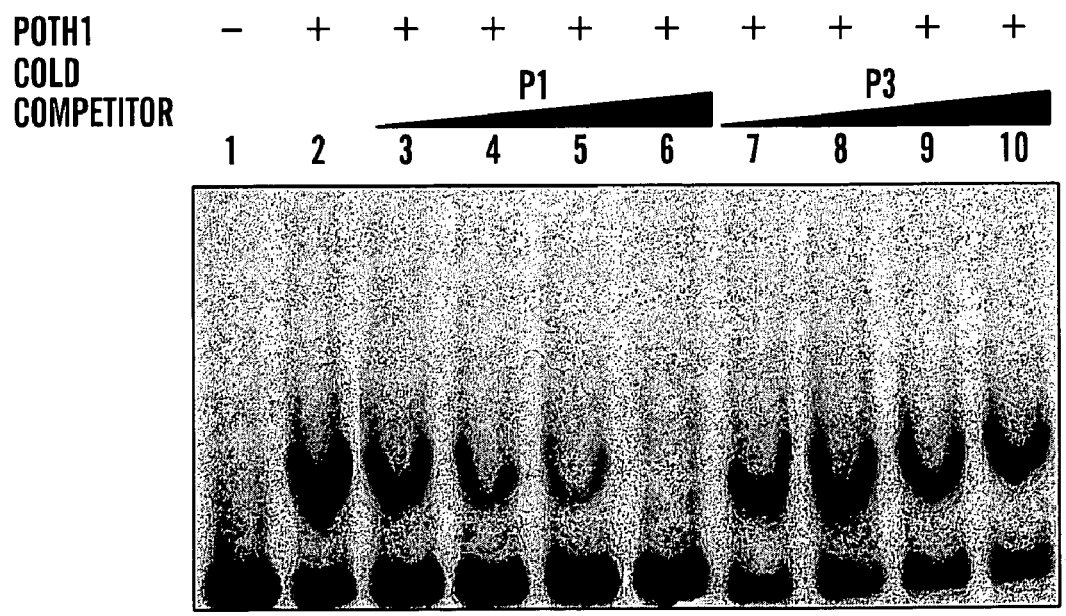

Recombinant StBEL-05 protein expressed from *E. coli* retarded the mobility of all three promoter sequences and the first intron (FIGS. 18A and B). POTH1 only formed a complex with P1. StBEL-05 and POTH1 together produced a supershifted band with P1, which had stronger signal intensity and migrated much slower than either the StBEL-05-P1 or POTH1-P1 complexes (FIG. 18A). Competition assays were performed with labeled P1 and unlabeled P1 or unlabeled P3. With increased unlabeled P1, the P1-StBEL-05 complex quickly disappeared (FIG. 21A). With unlabeled P3, however, even at a concentration 100-fold more than labeled P1, the shifted band was still present (FIG. 21A). Unlabeled P1 also reduced the P1-POTH1 complex formation, but unlabeled P3 had no effect on the P1-POTH1 complex (FIG. 21B).

Figure 22:
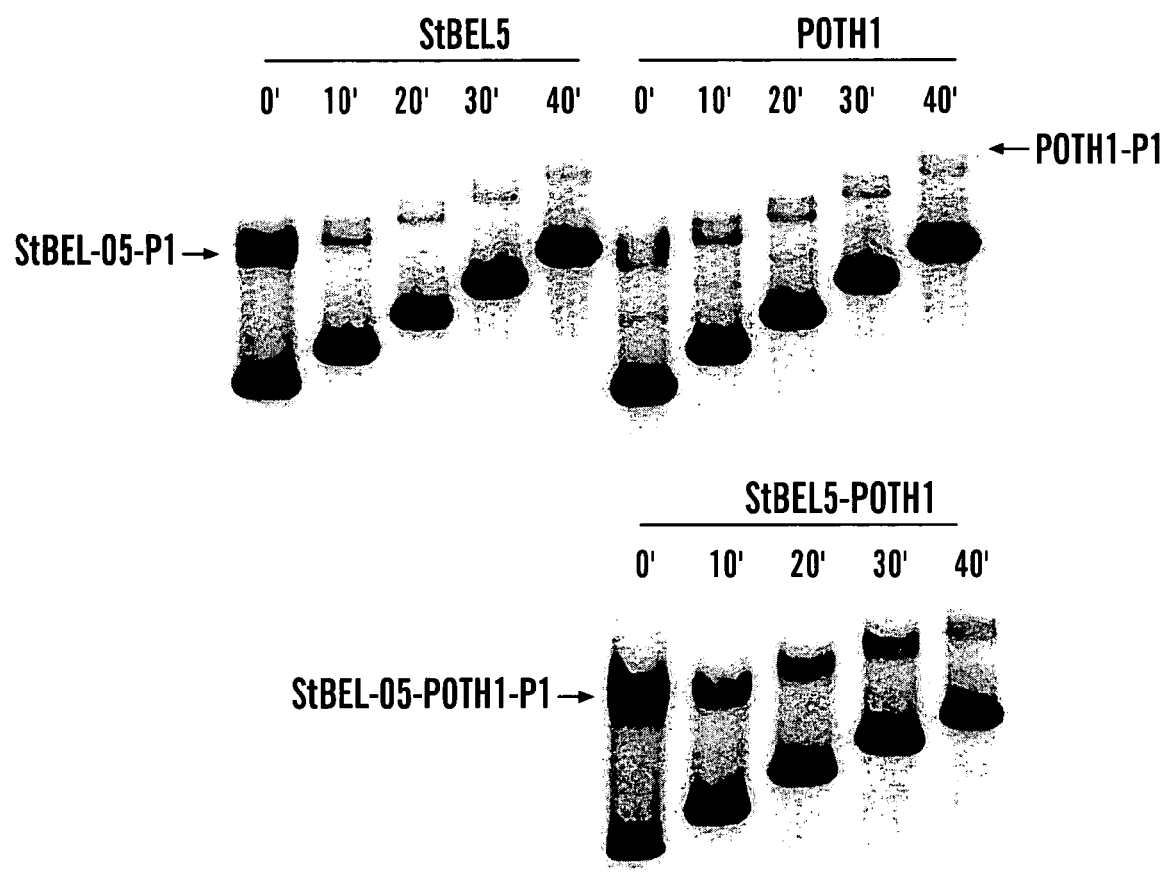
FIG. 22 shows a dissociation rate analysis of StBEL-05-P1, POTH1-P1, and StBEL-05-POTH1-P1 complexes. Labeled P1 was incubated on ice for 30 minutes with recombinant proteins, as indicated on the top. Then a 500-fold molar excess of unlabeled P1 was added and aliquots analyzed by gel mobility shift assay after the indicated time. The arrows show the DNA-protein complexes.

Consistent with the increased signal intensity of the StBEL-05-POTH1-P1 complex, the dissociation rate of this complex was much slower than either the StBEL-05-P1 or POTH1-P1 complexes (FIG. 22). Although StBEL-05 could bind to P2, P3, and the intron fragments, there was no supershifted band formed when both StBEL-05 and POTH1 were incubated with these three DNA fragments (FIG. 18A). These results indicate that both StBEL-05 and POTH1 are required for binding to the P1 DNA fragment. Based on these results, at least two TALE homeodomain binding sites may be present in P1. To support this premise, excessive amounts of a truncated protein containing only the HD portion of StBEL-05 produced a supershifted band similar to the POTH1-StBEL-05-P1 complex. Apparently, there were two binding sites recognized by StBEL-05 in P1. No supershifted band was detected, however, when P1 was incubated with excessive amounts of full-length StBEL-05 or POTH1. This indicates that the two binding sites in P1 are in close proximity to one other and that two full-length StBEL-05 molecules cannot bind to both sites at the same time because of size constraints.

Example 39—Results: The StBEL-05-POTH1 Heterodimer Binds Specifically to the TGA(C/G)(T/A)TGAC Site Based on the *Arabidopsis* KNOX-BEL heterodimer binding site TGACAG(G/C)T (SEQ ID NO:25) (Smith et al., "Selective Interaction of Plant Homeodomain Proteins Mediates High DNA-Binding Affinity," *Proc. Natl. Acad. Sci.* 99:9579-9584 (2002), which is hereby incorporated by reference in its entirety) and the TGAC binding core confirmed for MEINOX proteins (Smith et al., "Selective Interaction of Plant Homeodomain Proteins Mediates High DNA-Binding Affinity," *Proc. Natl. Acad. Sci.* 99:9579-9584 (2002); Tejada et al., "Determinants of the DNA-Binding Specificity of the Avian Homeodomain Protein, AKR," *DNA and Cell Biol.* 18:791-804 (1999), which are hereby incorporated by reference in their entirety, one putative site, TTGACTTGAC (SEQ ID NO:20), in the potato ga20ox1 promoter P1 region was identified. Oligonucleotides with serial point mutations across this site were used as probes in gel-retardation assays in the presence of StBEL-05, POTH1, or both. Point mutations across this site did not affect the binding of either StBEL-05 or POTH1 alone, but most mutations in TGACTTGAC (SEQ ID NO:26) abolished the binding by StBEL-05-POTH1 heterodimer. Based on these results, it was deduced that the consensus sequence of the StBEL-05-POTH1 heterodimer is TGA(C/G)(T/A)TGAC (SEQ ID NO:27).

Example 40—Results: Repression of ga20ox1 Promoter Requires the Interaction of StBEL-05 and POTH1

Figure 23A:
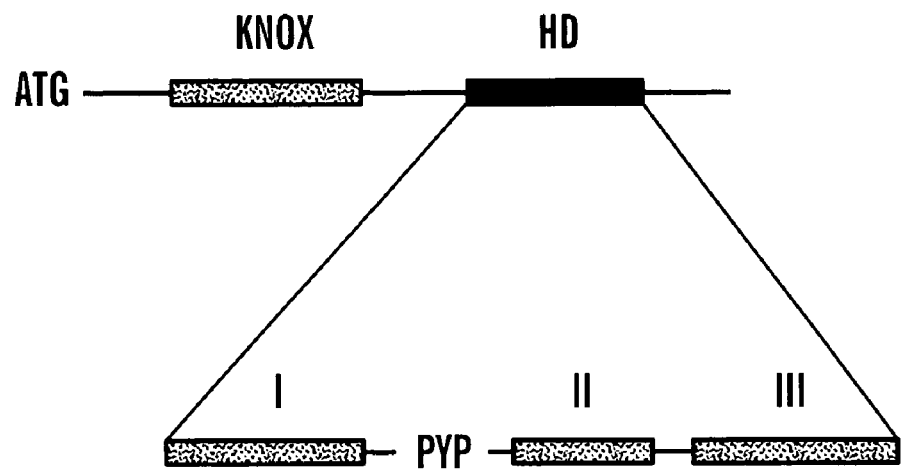
FIGS. 23A-B show the protein structures of POTH1 (FIG. 23A) and StBEL-05 (FIG. 23B). Conserved regions are labeled. These include the protein-binding regions for POTH1, KNOX I and KNOX II, and for StBEL-05, the Sky box and the BELL domains. The DNA-binding domains (HD) consisting of three helices and the characteristic proline-tyrosine-proline TALE are also designated. POTH1 is 345 aa in length, whereas StBEL-05 is 688 aa. The schematics of protein structure presented here are not drawn to scale to enhance visual clarity.
Figure 23B:
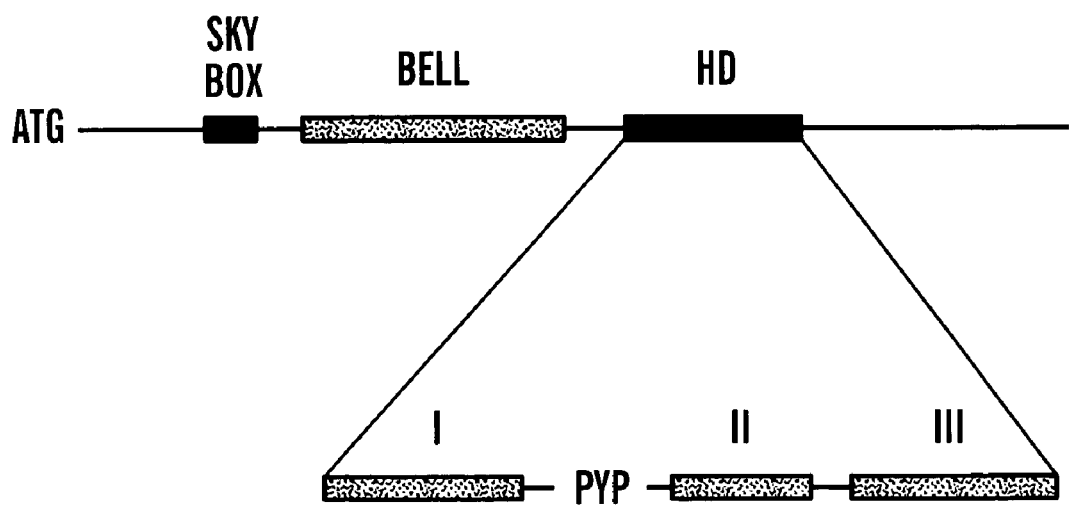

POTH1 encodes for a 345-residue protein estimated to have a mass of 37.95 kDa. The coding sequence of the protein includes the 97-aa KNOX domain and the 64-aa homeodomain consisting of three helices (FIG. 23A). The KNOX domain of POTH1 contains two conserved regions, designated Knox I and II. StBEL-05 is 688 aa in length with an estimated mass of 75.68 kDa. The coding sequence of StBEL-05 contains the conserved sky box, BELL domain, homeodomain, and the proline-tyrosine-proline (P-Y-P) loop between helices I and II (FIG. 23B). The BELL domain is 120 aa in length and the HD of StBEL-05 is 61 aa.

Figure 24A:
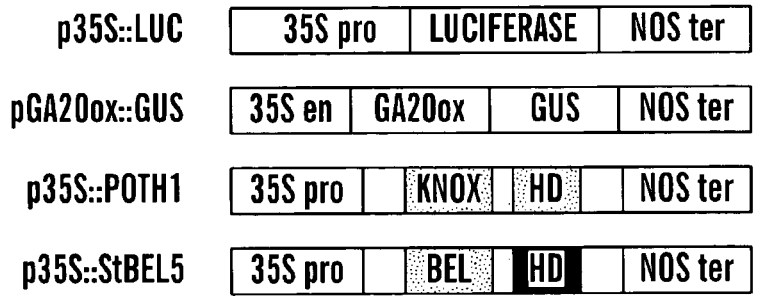
FIGS. 24A-C show schematics of constructs (FIG. 24A) and the repression effect of StBEL-05 and POTH1 on the ga20ox1 promoter (FIG. 24B) and on the 35S CaMV promoter (FIG. 24C). The construct with the LUC gene under the control of the cauliflower mosaic virus (CaMV) 35S promoter was used as an internal control. Each transfection was performed three times. Relative GUS-LUC activity was calculated with reporter alone set as 100%. Data are means±SE.
Figure 24B:
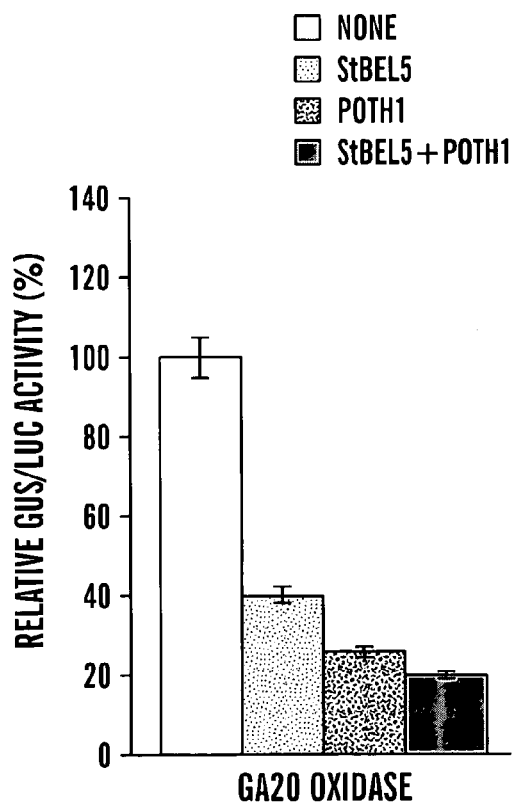
Figure 24C:
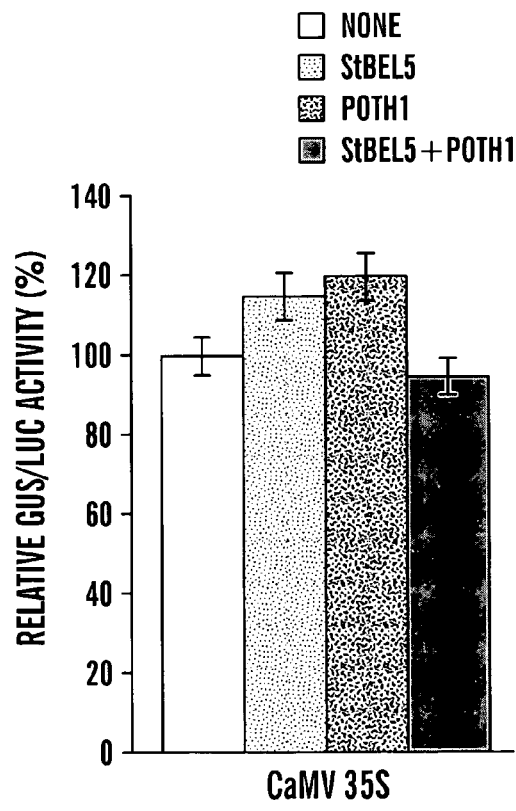
Figure 25A:
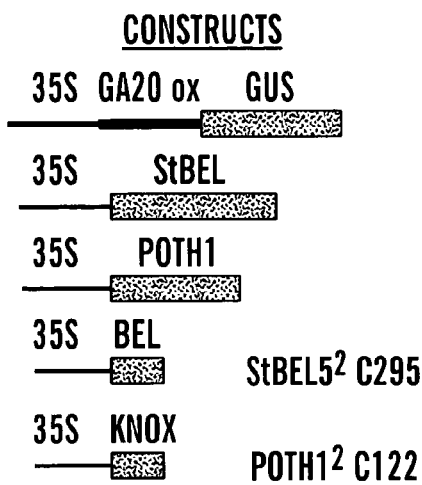
FIGS. 25 A-C show schematics of constructs (FIG. 25A) and the effect of dominant negative constructs of either StBEL-05 or POTH1 on the repression activity of StBEL-05 (FIG. 25B) or POTH1 (FIG. 25C), respectively. The construct with the LUC gene under the CaMV 35S promoter was used as a control. Each transfection was performed three times. Relative GUS-LUC activity was calculated with reporter alone set as 100%. Data are means±SE.
Figure 25B:
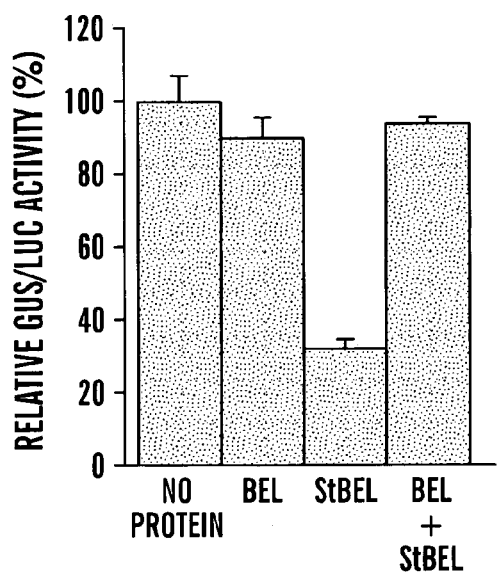
Figure 25C:
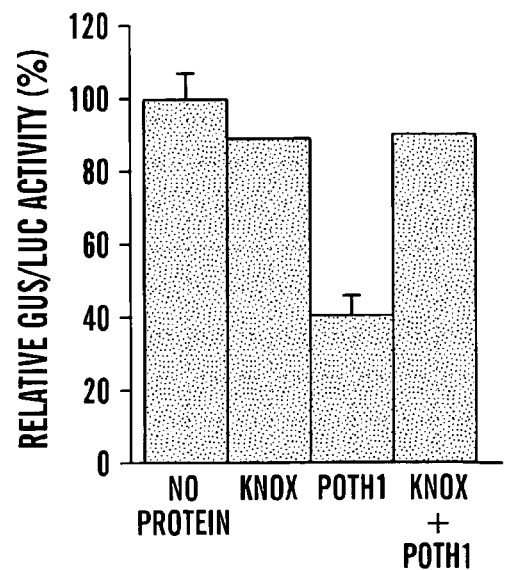

When co-transfected with effector p35S::StBEL5, p35S::POTH1, or both (FIG. 24A), relative GUS-LUC activity of the pGAOP::GUS reporter construct decreased by more than half (FIG. 24B). Neither StBEL-05 nor POTH1 showed any effect on the activity of the CaMV 35S promoter (FIG. 24C). To eliminate the possibility that endogenous BEL1-like or KNOX proteins cooperatively interact with POTH1 or StBEL-05, respectively, truncated forms of StBEL-05 and POTH1, StBEL5ΔC295 and POTH1ΔC122 (FIG. 25A), were generated to use as dominant negatives in the transcription assays. StBEL5ΔC295 and POTH1ΔC122 contain the intact protein-binding domain, but lack the carboxy-terminal region including the homeodomain. StBEL5ΔC295 and POTH1ΔC122 can interact with endogenous KNOX or BEL1-like proteins, respectively. Such heterodimers are not functional due to the lack of the homeodomain from the truncated proteins. In transcription assays with pGAOP::GUS as reporter, StBEL5ΔC295 had little effect on the activity of the ga20ox1 promoter (FIG. 25B). When co-transfected with StBEL-05, StBEL5ΔC295 abolished almost all of the repression activity of StBEL-05 (FIG. 25B). POTH1ΔC122 had a similar effect on the repression activity of POTH1 (FIG. 25C).

Example 41—Results: The Binding Site in the ga20ox1 Promoter Acts as a cis-Element for the Repression by StBEL-05-POTH1 Heterodimer To investigate whether the StBEL-05-POTH1 binding site identified through EMSA studies functions as a cis-element, a reporter construct with a point mutation in the binding site was used for the transcription assay (FIG. 26A). Constructs containing this single mutation exhibited no detectable repression of promoter activity when co-transfected with either StBEL-05, POTH1, or both (FIGS. 26B-C).

Figure 18B:
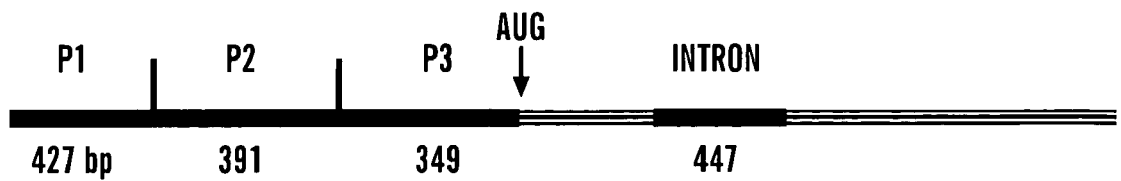

Example 42—Discussion: Cooperative Interaction Between StBEL-05 and POTH1 Mediates Binding Affinity for the ga20ox1 Promoter To regulate target gene expression, a transcription factor binds to the regulatory sequence of its target gene or interacts with another protein that does. Gel-retardation assays showed that both StBEL-05 and POTH1 bound to the promoter region of potato ga20ox1 gene, and StBEL-05 could also bind with the first intron sequence (FIGS. 18A-B). Unlabeled P3 competed with the StBEL-05-P1 complex, but not as effectively as unlabeled P1 (FIG. 21A), whereas P3 had no competition effect with the POTH1-P1 complex (FIG. 21B). These results indicated that the interaction between these two TALE HD proteins and P1 was specific and that StBEL-05 bound to P1 more strongly than to P3. It is highly likely then that P1 contains the cis element that functions with this protein complex in planta. The tobacco KNOX protein, NTH15, binds to both the promoter and the first intron of GA20 oxidase, but with higher affinity to the first intron (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety). NTH15 is not the tobacco homolog of POTH1 and this may explain the disparity in binding affinities. No BEL partners were tested for binding with the tobacco KNOX protein or the GA20 oxidase promoter.

Several consensus binding sites for KNOX proteins have been identified from either target gene promoters or in vitro binding site selection by using KNOX HD proteins from barley (Krusell et al., "DNA Binding Sites Recognized in Vitro by a Knotted Class 1 Homeodomain Protein Encoded by the Hooded Gene, K, in Barley (*Hordeum vulgare*)," *FEBS Lett.* 408:25-29 (1997), which is hereby incorporated by reference in its entirety, tobacco (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety), and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety). Because the homeodomains, especially the third α-helix in the HD region, of these KNOX proteins are almost identical, the consensus sequences recognized by them share a core TGTCAC motif (Nagasaki et al., "Functional Analysis of the Conserved Domains of a Rice KNOX Homeodomain Protein, OSH15," *Plant Cell* 13:2085-2098 (2001), which is hereby incorporated by reference in its entirety). Two interacting TALE proteins of vertebrates, Meis1 and Pbx1, dimerize on the composite DNA sequence, TGATTGACAG (SEQ ID NO:28), containing 5'-Pbx and 3'-Meis half sites (Chang et al., "Meis Proteins are Major in Vivo DNA Binding Partners for Wild-Type But Not Chimeric Pbx Proteins," *Mol. Cell. Biol.* 7:5679-5687 (1997), which is hereby incorporated by reference in its entirety). Using random oligonucleotide selection, the consensus sequence, TGACAG(G/C)T (SEQ ID NO:25), was identified for the *Arabidopsis* BEL-KNOX heterodimeric complex (Smith et al., "Selective Interaction of Plant Homeodomain Proteins Mediates High DNA-Binding Affinity," *Proc. Natl. Acad. Sci.* 99:9579-9584 (2002), which is hereby incorporated by reference in its entirety). Because the StBEL-05-POTH1-P1 complex requires both proteins to bind the target DNA, and increased amounts of the StBEL-05 homeodomain lead to a supershifted band, this indicates that there are two closely located TALE homeodomain binding sites in the P1 region similar to the two half binding sites for Meis1 and Pbx1 (Chang et al., "Meis Proteins are Major in Vivo DNA Binding Partners for Wild-Type But Not Chimeric Pbx Proteins," *Mol. Cell. Biol.* 7:5679-5687 (1997), which is hereby incorporated by reference in its entirety). Based on these results and comparisons to the known binding motifs, a potential StBEL5-POTH1 binding site, TTGACTTGAC (SEQ ID NO:25), has been identified in the P1 fragment. Gel-retardation assays confirmed that this oligo was sufficient for binding to StBEL-05, POTH1, and StBEL5-POTH1. Mutational gel-retardation analysis of this BEL-KNOX binding site showed that the StBEL-05-POTH1 heterodimer recognizes the 9-bp sequence, TGA(C/G)(T/A)TGAC (SEQ ID NO:27), containing two TGAC cores. StBEL-05 and POTH1 could bind to either one of the TGAC cores, because serial mutations had no effect on the DNA-binding ability of StBEL-05 or POTH1.

It has been a paradox for HD proteins regarding their high level of functional specificity in directing developmental programs and their high degree of redundancy in binding site specificity. Besides the low affinity and high redundancy in binding sites, the 5-base consensus sequences recognized by HD proteins randomly show up on average once every 1.0 kb in eukaryotic genomes (Mann et al., "Extra Specificity From Extradenticle: The Partnership Between Hox and Exd-Pbx Homeodomain Proteins. *Trends Genet.* 12:258-262 (1996), which is hereby incorporated by reference in its entirety). Therefore, it is likely that interaction with other DNA-binding transcription factors is necessary for HDs to affect binding affinity and specificity. Monomeric HD proteins have modest specificity for DNA binding, but their specificity is greatly increased through cooperative binding with other DNA binding partners (Mann et al., "Extra Specificity From Extradenticle: The Partnership Between Hox and Exd-Pbx Homeodoamin Proteins. *Trends Genet.* 12:258-262 (1996), which is hereby incorporated by reference in its entirety). The gel-retardation assays also showed that StBEL-05 and POTH1 in tandem formed a complex with P1 with greater signal intensity than either POTH1-P1 or StBEL5-P1 complexes (FIG. 18A), and that the StBEL-05-POTH1-DNA complex had a much slower dissociation rate (FIG. 22). Both of these results indicate that the BEL-KNOX heterodimer has an increased binding affinity for the target site.

Example 43—Discussion: STBEL-05-POTH1 Heterodimer Mediates the Repression of the ga20ox1 Promoter The previous examples showed that both StBEL-05 and POTH1 overexpression mutants exhibited decreased ga20ox1 mRNA levels in stolons and leaves, respectively (see Examples 1-32). Gel-retardation assay results showed that these two transcription factors bound to the promoter and the first intron of ga20ox1. These results indicate that StBEL-05 and POTH1 directly represses ga20ox1 transcription by binding to the promoter region. Results from the transcription assay showed that either StBEL-05 or POTH1 alone could repress reporter gene activity by more than 50%. The fact that neither POTH1 nor StBEL-05 affected CaMV 35S promoter activity (FIG. 24C) confirmed that such repression was not due to inhibition of the general transcription machinery. Direct repression of GA20 oxidase gene transcription by the KNOX protein NTH15 has also been reported in tobacco (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety).

Although either StBEL-05 or POTH1 could repress ga20ox1 promoter in the transcription assay, the KNOX-BEL heterodimers were possibly still formed with endogenous partners to function in tobacco protoplasts. There are three lines of evidence to support this possibility. First, of the seven BEL proteins identified in potato, all seven interacted with four tobacco KNOX proteins (see above). Second, the protein binding domains of the tobacco KNOX NTHs were most important in determining the severity of transgenic plant phenotypes (Sakamoto et al., "The Conserved KNOX Domain Mediates Specificity of Tobacco KNOTTED-1 type Homeodomain Proteins. *Plant Cell* 11:1419-1431 (1999), which is hereby incorporated by reference in its entirety), implying that interaction with protein partners, most probably the BEL1-like proteins, is essential for KNOX function. Third, the identification of BEL-KNOX binding sites (Smith et al., "Selective Interaction Of Plant Homeodomain Proteins Mediates High DNA-Binding Affinity. *Proc. Natl. Acad. Sci.* 99:9579-9584 (2002), which is hereby incorporated by reference in its entirety) and the StBEL-05-POTH1 binding site in this study, further implies that the BEL-KNOX dimer is involved in the regulation of target genes. In the transcription assays, constructs of the dominant negatives, StBEL5ΔC295 or POTH1ΔC122, abolished the repression activity of StBEL-05 or POTH1, respectively (FIG. 25). Therefore, StBEL-05 or POTH1 protein alone is not sufficient for the repression of ga20ox1 promoter. The BEL-KNOX heterodimeric complex is required for repression of transcription to occur.

Figure 27:
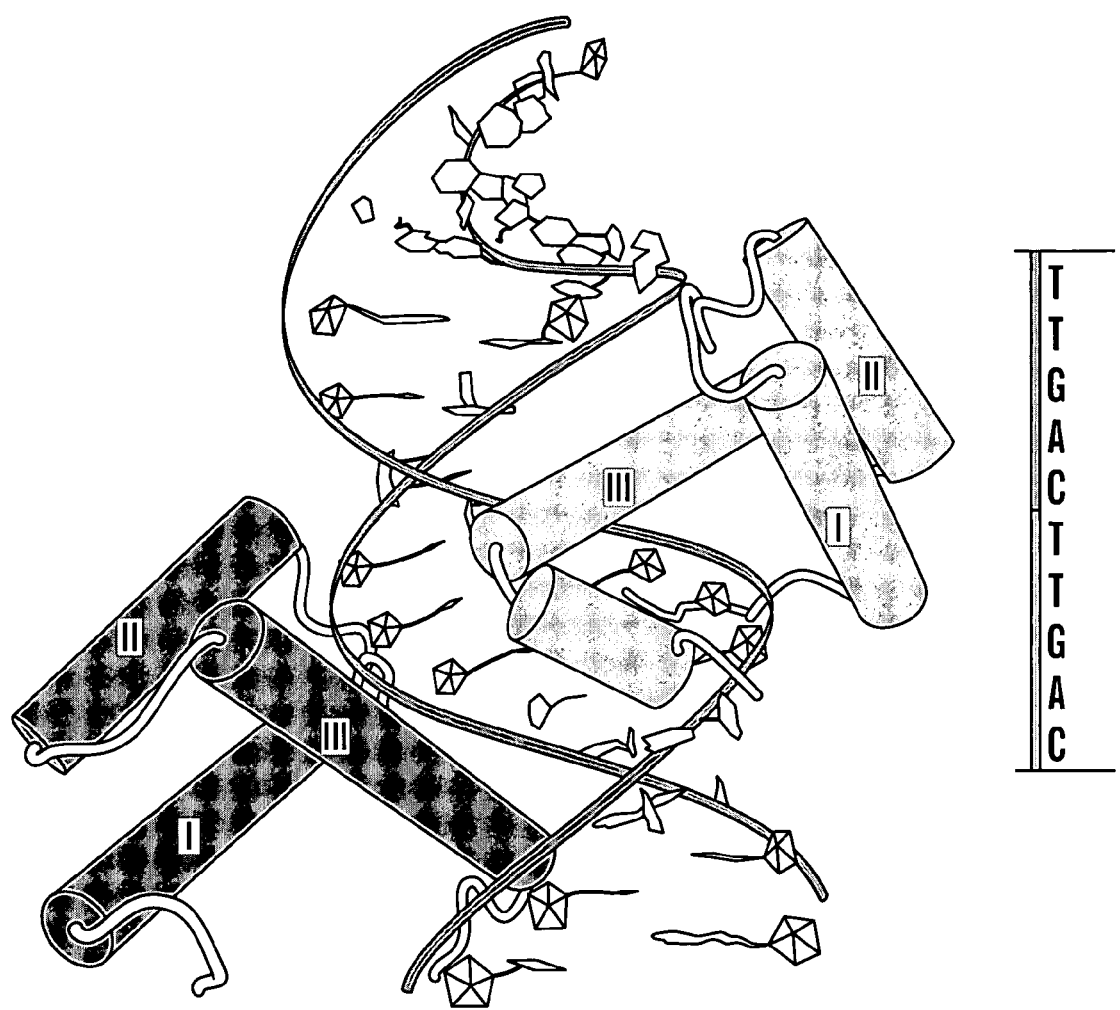
FIG. 27 shows a model of BEL/KNOX binding to target DNA. Light grey=StBEL-05 homeodomain; dark grey=POTH1 homeodomain. The three helices are indicated as I, II, or III. The schematics of protein structure presented here are not drawn to scale to enhance visual clarity. The third helix of the homeodomains of both POTH1 and StBEL-05 fit in the major groove of the DNA double helix.

The results above showed that the mutated P1 binding site of the ga20ox1 promoter did not respond to StBEL-05-POTH1-mediated repression, indicating that this binding site functions as a cis-element for the StBEL-05-POTH1 heterodimer. Based on the results from gel-retardation analysis of serial mutations in this site, the mutated promoter was capable of binding with StBEL-05 or POTH1 separately, but not the StBEL-05-POTH1 heterodimer. This is further evidence that it is the BEL-KNOX heterodimer and not the individual BEL or KNOX proteins that affect repression. The interaction of StBEL-05/POTH1 to affect transcription is summarized in the model of FIG. 27. The partner proteins interact through conserved protein binding domains. For StBEL-05, this includes the two amino-terminal helices of the BELL domain and the sky box (Chen et al., "Interacting Transcription Factors From the TALE Superclass Regulate Tuber Formation," *Plant Physiol.* (in press) (2003), which is hereby incorporated by reference in its entirety). For POTH1, this includes the KNOX domain with Knox II playing the most significant role (Sakamoto et al., "The Conserved KNOX Domain Mediates Specificity of Tobacco KNOTTED-1 type Homeodomain Proteins. *Plant Cell* 11:1419-1431 (1999), which is hereby incorporated by reference in its entirety). The sky box contributes to the tandem formation and interacts weakly with Knox I. Interaction between the respective protein binding domains and the spatial arrangement of the first two helices of the homeodomain bring the third helices of both TFs together in a major groove of the DNA helix. Specificity is then provided within the spatial constraints of the three components (StBEL-05, POTH1, and the helical groove) through recognition of the binding motif. In this case, the BEL/KNOX complex may repress transcription by interfering with the binding of critical components of the transcriptional machinery. Other BEL/KNOX complexes may affect gene expression differentially by recognizing other cis-elements as a result of slight modifications in protein structure.

The results indicate that similar to HDs in animals, collaboration of HD proteins to modulate the expression of target genes also occurs in plants. The interaction of HD proteins not only enhances their DNA-binding affinity, but also imparts another level of regulation to these complexes in fine-tuning developmental processes. It is very likely that the numerous potential BEL/KNOX protein interactions participate in a comprehensive system of regulation that coordinates plant growth.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated nucleic acid molecule encoding a BEL transcription factor from *Solanum tuberosum*, wherein said isolated nucleic acid molecule:
   (a) comprises the nucleotide sequence of SEQ ID NO:1; or
   (b) hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant results in tuber formation in the transgenic plant when grown under long-day conditions; or
   (c) encodes a protein or polypeptide comprising the amino acid sequence of SEQ ID NO:2.

2. The isolated nucleic acid molecule according to claim 1, wherein the nucleic acid molecule has the nucleotide sequence of SEQ ID NO:1.

3. The isolated nucleic acid molecule according to claim 1, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant results in tuber formation in the transgenic plant when grown under long-day conditions.

4. The isolated nucleic acid molecule according to claim 1, wherein the nucleic acid molecule encodes a protein or polypeptide comprising the amino acid sequence of SEQ ID NO:2.

5. A DNA construct comprising:
   the nucleic acid molecule according to claim 1, and
   an operably linked promoter and 3' regulatory region.

6. An expression vector comprising the DNA construct of claim 5.

7. The expression vector according to claim 6, wherein the nucleic acid molecule is in proper sense orientation and correct reading frame.

8. A host cell transduced with the nucleic acid molecule according to claim 1.

9. The host cell according to claim 8, wherein the cell is selected from the group consisting of a bacterial cell, a virus, a yeast cell, an insect cell, a plant cell, and an isolated mammalian cell.

10. A transgenic plant transformed with the nucleic acid molecule according to claim 1.

11. The transgenic plant according to claim 10, wherein the nucleic acid molecule has the nucleotide sequence of SEQ ID NO:1.

12. The transgenic plant according to claim 10, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in the transgenic plant results in tuber formation in the transgenic plant when grown under long-day conditions.

13. The transgenic plant according to claim 10, wherein the nucleic acid molecule encodes a protein or polypeptide comprising the amino acid sequence of SEQ ID NO:2.

14. The transgenic plant according to claim 10, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labiatae, Solanaceae, Cucurbitaceae, Compositae, and Rubiaceae.

15. A transgenic plant seed transformed with the nucleic acid molecule according to claim 1.

16. The transgenic plant seed according to claim 15, wherein the nucleic acid molecule has the nucleotide sequence of SEQ ID NO:1.

17. The transgenic plant seed according to claim 15, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant grown from the transgenic plant seed results in tuber formation in the transgenic plant when grown under long-day conditions.

18. The transgenic plant seed according to claim 15, wherein the nucleic acid molecule encodes a protein or polypeptide comprising the amino acid sequence of SEQ ID NO:2.

19. The transgenic plant seed according to claim 15, wherein the plant seed is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labiatae, Solanaceae, Cucurbitaceae, Compositae, and Rubiaceae.

20. A method for increasing rate of growth of a plant comprising: transforming a plant with the DNA construct according to claim 5, whereby the rate of growth of the plant is increased compared to a non-transformed plant of the same species.

21. The method according to claim 20, wherein the nucleic acid molecule has the nucleotide sequence of SEQ ID NO:1.

22. The method according to claim 20, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in the transgenic plant results in tuber formation in the transgenic plant when grown under long-day conditions.

23. The method according to claim 20, wherein the nucleic acid molecule encodes a protein or polypeptide comprising the amino acid sequence of SEQ ID NO:2.

24. The method according to claim 20, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labiatae, Solanaceae, Cucurbitaceae, Compositae, and Rubiaceae.

25. The DNA construct according to claim 5, wherein the nucleic acid molecule has the nucleotide sequence of SEQ ID NO:1.

26. The DNA construct according to claim 5, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant results in tuber formation in the transgenic plant when grown under long-day conditions.

27. The DNA construct according to claim 5, wherein the nucleic acid molecule encodes a protein or polypeptide comprising the amino acid sequence of SEQ ID NO:2.

28. The expression vector according to claim 6, wherein the nucleic acid molecule has the nucleotide sequence of SEQ ID NO:1.

29. The expression vector according to claim 6, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant results in tuber formation in the transgenic plant when grown under long-day conditions.

30. The expression vector according to claim 6, wherein the nucleic acid molecule encodes a protein or polypeptide comprising the amino acid sequence of SEQ ID NO:2.

31. The host cell according to claim 8, wherein the nucleic acid molecule has the nucleotide sequence of SEQ ID NO:1.

32. The host cell according to claim 8, wherein the nucleic acid molecule hybridizes to the nucleotide sequence of SEQ ID NO:1 under high stringency conditions characterized by hybridization in a buffer of 4-5×SSC/0.1% w/v SDS at 54° C. for 1-3 hours and in 4×SSC at 65° C., followed by a washing in 0.1×SSC at 65° C. for about one hour, wherein overexpression of the BEL transcription factor in a transgenic plant results in tuber formation in the transgenic plant when grown under long-day conditions.

33. The host cell according to claim 8, wherein the nucleic acid molecule encodes a protein or polypeptide comprising the amino acid sequence of SEQ ID NO:2.

* * * * *

SEQUENCE LISTING

```
<160> NUMBER OF SEQ ID NOS: 28

<210> SEQ ID NO 1
<211> LENGTH: 2735
<212> TYPE: DNA
<213> ORGANISM: Solanum tuberosum

<400> SEQUENCE: 1
catgcagaga taaaaatata gatcagtctg acaagaaggc aacttctcaa agcttagaga      60
gctaccaccc gaagatagac agttagttac atgtactgtt atagataaaa ggagaaatcc     120
gaagaagaaa gaattttttt tgcagatatg tactatcaag gaacctcgga taatactaat     180
atacaagctg atcatcaaca acgtcataat catgggaata gtaataataa taatattcag     240
acactttatt tgatgaaccc taacaattat atgcaaggct acactacttc tgacacacag     300
cagcagcagc agttacttt cctgaattct tcaccagcag caagcaacgc gctttgccat      360
gcgaatatac aacacgcgcc gctgcaacag cagcactttg tcggtgtgcc tcttccggca     420
gtaagtttgc acgatcagat caatcatcat ggacttttac agcgcatgtg gaacaaccaa     480
gatcaatctc agcaggtgat agtaccatcg tcgacggggg tttctgccac gtcatgtggc     540
```

-continued

```
gggatcacca cggacttggc gtctcaattg gcgtttcaga ggccgattcc gacaccacaa      600
caccgacagc agcaacaaca gcaaggcggt ctatctctaa gcctttctcc tcagctacaa      660
cagcaaatta gtttcaataa caatatttca tcctcatcac caaggacaaa taatgttact      720
attagggaa cattagatgg aagttctagc aacatggttt taggctctaa gtatctgaaa      780
gctgcacaag agcttcttga tgaagttgtt aatattgttg gaaaaagcat caaaggagat      840
gatcaaaaga aggataattc aatgaataaa gaatcaatgc ctttggctag tgatgtcaac      900
actaatagtt ctggtggtgg tgaaagtagc agcaggcaga aaaatgaagt tgctgttgag      960
cttacaactg ctcaaagaca agaacttcaa atgaaaaaag ccaagcttct tgccatgctt     1020
gaagaggtgg agcaaaggta cagacagtac catcaccaaa tgcaaataat tgtattatca     1080
tttgagcaag tagcaggaat tggatcagcc aaatcataca ctcaattagc tttgcatgca     1140
atttcgaagc aattcagatg cctaaaggat gcaattgctg agcaagtaaa ggcgacgagc     1200
aagagtttag gtgaagagga aggcttggga gggaaaatcg aaggctcaag actcaaattt     1260
gtggaccatc atctaaggca acaacgcgcg ctgcaacaga taggaatgat gcaaccaaat     1320
gcttggagac cccaaagagg tttacctgaa agagctgtct ctgtccttcg tgcttggctt     1380
ttcgagcatt ttcttcatcc ttacccaaag gattcagaca aaatcatgct tgctaagcaa     1440
acggggctaa caaggagcca ggtgtctaac tggttcataa atgctcgagt tcgattatgg     1500
aagccaatgg tagaagaaat gtacttggaa gaagtgaaga atcaagaaca aaacagtact     1560
aatacttcag gagataacaa aaacaaagag accaatataa gtgctccaaa tgaagagaaa     1620
catccaatta ttactagcag cttattacaa gatggtatta ctactactca agcagaaatt     1680
tctacctcaa ctatttcaac ttcccctact gcaggtgctt cacttcatca tgctcacaat     1740
ttctccttcc ttggttcatt caacatggat aatactacta ctactgttga tcatattgaa     1800
aacaacgcga aaaagcaaag aaatgacatg cacaagtttt ctccaagtag tattctttca     1860
tctgttgaca tggaagccaa agctagagaa tcatcaaata aagggtttac taatcccttta     1920
atggcagcat acgcgatggg agattttgga aggtttgatc ctcatgatca acaaatgacc     1980
gcgaattttc atggaaataa tggtgtctct cttactttag gacttcctcc ttctgaaaac     2040
ctagccatgc cagtgagcca acaaaattac ctttctaatg acttgggaag taggtctgaa     2100
atggggagtc attacaatag aatgggatat gaaaacattg atttttcagag tgggaataag     2160
cgatttccga ctcaactatt accagatttt gttacaggta atctaggaac atgaatacca     2220
gaaagtctcg tattgatagc tgaaaagata aaggaagtt agggatactc ttatattgtg     2280
tgaggccttc tggcccaagt cggaggaccc aatttgatac aacctatcat aggagaaaag     2340
aagtggagac taaattaaag taacaaaatt ttaaagcaca ctttctagta tatatacttc     2400
ttttttttat agtatagaaa agaagagatt ttgtgcttta gtgtatagat agagtctact     2460
tagtataggt tatacttcta gttccttgag aagattgata caactagtag tattttttt      2520
cttttgggtt ggcttggagt actatttta gttattggaa actagctata gtaaatgttg      2580
taaagttgtg atattgttcc tctcaatttg catataattt gaaatatttt gtacctacta     2640
gctagtctct aaattatgtt tccattgctt gtaattgcaa ttttatttga attttgtgct     2700
atcattatta gattagcaaa aaaaaaaaa aaaaa                                 2735
```

<210> SEQ ID NO 2
<211> LENGTH: 688
<212> TYPE: PRT
<213> ORGANISM: Solanum tuberosum -continued

```
<400> SEQUENCE: 2

Met Tyr Tyr Gln Gly Thr Ser Asp Asn Thr Asn Ile Gln Ala Asp His
1               5                   10                  15

Gln Gln Arg His Asn His Gly Asn Ser Asn Asn Asn Ile Gln Thr
            20                  25                  30

Leu Tyr Leu Met Asn Pro Asn Asn Tyr Met Gln Gly Tyr Thr Thr Ser
        35                  40                  45

Asp Thr Gln Gln Gln Gln Leu Leu Phe Leu Asn Ser Ser Pro Ala
    50                  55                  60

Ala Ser Asn Ala Leu Cys His Ala Asn Ile Gln His Ala Pro Leu Gln
65              70                  75                  80

Gln Gln His Phe Val Gly Val Pro Leu Pro Ala Val Ser Leu His Asp
            85                  90                  95

Gln Ile Asn His His Gly Leu Leu Gln Arg Met Trp Asn Asn Gln Asp
            100                 105                 110

Gln Ser Gln Gln Val Ile Val Pro Ser Ser Thr Gly Val Ser Ala Thr
        115                 120                 125

Ser Cys Gly Gly Ile Thr Thr Asp Leu Ala Ser Gln Leu Ala Phe Gln
    130                 135                 140

Arg Pro Ile Pro Thr Pro Gln His Arg Gln Gln Gln Gln Gln Gln Gly
145                 150                 155                 160

Gly Leu Ser Leu Ser Leu Ser Pro Gln Leu Gln Gln Ile Ser Phe
            165                 170                 175

Asn Asn Asn Ile Ser Ser Ser Pro Arg Thr Asn Asn Val Thr Ile
            180                 185                 190

Arg Gly Thr Leu Asp Gly Ser Ser Asn Met Val Leu Gly Ser Lys
        195                 200                 205

Tyr Leu Lys Ala Ala Gln Glu Leu Leu Asp Glu Val Val Asn Ile Val
    210                 215                 220

Gly Lys Ser Ile Lys Gly Asp Asp Gln Lys Lys Asp Asn Ser Met Asn
225                 230                 235                 240

Lys Glu Ser Met Pro Leu Ala Ser Asp Val Asn Thr Asn Ser Ser Gly
                245                 250                 255

Gly Gly Glu Ser Ser Ser Arg Gln Lys Asn Glu Val Ala Val Glu Leu
            260                 265                 270

Thr Thr Ala Gln Arg Gln Glu Leu Gln Met Lys Lys Ala Lys Leu Leu
        275                 280                 285

Ala Met Leu Glu Glu Val Glu Gln Arg Tyr Arg Gln Tyr His His Gln
290                 295                 300

Met Gln Ile Ile Val Leu Ser Phe Glu Gln Val Ala Gly Ile Gly Ser
305                 310                 315                 320

Ala Lys Ser Tyr Thr Gln Leu Ala Leu His Ala Ile Ser Lys Gln Phe
            325                 330                 335

Arg Cys Leu Lys Asp Ala Ile Ala Glu Gln Val Lys Ala Thr Ser Lys
        340                 345                 350

Ser Leu Gly Glu Glu Gly Leu Gly Lys Ile Glu Gly Ser Arg
    355                 360                 365

Leu Lys Phe Val Asp His His Leu Arg Gln Gln Arg Ala Leu Gln Gln
    370                 375                 380

Ile Gly Met Met Gln Pro Asn Ala Trp Arg Pro Gln Arg Gly Leu Pro
385                 390                 395                 400

Glu Arg Ala Val Ser Val Leu Arg Ala Trp Leu Phe Glu His Phe Leu
```

```
                405                 410                 415
His Pro Tyr Pro Lys Asp Ser Asp Lys Ile Met Leu Ala Lys Gln Thr
            420                 425                 430

Gly Leu Thr Arg Ser Gln Val Ser Asn Trp Phe Ile Asn Ala Arg Val
            435                 440                 445

Arg Leu Trp Lys Pro Met Val Glu Met Tyr Leu Glu Glu Val Lys
            450                 455                 460

Asn Gln Glu Gln Asn Ser Thr Asn Thr Ser Gly Asp Asn Lys Asn Lys
465                 470                 475                 480

Glu Thr Asn Ile Ser Ala Pro Asn Glu Glu Lys His Pro Ile Ile Thr
                485                 490                 495

Ser Ser Leu Leu Gln Asp Gly Ile Thr Thr Thr Gln Ala Glu Ile Ser
                500                 505                 510

Thr Ser Thr Ile Ser Thr Ser Pro Thr Ala Gly Ala Ser Leu His His
            515                 520                 525

Ala His Asn Phe Ser Phe Leu Gly Ser Phe Asn Met Asp Asn Thr Thr
            530                 535                 540

Thr Thr Val Asp His Ile Glu Asn Asn Ala Lys Lys Gln Arg Asn Asp
545                 550                 555                 560

Met His Lys Phe Ser Pro Ser Ile Leu Ser Ser Val Asp Met Glu
                565                 570                 575

Ala Lys Ala Arg Glu Ser Ser Asn Lys Gly Phe Thr Asn Pro Leu Met
            580                 585                 590

Ala Ala Tyr Ala Met Gly Asp Phe Gly Arg Phe Asp Pro His Asp Gln
            595                 600                 605

Gln Met Thr Ala Asn Phe His Gly Asn Asn Gly Val Ser Leu Thr Leu
            610                 615                 620

Gly Leu Pro Pro Ser Glu Asn Leu Ala Met Pro Val Ser Gln Gln Asn
625                 630                 635                 640

Tyr Leu Ser Asn Asp Leu Gly Ser Arg Ser Glu Met Gly Ser His Tyr
                645                 650                 655

Asn Arg Met Gly Tyr Glu Asn Ile Asp Phe Gln Ser Gly Asn Lys Arg
            660                 665                 670

Phe Pro Thr Gln Leu Leu Pro Asp Phe Val Thr Gly Asn Leu Gly Thr
            675                 680                 685

<210> SEQ ID NO 3
<211> LENGTH: 1898
<212> TYPE: DNA
<213> ORGANISM: Solanum tuberosum

<400> SEQUENCE: 3
atgactttca ggtctagtct tccactagac ctccgtgaaa tttcaacaac aaatcatcaa    60
gttggaatac tatcatcatc accattacca tcaccaggaa caaataccaa taatatcaat   120
catactcgag gattaggggc atcatcatct ttttcgattt ctaatgggat gatattgggt   180
tctaagtacc taaagttgc acaagatctt cttgatgaag ttgttaatgt tggaaaaaac   240
atcaaattat cagatggctt agagagtggt gcaaaggaga acacaaatt ggacaatgaa   300 ttaatatctt tggctagtga tgatgttgaa agcagcagcc aaaaaaatag tggtgttgaa   360
cttacaacag ctcaaagaca agaacttcaa atgaagaaag ccaagcttgt tagcatgctt   420
gatgaggtgg atcaaggta tagacaatac catcaccaaa tgcaaatgat tgcaacatca   480
tttgagcaaa caacaggaat tggatcatca aaatcataca cacaacttgc tttgcacaca   540
```

```
atttcaaagc aatttagatg tttaaaagat gcaatttctg ggcaaataaa ggacactagc      600
aaaactttag gggaagaaga aaacattgga ggcaaaattg aaggatcaaa gttgaaattt      660
gtggatcatc atttacgcca acaacgtgca ctacaacaat tagggatgat gcaaaccaat      720
gcatggaagc ctcaaagagg tttgccagaa agagcggttt cagttctccg cgcttggctt      780
ttcgagcatt ttcttcatcc gtatcccaaa gattcagata aaatcatcct tgctaagcaa      840
acagggctaa caaggagcca ggtatcaaat tggtttataa atgctagagt tagactatgg      900
aagccaatgg tagaagaaat gtacatggaa gaagtgaaga aaaacaatca gaacaaaat       960
attgagccta ataacaatga aattgttggc tcaaaatcaa gtgttccaca agagaaatta     1020
ccaattagta gcaatattat tcataatgct tctccaaatg atatttctac ttccaccatt     1080
tcaacatctc cgacgggtgg cggcggttcg attccgactc agacggttgc aggtttctcc     1140
ttcattaggt cattaaacat ggagaacatt gatgatcaaa ggaacaacaa aaaggcaaga     1200
aatgagatgc aaaattgttc aactagtact attctctcaa tggaaagaga atcataaat      1260
aaagttgtgc aagatgagac aatcaaaagt gaaaagttca acaacacaca acaagagaa      1320
tgttactctc taatgactcc aaattacaca atggatgatc aatttggaac aaggttcaat     1380
aatcaaaatc atgaacaatt ggcaacaaca acaacttttc atcaaggaaa tggtcatgtt     1440
tctcttactt tagggcttcc accaaattct gaaaaccaac acaattacat tggattggaa     1500
atcattaca atcaacctac acatcatcca aatattagct atgaaaacat tgatttttcag    1560
agtggaaagc gatacgccac tcaactatta caagattttg tttcttgatg atatatataa     1620
tttgcaggta aatcagcttg aaattacatc atgacaggtc ttgaataaaa gaaggggagt     1680
tgagatttag tgatcatata aatatgtata ggtagaaatt ttagttagta tatataggtt     1740
atacttctag tttcttaatg aagatacaag ttttgttgtt attttttgtat tgaggtaact     1800
agctagcttg gattatttaa agttggtgca tgcaactaaa gaagaagaaa aaataatcta     1860
tatatgcaaa ctacagtata ttgtaaattt tgtgcttc                             1898
```

<210> SEQ ID NO 4
<211> LENGTH: 535
<212> TYPE: PRT
<213> ORGANISM: Solanum tuberosum

<400> SEQUENCE: 4

```
Met Thr Phe Arg Ser Ser Leu Pro Leu Asp Leu Arg Glu Ile Ser Thr
  1               5                  10                  15

Thr Asn His Gln Val Gly Ile Leu Ser Ser Ser Pro Leu Pro Ser Pro
             20                  25                  30

Gly Thr Asn Thr Asn Asn Ile Asn His Thr Arg Gly Leu Gly Ala Ser
         35                  40                  45

Ser Ser Phe Ser Ile Ser Asn Gly Met Ile Leu Gly Ser Lys Tyr Leu
     50                  55                  60

Lys Val Ala Gln Asp Leu Leu Asp Glu Val Val Asn Val Gly Lys Asn
 65                  70                  75                  80

Ile Lys Leu Ser Asp Gly Leu Glu Ser Gly Ala Lys Glu Lys His Lys
                 85                  90                  95

Leu Asp Asn Glu Leu Ile Ser Leu Ala Ser Asp Val Glu Ser Ser
            100                 105                 110

Ser Gln Lys Asn Ser Gly Val Glu Leu Thr Thr Ala Gln Arg Gln Glu
        115                 120                 125

Leu Gln Met Lys Lys Ala Lys Leu Val Ser Met Leu Asp Glu Val Asp
```

```
            130                 135                 140
Gln Arg Tyr Arg Tyr His His Gln Met Gln Met Ile Ala Thr Ser
145                 150                 155                 160

Phe Glu Gln Thr Thr Gly Ile Gly Ser Ser Lys Ser Tyr Thr Gln Leu
                165                 170                 175

Ala Leu His Thr Ile Ser Lys Gln Phe Arg Cys Leu Lys Asp Ala Ile
                180                 185                 190

Ser Gly Gln Ile Lys Asp Thr Ser Lys Thr Leu Gly Glu Glu Asn
            195                 200                 205

Ile Gly Gly Lys Ile Glu Gly Ser Lys Leu Lys Phe Val Asp His His
210                 215                 220

Leu Arg Gln Gln Arg Ala Leu Gln Gln Leu Gly Met Met Gln Thr Asn
225                 230                 235                 240

Ala Trp Lys Pro Gln Arg Gly Leu Pro Glu Arg Ala Val Ser Val Leu
                245                 250                 255

Arg Ala Trp Leu Phe Glu His Phe Leu His Pro Tyr Pro Lys Asp Ser
            260                 265                 270

Asp Lys Ile Ile Leu Ala Lys Gln Thr Gly Leu Thr Arg Ser Gln Val
        275                 280                 285

Ser Asn Trp Phe Ile Asn Ala Arg Val Arg Leu Trp Lys Pro Met Val
        290                 295                 300

Glu Glu Met Tyr Met Glu Glu Val Lys Lys Asn Asn Gln Glu Gln Asn
305                 310                 315                 320

Ile Glu Pro Asn Asn Glu Ile Val Gly Ser Lys Ser Val Pro
                325                 330                 335

Gln Glu Lys Leu Pro Ile Ser Ser Asn Ile Ile His Asn Ala Ser Pro
            340                 345                 350

Asn Asp Ile Ser Thr Ser Thr Ile Ser Thr Ser Pro Thr Gly Gly Gly
        355                 360                 365

Gly Ser Ile Pro Thr Gln Thr Val Ala Gly Phe Ser Phe Ile Arg Ser
    370                 375                 380

Leu Asn Met Glu Asn Ile Asp Asp Gln Arg Asn Asn Lys Lys Ala Arg
385                 390                 395                 400

Asn Glu Met Gln Asn Cys Ser Thr Ser Thr Ile Leu Ser Met Glu Arg
                405                 410                 415

Glu Ile Ile Asn Lys Val Val Gln Asp Glu Thr Ile Lys Ser Glu Lys
                420                 425                 430

Phe Asn Asn Thr Gln Thr Arg Glu Cys Tyr Ser Leu Met Thr Pro Asn
            435                 440                 445

Tyr Thr Met Asp Asp Gln Phe Gly Thr Arg Phe Asn Asn Gln Asn His
    450                 455                 460

Glu Gln Leu Ala Thr Thr Thr Phe His Gln Gly Asn Gly His Val
465                 470                 475                 480

Ser Leu Thr Leu Gly Leu Pro Pro Asn Ser Glu Asn Gln His Asn Tyr
                485                 490                 495

Ile Gly Leu Glu Asn His Tyr Asn Gln Pro Thr His Pro Asn Ile
            500                 505                 510

Ser Tyr Glu Asn Ile Asp Phe Gln Ser Gly Lys Arg Tyr Ala Thr Gln
        515                 520                 525

Leu Leu Gln Asp Phe Val Ser
530                 535

<210> SEQ ID NO 5
```

<211> LENGTH: 1920
<212> TYPE: DNA
<213> ORGANISM: Solanum tuberosum

<400> SEQUENCE: 5

```
ggggagcgag tggttccgac aaggtatggt aatgggtgga ggtgcaagta gtcaacaatt      60
gggatatgca aaaatcata ctcctaatgt ggcggagtcc atgcaacttt ttctaatgaa      120
tccacaacca aggtcacctt ctccatctcc tcctaattca acttcttcta cgcttcacat     180
gttgttacca aacccatcat ctacttcaac acttcaaggg tttcctaatc cggccgaagg     240
atctttcggt caattcatta catggggaa tggaggagca agtgctgcca cagccaccca     300
tcatctcaat gcccagaatg aaatcggagg agtaaacgtt gtagaaagtc aaggcctatc     360
tctatccttg tcttcttcgt tacagcacaa ggcggaggaa ttacaaatga gcggagaagc     420
tggaggaatg atgttcttca atcaaggagg gtctagtact tccgggcagt atcgatacaa     480
gaatttgaat atgggtggat caggagtaag cccaaacatt catcaagtcc atgttgggta     540
tgggtcatca ttaggagtgg tcaatgtgtt gaggaattcc aaatacgcga agctgccca      600
agaactactg gaagaattct gcagtgttgg aagaggtaaa ttgaagaaga ctaacaacaa     660
agcagcagcc aataaccta atacgaaccc tagtggcgct aacaatgaag cttcttcaaa     720
agatgttcct actttgtccg ctgctgatag aattgagcat cagagaagga aggtcaaact     780
tttatctatg gttgatgagg tagataggag gtacaatcat tactgtgaac aaatgcagat     840
ggttgtaaat tcgtttgatt tagtgatggg tttcggcaca gcagttccct acacagcact     900
tgcacagaag gcaatgtcaa gacatttcag gtgtttaaag gatgcaatag gagcacaatt     960
gaagcagagt tgtgagttat taggagagaa agatgcagga aattcgggat tgactaaagg    1020
agaaactccg aggcttaaga tgcttgaaca aagtttgagg caacaagggg cgtttcacca    1080
aatgggaatg atggaacaag aagcttggag accacaaaga ggcttacctg aacgttctgt    1140
caacatttta agagcttggc tttttgagca ttttctacac ccgtatccaa gtgatgctga    1200
taaacatctg ttggcaagac agactggtct ctccagaaat caggtatcaa attggttcat    1260
taatgctagg gttcggttgt ggaaacccat ggtagaagat atgtatcaac aagaagccaa    1320
agatgaagat ggagatggag atgagaagag ccaaagccaa aacagtggca ataacataat    1380
tgcacaaaca ccaacgccta atagcctgac taacacttca tctactaata tgacgacgac    1440
aacagcccct acaactacga cagctctagc tgctgcagag acaggaacag ctgccactcc    1500
cataactgtt acctcaagca aaagatccca aatcaatgcc acgatagtg accacttcact    1560
tgtagcaatc aattccttct ctgaaaacca agctactttt ccgaccaaca ttcatgatcc    1620
cgacgattgc cgtcgcggca acttatccgg tgacgacggg accaccacac atgatcatat    1680
ggggtccacc atgataaggt ttgggaccac tgctggtgac gtgtcactca ccttagggtt    1740
acgacatgca ggaaatttac cagagaatac tcatttcttt ggttaattaa tacgtattttt   1800
ccccatagta attaattaaa actgaattag cttgagctca tcataattta tgcattgctt    1860
tttgttataa gaaattccat aaattagctt tgtgttaaaa aaaaaaaaa aaaaaaaaa       1920
```

<210> SEQ ID NO 6
<211> LENGTH: 586
<212> TYPE: PRT
<213> ORGANISM: Solanum tuberosum

<400> SEQUENCE: 6

Met Val Met Gly Gly Gly Ala Ser Ser Gln Gln Leu Gly Tyr Ala Lys

```
              1               5              10              15
Asn His Thr Pro Asn Val Ala Glu Ser Met Gln Leu Phe Leu Met Asn
                20                  25                  30

Pro Gln Pro Arg Ser Pro Ser Pro Ser Pro Pro Asn Ser Thr Ser Ser
                35                  40                  45

Thr Leu His Met Leu Leu Pro Asn Pro Ser Ser Thr Ser Thr Leu Gln
                50                  55                  60

Gly Phe Pro Asn Pro Ala Glu Gly Ser Phe Gly Gln Phe Ile Thr Trp
 65                  70                  75                  80

Gly Asn Gly Gly Ala Ser Ala Ala Thr Ala Thr His His Leu Asn Ala
                85                  90                  95

Gln Asn Glu Ile Gly Gly Val Asn Val Val Glu Ser Gln Gly Leu Ser
               100                 105                 110

Leu Ser Leu Ser Ser Ser Leu Gln His Lys Ala Glu Glu Leu Gln Met
               115                 120                 125

Ser Gly Glu Ala Gly Gly Met Met Phe Phe Asn Gln Gly Gly Ser Ser
               130                 135                 140

Thr Ser Gly Gln Tyr Arg Tyr Lys Asn Leu Asn Met Gly Gly Ser Gly
145                 150                 155                 160

Val Ser Pro Asn Ile His Gln Val His Val Gly Tyr Gly Ser Ser Leu
               165                 170                 175

Gly Val Val Asn Val Leu Arg Asn Ser Lys Tyr Ala Lys Ala Ala Gln
               180                 185                 190

Glu Leu Leu Glu Glu Phe Cys Ser Val Gly Arg Gly Lys Leu Lys Lys
               195                 200                 205

Thr Asn Asn Lys Ala Ala Ala Asn Asn Pro Asn Thr Asn Pro Ser Gly
210                 215                 220

Ala Asn Asn Glu Ala Ser Ser Lys Asp Val Pro Thr Leu Ser Ala Ala
225                 230                 235                 240

Asp Arg Ile Glu His Gln Arg Arg Lys Val Lys Leu Leu Ser Met Val
               245                 250                 255

Asp Glu Val Asp Arg Arg Tyr Asn His Tyr Cys Glu Gln Met Gln Met
               260                 265                 270

Val Val Asn Ser Phe Asp Leu Val Met Gly Phe Gly Thr Ala Val Pro
               275                 280                 285

Tyr Thr Ala Leu Ala Gln Lys Ala Met Ser Arg His Phe Arg Cys Leu
               290                 295                 300

Lys Asp Ala Ile Gly Ala Gln Leu Lys Gln Ser Cys Glu Leu Leu Gly
305                 310                 315                 320

Glu Lys Asp Ala Gly Asn Ser Gly Leu Thr Lys Gly Glu Thr Pro Arg
               325                 330                 335

Leu Lys Met Leu Glu Gln Ser Leu Arg Gln Arg Ala Phe His Gln
               340                 345                 350

Met Gly Met Met Glu Gln Glu Ala Trp Arg Pro Gln Arg Gly Leu Pro
               355                 360                 365

Glu Arg Ser Val Asn Ile Leu Arg Ala Trp Leu Phe Glu His Phe Leu
               370                 375                 380

His Pro Tyr Pro Ser Asp Ala Asp Lys His Leu Leu Ala Arg Gln Thr
385                 390                 395                 400

Gly Leu Ser Arg Asn Gln Val Ser Asn Trp Phe Ile Asn Ala Arg Val
               405                 410                 415

Arg Leu Trp Lys Pro Met Val Glu Asp Met Tyr Gln Gln Glu Ala Lys
               420                 425                 430
```

```
Asp Glu Asp Gly Asp Gly Asp Glu Lys Ser Gln Ser Gln Asn Ser Gly
            435                 440                 445

Asn Asn Ile Ile Ala Gln Thr Pro Thr Pro Asn Ser Leu Thr Asn Thr
    450                 455                 460

Ser Ser Thr Asn Met Thr Thr Thr Thr Ala Pro Thr Thr Thr Thr Ala
465                 470                 475                 480

Leu Ala Ala Ala Glu Thr Gly Thr Ala Ala Thr Pro Ile Thr Val Thr
                485                 490                 495

Ser Ser Lys Arg Ser Gln Ile Asn Ala Thr Asp Ser Asp Pro Ser Leu
            500                 505                 510

Val Ala Ile Asn Ser Phe Ser Glu Asn Gln Ala Thr Phe Pro Thr Asn
            515                 520                 525

Ile His Asp Pro Asp Asp Cys Arg Arg Gly Asn Leu Ser Gly Asp Asp
        530                 535                 540

Gly Thr Thr Thr His Asp His Met Gly Ser Thr Met Ile Arg Phe Gly
545                 550                 555                 560

Thr Thr Ala Gly Asp Val Ser Leu Thr Leu Gly Leu Arg His Ala Gly
                565                 570                 575

Asn Leu Pro Glu Asn Thr His Phe Phe Gly
            580                 585

<210> SEQ ID NO 7
<211> LENGTH: 2103
<212> TYPE: DNA
<213> ORGANISM: Solanum tuberosum
<220> FEATURE:
<221> NAME/KEY: unsure
<222> LOCATION: (5)
<223> OTHER INFORMATION: N at position 5 is a, c, t, or g
<220> FEATURE:
<221> NAME/KEY: unsure
<222> LOCATION: (1768)
<223> OTHER INFORMATION: N at position 1768 is a, c, t, or g
<220> FEATURE:
<221> NAME/KEY: unsure
<222> LOCATION: (1780)
<223> OTHER INFORMATION: N at position 1780 is a, c, t, or g
<220> FEATURE:
<221> NAME/KEY: unsure
<222> LOCATION: (1783)
<223> OTHER INFORMATION: N at position 1783 is a, c, t, or g
<220> FEATURE:
<221> NAME/KEY: unsure
<222> LOCATION: (1785)
<223> OTHER INFORMATION: N at position 1785 is a, c, t, or g
<220> FEATURE:
<221> NAME/KEY: unsure
<222> LOCATION: (1794)
<223> OTHER INFORMATION: N at position 1794 is a, c, t, or g
<220> FEATURE:
<221> NAME/KEY: unsure
<222> LOCATION: (1802)
<223> OTHER INFORMATION: N at position 1802 is a, c, t, or g
<220> FEATURE:
<221> NAME/KEY: unsure
<222> LOCATION: (1805)
<223> OTHER INFORMATION: N at position 1805  is a, c, t, or g
<220> FEATURE:
<221> NAME/KEY: unsure
<222> LOCATION: (1811)
<223> OTHER INFORMATION: N at position 1811 is a, c, t, or g
<220> FEATURE:
<221> NAME/KEY: unsure
<222> LOCATION: (1813)
<223> OTHER INFORMATION: N at position 1813 is a, c, t, or g
<220> FEATURE:
<221> NAME/KEY: unsure
<222> LOCATION: (1818)
```

-continued

```
<223> OTHER INFORMATION: N at position 1818 is a, c, t, or g
<220> FEATURE:
<221> NAME/KEY: unsure
<222> LOCATION: (1831)
<223> OTHER INFORMATION: N at position 1831 is a, c, t, or g
<220> FEATURE:
<221> NAME/KEY: unsure
<222> LOCATION: (1862)
<223> OTHER INFORMATION: N at position 1862 is a, c, t, or g
<220> FEATURE:
<221> NAME/KEY: unsure
<222> LOCATION: (1869)
<223> OTHER INFORMATION: N at position 1869 is a, c, t, or g
<220> FEATURE:
<221> NAME/KEY: unsure
<222> LOCATION: (1872)
<223> OTHER INFORMATION: N at position 1872 is a, c, t, or g
<220> FEATURE:
<221> NAME/KEY: unsure
<222> LOCATION: (1896)
<223> OTHER INFORMATION: N at position 1896 is a, c, t, or g
<220> FEATURE:
<221> NAME/KEY: unsure
<222> LOCATION: (1911)
<223> OTHER INFORMATION: N at position 1911 is a, c, t, or g
<220> FEATURE:
<221> NAME/KEY: unsure
<222> LOCATION: (1926)
<223> OTHER INFORMATION: N at position 1926 is a, c, t, or g
<220> FEATURE:
<221> NAME/KEY: unsure
<222> LOCATION: (1932)
<223> OTHER INFORMATION: N at position 1932 is a, c, t, or g
<220> FEATURE:
<221> NAME/KEY: unsure
<222> LOCATION: (1960)
<223> OTHER INFORMATION: N at position 1960 is a, c, t, or g
<220> FEATURE:
<221> NAME/KEY: unsure
<222> LOCATION: (1967)
<223> OTHER INFORMATION: N at position 1967 is a, c, t, or g
<220> FEATURE:
<221> NAME/KEY: unsure
<222> LOCATION: (1988)
<223> OTHER INFORMATION: N at position 1988 is a, c, t, or g
<220> FEATURE:
<221> NAME/KEY: unsure
<222> LOCATION: (2002)
<223> OTHER INFORMATION: N at position 2002 is a, c, t, or g
<220> FEATURE:
<221> NAME/KEY: unsure
<222> LOCATION: (2022)
<223> OTHER INFORMATION: N at position 2022 is a, c, t, or g
<220> FEATURE:
<221> NAME/KEY: unsure
<222> LOCATION: (2034)
<223> OTHER INFORMATION: N at position 2034 is a, c, t, or g
<220> FEATURE:
<221> NAME/KEY: unsure
<222> LOCATION: (2036)
<223> OTHER INFORMATION: N at position 2036 is a, c, t, or g
<220> FEATURE:
<221> NAME/KEY: unsure
<222> LOCATION: (2039)
<223> OTHER INFORMATION: N at position 2039 is a, c, t, or g
<220> FEATURE:
<221> NAME/KEY: unsure
<222> LOCATION: (2041)
<223> OTHER INFORMATION: N at position 2041 is a, c, t, or g
<220> FEATURE:
<221> NAME/KEY: unsure
<222> LOCATION: (2049)
<223> OTHER INFORMATION: N at position 2049 is a, c, t, or g
<220> FEATURE:
<221> NAME/KEY: unsure
<222> LOCATION: (2057)
<223> OTHER INFORMATION: N at position 2057 is a, c, t, or g
<220> FEATURE:
<221> NAME/KEY: unsure
```

```
<222> LOCATION: (2068)
<223> OTHER INFORMATION: N at position 2068 is a, c, t, or g
<220> FEATURE:
<221> NAME/KEY: unsure
<222> LOCATION: (2072)
<223> OTHER INFORMATION: N at position 2072 is a, c, t, or g
<220> FEATURE:
<221> NAME/KEY: unsure
<222> LOCATION: (2076)
<223> OTHER INFORMATION: N at position 2076 is a, c, t, or g
<220> FEATURE:
<221> NAME/KEY: unsure
<222> LOCATION: (2091)
<223> OTHER INFORMATION: N at position 2091 is a, c, t, or g

<400> SEQUENCE: 7
aaccnaaaaa agagatcgaa ttcggcacga gtgatcatgg tccttcgtct tctaagaaca      60
ttattagtga acaattttac caacatggta gtcatgaaaa tatgttgaca acaacaacta     120
ctcatcatga tgatcatcaa ggctcgtggc atcacgataa taacagaaca ttacttgttg     180
atgatccatc tatgagatgt gttttccctt gtgaaggaaa tgaaaggcca agtcatggac     240
tttcattatc tctttgttcc tcaaatccat caagtattgg tttacaatct tttgaactta     300
gacatcaaga tttgcaacaa ggattaatac atgatggatt tttgggtaaa tctacaaata     360
tacaacaagg gtattttcat catcatcatc aagttaggga ctcgaaatat ttaggtccgg     420
ctcaagagtt gctcagtgag ttctgtagtc tcggaataaa gaagaataat gatcattctt     480
cttcaaaagt acttctaaag caacatgaga gtactgctag tacttcaaaa agcaactttt     540
tacagtctct tgacctttg gaacttcaaa aagaaagac aaaattgctt caaatgcttg     600
aagaggtgga tagaaggtac aagcattatt gtgatcaaat gaaggctgtt gtatcatcat     660
ttgaagcagt ggctggaaat ggagcagcaa cagtttactc agccttagca tcaagggcta     720
tgtcaaggca ttttagatgt taagagatg gaattgtggc acaaattaag gccacaaaaa     780
tggctatggg agaaaaagac agtactagta ctcttattcc tggttcaaca agaggtgaaa     840
caccaagact cagacttctt gatcaaactt taaggcaaca aaaggctttc caacagatga     900
atatgatgga gactcatcca tggagaccgc aacgtggtct cccagaaaga tcagtctccg     960
ttctccgcgc ttggctcttt gaacactttc ttcacccgta cccaagtgat gttgataaac    1020
acattttagc tcgccaaact ggtctttcaa gaagccaggt gtctaattgg ttcattaatg    1080
caagggtaag gctatggaag ccaatggtgg aagaaatgta cttagaagaa acaaaagaag    1140
aagaaaatgt tggatctcca gatggatcaa agcccctaat tgatgacatg acaattcatc    1200
aatcacacat tgatcatcat caagctgatc aaaagccaaa tcttgtaaga attgactctg    1260
aatgcatatc ttccatcata aatcatcaac ctcatgagaa aaatgatcaa aactatggag    1320
taattagagg tggagatcaa tcgtttggcg cgattgagct agattttca acaaatattg    1380 cttatggtac tagtggtggt gaccatcatc atcatggagg gggtgtttct ttaacattgg    1440
gattacaaca acatggtgga agtggtggat catcaatggg gttaactaca ttttcatcac    1500
aaccatctca taatcaaagt tcactttttt atccaagaga tgatgatcaa gttcaatatt    1560
catcactttt ggatagtgaa aatcagaatt tgccatatag aaaccttgat gggggcacaa    1620
cttcttcatg atttggctgg ttaaaaaatg acagagattc ttcattttgg accttattat    1680
atactctaat tttaatatat attggtgatg aatgatgata aaaaaaaaa aaaaaaaaa    1740 aaaaaaaaa aaaaaaaaa acctcgancc cggtcgactn tanacccta tagngagtcg    1800 tnttnctgca nanatctntg aatcgtaaat nctgaaaaac cccgcaagtt cacttcaact    1860
```

| | | |
|---|---|---|
| gngcatcgng cnccatctca atttctttca tttatncatc gttttgcctt nttttatgta | 1920 |
| actatnctcc tntaagtttc aatcttggcc atgtaacctn tgatctntaa aatttttaa | 1980 |
| atgactanaa ttaatgccca tntttttttt ggacctaaat tnttcatgaa aatntnttnc | 2040 |
| nagggcttnt tcaaaancttt tggacttntt cnccanaggt ttggtcaagt ntccaatcaa | 2100 |
| ggt | 2103 |

<210> SEQ ID NO 8
<211> LENGTH: 589
<212> TYPE: PRT
<213> ORGANISM: Solanum tuberosum

<400> SEQUENCE: 8

```
Met Val Asn His Gln Leu Gln Asn Phe Glu Thr Asn Pro Glu Met Tyr
  1               5                  10                  15

Asn Leu Ser Ser Thr Thr Ser Ser Met Asp Gln Met Ile Gly Phe Pro
             20                  25                  30

Pro Asn Asn Asn Pro His His Val Leu Trp Lys Gly Asn Phe Pro
         35                  40                  45

Asn Lys Ile Asn Gly Val Asp Asp Asp His Gly Pro Ser Ser Ser
     50                  55                  60

Lys Asn Ile Ile Ser Glu Gln Phe Tyr Gln His Gly Ser His Glu Asn
 65                  70                  75                  80

Met Leu Thr Thr Thr Thr His His Asp Asp His Gln Gly Ser Trp
                 85                  90                  95

His His Asp Asn Asn Arg Thr Leu Leu Val Asp Asp Pro Ser Met Arg
            100                 105                 110

Cys Val Phe Pro Cys Glu Gly Asn Glu Arg Pro Ser His Gly Leu Ser
        115                 120                 125

Leu Ser Leu Cys Ser Ser Asn Pro Ser Ser Ile Gly Leu Gln Ser Phe
    130                 135                 140

Glu Leu Arg His Gln Asp Leu Gln Gln Gly Leu Ile His Asp Gly Phe
145                 150                 155                 160

Leu Gly Lys Ser Thr Asn Ile Gln Gln Gly Tyr Phe His His His
                165                 170                 175

Gln Val Arg Asp Ser Lys Tyr Leu Gly Pro Ala Gln Glu Leu Leu Ser
            180                 185                 190

Glu Phe Cys Ser Leu Gly Ile Lys Lys Asn Asn Asp His Ser Ser Ser
        195                 200                 205

Lys Val Leu Leu Lys Gln His Glu Ser Thr Ala Ser Thr Ser Lys Lys
    210                 215                 220

Gln Leu Leu Gln Ser Leu Asp Leu Leu Glu Leu Gln Lys Arg Lys Thr
225                 230                 235                 240

Lys Leu Leu Gln Met Leu Glu Glu Val Asp Arg Arg Tyr Lys His Tyr
                245                 250                 255

Cys Asp Gln Met Lys Ala Val Val Ser Ser Phe Glu Ala Val Ala Gly
            260                 265                 270

Asn Gly Ala Ala Thr Val Tyr Ser Ala Leu Ala Ser Arg Ala Met Ser
        275                 280                 285

Arg His Phe Arg Cys Leu Arg Asp Gly Ile Val Ala Gln Ile Lys Ala
    290                 295                 300

Thr Lys Met Ala Met Gly Glu Lys Asp Ser Thr Ser Thr Leu Ile Pro
305                 310                 315                 320

Gly Ser Thr Arg Gly Glu Thr Pro Arg Leu Arg Leu Leu Asp Gln Thr
```

```
                       325                 330                 335
Leu Arg Gln Gln Lys Ala Phe Gln Gln Met Asn Met Met Glu Thr His
            340                 345                 350

Pro Trp Arg Pro Gln Arg Gly Leu Pro Glu Arg Ser Val Ser Val Leu
        355                 360                 365

Arg Ala Trp Leu Phe Glu His Phe Leu His Pro Tyr Pro Ser Asp Val
    370                 375                 380

Asp Lys His Ile Leu Ala Arg Gln Thr Gly Leu Ser Arg Ser Gln Val
385                 390                 395                 400

Ser Asn Trp Phe Ile Asn Ala Arg Val Arg Leu Trp Lys Pro Met Val
                405                 410                 415

Glu Glu Met Tyr Leu Glu Glu Thr Lys Glu Glu Asn Val Gly Ser
            420                 425                 430

Pro Asp Gly Ser Lys Ala Leu Ile Asp Asp Met Thr Ile His Gln Ser
        435                 440                 445

His Ile Asp His His Gln Ala Asp Gln Lys Pro Asn Leu Val Arg Ile
    450                 455                 460

Asp Ser Glu Cys Ile Ser Ser Ile Ile Asn His Gln Pro His Glu Lys
465                 470                 475                 480

Asn Asp Gln Asn Tyr Gly Val Ile Arg Gly Gly Asp Gln Ser Phe Gly
                485                 490                 495

Ala Ile Glu Leu Asp Phe Ser Thr Asn Ile Ala Tyr Gly Thr Ser Gly
            500                 505                 510

Gly Asp His His His Gly Gly Val Ser Leu Thr Leu Gly Leu
        515                 520                 525

Gln Gln His Gly Gly Ser Gly Gly Ser Ser Met Gly Leu Thr Thr Phe
    530                 535                 540

Ser Ser Gln Pro Ser His Asn Gln Ser Ser Leu Phe Tyr Pro Arg Asp
545                 550                 555                 560

Asp Asp Gln Val Gln Tyr Ser Ser Leu Leu Asp Ser Glu Asn Gln Asn
                565                 570                 575

Leu Pro Tyr Arg Asn Leu Asp Gly Gly Thr Thr Ser Ser
            580                 585
```

<210> SEQ ID NO 9
<211> LENGTH: 1939
<212> TYPE: DNA
<213> ORGANISM: Solanum tuberosum

<400> SEQUENCE: 9

```
acgagcgttt atgagacagc cgggttgttg tctgaaatgt tcaattttca gacaacatcc     60
acggctgcaa ctgaattgtt gcagaatcaa ttgtcaaata actatagaca cccgaatcaa    120
cagccacatc atcaacctcc gaccagggag tggtttggta acagacaaga gatcgtagtt    180
ggtggaagtt tgcaggtaac atttggggat acaaaagatg atgtgaatgc gaaggtatta    240
ttgagtaacc gtgatagtgt aactgattat tatcagcgtc aacacaatca agtaccaagt    300
ataaataccg cggagtccat gcaactttt cttatgaatc cacaaccaag ttcaccatca    360
caatctactc cttcaactct tcatcaaggg ttttctagcc cggtcggagg gcatttagt    420
caattcatgt gtggaggagc aagtacttct tcaaatccaa ttggaggagt aaatgtgatt    480
gatcaaggc aaggtctttc attgtccttg tcatctactt tacaacattt ggaagcatcc    540
aaagtggaag atttgaggat gaatagtgga ggagaaatgt tgttttttcaa tcaagaaagt    600
caaaatcatc ataatattgg ttttgggtca tcactaggac tagtcaatgt gttgaggaat    660
```

-continued

```
tcaaagtatg tcaaagcaac acaagagttg ttggaagagt tttgttgtgt tgggaagggt      720
caattgttca agaaaatcaa caaagtttct aggaataaca acacaagtac atcacccatt      780 attaaccota gtggaagtaa taacaataat tcatcttctt caaaggctat tatccctcct      840
aatttgtcaa ctgcagagag acttgatcat caaagaagga aggtcaaact tttatccatg      900
cttgatgagg tagagaaaag atacaaccac tattgtgaac aaatgcagat ggtagtaaac      960
tcattcgatc tagtgatggg ttttggagct gcagttcctt acacagcact agcacagaaa     1020
gccatgtcta ggcatttcaa gtgtttaaaa gatggcgtgg cggcgcaatt gaagaagaca     1080
tgtgaggcac taggtgaaaa agatgcaagc agtagttcag gactgactaa aggagaaaca     1140
ccaaggctta aggtgcttga acaaagcttg aggcaacaaa gagcttttca acaaatggga     1200
atgatggaac aagaagcttg gaggccacaa agaggattgc ctgaacgatc tgtcaatatt     1260
ttaagagctt ggcttttcga acattttcta catccgtatc caagtgatgc agataagcat     1320
cttttggcac gacagactgg tctctccaga aaccaggtag caaactggtt cataaatgcg     1380
agggtgagat tgtggaaacc catggtagaa gaaatgtatc aaagagaggt taatgaagat     1440
gatgttgatg acatgcaaga aaaccaaaac agtacaaata cacaaatacc aacgcctaat     1500
attattatta caaccaattc taacattaca gaaacaaaat cagctgccac tgccacaatt     1560
gcttcagaca aaaaaccoca aatcaatgtc tctgaaattg accttcaat tgtcgcaatg     1620 aatacacatt attcttcctc tatgccaact caattaacca atttccccac tattcaagat     1680
gagtccgacc acatcttata tcgccgcagt ggagcggaat atgggaccac aaaatatggct     1740 agtaattctg aaattggatc caacatgata acatttggga ccactacggc tagtgatgtt     1800
tcacttacct taggactgcg ccatgcgggt aatttacctg agaatactca tttttccggt     1860
taattaagat agtgtattca aacactgcta cataaattat gattttatat atatatatat     1920
tgtcatccga ttagtttat                                                  1939
```

<210> SEQ ID NO 10  
<211> LENGTH: 620  
<212> TYPE: PRT  
<213> ORGANISM: Solanum tuberosum

<400> SEQUENCE: 10

```
Thr Ser Val Tyr Glu Thr Ala Gly Leu Leu Ser Glu Met Phe Asn Phe
  1               5                  10                  15

Gln Thr Thr Ser Thr Ala Ala Thr Glu Leu Leu Gln Asn Gln Leu Ser
             20                  25                  30

Asn Asn Tyr Arg His Pro Asn Gln Gln Pro His His Gln Pro Pro Thr
         35                  40                  45

Arg Glu Trp Phe Gly Asn Arg Gln Glu Ile Val Val Gly Gly Ser Leu
     50                  55                  60

Gln Val Thr Phe Gly Asp Thr Lys Asp Val Asn Ala Lys Val Leu
 65                  70                  75                  80

Leu Ser Asn Arg Asp Ser Val Thr Asp Tyr Tyr Gln Arg Gln His Asn
                 85                  90                  95

Gln Val Pro Ser Ile Asn Thr Ala Glu Ser Met Gln Leu Phe Leu Met
            100                 105                 110

Asn Pro Gln Pro Ser Ser Pro Ser Gln Ser Thr Pro Ser Thr Leu His
        115                 120                 125

Gln Gly Phe Ser Ser Pro Val Gly Gly His Phe Ser Gln Phe Met Cys
    130                 135                 140
```

-continued

```
Gly Gly Ala Ser Thr Ser Ser Asn Pro Ile Gly Gly Val Asn Val Ile
145                 150                 155                 160

Asp Gln Gly Gln Gly Leu Ser Leu Ser Leu Ser Ser Thr Leu Gln His
            165                 170                 175

Leu Glu Ala Ser Lys Val Glu Asp Leu Arg Met Asn Ser Gly Gly Glu
            180                 185                 190

Met Leu Phe Phe Asn Gln Glu Ser Gln Asn His His Asn Ile Gly Phe
            195                 200                 205

Gly Ser Ser Leu Gly Leu Val Asn Val Leu Arg Asn Ser Lys Tyr Val
210                 215                 220

Lys Ala Thr Gln Glu Leu Leu Glu Glu Phe Cys Cys Val Gly Lys Gly
225                 230                 235                 240

Gln Leu Phe Lys Lys Ile Asn Lys Val Ser Arg Asn Asn Asn Thr Ser
            245                 250                 255

Thr Ser Pro Ile Ile Asn Pro Ser Gly Ser Asn Asn Asn Asn Ser Ser
            260                 265                 270

Ser Ser Lys Ala Ile Ile Pro Pro Asn Leu Ser Thr Ala Glu Arg Leu
275                 280                 285

Asp His Gln Arg Arg Lys Val Lys Leu Leu Ser Met Leu Asp Glu Val
290                 295                 300

Glu Lys Arg Tyr Asn His Tyr Cys Glu Gln Met Gln Met Val Val Asn
305                 310                 315                 320

Ser Phe Asp Leu Val Met Gly Phe Gly Ala Ala Val Pro Tyr Thr Ala
            325                 330                 335

Leu Ala Gln Lys Ala Met Ser Arg His Phe Lys Cys Leu Lys Asp Gly
            340                 345                 350

Val Ala Ala Gln Leu Lys Lys Thr Cys Glu Ala Leu Gly Glu Lys Asp
            355                 360                 365

Ala Ser Ser Ser Ser Gly Leu Thr Lys Gly Glu Thr Pro Arg Leu Lys
370                 375                 380

Val Leu Glu Gln Ser Leu Arg Gln Gln Arg Ala Phe Gln Gln Met Gly
385                 390                 395                 400

Met Met Glu Gln Glu Ala Trp Arg Pro Gln Arg Gly Leu Pro Glu Arg
            405                 410                 415

Ser Val Asn Ile Leu Arg Ala Trp Leu Phe Glu His Phe Leu His Pro
            420                 425                 430

Tyr Pro Ser Asp Ala Asp Lys His Leu Leu Ala Arg Gln Thr Gly Leu
            435                 440                 445

Ser Arg Asn Gln Val Ala Asn Trp Phe Ile Asn Ala Arg Val Arg Leu
450                 455                 460

Trp Lys Pro Met Val Glu Glu Met Tyr Gln Arg Glu Val Asn Glu Asp
465                 470                 475                 480

Asp Val Asp Asp Met Gln Glu Asn Gln Asn Ser Thr Asn Thr Gln Ile
            485                 490                 495

Pro Thr Pro Asn Ile Ile Ile Thr Thr Asn Ser Asn Ile Thr Glu Thr
            500                 505                 510

Lys Ser Ala Ala Thr Ala Thr Ile Ala Ser Asp Lys Lys Pro Gln Ile
            515                 520                 525

Asn Val Ser Glu Ile Asp Pro Ser Ile Val Ala Met Asn Thr His Tyr
            530                 535                 540

Ser Ser Ser Met Pro Thr Gln Leu Thr Asn Phe Pro Thr Ile Gln Asp
545                 550                 555                 560
```

```
                                      -continued

Glu Ser Asp His Ile Leu Tyr Arg Arg Ser Gly Ala Glu Tyr Gly Thr
                565                 570                 575

Thr Asn Met Ala Ser Asn Ser Glu Ile Gly Ser Asn Met Ile Thr Phe
            580                 585                 590

Gly Thr Thr Thr Ala Ser Asp Val Ser Leu Thr Leu Gly Leu Arg His
        595                 600                 605

Ala Gly Asn Leu Pro Glu Asn Thr His Phe Ser Gly
    610                 615                 620

<210> SEQ ID NO 11
<211> LENGTH: 2128
<212> TYPE: DNA
<213> ORGANISM: Solanum tuberosum
<220> FEATURE:
<221> NAME/KEY: unsure
<222> LOCATION: (2078)
<223> OTHER INFORMATION: N at position 2078 is a, c, t, or g

<400> SEQUENCE: 11
caagggcttt cacttagcct gtcctcgtcc cagcagccgg ggtttgggaa cttcacggcg     60
gcgcgtgagc ttgtttcttc gccttcgggt tcggcttcag cttcagggat acaacaacaa    120
caacagcaac aacagagtat tagtagtgtg cctttgagtt ctaagtacat gaaggctgca    180
caagagctac ttgatgaagt tgtaaatgtt ggaaaatcaa tgaaaagtac taatagtact    240
gatgttgttg ttaataatga tgtcaagaaa tcgaagaata tgggcgatat ggacggacag    300
ttagacggag ttggagcaga caaagacgga gctccaacaa ctgagctaag tacaggggag    360
agacaagaaa ttcaaatgaa gaaagcaaaa cttgttaaca tgcttgacga ggtggagcag    420
aggtatagac attatcatca ccaaatgcag tcagtgatac attggttaga gcaagctgct    480
ggcattggat cagcaaaaac atatacagca ttggctttgc agacgatttc gaagcaattt    540
aggtgtctta aggacgcgat aattggtcaa atacgatcag caagccagac gttaggcgaa    600
gaagatagtt tgggagggaa gattgaaggt tcaaggctta aatttgttga taatcagcta    660
agacagcaaa gggcttttgca acaattggga atgatccagc ataatgcttg agacctcag    720 agaggattgc ccgaacgagc tgtttctgtt cttcgcgctt ggcttttttga acatttcctc    780 catccttatc ccaaggattc agacaaaatg atgctagcaa acaaacagg actaactagg    840 agtcaggtgt cgaattggtt catcaatgct cgagttcgtc tttggaagcc aatggtggaa    900
gagatgtact ggaagagat aaagaacac gaacagaatg ggttgggtca agaaaagacg    960
agcaaattag gtgaacagaa cgaagattca acaacatcaa gatccattgc tacacaagac   1020
aaaagccctg gttcagatag ccaaaacaag agttttgtct caaaacagga caatcatttg   1080
cctcaacaca accctgcttc accaatgccc gatgtccaac gccacttcca tacccctatc   1140
ggtatgacca tccgtaatca gtctgctggt ttcaacctca ttggatcacc agagatcgaa   1200
agcatcaaca ttactcaagg gagtccaaag aaaccgagga caacgagat gttgcattca   1260 ccaaacagca ttccatccat caacatggat gtaaagccta acgaggaaca atgtcgatg    1320 aagtttggtg atgataggca ggacagagat ggattctcac taatgggagg accgatgaac   1380
ttcatgggag gattcggagc ctatcccatt ggagaaattg ctcggtttag caccgagcaa   1440
ttctcagcac catactcaac cagtggcaca gtttcactca ctcttggcct accacataac   1500 gaaacctct caatgtctgc aacacaccac agtttccttc caattccaac acaaacatc    1560 caaattggaa gtgaaccaaa tcatgagttt ggtagcttaa acacaccaac atcagctcac   1620
tcaacatcaa gcgtctatga aaccttcaac attcagaaca gaaagaggtt cgccgcaccc   1680
```

-continued

```
ttgttaccag attttgttgc ctgatcacaa aaacaaaaac aggttttggc aacagacaaa    1740
cttctgtcgc taaacaagga catgatttag cgacagataa cttcagtcgc taacttagcg    1800
actgaaaact tctgtcgcta agcatgaaca tgtattagcg acatacagta tgcaactgta    1860
tgtcactaaa caagaacatg atgaattagt gacggacaac ttctgtcgct aaacaacaaa    1920
aaaaaatcca tgttttagta tattgtttct cattctatca tatcatggta gtgtaaagaa    1980
tcaagaaaca agttttacat agtaacagtc tttatacatt ggagatgaag aaccatttaa    2040
gttcttcaaa atagatagat tttctaggtt acttctanaa gatatatata tggttgaggg    2100
tttgtatatt aaaaaaaaaa aaaaaaaa                                       2128
```

<210> SEQ ID NO 12
<211> LENGTH: 567
<212> TYPE: PRT
<213> ORGANISM: Solanum tuberosum

<400> SEQUENCE: 12

```
Gln Gly Leu Ser Leu Ser Leu Ser Ser Gln Gln Pro Gly Phe Gly
  1               5                  10                  15

Asn Phe Thr Ala Ala Arg Glu Leu Val Ser Ser Pro Ser Gly Ser Ala
                 20                  25                  30

Ser Ala Ser Gly Ile Gln Gln Gln Gln Gln Gln Gln Ser Ile Ser
             35                  40                  45

Ser Val Pro Leu Ser Ser Lys Tyr Met Lys Ala Ala Gln Glu Leu Leu
         50                  55                  60

Asp Glu Val Val Asn Val Gly Lys Ser Met Lys Ser Thr Asn Ser Thr
 65                  70                  75                  80

Asp Val Val Val Asn Asn Asp Val Lys Lys Ser Lys Asn Met Gly Asp
                     85                  90                  95

Met Asp Gly Gln Leu Asp Gly Val Gly Ala Asp Lys Asp Gly Ala Pro
                100                 105                 110

Thr Thr Glu Leu Ser Thr Gly Glu Arg Gln Glu Ile Gln Met Lys Lys
            115                 120                 125

Ala Lys Leu Val Asn Met Leu Asp Glu Val Glu Gln Arg Tyr Arg His
        130                 135                 140

Tyr His His Gln Met Gln Ser Val Ile His Trp Leu Glu Gln Ala Ala
145                 150                 155                 160

Gly Ile Gly Ser Ala Lys Thr Tyr Thr Ala Leu Ala Leu Gln Thr Ile
                165                 170                 175

Ser Lys Gln Phe Arg Cys Leu Lys Asp Ala Ile Ile Gly Gln Ile Arg
            180                 185                 190

Ser Ala Ser Gln Thr Leu Gly Glu Glu Asp Ser Leu Gly Gly Lys Ile
        195                 200                 205

Glu Gly Ser Arg Leu Lys Phe Val Asp Asn Gln Leu Arg Gln Gln Arg
    210                 215                 220

Ala Leu Gln Gln Leu Gly Met Ile Gln His Asn Ala Trp Arg Pro Gln
225                 230                 235                 240

Arg Gly Leu Pro Glu Arg Ala Val Ser Val Leu Arg Ala Trp Leu Phe
                245                 250                 255

Glu His Phe Leu His Pro Tyr Pro Lys Asp Ser Asp Lys Met Met Leu
            260                 265                 270

Ala Lys Gln Thr Gly Leu Thr Arg Ser Gln Val Ser Asn Trp Phe Ile
        275                 280                 285
```

```
Asn Ala Arg Val Arg Leu Trp Lys Pro Met Val Glu Glu Met Tyr Leu
    290                 295                 300
Glu Glu Ile Lys Glu His Glu Gln Asn Gly Leu Gly Gln Glu Lys Thr
305                 310                 315                 320
Ser Lys Leu Gly Glu Gln Asn Glu Asp Ser Thr Thr Ser Arg Ser Ile
                325                 330                 335
Ala Thr Gln Asp Lys Ser Pro Gly Ser Asp Ser Gln Asn Lys Ser Phe
            340                 345                 350
Val Ser Lys Gln Asp Asn His Leu Pro Gln His Asn Pro Ala Ser Pro
        355                 360                 365
Met Pro Asp Val Gln Arg His Phe His Thr Pro Ile Gly Met Thr Ile
    370                 375                 380
Arg Asn Gln Ser Ala Gly Phe Asn Leu Ile Gly Ser Pro Glu Ile Glu
385                 390                 395                 400
Ser Ile Asn Ile Thr Gln Gly Ser Pro Lys Lys Pro Arg Asn Asn Glu
                405                 410                 415
Met Leu His Ser Pro Asn Ser Ile Pro Ser Ile Asn Met Asp Val Lys
            420                 425                 430
Pro Asn Glu Glu Gln Met Ser Met Lys Phe Gly Asp Asp Arg Gln Asp
        435                 440                 445
Arg Asp Gly Phe Ser Leu Met Gly Pro Met Asn Phe Met Gly Gly
    450                 455                 460
Phe Gly Ala Tyr Pro Ile Gly Glu Ile Ala Arg Phe Ser Thr Glu Gln
465                 470                 475                 480
Phe Ser Ala Pro Tyr Ser Thr Ser Gly Thr Val Ser Leu Thr Leu Gly
                485                 490                 495
Leu Pro His Asn Glu Asn Leu Ser Met Ser Ala Thr His His Ser Phe
            500                 505                 510
Leu Pro Ile Pro Thr Gln Asn Ile Gln Ile Gly Ser Glu Pro Asn His
        515                 520                 525
Glu Phe Gly Ser Leu Asn Thr Pro Thr Ser Ala His Ser Thr Ser Ser
    530                 535                 540
Val Tyr Glu Thr Phe Asn Ile Gln Asn Arg Lys Arg Phe Ala Ala Pro
545                 550                 555                 560
Leu Leu Pro Asp Phe Val Ala
                565
```

<210> SEQ ID NO 13
<211> LENGTH: 2065
<212> TYPE: DNA
<213> ORGANISM: Solanum tuberosum

<400> SEQUENCE: 13

```
atctccaagt aaaaggtta ttgagaaaag taacacagat ggcgacttat tttcctagtc    60
caaacaatca aagagatgct gatcagacat ttcatatttt taggcaatct ttgcctgagt   120
cttattcaga agcttcaaat gctccagaaa acatgatggt attcatgaac tattcttctt   180
ctggggcata ttcagatatg ttgacgggta cttcccaaca acaacacaac tgcatcgata   240
tcccatctat aggagccacg cctttcaaca catcccaaca agaaatattg tcaaatcttg   300
gaggatcgca gatggggatt caggattttt cttcatggag agatagcaga atgagatgc   360
tagctgataa tgtctttcaa gttgcacaaa atgtgcaggg tcaaggatta ccctcagtc   420
ttggctccaa ataccatct ggaattggaa tttcacatgt ccaatctcag atcctaacc   480
aaggtggcgg ttttaacatg tcctttggag atggtgataa ttcccaacca aaagaacaaa  540
```

```
gaaatgcaga ttattttcct ccggataatc ctggaaggga cttggatgct atgaaagggt    600
ataattctcc atatggtacg tcgagtattg caaggaccat cccagctcg aagtatttga    660 aagcagctca atatttgctt gatgaggttg ttagtgtcag aaaggccatc aaggagcaaa    720
attctaagaa agagttgaca aaggattcca gagagtctga tgtggactcg aaaaatatat    780
catcagatac tcctgcaaat gggggttcaa atcctcatga gtccaaaaac aaccaaagtg    840
aactttcacc taccgagaag caagaagtgc agaacaaact ggccaaactt ctgtcaatgc    900
tggatgagat tgatagaagg tacagacaat attatcatca gatgcaaata gtggtttcat    960
catttgatgt ggtagctgga gaaggagcag ctaaaccata cacagctctt gctctccaga   1020
caatttcccg acacttccgt tgcttgcgtg atgcaatctg cgatcagatt cgagcatcac   1080
gaagaagtct tggagagcaa gatgcttcag aaaacagcaa agcgattgga atatcacgcc   1140
tgcgttttgt ggatcatcat attagacagc agagagccct gcagcagctt ggtatgatgc   1200
aacaacatgc ctggaggcct cagaggggat tgcctgaaag ctctgtttca gttttgcgtg   1260
cttggctctt tgagcacttt cttcatccct acccgaaaga ttctgacaaa attatgctag   1320
caaggcaaac tggcttaacg agaagtcagg tatcaaattg gttcataaat gcacgggtgc   1380
gtctttggaa acccatggtt gaggaaatgt acaaagaaga ggctggtgat gctaaaatag   1440
actcaaattc ttcatcggat gttgcccca gacttgcaac aaaagactca aagttgaag     1500 aaagaggaga attgcaccag aatgcagctt cagaatttga gcagtacaat agtggccaaa   1560
tcctggagtc aaaatctaac catgaagctg atgtagaaat ggagggagca agtaatgcag   1620
aaactcaaag tcaatctgga atggaaaacc aaacaggcga accctgcct gctatggata    1680 attgcaccct ttttcaggac gcatttgttc aaagcaacga tagattctca gaatttggta   1740
gttttggaag tggaaatgta ctacccaatg gagtttcact tacattgggg ctgcagcaag   1800
gtgaaggaag caacctacct atgtccatcg aaactcacgt tagttatgta ccattaaggg   1860
cagatgacat gtatagtaca gcacctacta ctatggtccc tgaaacagca gaattcaact   1920
gcttggattc tgggaatagg cagcaaccat tttggctcct accatctgct acatgatttt   1980
gtatgtgttg tagaattaaa ctgcaagttt tgagtacatc aacattcatc ttcaaaaaaa   2040
aaaaaaaaaa aaaaaaaaaa aaaaa                                          2065
```

<210> SEQ ID NO 14
<211> LENGTH: 645
<212> TYPE: PRT
<213> ORGANISM: Solanum tuberosum

<400> SEQUENCE: 14

```
Met Ala Thr Tyr Phe Pro Ser Pro Asn Asn Gln Arg Asp Ala Asp Gln
 1               5                  10                  15

Thr Phe Gln Tyr Phe Arg Gln Ser Leu Pro Glu Ser Tyr Ser Glu Ala
             20                  25                  30

Ser Asn Ala Pro Glu Asn Met Met Val Phe Met Asn Tyr Ser Ser Ser
         35                  40                  45

Gly Ala Tyr Ser Asp Met Leu Thr Gly Thr Ser Gln Gln Gln His Asn
     50                  55                  60

Cys Ile Asp Ile Pro Ser Ile Gly Ala Thr Pro Phe Asn Thr Ser Gln
 65                  70                  75                  80

Gln Glu Ile Leu Ser Asn Leu Gly Gly Ser Gln Met Gly Ile Gln Asp
                 85                  90                  95
```

```
Phe Ser Ser Trp Arg Asp Ser Arg Asn Glu Met Leu Ala Asp Asn Val
            100                 105                 110
Phe Gln Val Ala Gln Asn Val Gln Gly Gln Gly Leu Ser Leu Ser Leu
        115                 120                 125
Gly Ser Asn Ile Pro Ser Gly Ile Gly Ile Ser His Val Gln Ser Gln
    130                 135                 140
Asn Pro Asn Gln Gly Gly Gly Phe Asn Met Ser Phe Gly Asp Gly Asp
145                 150                 155                 160
Asn Ser Gln Pro Lys Glu Gln Arg Asn Ala Asp Tyr Phe Pro Pro Asp
                165                 170                 175
Asn Pro Gly Arg Asp Leu Asp Ala Met Lys Gly Tyr Asn Ser Pro Tyr
            180                 185                 190
Gly Thr Ser Ser Ile Ala Arg Thr Ile Pro Ser Ser Lys Tyr Leu Lys
        195                 200                 205
Ala Ala Gln Tyr Leu Leu Asp Glu Val Val Ser Val Arg Lys Ala Ile
    210                 215                 220
Lys Glu Gln Asn Ser Lys Lys Glu Leu Thr Lys Asp Ser Arg Glu Ser
225                 230                 235                 240
Asp Val Asp Ser Lys Asn Ile Ser Ser Asp Thr Pro Ala Asn Gly Gly
                245                 250                 255
Ser Asn Pro His Glu Ser Lys Asn Asn Gln Ser Glu Leu Ser Pro Thr
            260                 265                 270
Glu Lys Gln Glu Val Gln Asn Lys Leu Ala Lys Leu Leu Ser Met Leu
        275                 280                 285
Asp Glu Ile Asp Arg Arg Tyr Arg Gln Tyr Tyr His Gln Met Gln Ile
    290                 295                 300
Val Val Ser Ser Phe Asp Val Ala Gly Glu Gly Ala Ala Lys Pro
305                 310                 315                 320
Tyr Thr Ala Leu Ala Leu Gln Thr Ile Ser Arg His Phe Arg Cys Leu
                325                 330                 335
Arg Asp Ala Ile Cys Asp Gln Ile Arg Ala Ser Arg Arg Ser Leu Gly
            340                 345                 350
Glu Gln Asp Ala Ser Glu Asn Ser Lys Ala Ile Gly Ile Ser Arg Leu
        355                 360                 365
Arg Phe Val Asp His His Ile Arg Gln Gln Arg Ala Leu Gln Gln Leu
    370                 375                 380
Gly Met Met Gln Gln His Ala Trp Arg Pro Gln Arg Gly Leu Pro Glu
385                 390                 395                 400
Ser Ser Val Ser Val Leu Arg Ala Trp Leu Phe Glu His Phe Leu His
                405                 410                 415
Pro Tyr Pro Lys Asp Ser Asp Lys Ile Met Leu Ala Arg Gln Thr Gly
            420                 425                 430
Leu Thr Arg Ser Gln Val Ser Asn Trp Phe Ile Asn Ala Arg Val Arg
        435                 440                 445
Leu Trp Lys Pro Met Val Glu Glu Met Tyr Lys Glu Ala Gly Asp
    450                 455                 460
Ala Lys Ile Asp Ser Asn Ser Ser Ser Asp Val Ala Pro Arg Leu Ala
465                 470                 475                 480
Thr Lys Asp Ser Lys Val Glu Glu Arg Gly Glu Leu His Gln Asn Ala
                485                 490                 495
Ala Ser Glu Phe Glu Gln Tyr Asn Ser Gly Gln Ile Leu Glu Ser Lys
            500                 505                 510
Ser Asn His Glu Ala Asp Val Glu Met Glu Gly Ala Ser Asn Ala Glu
```

|  |  | 515 |  |  | 520 |  |  | 525 |  |
|---|---|---|---|---|---|---|---|---|---|

Thr Gln Ser Gln Ser Gly Met Glu Asn Gln Thr Gly Glu Pro Leu Pro
        530                  535                540

Ala Met Asp Asn Cys Thr Leu Phe Gln Asp Ala Phe Val Gln Ser Asn
545                  550                555              560

Asp Arg Phe Ser Glu Phe Gly Ser Phe Gly Ser Gly Asn Val Leu Pro
                565              570                575

Asn Gly Val Ser Leu Thr Leu Gly Leu Gln Gln Gly Glu Gly Ser Asn
                580              585                590

Leu Pro Met Ser Ile Glu Thr His Val Ser Tyr Val Pro Leu Arg Ala
        595                  600              605

Asp Asp Met Tyr Ser Thr Ala Pro Thr Thr Met Val Pro Glu Thr Ala
610                  615                620

Glu Phe Asn Cys Leu Asp Ser Gly Asn Arg Gln Gln Pro Phe Trp Leu
625                  630                635              640

Leu Pro Ser Ala Thr
                645

<210> SEQ ID NO 15
<211> LENGTH: 7
<212> TYPE: PRT
<213> ORGANISM: Solanum tuberosum

<400> SEQUENCE: 15

Val Ser Leu Thr Leu Gly Leu
  1              5

<210> SEQ ID NO 16
<211> LENGTH: 1383
<212> TYPE: DNA
<213> ORGANISM: Solanum tuberosum

<400> SEQUENCE: 16

```
gagtttctct ccctttaaa aagaaaaaa aaaacacaac acccacttca aatatcaaac      60
aaatttctca tttgattatt tctaagtgat ttacactact ttgtattttt gtttgttttt     120
ttttagatat atatatggat gatgaaatgt atggttttca ttcaacaaga gacgattacg    180
cggataaagc tttgatgtca ccggagaatt tgatgatgca aactgagtac aacaatttcc    240
acaactatac caactcgtcc atcttgactt ctaatccgat gatgtttgga tccgatgata    300
ttcaattatc atcggaacaa actaattctt tcagtactat gactcttcaa ataatgata    360
atatttatca aattagaagt ggaaattgtg gcggaggcag tggcagtggt ggtagcagta    420
aggatcataa tgataataac aataataatg aagattatga tgaagatggt tcaaatgtta    480
tcaaggctaa aatcgtctca catccttatt atcctaaatt actcaacgct tatattgatt    540
gccaaaaggt tggagcacca gcgggtatag taaatctgct ggaagaaata aggcaacaaa    600
ctgattttcg taaaccaaac gctacttcta tatgtatagg agctgatcct gaacttgatg    660
agtttatgga aacgtattgt gatatattgt tgaagtataa gtccgatctg tctaggcctt    720
ttgatgaagc aacaacgttc ctcaacaaga ttgaaatgca actaggtaat ctttgcaaag    780
atgatggtgg tgtatcatca gatgaggagt taagttgtgg tgaggcagat gcatcaatga    840
gaagtgagga taatgaactc aaagatagac tcctacgtaa gtttggaagt catttaagta    900
gtctaaagtt ggaattttca aagaaaaaga agaaagggaa gctaccaaaa gaggcaaggc    960
aaatgttact tgcatggtgg gatgatcact ttagatggcc ttaccctacg gaggctgata   1020
```

```
agaattcact agcagaatca acaggacttg atccaaagca gatcaacaat tggtttataa    1080
atcaaaggaa gagacattgg aaaccatcag agaatatgca gttagctgtt atggataatc    1140
taagctctca gttcttctca tcagatgatt gagtttgaat ggaaattgtg aaaatactgc    1200
tcttcatttc tctttttatt atatataata tataaatagt atattttggg gaaagaaaga    1260
agttatttta ttaatcaaaa tctctataaa taatggtaga gattaattaa tgttgaattc    1320
ttcttgatca tgtaaatatt caatctagct aattgtcaaa attaatgctt acctaaaaaa    1380
aaa                                                                 1383
```

<210> SEQ ID NO 17
<211> LENGTH: 345
<212> TYPE: PRT
<213> ORGANISM: Solanum tuberosum

<400> SEQUENCE: 17

```
Met Asp Asp Glu Met Tyr Gly Phe His Ser Thr Arg Asp Asp Tyr Ala
  1               5                  10                  15

Asp Lys Ala Leu Met Ser Pro Glu Asn Leu Met Met Gln Thr Glu Tyr
             20                  25                  30

Asn Asn Phe His Asn Tyr Thr Asn Ser Ser Ile Leu Thr Ser Asn Pro
         35                  40                  45

Met Met Phe Gly Ser Asp Asp Ile Gln Leu Ser Ser Glu Gln Thr Asn
     50                  55                  60

Ser Phe Ser Thr Met Thr Leu Gln Asn Asn Asp Asn Ile Tyr Gln Ile
 65                  70                  75                  80

Arg Ser Gly Asn Cys Gly Gly Ser Gly Ser Gly Ser Lys
                 85                  90                  95

Asp His Asn Asp Asn Asn Asn Asn Glu Asp Tyr Asp Glu Asp Gly
                100                 105                 110

Ser Asn Val Ile Lys Ala Lys Ile Val Ser His Pro Tyr Tyr Pro Lys
                115                 120                 125

Leu Leu Asn Ala Tyr Ile Asp Cys Gln Lys Val Gly Ala Pro Ala Gly
            130                 135                 140

Ile Val Asn Leu Leu Glu Glu Ile Arg Gln Gln Thr Asp Phe Arg Lys
145                 150                 155                 160

Pro Asn Ala Thr Ser Ile Cys Ile Gly Ala Asp Pro Glu Leu Asp Glu
                165                 170                 175

Phe Met Glu Thr Tyr Cys Asp Ile Leu Leu Lys Tyr Lys Ser Asp Leu
            180                 185                 190

Ser Arg Pro Phe Asp Glu Ala Thr Thr Phe Leu Asn Lys Ile Glu Met
        195                 200                 205

Gln Leu Gly Asn Leu Cys Lys Asp Asp Gly Gly Val Ser Ser Asp Glu
    210                 215                 220

Glu Leu Ser Cys Gly Glu Ala Asp Ala Ser Met Arg Ser Glu Asp Asn
225                 230                 235                 240

Glu Leu Lys Asp Arg Leu Leu Arg Lys Phe Gly Ser His Leu Ser Ser
                245                 250                 255

Leu Lys Leu Glu Phe Ser Lys Lys Lys Lys Gly Lys Leu Pro Lys
            260                 265                 270

Glu Ala Arg Gln Met Leu Leu Ala Trp Trp Asp His Phe Arg Trp
        275                 280                 285

Pro Tyr Pro Thr Glu Ala Asp Lys Asn Ser Leu Ala Glu Ser Thr Gly
    290                 295                 300
```

```
Leu Asp Pro Lys Gln Ile Asn Asn Trp Phe Ile Asn Gln Arg Lys Arg
305                 310                 315                 320

His Trp Lys Pro Ser Glu Asn Met Gln Leu Ala Val Met Asp Asn Leu
            325                 330                 335

Ser Ser Gln Phe Phe Ser Ser Asp Asp
            340                 345
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
aagaagaaga agaaagggaa                                             20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 19
atgaaccagt tgttgat                                                17

<210> SEQ ID NO 20
<211> LENGTH: 10
<212> TYPE: DNA
<213> ORGANISM: Solanum tuberosum

<400> SEQUENCE: 20
ttgacttgac                                                        10

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 21
ggatccttga agtggctctt ctct                                        24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22
aatctagaga cactctcttt ttcgt                                       25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
ctatttgact tcacacggtt attt                                        24

```
<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 24
aaataaccgt gtgaagtcaa atag                                          24

<210> SEQ ID NO 25
<211> LENGTH: 8
<212> TYPE: DNA
<213> ORGANISM: Solanum tuberosum

<400> SEQUENCE: 25 tgacagst                                                             8

<210> SEQ ID NO 26
<211> LENGTH: 9
<212> TYPE: DNA
<213> ORGANISM: Solanum tuberosum

<400> SEQUENCE: 26 tgacttgac                                                            9

<210> SEQ ID NO 27
<211> LENGTH: 9
<212> TYPE: DNA
<213> ORGANISM: Solanum tuberosum

<400> SEQUENCE: 27 tgaswtgac                                                            9

<210> SEQ ID NO 28
<211> LENGTH: 10
<212> TYPE: DNA
<213> ORGANISM: Solanum tuberosum

<400> SEQUENCE: 28
tgattgacag                                                          10
```